United States Patent

De et al.

[11] Patent Number: 5,164,388
[45] Date of Patent: Nov. 17, 1992

[54] HETEROCYCLIC PEPTIDE RENIN INHIBITORS

[75] Inventors: Biswanath De, Vernon Hills; Hwan S. Jae, Glencoe, both of Ill.

[73] Assignee: Abbott Laboratories, Abbott Park, Ill.

[21] Appl. No.: 678,266

[22] PCT Filed: Oct. 18, 1989

[86] PCT No.: PCT/US89/04649
§ 371 Date: Apr. 18, 1991
§ 102(e) Date: Apr. 18, 1991

[87] PCT Pub. No.: WO90/04917
PCT Pub. Date: May 5, 1990

Related U.S. Application Data

[63] Continuation-in-part of Ser. No. 390,571, Aug. 7, 1989, abandoned, which is a continuation-in-part of Ser. No. 259,959, Oct. 19, 1988, abandoned.

[51] Int. Cl.$^5$ .......................... A61K 31/495
[52] U.S. Cl. .................. 514/235.8; 514/210; 514/230.8; 514/231.5; 514/252; 514/255; 514/315; 514/326; 514/345; 514/397; 514/18; 540/492; 544/121; 544/132; 544/295; 544/357; 544/360; 544/369; 544/370; 544/375; 544/384; 544/385; 544/392; 544/398; 544/95; 544/99; 546/184; 546/209; 546/210; 546/216; 548/204; 548/215; 548/228; 548/318; 548/336; 548/341; 548/541; 530/332; 560/45; 560/51; 562/444
[58] Field of Search .................. 514/18, 252, 235.8; 530/332; 544/295, 357, 360, 369, 370, 375

[56] References Cited

U.S. PATENT DOCUMENTS

| | | | |
|---|---|---|---|
| 2,501,455 | 3/1950 | Stekol | 544/385 |
| 3,121,717 | 2/1964 | Fisher et al. | 544/385 |
| 3,796,703 | 3/1974 | Fauraw et al. | 544/360 |
| 4,029,650 | 6/1977 | Raynaud et al. | 544/360 |
| 4,548,926 | 10/1985 | Matsueda . | |
| 4,585,774 | 4/1986 | Tomiuaga | 544/357 |
| 4,645,759 | 2/1987 | Luly et al. | 530/330 |
| 4,652,551 | 3/1987 | Luly et al. | 530/330 |
| 4,657,931 | 4/1987 | Baran et al. . | |
| 4,680,284 | 7/1987 | Luly | 530/330 |
| 4,705,846 | 11/1987 | Thaisrivongs | 530/330 |
| 4,713,445 | 12/1987 | Szelke et al. | 530/330 |
| 4,725,580 | 2/1988 | Wagnon | 530/332 |
| 4,727,060 | 2/1988 | Buhlmayer et al. . | |
| 4,755,592 | 7/1988 | Raddatz et al. . | |
| 4,758,584 | 7/1988 | Buhlmayer et al. . | |
| 4,782,043 | 11/1988 | Boger . | |
| 4,812,442 | 3/1989 | Boger . | |
| 4,826,815 | 5/1989 | Luly et al. | 530/331 |
| 4,826,958 | 5/1989 | Sham | 548/229 |
| 4,837,204 | 6/1989 | Rosenberg et al. | 530/331 |
| 4,994,477 | 2/1991 | Kempf et al. | 548/429 |
| 5,032,577 | 7/1991 | Fung et al. | 530/332 |
| 5,055,466 | 10/1991 | Weller et al. | 544/369 |
| 5,059,589 | 10/1991 | Stein et al. | 514/18 |
| 5,063,208 | 11/1991 | Rosenberg et al. | 530/332 |
| 5,098,924 | 3/1992 | Poss | 544/370 |

FOREIGN PATENT DOCUMENTS

| | | |
|---|---|---|
| 76222/87 | 2/1988 | Australia . |
| 0189203 | 7/1986 | European Pat. Off. . |
| 0228192 | 7/1987 | European Pat. Off. . |
| 0229667 | 7/1987 | European Pat. Off. . |
| 0231919 | 8/1987 | European Pat. Off. . |
| 0310070 | 4/1989 | European Pat. Off. . |
| 0310071 | 4/1989 | European Pat. Off. . |
| 0310072 | 4/1989 | European Pat. Off. . |
| 0310073 | 4/1989 | European Pat. Off. . |
| 0311012 | 4/1989 | European Pat. Off. . |
| 3721855 | 9/1988 | Fed. Rep. of Germany . |
| WO87/02581 | 5/1987 | PCT Int'l Appl. . |
| WO87/02986 | 5/1987 | PCT Int'l Appl. . |
| WO87/05302 | 9/1987 | PCT Int'l Appl. . |
| WO88/02374 | 4/1988 | PCT Int'l Appl. . |
| WO88/05050 | 7/1988 | PCT Int'l Appl. . |

OTHER PUBLICATIONS

Chem. Abstr. vol. 108, Entry 38432d (1988) Abstract Ger. 3,601,248 (Breipohl).
Hansen, Biochem. Biophys. Res. Commun. 132 155 (1985).
Moore, Biochem. Biophys. Res. Commun., 159 420 (1989).
Billich, J. Biol. Chem., 263 1790S (1988).
Richards, FEBS Lett., 247 113 (1989).

*Primary Examiner*—Donald G. Daus
*Attorney, Agent, or Firm*—Steven R. Crowley

[57] ABSTRACT

A renin inhibiting compound of the formula

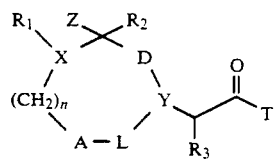

wherein X is N, O or CH; $R_1$ is absent or a functional group; A and L are independently selected from absent, C=O, $SO_2$ and $CH_2$; D is C=O, $SO_2$ or $CH_2$; Y is N or CH; $R_2$ is hydrogen, loweralkyl or substituted alkyl; Z is a functional group; $R_3$ is loweralkyl or substituted alkyl; n is 0 or 1; and T is a mimic of the Leu-Val cleavage site of angiotensinogen; or a pharmaceutically acceptable salt, ester or prodrug thereof.

14 Claims, No Drawings

HETEROCYCLIC PEPTIDE RENIN INHIBITORS

This is a continuation-in-part of U.S. patent application Ser. No. 390,571, filed Aug. 7, 1989, which is a continuation-in-part of U.S. patent application Ser. No. 259,959, filed Oct. 19, 1988 both are now abandoned.

TECHNICAL FIELD

The present invention relates to novel compounds and compositions which inhibit renin, processes for making such compounds, synthetic intermediates employed in these processes, and a method of treating hypertension or congestive heart failure with such compounds or in combination with another antihypertensive agent. The present invention also relates to compositions and a method for treating glaucoma with such compounds and a method of inhibiting retroviral proteases and treating a retroviral infection with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharamacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. Sodium retention causes blood volume to increase, which leads to hypertension. AII is cleaved by an aminopeptidase to form angiotensin III (AIII), which, compared to AII, is a less potent vasoconstrictor but a more potent inducer of aldosterone release.

Angiotensinogen, the natural substrate for human renin has the following amino acid sequence.

renin. When these two parts are combined in one compound, the compound binds to renin but is not cleaved. Thus, renin is inhibited from acting on its natural substrate angiotensinogen.

Inhibitors of renin have been sought as agents for control of hypertension and as diagnostic agents for identification of cases of hypertension due to renin excess.

With these objectives in mind, the renin-angiotensin system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavorial and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (*Nature*, Vol. 303, p. 81, 1983). In addition, Szelke and co-workers have described polypeptide analogs containing a non-peptide link, (*Nature*, Vol. 299, p. 555, 1982) which also cause potent renin inhibition and show a high specificity for this enzyme. Recent patents have disclosed novel small peptide renin inhibitors which contain novel dipeptide isosteres as transition state analogs (Szelke, et al., U.S. Pat. No. 4,609,643; Boger, et al., U.S. Pat. No. 4,668,770; Baran, et al., U.S. Pat. No. 4,657,931; Matsueda, et al., U.S. Pat. No. 4,548,926; Luly, et al., U.S. Pat. No. 4,645,759; and Luly, et al., U.S. Pat. No. 4,680,284).

The following references disclose peptide renin inhibitors which incorporate hydroxyl, substituted amide and heterocyclic derivatives of statine and statine analogs:

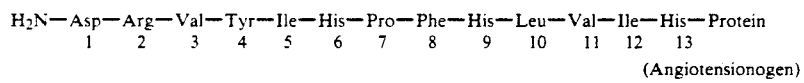

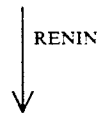

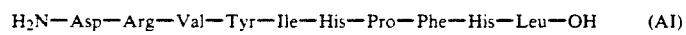

Renin cleaves angiotensinogen at the amide bond between amino acid residues 10 and 11 to give angiotensin I (AI).

Compounds which are inhibitors of renin generally comprise two parts. One part of the compound mimics the first 9 amino acid residues of angiotensinogen. The other part mimics the Leu-Val cleavage site of angiotensinogen and is designed to be non-cleavable by Luly, et al., U.S. Pat. No. 4,845,079, issued Jul. 4, 1989;

Fung, et al., PCT Patent Application No. WO88/05050, published Jul. 14, 1988;

Luly, et al., U.S. Pat. No. 4,725,584, issued Feb. 16, 1988;

Luly, et al., U.S. Pat. No. 4,680,284, issued Jul. 14, 1987;

Rosenberg, et al., U.S. Pat. No. 4,837,204, issued Jun. 6, 1989;

Baran, et al., U.S. Pat. No. 4,657,931, issued Apr. 14, 1987;

Matsueda, et al., U.S. Pat. No. 4,548,926, issued Oct. 22, 1985;

Morisawa, et al., European Patent Application No. 0228192, published Jul. 8, 1987;

Ten Brink, PCT Patent Application No. WO87/02986, published May 21, 1987;

Buhlmayer, et al., U.S. Pat. No. 4,727,060, issued Feb. 23, 1988;

Buhlmayer, et al., U.S. Pat. No. 4,758,584, issued Jul. 19, 1988;

Szelke, et al., U.S. Pat. No. 4,713,445, issued Dec. 15, 1987;

Raddatz, et al., U.S. Pat. No. 4,755,592, issued Jul. 5, 1988;

Raddatz, et al., Australian Patent Application No. AU 76222/87, published Feb. 4, 1988;

Ryono, et al., European Patent Application No. EP 0231919, published Aug. 12, 1987;

Hanson, Biochem. Biophys. Res. Commun. 132155 (1985); Luly, European Patent Application No. EP0189203, published Jul. 30, 1986;

Hanson, et al., European Patent Application No. EP0310070, published Apr. 5, 1989;

Hanson, et al., European Patent Application No. EP0310071, published Apr. 5, 1989;

Hanson, et al., European Patent Application No. EP0310072, published Apr. 5, 1989;

Hanson, et al., European Patent Application No. EP0310073, published Apr. 5, 1989; and Gante, et al., German Patent Application No. DE3721855, published Sep. 22, 1988.

Thaisrivongs, U.S. Pat. No. 4,705,846, issued Nov. 10, 1987, discloses peptide renin inhibitors incorporating a 5- or 6-membered lactam.

Schostarez, et al., PCT Patent Application No. WO88/02374, published Apr. 7, 1988, discloses peptide renin inhibitors incorporating a lactam.

Thaisrivongs, PCT Patent Application No. WO87/05302, published Sep. 11, 1987, discloses peptide renin inhibitors incorporating a lactam.

Szelke, et al., U.S. Pat. No. 4,713,445, issued Dec. 15, 1987, discloses peptide renin inhibitors incorporating an azalactam.

Boger, et al., U.S. Pat. No. 4,782,043, issued Nov. 1, 1988, discloses cyclic peptide renin inhibitors in combination with other antihypertensive agents.

Boger, et al., U.S. Pat. No. 4,812,442, issued Mar. 14, 1989, discloses tripeptide renin inhibitors in combination with other antihypertensive agents.

Watkins, PCT Patent Application No. WO87/02581, published May 7, 1987, discloses the use of renin inhibitors for the treatment of glaucoma.

Stein, et al., European Patent Application No. EP0311012, published Apr. 12, 1989, discloses renin inhibitors having a diol substituent which are antiglaucoma agents.

Peptidyl inhibitors of HIV protease are disclosed by Moore, Biochem. Biophys. Res. Commun., 159 420 (1989); Billich, J. Biol. Chem., 263 1790S (1988); and Richards, FEBS Lett., 247 113 (1989).

DISCLOSURE OF THE INVENTION

In accordance with the present invention, there are renin inhibiting compounds of the formula:

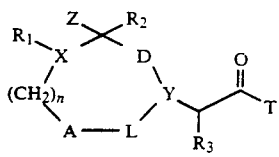

or a pharmaceutically acceptable salt, ester or prodrug thereof.

X is
(I) N,
(II) O or
(III) CH.

$R_1$ is
(I) absent,
(II) hydrogen,
(III) an N-protecting group,
(IV) aryl,
(V) heterocyclic, or
(VI) $R_6$—Q—wherein
 1) $R_6$ is
  i) loweralkyl,
  ii) amino,
  iii) alkylamino,
  iv) dialkylamino,
  v) (alkoxyalkyl)(alkyl)amino,
  vi) (alkoxyalkoxyalkyl)(alkyl)amino,
  vii) aryl,
  viii) arylalkyl,
  ix) aminoalkyl,
  x) (N-protected)aminoalkyl,
  xi) alkoxy,
  xii) substituted loweralkyl wherein the substituent is selected from alkoxy, thioalkoxy, halogen, alkylamino, (N-protected)(alkyl)amino and dialkylamino,

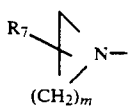

xiii)

wherein m is 1 to 5 and $R_7$ is hydrogen, hydroxy, alkoxy, thioalkoxy, alkoxyalkoxy, polyalkoxy, amino, (N-protected)amino, alkylamino, (N-protected)(alkyl)amino or dialkylamino; or

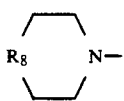

xiv)

wherein $R_8$ is O, S, $SO_2$, O=C or $R_9N$ wherein $R_9$ is hydrogen, loweralkyl or an N-protecting group; and
 2) Q is
  i) C=O or
  ii) $CH_2$,
with the proviso that X is N when $R_1$ is an N-protecting group;

(VII) $R_{54}S(O)_2$—wherein $R_{54}$ is
1) amino,
2) alkylamino,
3) dialkylamino,
4) loweralkyl,
5) haloalkyl,
6) aryl,
7) p-biphenyl,
8) heterocyclic or (VIII) $(R_{55})_2P(O)$—wherein $R_{55}$ is
1) alkoxy,
2) alkylamino or
3) dialkylamino.

A and L are independently selected from
(I) absent,
(II) C=O,
(III) $SO_2$ and
(IV) $CH_2$.

D is
(I) C=O,
(II) $SO_2$ or
(III) $CH_2$.

Y is
(I) N or
(II) CH.

$R_2$ is
(I) hydrogen,
(II) loweralkyl,
(III) cycloalkylalkyl,
(IV) $-CH_2-R_{10}-(CH_2)_q-R_{11}$ wherein
1) q is 0, 1 or 2,
2) $R_{10}$ is absent or $R_{10}$ is O, NH or S only when q is 1 or 2, and
3) $R_{11}$ is
i) aryl or
ii) heterocyclic.

Z is
(I) hydrogen or
(II) $-R_{28}C(O)R_{29}$, $-R_{28}S(O)_2R_{29}$ or $-R_{28}-C(S)R_{29}$ wherein
1) $R_{28}$ is
i) NH,
ii) $-N(R_{200})-$ wherein $R_{200}$ is loweralkyl or benzyl or
iii) $CH_2$ and
2) $R_{29}$ is
i) alkoxy,
ii) benzyloxy,
iii) alkylamino,
iv) dialkylamino,
v) aryl or
vi) heterocyclic.

$R_3$ is
(I) hydrogen,
(II) loweralkyl,
(III) loweralkenyl,
(IV) cycloalkylalkyl,
(V) cycloalkenylalkyl,
(VI) alkoxyalkyl,
(VII) thioalkoxyalkyl,
(VIII) (alkoxyalkoxy)alkyl,
(IX) (polyalkoxy)alkyl,
(X) arylalkyl or
(XI) (heterocyclic)alkyl.

n is 0 or 1.

T is a mimic of the Leu-Val cleavage site of angiotensinogen.

The term "mimic of the Leu-Val cleavage site of angiotensinogen" as used herein includes

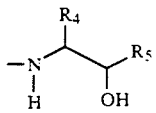

wherein
$R_4$ is
(I) loweralkyl,
(II) cycloalkylalkyl or
(III) arylalkyl; and $R_5$ is

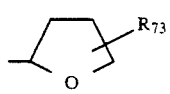

(I)

wherein $R_{73}$ is loweralkyl,

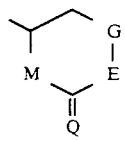

(II)

wherein
1) M is
i) O,
ii) S or
iii) NH;
2) Q is
i) O or
ii) S;
3) E is
i) O,
ii) S,
iii) $CHR_{61}$ wherein $R_{61}$ loweralkyl,
iv) $C\odot CH_2$ or
v) $NR_{18}$ wherein $R_{18}$ is
a) hydrogen,
b) loweralkyl,
c) hydroxyalkyl,
d) hydroxy,
e) alkoxy,
f) amino or
g) alkylamino; and
4) G is
i) absent,
ii) $CH_2$ or
iii) $NR_{19}$ wherein $R_{19}$ is hydrogen or loweralkyl, with the proviso that when G is $NR_{19}$, then $R_{18}$ is loweralkyl or hydroxyalkyl;

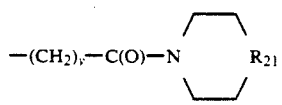

(III)

wherein
1) v is 0 or 1 and
2) $R_{21}$ is
i) NH,
ii) O, iii) S or
iv) SO₂; or (IV) a substituted methylene group.

The term "mimic of the Leu-Val cleavage site of angiotensinogen" as used herein also includes the substituents (T) disclosed in the following references:

Luly, et al., U.S. Pat. No. 4,645,759, issued Feb. 24, 1987, which is hereby incorporated by reference, discloses mimics of the Leu-Val cleavage site of angiotensinogen having the formula

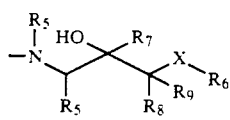

wherein $R_4$, $R_5$, $R_6$, $R_7$, $R_8$, $R_9$ and X are as defined therein;

Luly, et al., U.S. Pat. No. 4,652,551, issued Mar. 24, 1987, which is hereby incorporated by reference, discloses mimics of the Leu-Val cleavage site of angiotensinogen having the formula

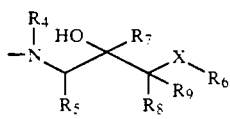

wherein $R_4$, $R_5$, $R_6$, $R_7$, $R_8$, $R_9$ and X are as defined therein;

Luly, et al., U.S. Pat. No. 4,680,284, issued Jul. 14, 1987, which is hereby incorporated by reference, discloses mimics of the Leu-Val cleavage site of angiotensinogen having the formula

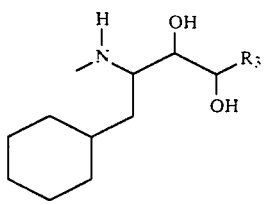

wherein $R_3$ is as defined therein;

Luly, et al., U.S. Pat. No. 4,725,584, issued Feb. 16, 1988, which is hereby incorporated by reference, discloses mimics of the Leu-Val cleavage site of angiotensinogen having the formula

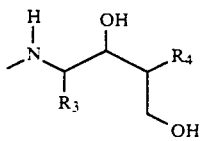

wherein $R_3$ and $R_4$ are as defined therein;

Luly, et al., U.S. Pat. No. 4,725,583, issued Feb. 16, 1988, which is hereby incorporated by reference, discloses mimics of the Leu-Val cleavage site of angiotensinogen having the formula

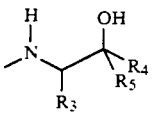

wherein $R_3$, $R_4$ and $R_5$ are as defined therein;

Rosenberg, et al., U.S. Pat. No. 4,837,204, issued Jun. 6, 1989, which is hereby incorporated by reference, discloses mimics of the Leu-Val cleavage site of angiotensinogen having the formula

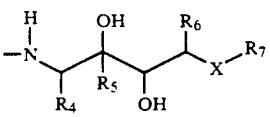

wherein $R_4$, $R_5$, $R_6$, $R_7$ and X are as defined therein;

Luly, et al., U.S. Pat. No. 4,845,079, issued Jul. 4, 1989, which is hereby incorporated by reference, discloses mimics of the Leu-Val cleavage site of angiotensinogen having the formula

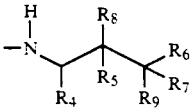

wherein $R_4$, $R_5$, $R_6$, $R_7$, $R_8$ and $R_9$ are as defined therein;

Sham, U.S. Pat. No. 4,826,958, issued May 2, 1989, which is hereby incorporated by reference, discloses mimics of the Leu-Val cleavage site of angiotensinogen having the formula

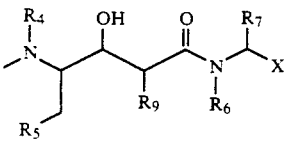

wherein $R_4$, $R_5$, $R_6$, $R_7$, $R_9$ and X are as defined therein;

Rosenberg et al., U.S. Pat. No. 4,857,507, issued Aug. 15, 1989, which is hereby incorporated by reference, discloses mimics of the Leu-Val cleavage site of angiotensinogen having the formula

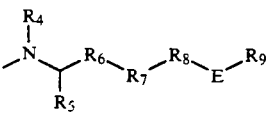

wherein $R_4$, $R_5$, $R_6$, $R_7$, $R_8$, $R_9$ and E are as defined therein;

Luly, et al., U.S. Pat. No. 4,826,815, issued May 2, 1989, which is hereby incorporated by reference, discloses mimics of the Leu-Val cleavage site of angiotensinogen having the formula

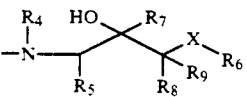

wherein $R_4$, $R_5$, $R_6$, $R_7$, $R_8$, $R_9$ and X are as defined therein;

Bender, et al., U.S. Pat. No. 4,818,748, issued Apr. 4, 1989, which is hereby incorporated by reference, discloses mimics of the Leu-Val cleavage site of angiotensinogen having the formula

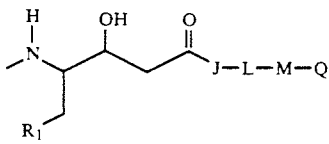

wherein $R_1$, J, L, M and Q are as defined therein;

Fuhrer, et al., U.S. Pat. No. 4,613,676, issued Sep. 23, 1986, which is hereby incorporated by reference, discloses mimics of the Leu-Val cleavage site of angiotensinogen having the formula

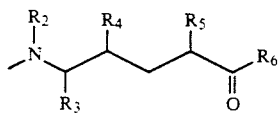

wherein $R_2$, $R_3$, $R_4$, $R_5$ and $R_6$ are as defined therein;

Riniker, et al., U.S. Pat. No. 4,595,677, issued Jun. 17, 1986, which is hereby incorporated by reference, discloses mimics of the Leu-Val cleavage site of angiotensinogen having the formula

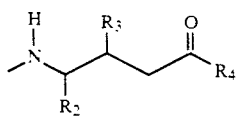

wherein $R_2$, $R_3$ and $R_4$ are as defined therein;

Buhlmayer, et al., U.S. Pat. No. 4,727,060, issued Feb. 23, 1988, which is hereby incorporated by reference, discloses mimics of the Leu-Val cleavage site of angiotensinogen having the formula

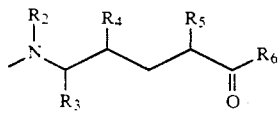

wherein $R_2$, $R_3$, $R_4$, $R_5$ and $R_6$ are as defined therein;

Buhlmayer, et al., U.S. Pat. No. 4,758,584, issued Jul. 19, 1988, which is hereby incorporated by reference, discloses mimics of the Leu-Val cleavage site of angiotensinogen having the formula

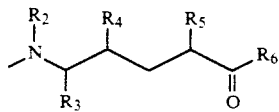

wherein $R_2$, $R_3$, $R_4$, $R_5$ and $R_6$ are as defined therein;

Szelke, et al., U.S. Pat. No. 4,609,643, issued Sep. 2, 1986, which is hereby incorporated by reference, discloses mimics of the Leu-Val cleavage site of angiotensinogen having the formula

—A—B—Z—W wherein A, B, Z and W are as defined therein;

Szelke, et al., U.S. Pat. No. 4,650,661, issued Mar. 17, 1987, which is hereby incorporated by reference, discloses mimics of the Leu-Val cleavage site of angiotensinogen having the formula

—A—B—Z—W wherein A, B, Z and W are as defined therein;

Szelke, et al., U.S. Pat. No. 4,713,445, issued Dec. 15, 1987, which is hereby incorporated by reference, discloses mimics of the Leu-Val cleavage site of angiotensinogen having the formula

—A—B—Z—W wherein A, B, Z and W are as defined therein;

Iizuka, et al., U.S. Pat. No. 4,656,269, issued Apr. 7, 1987, which is hereby incorporated by reference, discloses mimics of the Leu-Val cleavage site of angiotensinogen having the formula

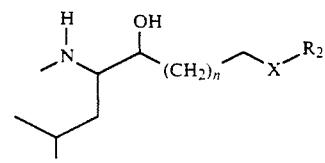

wherein n, X and $R_2$ are as defined therein;

Iizuka, et al., U.S. Pat. No. 4,711,958, issued Dec. 8, 1987, which is hereby incorporated by reference, discloses mimics of the Leu-Val cleavage site of angiotensinogen having the formula

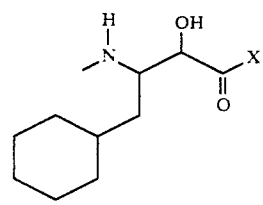

wherein X is as defined therein;

Kleinman, et al., U.S. Pat. No. 4,729,985, issued Mar. 8, 1988, which is hereby incorporated by reference, discloses mimics of the Leu-Val cleavage site of angiotensinogen having the formula

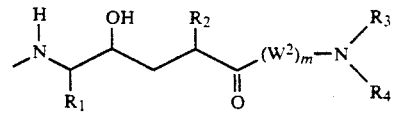

wherein $R_1$, $R_2$, m, $W^2$, $R_3$ and $R_4$ are as defined therein;

Hoover, U.S. Pat. No. 4,668,769, issued May 26, 1987, which is hereby incorporated by reference, discloses mimics of the Leu-Val cleavage site of angiotensinogen having the formula

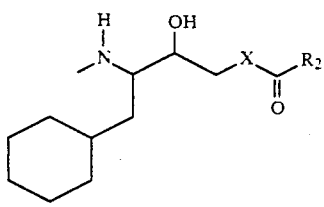

wherein X and R₂ are as defined therein;

Hoover, et al., U.S. Pat. No. 4,814,342, issued Mar. 21, 1989, which is hereby incorporated by reference, discloses mimics of the Leu-Val cleavage site of angiotensinogen having the formula

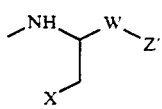

wherein X, W and Z¹ are as defined therein;

Bindra, et al., U.S. Pat. No. 4,749,687, issued Jun. 7, 1988, which is hereby incorporated by reference, discloses mimics of the Leu-Val cleavage site of angiotensinogen having the formula

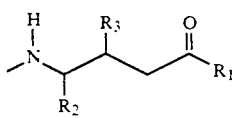

wherein $R_1$, $R_2$ and $R_3$ are as defined therein;

Hoover, et al., U.S. Pat. No. 4,814,342, issued Mar. 1, 1989, which is hereby incorporated by reference, discloses mimics of the Leu-Val cleavage site of angiotensinogen having the formula

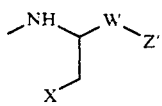

wherein X, W and Z¹ are as defined therein;

Matsueda, et al., U.S. Pat. No. 4,698,329, issued Oct. 6, 1987, which is hereby incorporated by reference, discloses mimics of the Leu-Val cleavage site of angiotensinogen having the formula

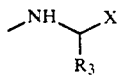

wherein $R_3$ and X are as defined therein;

Matsueda, et al., U.S. Pat. No. 4,548,926, issued Oct. 22, 1985, which is hereby incorporated by reference, discloses mimics of the Leu-Val cleavage site of angiotensinogen having the formula

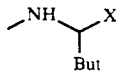

wherein But and X are as defined therein;

Wagnon, et al., U.S. Pat. No. 4,725,580, issued Feb. 16, 1988, which is hereby incorporated by reference, discloses mimics of the Leu-Val cleavage site of angiotensinogen having the formula

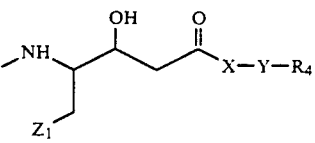

wherein $Z_1$, X, Y and $R_4$ are as defined therein;

Wagnon, et al., U.S. Pat. No. 4,746,648, issued May 24, 1988, which is hereby incorporated by reference, discloses mimics of the Leu-Val cleavage site of angiotensinogen having the formula

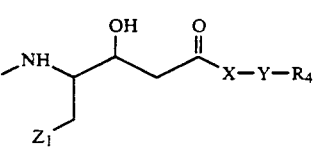

wherein $Z_1$, X, Y and $R_4$ are as defined therein;

Cazaubon, et al., U.S. Pat. No. 4,481,192, issued Nov. 6, 1984, which is hereby incorporated by reference, discloses mimics of the Leu-Val cleavage site of angiotensinogen having the formula

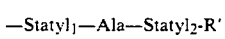

—Statyl₁—Ala—Statyl₂-R' wherein Statyl₁, Ala, Statyl₂ and R' are as defined therein;

Hansen, et al., U.S. Pat. No. 4,722,922, issued Feb. 2, 1988, which is hereby incorporated by reference, discloses mimics of the Leu-Val cleavage site of angiotensinogen having the formula

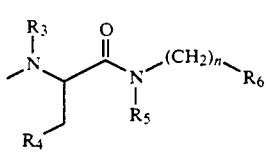

wherein $R_3$, $R_4$, $R_5$, n and $R_6$ are as defined therein;

Hansen, et al., U.S. Pat. No. 4,510,085, issued Apr. 9, 1985, which is hereby incorporated by reference, discloses mimics of the Leu-Val cleavage site of angiotensinogen having the formula

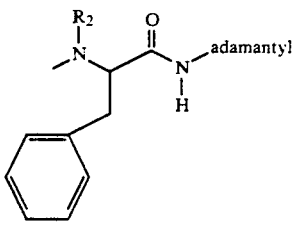

wherein $R_2$ is as defined therein;

Baran, et al., U.S. Pat. No. 4,657,931, issued Apr. 14, 1987, which is hereby incorporated by reference, discloses mimics of the Leu-Val cleavage site of angiotensinogen having the formula

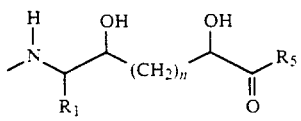

wherein $R_1$, n and $R_5$ are as defined therein;

Hansen, et al., U.S. Pat. No. 4,514,332 issued Apr. 30, 1985, which is hereby incorporated by reference, discloses mimics of the Leu-Val cleavage site of angiotensinogen having the formula

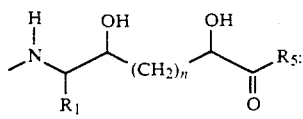

Natarajan, et al., U.S. Pat. No. 4,757,050, issued Jul. 12, 1988, which is hereby incorporated by reference, discloses mimics of the Leu-Val cleavage site of angiotensinogen having the formula

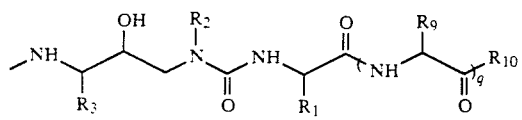

wherein $R_1$, $R_2$, $R_3$, q, $R_9$ and $R_{10}$ are as defined therein;

Gordon, U.S. Pat. No. 4,749,781, issued Jun. 7, 1988, which is hereby incorporated by reference, discloses mimics of the Leu-Val cleavage site of angiotensinogen having the formula

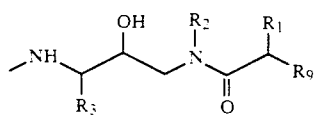

wherein $R_1$, $R_2$, $R_3$ and $R_9$ are as defined therein;

Ryono, et al., U.S. Pat. No. 4,665,193, issued May 12, 1987, which is hereby incorporated by reference, discloses mimics of the Leu-Val cleavage site of angiotensinogen having the formula

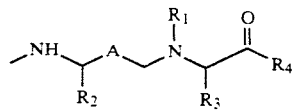

wherein $R_1$, $R_2$, $R_3$, $R_4$ and A are as defined therein;

Ryono, et al., U.S. Pat. No. 4,616,088, issued Oct. 1, 1986, which is hereby incorporated by reference, discloses mimics of the Leu-Val cleavage site of angiotensinogen having the formula

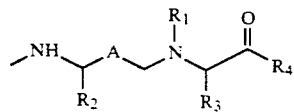

wherein $R_1$, $R_2$, $R_3$, $R_4$ and A are as defined therein;

Ryono, et al., U.S. Pat. No. 4,629,724, issued Dec. 16, 1986, which is hereby incorporated by reference, discloses mimics of the Leu-Val cleavage site of angiotensinogen having the formula

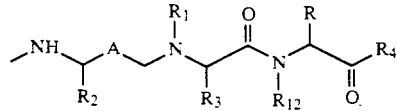

wherein $R_1$, $R_2$, $R_3$, $R_4$, R, $R_{12}$ and A are as defined therein;

Patel, U.S. Pat. No. 4,820,691, issued Apr. 11, 1989, which is hereby incorporated by reference, discloses mimics of the Leu-Val cleavage site of angiotensinogen having the formula

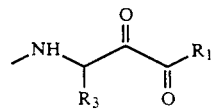

wherein $R_1$ and $R_3$ are as defined therein;

Thaisrivongs, U.S. Pat. No. 4,705,846, issued Nov. 10, 1987, which is hereby incorporated by reference, discloses mimics of the Leu-Val cleavage site of angiotensinogen having the formula

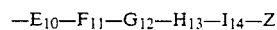

$$-E_{10}-F_{11}-G_{12}-H_{13}-I_{14}-Z$$

wherein $E_{10}$, $F_{11}$, $G_{12}$, $H_{13}$, $I_{14}$ and Z are as defined therein;

Hudspeth, et al., U.S. Pat. No. 4,743,585, issued May 10, 1988, which is hereby incorporated by reference, discloses mimics of the Leu-Val cleavage site of angiotensinogen having the formula

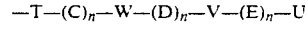

$$-T-(C)_n-W-(D)_n-V-(E)_n-U$$

wherein T, C, W, D, V, E, U and n are as defined therein;

Hudspeth, et al., U.S. Pat. No. 4,735,933, issued Apr. 5, 1988, which is hereby incorporated by reference, discloses mimics of the Leu-Val cleavage site of angiotensinogen having the formula

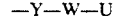

$$-Y-W-U$$

wherein Y, W and U are as defined therein;

Kaltenbronn, et al., U.S. Pat. No. 4,804,743, issued Feb. 14, 1989, which is hereby incorporated by reference, discloses mimics of the Leu-Val cleavage site of angiotensinogen having the formula

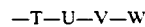

$$-T-U-V-W$$

wherein T, U, V and W are as defined therein;

Pinori, et al., U.S. Pat. No. 4,560,505, issued Dec. 24, 1985, which is hereby incorporated by reference, discloses mimics of the Leu-Val cleavage site of angiotensinogen having the formula

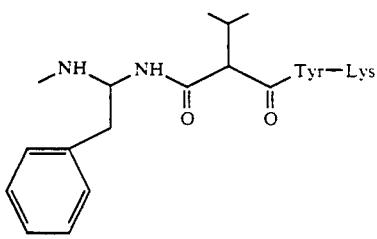

wherein Tyr and Lys are as defined therein;

Yamato, et al., U.S. Pat. No. 4,683,220, issued July 28, 1987, which is hereby incorporated by reference, discloses mimics of the Leu-Val cleavage site of angiotensinogen having the formula

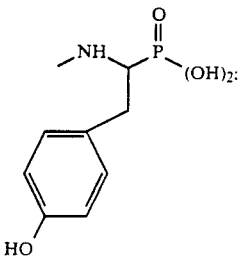

Boger, et al., U.S. Pat. No. 4,668,770, issued May 26, 1987, which is hereby incorporated by reference, discloses mimics of the Leu-Val cleavage site of angiotensinogen having the formula

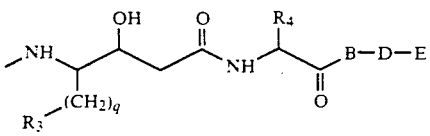

wherein $R_3$, $R_4$, q, B, D and E are as defined therein;

Boger, U.S. Pat. No. 4,668,663, issued May 26, 1987, which is hereby incorporated by reference, discloses mimics of the Leu-Val cleavage site of angiotensinogen having the formula

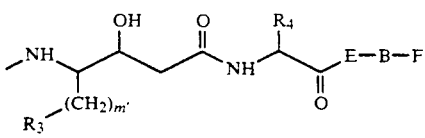

wherein $R_3$, $R_4$, m, E, B and F are as defined therein;

Bock, et al., U.S. Pat. No. 4,636,491, issued Jan. 3, 1987, which is hereby incorporated by reference, discloses mimics of the Leu-Val cleavage site of angiotensinogen having the formula

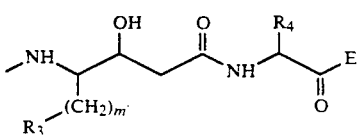

wherein $R_3$, $R_4$, m' and E are as defined therein;

Bock, et al., U.S. Pat. No. 4,663,310, issued May 5, 1987, which is hereby incorporated by reference, discloses mimics of the Leu-Val cleavage site of angiotensinogen having the formula

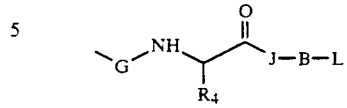

wherein G, $R_4$, J, B and L are as defined therein;

Boger, et al., U.S. Pat. No. 4,661,473, issued Apr. 28, 1987, which is hereby incorporated by reference, discloses mimics of the Leu-Val cleavage site of angiotensinogen having the formula

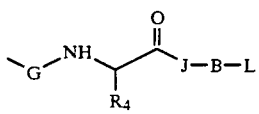

wherein G, $R_4$, J, B and L are as defined therein;

Veber, et al., U.S. Pat. No. 4,479,941, issued Oct. 30, 1984, which is hereby incorporated by reference, discloses mimics of the Leu-Val cleavage site of angiotensinogen having the formula

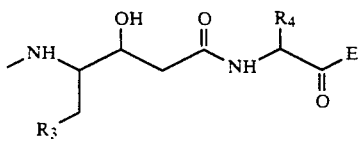

wherein $R_3$, $R_4$ and E are as defined therein;

Boger, et al., U.S. Pat. No. 4,470,971, issued Sep. 11, 1984, which is hereby incorporated by reference, discloses mimics of the Leu-Val cleavage site of angiotensinogen having the formula

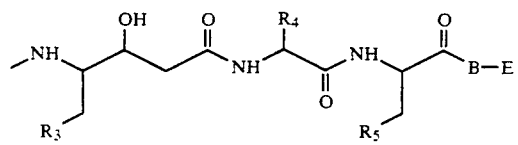

wherein $R_3$, $R_4$, $R_5$, B and E are as defined therein;

Veber, et al., U.S. Pat. No. 4,384,994, issued May 24, 1983, which is hereby incorporated by reference, discloses mimics of the Leu-Val cleavage site of angiotensinogen having the formula

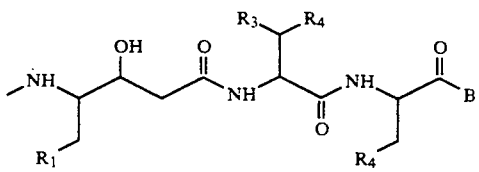

wherein $R_1$, $R_2$, $R_3$, $R_4$ and B are as defined therein;

Boger, et al., U.S. Pat. No. 4,812,442, issued Mar. 14, 1989, which is hereby incorporated by reference, discloses mimics of the Leu-Val cleavage site of angiotensinogen having the formula

—G—J wherein G and J are as defined therein;

Evans, U.S. Pat. No. 4,665,055, issued May 12, 1987, which is hereby incorporated by reference, discloses mimics of the Leu-Val cleavage site of angiotensinogen having the formula

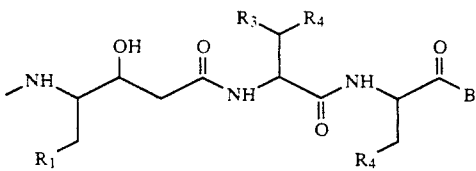

wherein $R_4$, $R_5$, B and C are as defined therein;

Evans, et al., U.S. Pat. No. 4,609,641, issued Sep. 2, 1986, which is hereby incorporated by reference, discloses mimics of the Leu-Val cleavage site of angiotensinogen having the formula

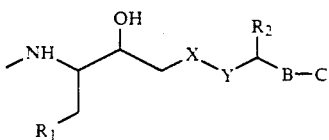

wherein $R_1$, $R_2$, X, Y, B and C are as defined therein;

Patchett, et al., U.S. Pat. No. 4,839,357, issued Jun. 13, 1989, which is hereby incorporated by reference, discloses mimics of the Leu-Val cleavage site of angiotensinogen having the formula

—G—J wherein G and J are as defined therein;

Boger, et al., U.S. Pat. No. 4,812,442, issued Mar. 14, 1989, which is hereby incorporated by reference, discloses mimics of the Leu-Val cleavage site of angiotensinogen having the formula

—G—J wherein G and J are as defined therein;

Boger, U.S. Pat. No. 4,665,052, issued May 12, 1987, which is hereby incorporated by reference, discloses mimics of the Leu-Val cleavage site of angiotensinogen having the formula

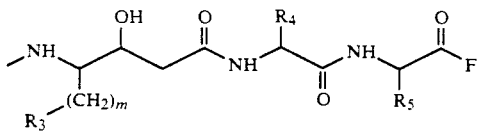

wherein $R_3$, $R_4$, $R_5$, m and F are as defined therein;

Veber, et al., U.S. Pat. No. 4,478,826, issued Oct. 23, 1984, which is hereby incorporated by reference, discloses mimics of the Leu-Val cleavage site of angiotensinogen having the formula

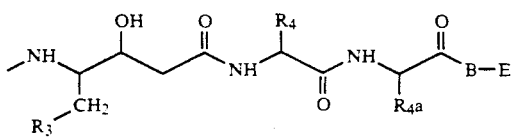

wherein $R_3$, $R_4$, $R_{4a}$, B and E are as defined therein;

Boger, et al., U.S. Pat. No. 4,485,099, issued Nov. 27, 1984, which is hereby incorporated by reference, discloses mimics of the Leu-Val cleavage site of angiotensinogen having the formula

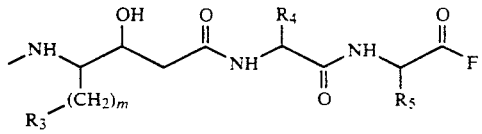

wherein $R_3$, $R_4$, $R_5$, m and F are as defined therein;

Boger, et al., U.S. Pat. No. 4,477,440 issued Oct. 16, 1984, which is hereby incorporated by reference, discloses mimics of the Leu-Val cleavage site of angiotensinogen having the formula

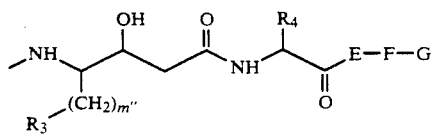

wherein $R_3$, $R_4$, m'', E, F and G are as defined therein;

Raddatz, et al., U.S. Pat. No. 4,721,776, issued Jan. 26, 1988, which is hereby incorporated by reference, discloses mimics of the Leu-Val cleavage site of angiotensinogen having the formula

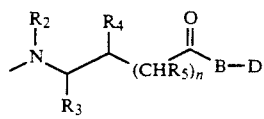

wherein $R_2$, $R_3$, $R_4$, $R_5$, n, B and D are as defined therein;

Holzemann, et al., U.S. Pat. No. 4,709,010, issued Nov. 24, 1987, which is hereby incorporated by reference, discloses mimics of the Leu-Val cleavage site of angiotensinogen having the formula

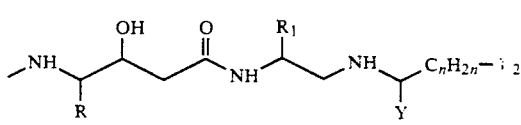

wherein R, $R_1$, $R_2$, n and Y are as defined therein;

Raddatz, et al., U.S. Pat. No. 4,812,555, issued Mar. 14, 1989, which is hereby incorporated by reference, discloses mimics of the Leu-Val cleavage site of angiotensinogen having the formula

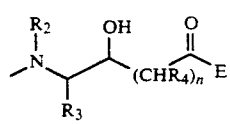

wherein $R_2$, $R_3$, $R_4$, n and E are as defined therein;

Raddatz, et al., U.S. Pat. No. 4,755,592, issued Jul. 5, 1988, which is hereby incorporated by reference, discloses mimics of the Leu-Val cleavage site of angiotensinogen having the formula

—W—E—W'—Y wherein W, E, W' and Y are as defined therein;

Raddatz, et al., U.S. Pat. No. 4,666,888, issued May 19, 1987, which is hereby incorporated by reference, discloses mimics of the Leu-Val cleavage site of angiotensinogen having the formula

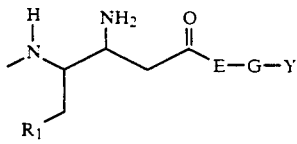

wherein $R_1$, E, G and Y are as defined therein;

Wagnon, et al., U.S. Pat. No. 4,840,935, issued Jun. 20, 1989, which is hereby incorporated by reference, discloses mimics of the Leu-Val cleavage site of angiotensinogen having the formula

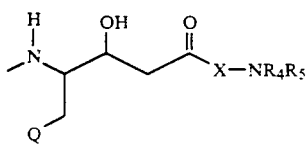

wherein $R_4$, $R_5$, Q and X are as defined therein;

Iizuka, et al., U.S. Pat. No. 4,841,067, issued Jun. 20, 1989, which is hereby incorporated by reference, discloses mimics of the Leu-Val cleavage site of angiotensinogen having the formula

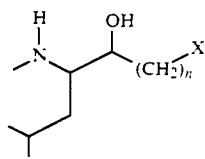

wherein n and X are as defined therein;

Raddatz, et al., U.S. Pat. No. 4,829,053, issued May 9, 1989, which is hereby incorporated by reference, discloses mimics of the Leu-Val cleavage site of angiotensinogen having the formula

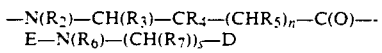

wherein n, s, $R_2$, $R_3$, $R_4$, $R_5$, $R_6$, $R_7$, E and D are as defined therein;

European Patent Application No. EP0264106, published Apr. 20, 1988, discloses mimics of the Leu-Val cleavage site of angiotensinogen having the formula

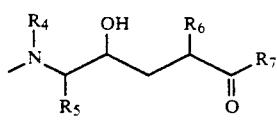

wherein $R_4$, $R_5$, $R_6$ and $R_7$ are as defined therein including $R_4$ is hydrogen or loweralkyl; $R_5$ is hydrogen, loweralkyl or an amino acid residue; $R_6$ is loweralkyl, cycloalkyl, cycloalkylalkyl or arylalkyl and $R_7$ is hydroxy, alkoxy, substituted alkoxy, amino, substituted amino or an N-heterocycle;

European Patent Application No. EP0272583, published Jun. 29, 1988, discloses mimics of the Leu-Val cleavage site of angiotensinogen having the formula

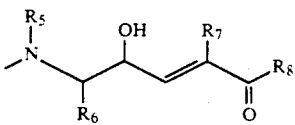

wherein $R_5$, $R_6$, $R_7$ and $R_8$ are as defined therein including $R_5$ is hydrogen or loweralkyl; $R_6$ is hydrogen, loweralkyl, cycloalkyl, cycloalkylalkyl, aryl, arylalkyl or an amino acid residue; and $R_7$ and $R_8$ are independently selected from hydrogen, loweralkyl, cycloalkyl, cycloalkylalkyl or arylalkyl;

European Patent Application No. EP0309766, published Apr. 5, 1989, discloses mimics of the Leu-Val cleavage site of angiotensinogen having the formula

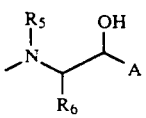

wherein $R_5$, $R_6$ and A are as defined therein including $R_5$ is hydrogen or loweralkyl; $R_6$ is hydrogen, loweralkyl, cycloalkyl, cycloalkylalkyl, aryl, aralkyl or heterocyclic; and A is $-CH(OH)-(CH)_q-R_7$ wherein q is 0-5 and $R_7$ is hydrogen, loweralkyl, cycloalkyl, cycloalkylalkyl, aryl, arylalkyl, heterocyclic, substituted thioalkyl, substituted sulfone, substituted sulfoxide, substituted amine, quaternized amine, heterocyclic, carboxyalkyl, alkoxycarbonylalkyl or amidoalkyl;

European Patent Application No. EP0300189, published Jan. 25, 1989, discloses mimics of the Leu-Val cleavage site of angiotensinogen having the formula

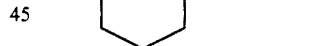

wherein $R_4$ is as defined therein including $R_4$ is loweralkyl;

European Patent Application No. EP0283970, published Sep. 28, 1988, discloses mimics of the Leu-Val cleavage site of angiotensinogen having the formula

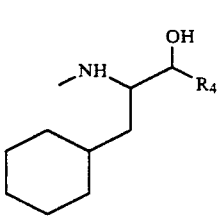

wherein $R_4$ is as defined therein including $R_4$ is loweralkyl;

European Patent Application No. EP0255082, published Feb. 3, 1988, discloses mimics of the Leu-Val cleavage site of angiotensinogen having the formula

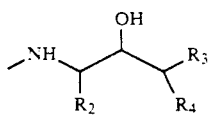

wherein $R_2$, $R_3$ and $R_4$ are as defined therein including $R_2$ is hydrogen, alkyl, cyclcoalkyl, cycloalkylalkyl, aryl or arylalkyl; $R_3$ is hydrogen, alkyl or arylalkyl; and $R_4$ is $-X-(CH_2)_{n'}R_7$ wherein X is absent, O or S, n' is 0–4 and $R_7$ is hydrogen, hydroxy, amino, heteroaryl or $-CH(R_9)-(CH_2)_p-Y-(CH_2)_q-R_{10}$ wherein p, q, Y and $R_{10}$ are as defined therein;

European Patent Application No. EP0230242, published Jul. 29, 1987, discloses mimics of the Leu-Val cleavage site of angiotensinogen having the formula

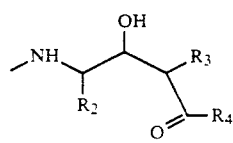

wherein $R_2$, $R_3$ and $R_4$ are as defined therein including $R_2$ is hydrogen, alkyl, cycloalkylalkyl, aryl or arylalkyl; $R_3$ is hydrogen, alkyl or alkenyl; and $R_4$ is $-N(R_5)-CH(R_6)-(CH_2)_n-Ar$ or $-N(R_5)-CH(R_6)-CH=CH-(CH_2)_m-Ar$ wherein n is 0–6, m is 0–4, $R_5$ is hydrogen or alkyl and $R_6$ is hydrogen, alkyl, hydroxyalkyl, alkoxyalkyl, thioalkoxyalkyl, carboxyalkyl, alkoxycarbonylalkyl, haloalkyl, alkylaminoalkyl, alkoxycarbonylaminoalkyl or arylalkoxycarbonylaminoalkyl;

European Patent Application No. EP0310015, published Apr. 5, 1989, discloses mimics of the Leu-Val cleavage site of angiotensinogen having the formula

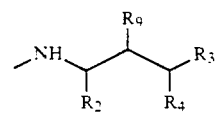

wherein $R_2$, $R_3$, $R_4$ and $R_9$ are as defined therein including $R_2$ is hydrogen, alkyl, cycloalkyl, cycloalkylalkyl, aryl or arylalkyl; $R_3$ is hydrogen, alkyl, aryl or arylalkyl; $R_9$ is hydroxy or fluoro; and $R_4$ is $-(CH_2)_p-X-(CH_2)_q-R_7$ wherein p is 0–4, q is 0–4, X is $-CF_2-$, $-C(O)-$ or $-CH(R_8)-$ wherein $R_8$ is alkyl, alkoxy, thioalkoxy, alkylamino, hydroxy, azido or halo and $R_7$ is hydrogen, hydroxy, amino, aryl or heteroaryl;

European Patent Application No. EP0315574, published May 10, 1989, discloses mimics of the Leu-Val cleavage site of angiotensinogen having the formula

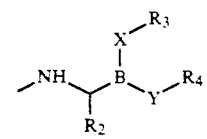

(B is a boron atom)

wherein $R_2$, X, Y, $R_3$ and $R_4$ are as defined therein including $R_2$ is hydrogen, alkyl, cycloalkyl, cycloalkylalkyl, aryl or heterocyclic; X and Y are independently selected from O or $-N(R_{13})-$ wherein $R_{13}$ is hydrogen, alkyl or substituted alkyl; and $R_3$ and $R_4$ are independently selected from hydrogen, alkyl or aryl; or the boron containing substituent is a boron containing cyclic group;

Japanese Patent Application No. J63275552, published Nov. 14, 1988 discloses mimics of the Leu-Val cleavage site of angiotensinogen having the formula

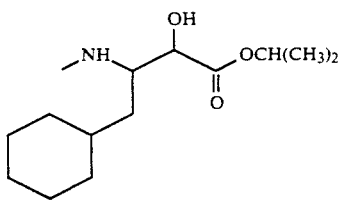

European Patent Application No. EP0252727, published Jan. 13, 1988, discloses mimics of the Leu-Val cleavage site of angiotensinogen having the formula

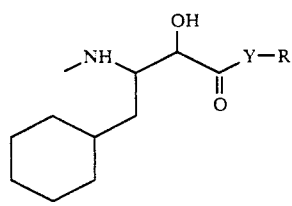

wherein Y and R are as defined therein including Y is O or NH and R is alkyl, cycloalkyl or halogenated alkyl;

European Patent Application No. EP0244083, published Nov. 4, 1987, discloses mimics of the Leu-Val cleavage site of angiotensinogen having the formula

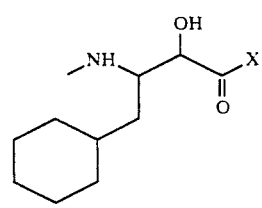

wherein X is as defined therein including X is alkoxy, alkyalamino, cycloalkyloxy, morpholino and haloalkoxy.

European Patent Application No. EP0216539, published Apr. 1, 1987, discloses mimics of the Leu-Val cleavage site of angiotensinogen having the formula

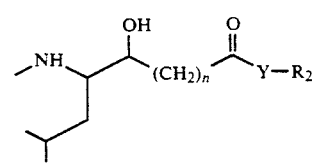

wherein n, Y and $R_2$ are as defined therein including n is 0–1, Y is O or NH and $R_2$ is alkyl;

European Patent Application No. EP0206807, published Dec. 30, 1986, discloses mimics of the Leu-Val cleavage site of angiotensinogen having the formula

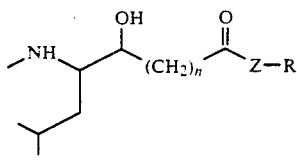

wherein n, Z and R are as defined therein including n is 0-1, Z is O or NH and R is alkyl;

European Patent Application No. EP0190891, published Aug. 13, 1986, discloses mimics of the Leu-Val cleavage site of angiotensinogen having the formula

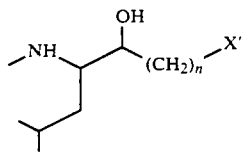

wherein n and X' are as defined therein including n is 0-1 and X' is alkoxycarbonyl, aralkoxycarbonyl, or —C(O)NR$_1$R$_2$ wherein R$_1$ is hydrogen, alkyl or aralkyl and R$_2$ is alkyl or —CH$_2$—Y—R wherein Y is O or NH and R is alkyl or aralkyl;

European Patent Application No. EP0181110, published May 14, 1986, discloses mimics of the Leu-Val cleavage site of angiotensinogen having the formula

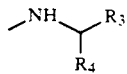

wherein R$_3$ and R$_4$ are as defined therein including R$_3$ is —CHO or —CH$_2$OH and R$_4$ is isobutyl or benzyl;

European Patent Application No. EP0297816, published Jan. 4, 1989, discloses mimics of the Leu-Val cleavage site of angiotensinogen having the formula

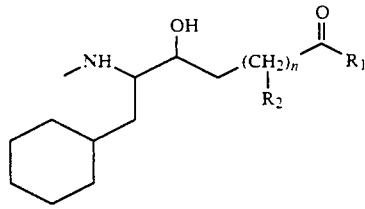

wherein n, R$_1$ and R$_2$ are as defined therein including n is 0-1, R$_1$ is —NH$_2$, alkylamino, alkoxy, or 2-alkoxycarbonylpyrrolidin-1-yl and R$_2$ is alkyl, alkenyl, haloalkenyl or azide substituted alkenyl;

European Patent Application No. EP0297815, published Jan. 4, 1989, discloses mimics of the Leu-Val cleavage site of angiotensinogen having the formula

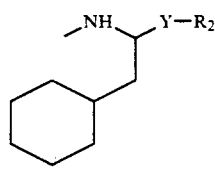

wherein Y and R$_2$ are as defined therein including Y is —CH(OH)— or —C(O)— and R$_2$ is —CF$_2$C(O)NHCH$_3$, —CF$_3$ or —CF$_2$C(CH$_2$CH(CH$_3$)$_2$)CO$_2$C$_2$H$_5$;

European Patent Application No. EP0212903, published Mar. 4, 1987, discloses mimics of the Leu-Val cleavage site of angiotensinogen having the formula

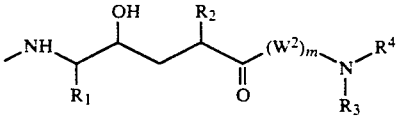

wherein m, R$_1$, R$_2$, R$_3$, R$_4$ and W$^2$ are as defined therein including m is 0-1, R$_1$ and R$_2$ are independently selected from hydrogen, alkyl, alkenyl, phenyl, naphthyl, cycloalkyl, cycloalkenyl, phenylalkyl, naphthylalkyl, cycloalkylalkyl and cycloalkenylalkyl, R$_3$ and R$_4$ are independently selected from alkyl, phenyl, naphthyl, cycloalkyl, adamantyl, phenylalkyl, naphthylalkyl, cycloalkylalkyl and adamantylalkyl; or R$_3$ is hydrogen and R$_4$ is —CH(R$_7$)(CH$_2$)$_p$(Q)$_r$CH(R$_8$)(CH$_2$)$_q$—Y wherein p and q are independently selected from 0,1,2,3,4,5 and 6, r is 0-1, Q is —CH$_2$—, —CH=CH—, —O—, —NH—, —CH(OH)—]or —C(O)—, Y is methyl, phenyl, —C(O)OR$_9$, C(O)NR$_9$R$_{10}$, —C(O)NHC(O)OCH$_2$C$_6$H$_5$, —NH$_2$, —NHC(O)CH$_2$C$_6$H$_5$, —NHCH(CH$_2$C$_6$H$_5$)C(O)OR$_9$ or —NHCH(CH$_2$C$_6$H$_5$)C(O)NR$_9$R$_{10}$ wherein R$_9$ and R$_{10}$ are independently selected from hydrogen, alkyl, phenyl, cycloalkyl, phenylalkyl, cycloalkylalkyl or adamantyl, and R$_7$ and R$_8$ are independently selected from hydrogen, alkyl, phenyl, cycloalkyl, phenylalkyl, cycloalkylalkyl or adamantyl; or R$_3$ and R$_4$ taken together with the nitrogen to which they are attached form a pyrrole, indoline, isoindoline, piperidine, 1,2,3,4-tetrahydroquinoline, 1,2,3,4-tetrahydroisoquinoline, perhydroazepine or morpholine ring; and W$^2$ is —NHCH((CH$_2$)$_3$R$_6$)—C(O)— wherein R$_6$ is —NH$_2$, —NHC(=NH)NH$_2$ or —CH$_2$NH$_2$;

PCT Patent Application No. WO 88/03022, published May 5, 1988, discloses mimics of the Leu-Val cleavage site of angiotensinogen having the formula

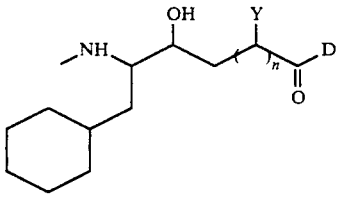

wherein n, Y and D are as defined therein including n is 0-1, Y is isobutyl, allyl or benzyl and D is 2-carboxypyrrolidin-1-yl or —ZR wherein Z is O or NH and R is alkyl, phenyl or substituted alkyl or substituted phenyl;

German Patent Application No. DE3725137, published Aug. 6, 1986, discloses mimics of the Leu-Val cleavage site of angiotensinogen having the formula

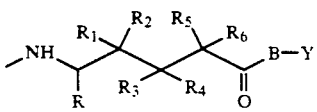

wherein R, R$_1$, R$_2$, R$_3$, R$_4$, R$_5$, R$_6$, B and Y are as defined therein including R is hydrogen, alkyl, cycloalkyl, cycloalkylalkyl, aryl, arylalkyl, heteroaryl or heteroarylalkyl, $R_1$ is hydroxy, alkoxy or aryloxy, $R_2$ is hydrogen or $R_1$ and $R_2$ taken together is oxo (=O), $R_3$, $R_4$, $R_5$ and $R_6$ are independently selected from hydrogen, fluoro, chloro, alkyl, cycloalkyl, cycloalkylalkyl, aryl, arylalkyl, heteroaryl and heteroarylalkyl, B is a peptide chain containing from 1 to 10 amino acid residues and Y is hydroxy or a protecting group for the peptide carboxy group;

British Patent Application No. GB2203740, published Oct. 26, 1988, discloses mimics of the Leu-Val cleavage site of angiotensinogen having the formula

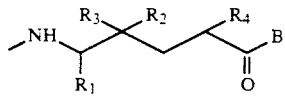

wherein $R_1$, $R_2$, $R_3$, $R_4$ and B are as defined therein including $R_1$ is a hydrophobic or hydrophilic side chain, $R_2$ is hydroxy or amino, $R_3$ is hydrogen or $R_2$ and $R_3$ taken together is oxo (=O), $R_4$ is a hydrophobic or hydrophilic side chain and B is —NHCH($R_6$)C($R_7$)($R_8$)C($R_9$)($R_{10}$)CH$_2$C(O)N$R_{11}R_{12}$ wherein $R_6$ is $R_1$, $R_7$ and $R_8$ are the same as $R_2$ and $R_3$, $R_9$ and $R_{10}$ are independently selected from hydrogen and fluoro and $R_{11}$ and $R_{12}$ are independently selected from hydrogen, alkyl, arylalkyl, heteroarylalkyl and —CH($R_{13}$)C(O)$R_{14}$ wherein $R_{13}$ is alkyl or hydroxyalkyl and $R_{14}$ is hydroxy, alkoxy, amino, alkylamino, aminomethylpyridyl or benzyl;

British Patent Application No. GB2200115, published Jul. 27, 1988, discloses mimics of the Leu-Val cleavage site of angiotensinogen having the formula

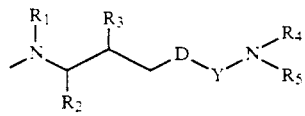

$R_1$, $R_2$, $R_3$, $R_4$, $R_5$, D and Y are as defined therein including $R_1$ is hydrogen or alkyl, $R_2$ is an amino acid side chain, $R_3$ is hydrogen, hydroxy, aryloxy or amino, $R_4$ and $R_5$ are independently selected from hydrogen, alkyl, arylalkyl, heteroarylalkyl and —CH($R_{12}$)C(O)$R_{13}$ wherein $R_{12}$ is alkyl or hydroxyalkyl and $R_{13}$ is hydroxy, alkoxy, amino, alkylamino, aminomethylpyridyl or benzyl; or —N$R_4R_5$ represents pyrrolidinyl, piperidinyl, morpholinyl, piperazinyl or substituted piperazinyl; D is a bond, O, —N($R_1$)— or —CH($R_1$)— and Y is —C(O)—, —S(O)$_2$— or —P(O)—;

German Patent Application No. DE3830825, published Mar. 23, 1989, discloses mimics of the Leu-Val cleavage site of angiotensinogen having the formula

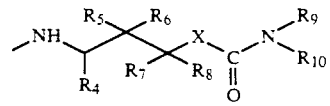

wherein $R_4$, $R_5$, $R_6$, $R_7$, $R_8$, $R_9$, $R_{10}$ and X are as defined therein including $R_4$ is a hydrophilic or hydrophobic amino acid side chain, $R_5$ is hydroxy or amino, $R_6$ is hydrogen or $R_5$ and $R_6$ taken together are oxo (=O), $R_7$ and $R_8$ are independently selected from hydrogen and fluoro, $R_9$ and $R_{10}$ are independently selected from hydrogen, alkyl and —CH($R_{11}$)C(O)$R_{12}$ wherein $R_{11}$ is alkyl or hydroxyalkyl and $R_{12}$ is hydroxy, alkoxy, amino, alkylamino, aminomethylpyridyl, benzyl or —NH—(CH$_2$CH$_2$)m—$R_1$ wherein m is 1–20 and $R_1$ is as defined therein; and X is a bond or O, NH or —C($R_{13}$)($R_{14}$)wherein $R_{13}$ and $R_{14}$ are independently selected from hydrogen, fluoro or $R_4$; Japanese Patent Application No. J62246546, published Oct. 27, 1987, discloses mimics of the Leu-Val cleavage site of angiotensinogen having the formula

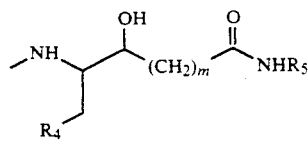

wherein m, $R_4$ and $R_5$ are as defined therein including m is 0–1, $R_4$ is alkyl, cycloalkyl or phenyl and $R_5$ is alkyl or substituted alkyl as defined therein;

European Patent Application No. EP0274259, published Jul. 13, 1988, discloses mimics of the Leu-Val cleavage site of angiotensinogen having the formula

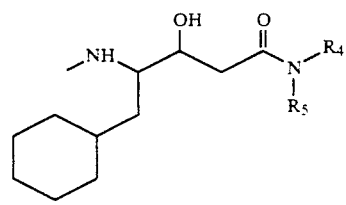

wherein $R_4$ and $R_5$ are as defined therein including $R_4$ is alkyl, hydroxyalkyl, (heterocyclic)alkyl, aminoalkyl, alkylaminoalkyl or dialkylaminoalkyl and $R_5$ is hydrogen or alkyl;

European Patent Application No. EP0228192, published Jul. 8, 1987, discloses mimics of the Leu-Val cleavage site of angiotensinogen having the formula

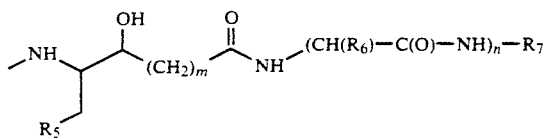

wherein m, n, $R_5$, $R_6$ and $R_7$ are as defined therein including m and n are independently selected from 0 and 1, $R_5$ is alkyl, cycloalkyl or phenyl, $R_6$ is alkyl and $R_7$ is alkyl or substituted alkyl as defined therein;

European Patent Application No. EP0273893, published Jul. 6, 1988, discloses mimics of the Leu-Val cleavage site of angiotensinogen having the formula

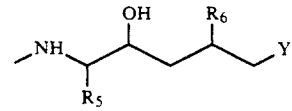

wherein $R_5$, $R_6$ and Y are as defined therein including $R_5$ is alkyl or cycloalkyl, $R_6$ is hydrogen or alkyl and Y is —SCH(CH$_3$)$_2$ or —S(O)$_2$CH(CH$_3$)$_2$;

European Patent Application No. EP0310070, published Apr. 5, 1989, discloses mimics of the Leu-Val cleavage site of angiotensinogen having the formula

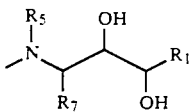

wherein $R_1$, $R_5$ and $R_7$ are as defined therein including $R_1$ is hydrogen, alkyl, haloalkyl, alkylcycloalkyl, alkylcycloalkenyl or alkoxycarbonyl, $R_5$ is hydrogen or alkyl and $R_7$ is cycloalkyl, phenyl, cycloalkylalkyl or phenylalkyl;

European Patent Application No. EP0310071, published Apr. 5, 1989, discloses mimics of the Leu-Val cleavage site of angiotensinogen having the formula

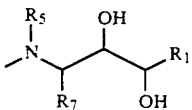

wherein $R_1$, $R_5$ and $R_7$ are as defined therein including $R_1$ is hydrogen, alkyl, haloalkyl, alkylcycloalkyl, alkylcycloalkenyl or alkoxycarbonyl, $R_5$ is hydrogen or alkyl and $R_7$ is cycloalkyl, phenyl, cycloalkylalkyl or phenylalkyl;

European Patent Application No. EP0310072, published Apr. 5, 1989, discloses mimics of the Leu-Val cleavage site of angiotensinogen having the formula

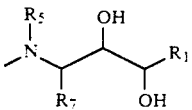

wherein $R_1$, $R_5$ and $R_7$ are as defined therein including $R_1$ is hydrogen, alkyl, haloalkyl, alkylcycloalkyl, alkylcycloalkenyl or alkoxycarbonyl, $R_5$ is hydrogen or alkyl and $R_7$ is cycloalkyl, phenyl, cycloalkylalkyl or phenylalkyl; European Patent Application No. EP0310073, published Apr. 5, 1989, discloses mimics of the Leu-Val cleavage site of angiotensinogen having the formula

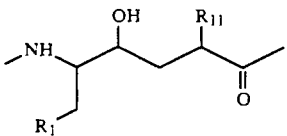

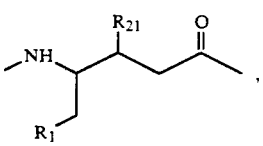

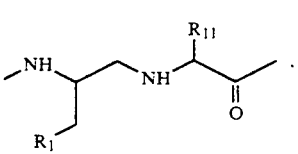

-continued

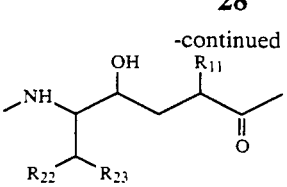

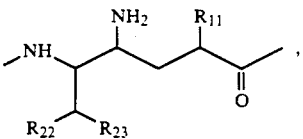

or

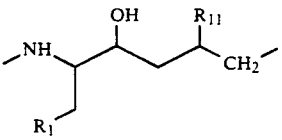

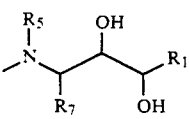

wherein $R_1$, $R_5$ and $R_7$ are as defined therein including $R_1$ is hydrogen, alkyl, haloalkyl, alkylcycloalkyl, alkylcycloalkenyl or alkoxycarbonyl, R5 is hydrogen or alkyl and $R_7$ is cycloalkyl, phenyl, cycloalkylalkyl or phenylalkyl;

European Patent Application No. EP0313847, published May 3, 1989, discloses mimics of the Leu-Val cleavage site of angiotensinogen having the formula

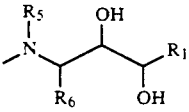

wherein $R_1$, $R_5$ and $R_6$ are as defined therein including $R_1$ is hydrogen, alkyl, haloalkyl, alkylcycloalkyl, alkylcycloalkenyl or alkoxycarbonyl, $R_5$ is hydrogen or alkyl and $R_6$ is cycloalkyl, phenyl, cycloalkylalkyl or phenylalkyl;

European Patent Application No. EP0296581, published Dec. 28, 1988, discloses mimics of the Leu-Val cleavage site of angiotensinogen having the formula

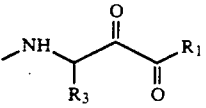

wherein $R_1$ and $R_3$ are as defined therein including $R_1$ is hydrogen, arylalkyl, aryl, (heterocyclic)alkyl or heterocyclic and $R_3$ is hydrogen, alkyl, haloalkyl, arylalkyl, (heterocyclic)alkyl, hydroxyalkyl, alkoxyalkyl, aminoalkyl, mercaptoalkyl, thioalkoxyalkyl, hydorxyalkoxyalkyl, aminoalkoxyalkyl, hydroxythioalkoxyalkyl, carboxyalkyl, aminothioalkoxyalkyl, guanidinoalkyl, aminocarbonylalkyl or imidazolylalkyl;

European Patent Application No. EP0231919, published Aug. 12, 1987, discloses mimics of the Leu-Val cleavage site of angiotensinogen having the formula

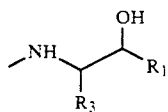

wherein $R_1$ and $R_3$ are as defined therein including $R_1$ is an N-heterocyclic ring and $R_3$ is hydrogen, alkyl, cycloalkylalkyl, haloalkyl, arylalkyl, (heterocyclic)alkyl, hydroxyalkyl, alkoxyalkyl, alkoxyalkyl, aminoalkyl, mercaptoalkyl, tioalkoxyalkyl, hydroxyalkoxyalkyl, aminoalkoxyalkyl, hydroxythioalkoxyalkyl, carboxyalkyl, aminothioalkoxyalkyl, guanidinoalkyl, aminocarbonylalkyl or imidazolylalkyl; PCT Patent Application No. WO 87/05302, published May 3, 1989, discloses mimics of the Leu-Val cleavage site of angiotensinogen having the formula

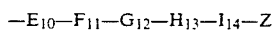

wherein $E_{10}$, $F_{11}$, $G_{12}$, $H_{13}$, $I_{14}$ and Z are as defined therein including —$E_{10}$—$F_{11}$— is

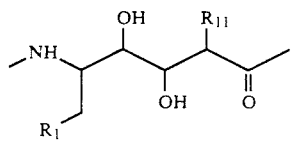

or

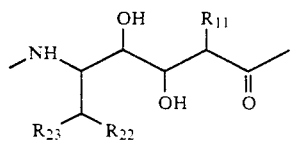

wherein $R_1$ is hydrogen, alkyl, aryl, cycloalkyl, heterocyclic, alkoxy or thioalkoxy, $R_{11}$ is hydrogen, alkyl, benzyl, cycloalkyl, hydroxyalkyl, cycloalkylalkyl, arylalkyl, (heterocyclic)alkyl, alkoxyalkyl or thioalkoxyalkyl, $R_{22}$ is hydrogen or alkyl and $R_{23}$ is hydroxyalkyl, aminoalkyl, aryl or alkyl, $G_{12}$ is absent or an amino acid residue, $H_{13}$ is absent or an amino acid residue, $I_{14}$ is absent or an amino acid residue and Z is hydroxy, substituted alkoxy, substituted amino or cyclic amino;

PCT Patent Application No. WO 87/02986, published May 21, 1987, discloses mimics of the Leu-Val cleavage site of angiotensinogen having the formula

wherein $E_{10}$, $F_{11}$, $G_{12}$, $H_{13}$, $I_{14}$ and Z are as defined therein including —$E_{10}$—$F_{11}$— is

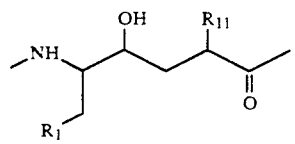

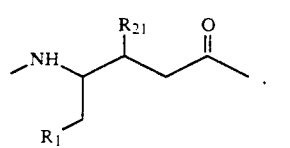

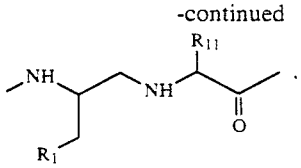

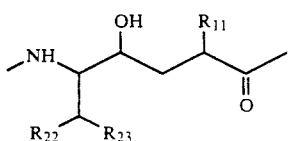

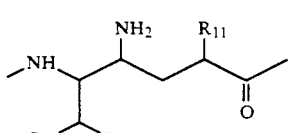

or

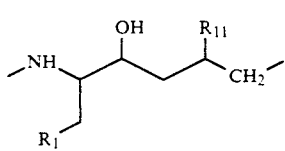

wherein $R_1$ is hydrogen, alkyl, aryl, cycloalkyl, heterocyclic, alkoxy or thioalkoxy, $R_{11}$ is hydrogen, alkyl, benzyl, cycloalkyl, hydroxyalkyl, cycloalkylalkyl, arylalkyl, (heterocyclic)alkyl, alkoxyalkyl or thioalkoxyalkyl, $R_{21}$ is hydroxy or amino, $R_{22}$ is hydrogen or alkyl and $R_{23}$ is hydroxy, amino, hydroxyalkyl, aminoalkyl, aryl or alkyl, $G_{12}$ is absent or an amino acid residue, $H_{13}$ is absent or an amino acid residue, $I_{14}$ is absent or an amino acid residue and Z is hydroxy, substituted alkoxy, substituted amino or cyclic amino;

PCT Patent Application No. WO 89/00161, published Jan. 12, 1989, discloses mimics of the Leu-Val cleavage site of angiotensinogen having the formula

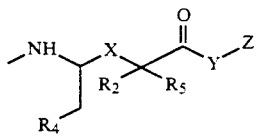

wherein $R_2$, $R_4$, $R_5$, X, Y and Z are as defined therein including $R_2$ is hydrogen or alkyl, $R_4$ is hydrogen, alkyl, cycloalkyl, aryl, heterocyclic, hydroxyalkyl or aminoalkyl, $R_5$ is hydrogen, alkyl, arylalkyl, (heterocyclic)alkyl or cycloalkyl, X is —CH(OH)—, —CH(NH$_2$)—, —C(O)—, —CH(OH)CH(OH)—, —CH(OH)CH$_2$—, —CH(NH$_2$)CH$_2$—, —C(O)—CH$_2$—, —CH$_2$—NH—, —CH$_2$—O— or —P(O)(A)B— wherein A is hydroxy or amino and B is absent, O, NH or CH$_2$, Y is absent or —NHCH($R_5$)C(O)— and Z is hydroxy, substituted alkoxy, substituted amino or N-heterocyclic;

PCT Patent Application No. WO 88/07053, published Sep. 22, 1988, discloses mimics of the Leu-Val cleavage site of angiotensinogen having the formula

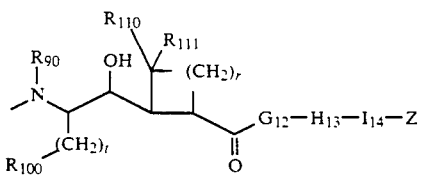

wherein r, t, $R_{90}$, $R_{100}$, $R_{110}$, $R_{111}$, $G_{12}$, $H_{13}$, $I_{14}$ and Z are as defined therein including r is 0–3, t is 0–3, $R_{90}$ is hydrogen or alkyl, $R_{100}$ is hydrogen, alkyl, aryl, cycloalkyl, heterocyclic, alkoxy or thioalkoxy, $R_{110}$ and $R_{111}$ are independently selected from hydrogen, alkyl, aryl, arylalkyl and halo, $G_{12}$ is absent, an amino acid residue or

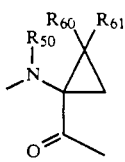

wherein $R_{50}$ is hydrogen, alkyl, arylalkyl, (heterocyclic)alkyl, cycloalkylalkyl or adamantyl, and $R_{60}$ and $R_{61}$ are independently selected from hydrogen, alkyl, aryl, arylalkyl, heterocyclic, (heterocyclic)alkyl, cycloalkyl, cycloalkylalkyl and adamantyl; or $R_{60}$ and $R_{61}$ taken together form a carbocyclic or heterocyclic spirocycle, $H_{13}$ is absent an amino acid residue or

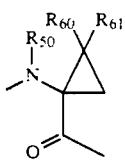

wherein $R_{50}$ is hydrogen, alkyl, arylalkyl, (heterocyclic)alkyl, cycloalkylalkyl or adamantyl, and $R_{60}$ and $R_{61}$ are independently selected from hydrogen, alkyl, aryl, arylalkyl, heterocyclic, (heterocyclic)alkyl, cycloalkyl, cycloalkylalkyl and adamantyl; or $R_{60}$ and $R_{61}$ taken together form a carbocyclic or heterocyclic spirocycle, $I_{14}$ is absent an amino acid residue or

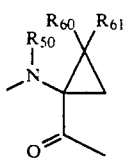

wherein $R_{50}$ is hydrogen, alkyl, arylalkyl, (heterocyclic)alkyl, cycloalkylalkyl or adamantyl, and $R_{60}$ and $R_{61}$ are independently selected from hydrogen, alkyl, aryl, arylalkyl, heterocyclic, (heterocyclic)alkyl, cycloalkyl, cycloalkylalkyl and adamantyl; or $R_{60}$ and $R_{61}$ taken together form a carbocyclic or heterocyclic spirocycle and Z is hydroxy, alkoxy, substituted alkoxy, amino, substituted amino or cyclic amino;

PCT Patent Application No. WO 88/02374, published Apr. 7, 1988, discloses mimics of the Leu-Val cleavage site of angiotensinogen having the formula $-E_{10}-F_{11}-C(=Y)-G_{12}-H_{13}-Z.$      a)

$-E_{10}-F_{11}-W.$      b)

$-E_{10}-F_{11}-G_{12}-H_{13}-W$ or      c)

$-E_{10}-F_{11}-G_{121}-H_{131}-I_{14}-Z$      d)

wherein $E_{10}$, $F_{11}$, $G_{12}$, $H_{13}$, $G_{121}$, $H_{131}$, $I_{14}$, W, Y and Z are as defined therein including $-E_{10}-F_{11}-$ is

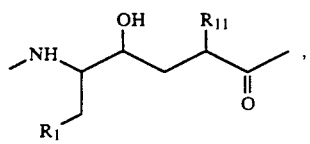

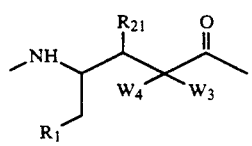

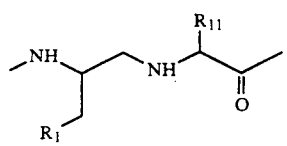

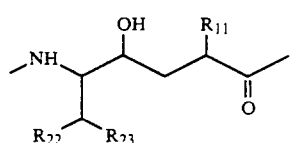

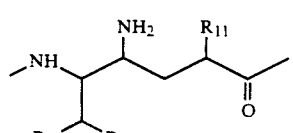

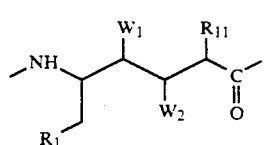

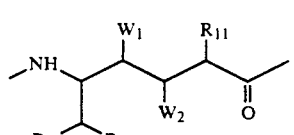

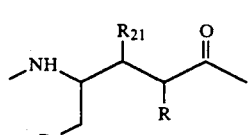

or

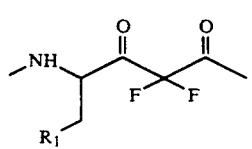

wherein R and $R_1$ are independently selected from alkyl, cycloalkyl, aryl, substituted alkyl as defined therein, alkoxy or thioalkoxy, $R_{11}$ is alkyl, cycloalkyl, aryl, substituted alkyl as defined therein, alkoxy, thioalkoxy, hydrogen, hydroxyalkyl, cycloalkylalkyl, arylalkyl, (heterocyclic)alkyl, alkoxyalkyl and thioalkoxyalkyl, $R_{22}$ is hydrogen or alkyl, $R_{23}$ is hydroxy, hydroxyalkyl, amino, aminoalkyl, aryl or alkyl, $R_{24}$ is aryl, amino, alkylamino, dialkylamino, trialkylamino, heterocyclic, hydroxy, alkoxy, alkanoyloxy, mercapto, carboxy, alkoxycarbonyl, dialkylaminoalkoxycarbonyl, aminocarbonyl, alkylaminocarbonyl, dialkylaminocarbonyl, cyclicamino, cycloalkylamino, guanidinyl, cyano, N-cyanoguanidinyl, cyanoamino, hydroxyalkylamino, di(hydroxyalkyl)amino, arylalkyl, aminoalkyl, alkylaminoalkyl, dialkylaminoalkyl, trialkylaminoalkyl, heterocyclicalkyl, hydroxyalkyl, alkoxyalkyl, alkanoyloxyalkyl, mercaptoalkyl, carboxyalkyl, alkoxycarbonylalkyl, dialkylaminoalkoxycarbonylalkyl, aminocarbonylalkyl, alkylaminocarbonylalkyl, dialkylaminocarbonylalkyl, cyclicaminoalkyl, cycloalkylaminoalkyl, guanidinylalkyl, cyanoalkyl, N-cyanoguanidinylalkyl, cyanoaminoalkyl, hydroxyalkylaminoalkyl or di(hydroxyalkyl)aminoalkyl, $W_1$ and $W_2$ are independently selected from hydroxy and amino, $W_3$ and $W_4$ are independently selected from hydrogen and fluoro, W is as defined therein, Y is O, S, NH or —N(alkyl)—, Z is as defined therein, $G_{12}$ is absent or an amino acid residue, $H_{13}$ is absent or an amino acid residue, $G_{121}$ is absent or an amino acid residue, $H_{131}$ is absent or an amino acid residue and $I_{14}$ is absent or an amino acid residue;

PCT Patent Application No. WO 86/06379, published Apr. 5, 1989, discloses mimics of the Leu-Val cleavage site of angiotensinogen having the formula

—E—F—G—H—Z wherein E, F, G, H and Z are as defined therein including —E—F— is

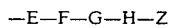

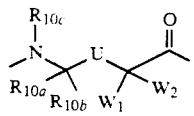

wherein $R_{10a}$ is hydrogen or alkyl, $R_{10b}$ is alkyl, cycloalkyl, cycloalkylalkyl, arylalkyl, (heterocyclic)alkyl, cycloalkenyl or cycloalkenylalkyl, $R_{10c}$ is hydrogen or alkyl, U is —C(O)—, —CH(OH)— or —CH(NH$_2$)— and $W_1$ and $W_2$ are independently selected from hydrogen, fluoro, chloro and bromo, G is absent or an amino acid residue, H is absent or an amino acid residue and Z is hydroxy, thiol, amino, substituted alkoxy, substituted thioalkoxy, substituted alkylamino, Lys-OH, Lys-NH$_2$, Ser-OH or Ser-NH$_2$;

European Patent Application No. EP0271862, published Jun. 22, 1988, discloses mimics of the Leu-Val cleavage site of angiotensinogen having the formula

—Y—W—U wherein Y, W and U are as defined therein including Y is Sta, Cysta or PhSta, W is Leu, Ile, N-MeLeu, Val or absent and U is —NHCH$_2$CH(CH$_3$)CH$_2$CH$_3$, —NHCH$_2$Ph, —NHCH(CH$_2$OH)CH(CH$_3$)CH$_2$CH$_3$, —NHCH$_2$CH(OH)CH$_2$SCH(CH$_3$)$_2$, —NHCH$_2$CH(OH)CH$_2$S(O)CH(CH$_3$)$_2$, —NHCH$_2$CH(OH)CH$_2$S(O)$_2$CH(CH$_3$)$_2$, —NHCH$_2$CH$_2$Ph, —NHCH$_2$(pyrid-2-yl), —NH$_2$, —NHCH$_2$CH=CH$_2$, —OEt, —OMe, —NH(piperidin-4-yl),

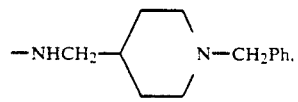

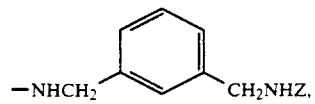

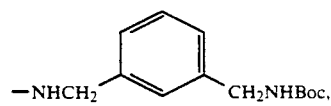

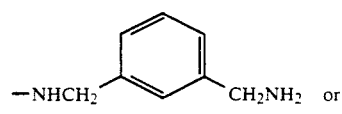

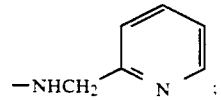

234

European Patent Application No. EP0275480, published Jul. 27, 1988, discloses mimics of the Leu-Val cleavage site of angiotensinogen having the formula

—W—U—V wherein W, U and V are as defined therein including W is Sta, PhSta or Cysta, U is absent, Leu, Ile, val, N-MeLeu or N-MeIle and V is —NHCH$_2$Ph, —NHCH$_2$cyclohexyl, —NH(piperidin-4-yl), —NHCH$_2$(pyrid-2-yl), —NHCH$_2$CH(CH$_3$)CH$_2$CH$_3$, —OMe, —OEt, —NHCH(CH$_2$OH)CH(CH$_3$)CH$_2$CH$_3$, —NHCH$_2$CH$_2$(morpholin-1-yl),

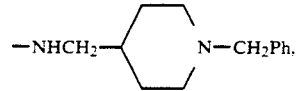

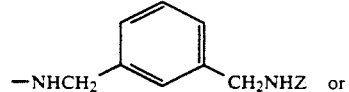

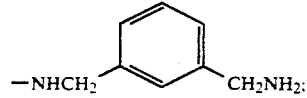

PCT Patent Application No. WO 88/03927, published Jun. 2, 1988, discloses mimics of the Leu-Val cleavage site of angiotensinogen having the formula —T—(C)$_n$—W—(D)$_n$—V—(E)$_n$—U wherein T, C, W, D, V, E, U and n are as defined therein including n is 0-1, T is Sta, PhSta, Cysta, Leu, CyclohexylAla or Phe, W is absent, Leu, Gly or Ile, V is absent, Leu or Ile, C is —CH$_2$NH—, —CH(OH)C-

H₂— or —CH(OH)—CH=CH—C(O)—, D is —CH₂NH—, E is —CH₂NH— or —CH₂N(Cbz)— and U is —NHCH₂Ph, —NHCH₂-cyclohexyl, —NH₂, —NH(piperidin-4-yl), —NHCH₂(pyrid-2-yl), —NHCH₂CH(CH₃)CH₂CH₃, —OMe, —OEt,

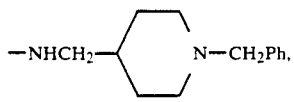

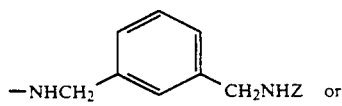

European Patent Application No. EP0314060, published May 3, 1989, discloses mimics of the Leu-Val cleavage site of angiotensinogen having the formula

wherein W and U are as defined therein including W is Sta, Cysta, PhSta, ChSta, DFKSta, DFKCys, DFKChs, ASta or ACys and U is —NHCH₂CH₂(morpholin-1-yl), —NHCH₂CH(CH₃)CH₂CH₃, —NHCH(CH₂OH)CH(CH₃)CH₂CH₃, —LeuNHCH₂Ph, —LeuNHCH₂-cyclohexyl, —LeuNH(piperidin-4-yl), —LeuNHCH₂(pyrid-2-yl) or

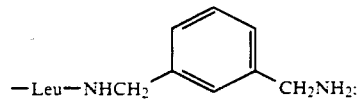

European Patent Application No. EP0310918, published Apr. 12, 1989, discloses mimics of the Leu-Val cleavage site of angiotensinogen having the formula

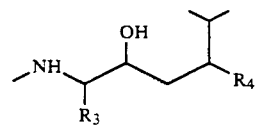

wherein R₃ and R₄ are as defined therein including R₃ is isobutyl, cyclohexylmethyl or benzyl and R₄ is phenyl, furyl, vinyl, ethyl or 1,2-dihydroxyethyl;

French Patent Application No. FR8700560, published Jul. 2, 1988, discloses mimics of the Leu-Val cleavage site of angiotensinogen having the formula

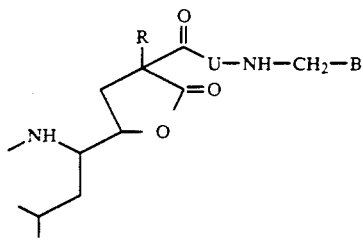

wherein R, U and B are as defined therein including R is hydrogen or hydroxyalkyl, U is Leu, Ala, Val or Ile and B is pyridyl;

European Patent Application No. EP0236948, published Sep. 16, 1987, discloses mimics of the Leu-Val cleavage site of angiotensinogen having the formula

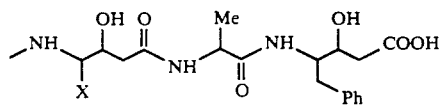

wherein X is as defined therein including X is isobutyl or benzyl;

European Patent Application No. EP0281316, published Sep. 7, 1988, discloses mimics of the Leu-Val cleavage site of angiotensinogen having the formula

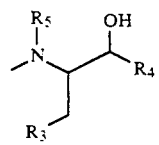

wherein R₃, R₄ and R₅ are as defined therein including R₃ is allyl, cyclohexyl or phenyl, R₄ is nitromethyl, alkoxycarbonyl or —CH₂S(O)ₙ—R$^d$ wherein n is 0–2 and R$^d$ is heterocyclic and R₅ is hydrogen or alkyl;

German Patent Application No. DE3825242, published Feb. 9, 1989, discloses mimics of the Leu-Val cleavage site of angiotensinogen having the formula

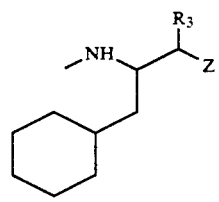

wherein R₃ and Z are as defined therein including R₃ is hydroxy or amino and Z is substituted carbonyl, substituted thiocarbonyl, substituted iminocarbonyl or unsubstituted or substituted phosphono, aminomethyl, thiomethyl, sulfinylmethyl, sulfonylmethyl or phosphonomethyl;

European Patent Application No. EP0275101, published Jul. 20, 1988, discloses mimics of the Leu-Val cleavage site of angiotensinogen having the formula

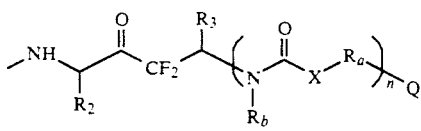

wherein $R_2$, $R_3$, $R_a$, $R_b$, n, X and Q are as defined therein including $R_2$ is an amino acid side chain, $R_3$ is hydrogen, alkyl, cyclohexyl, cyclohexylmethyl, phenyl, benzyl, 2-pyridylmethyl or an amino acid side chain, $R_a$ is an amino acid side chain, $R_b$ is hydrogen or alkyl or $R_a$ and $R_b$ taken together are —$CH_2$—$CH_2$—, n is 1-10, X is hydrogen, $CH_2$, alkoxy, substituted alkoxy, alkyl, phenyl, benzyl, cyclohexyl, cyclohexylmethyl or 2-pyridylmethyl and Q is hydrogen, alkyl, arylakyl, alkoxycarbonyl or an amino acid residue;

PCT Patent Application No. WO 89/01488, published Feb. 23, 1989, discloses mimics of the Leu-Val cleavage site of angiotensinogen having the formula $$E_{10}-F_{11}-G_{12}-H_{13}-I_{14}-Z$$

wherein $E_{10}$, $F_{11}$, $G_{12}$, $H_{13}$, $I_{14}$ and Z are as defined therein including —$E_{10}$—$F_{11}$— is

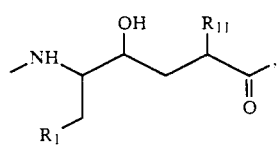

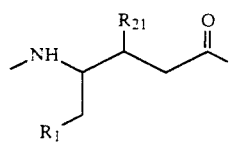

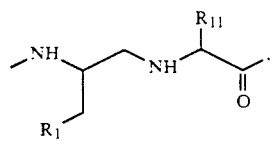

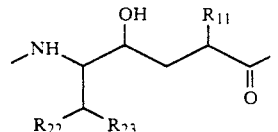

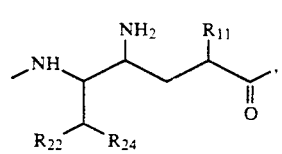

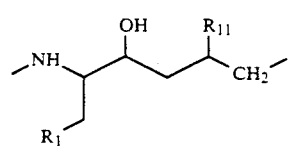

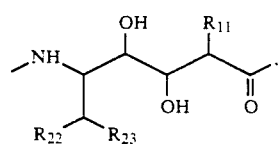

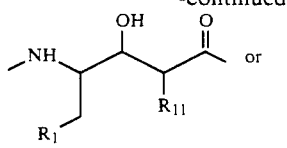

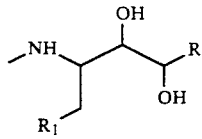

wherein $R_1$ is hydrogen, alkyl, aryl, cycloalkyl, heterocyclic, alkoxy or thioalkoxy, $R_{11}$ is hydrogen, alkyl, benzyl, cycloalkyl, hydroxyalkyl, cycloalkylalkyl, arylalkyl, (heterocyclic)alkyl, alkoxyalkyl or thioalkoxyalkyl, $R_{21}$ is hydroxy or amino, $R_{22}$ is hydrogen or alkyl and $R_{23}$ is hydroxy, amino, hydroxyalkyl, aminoalkyl, aryl or alkyl, $R_{24}$ is $R_1$ hydroxy, amino, hydroxyalkyl or aminoalkyl, $G_{12}$ is absent or an amino acid residue, $H_{13}$ is absent or an amino acid residue, $I_{14}$ is absent or an amino acid residue and Z is hydroxy, substituted alkoxy, substituted amino or cyclic amino;

European Patent Application No. EP0275101, published Jul. 20, 1988, discloses mimics of the Leu-Val cleavage site of angiotensinogen having the formula

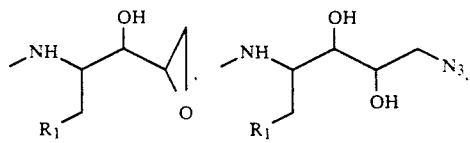

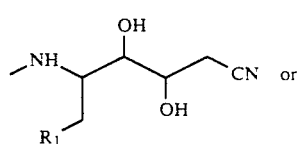

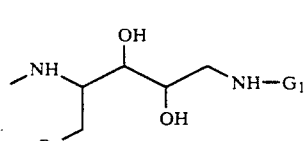

wherein $R_1$, $G_{12}$, $H_{13}$ and X are as defined therein including $R_1$ is hydrogen, alkyl, aryl, cycloalkyl, heterocyclic, alkoxy or thioalkoxy, $G_{12}$ is absent, an amino acid residue or an amino acid residue wherein the alpha-amino group has been replaced by O, $H_{13}$ is absent, an amino acid residue or an amino acid residue wherein the alpha-amino group has been replaced by 0 and X is hydrogen, alkyl or substituted alkyl as defined therein;

European Patent Application No. EP0312291, published Apr. 19, 1989, discloses mimics of the Leu-Val cleavage site of angiotensinogen having the formula

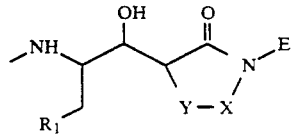

wherein $R_1$, Y, X and E are as defined therein including $R_1$ is hydrogen, alkyl, aryl, cycloalkyl, 1,3-dithiolan-2-yl or 1,3-dithian-2-yl, X is —$CH_2$—$C(R_{13})(R_{14})$ wherein $R_{13}$ and $R_{14}$ are independently selected from hydrogen, alkyl, alkenyl, carboxy, aminocarbonyl, substituted aminocarbonyl, substituted alkyl, alkanoyloxy, substituted aminocarbonyloxy, substituted carbonylamino, substituted aminocarbonylamino, substituted sulfinyl, substituted sulfonyl, substituted sulfide, amino, alkylamino, dialkylamino or heterocyclic, Y is $CH_2$, O, S, SO or $SO_2$ or X and Y taken together is $-(CH_2)_4-$ and E is hydrogen, aryl, heterocyclic, alkyl, cycloalkyl or substituted alkyl; European Patent Application No. EP0312283, published Apr. 19, 1989, discloses mimics of the Leu-Val cleavage site of angiotensinogen having the formula

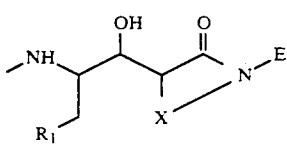

wherein $R_1$, X and E are as defined therein including $R_1$ is hydrogen, alkyl, aryl, cycloalkyl, 1,3-dithiolan-2-yl or 1,3-dithian-2-yl, X is $-CH_2-C(R_{13})(R_{14})-$ wherein $R_{13}$ and $R_{14}$ are independently selected from hydrogen, alkyl, alkenyl, carboxy, aminocarbonyl, substituted aminocarbonyl, substituted alkyl, alkanoyloxy, substituted aminocarbonyloxy, substituted carbonylamino, substituted aminocarbonylamino, substituted sulfinyl, substituted sulfonyl, substituted sulfide, amino, alkylamino, dialkylamino or heterocyclic and E is hydrogen, aryl, heterocyclic, alkyl, cycloalkyl or substituted alkyl;

European Patent Application No. EP0312158, published Apr. 19, 1989, discloses mimics of the Leu-Val cleavage site of angiotensinogen having the formula

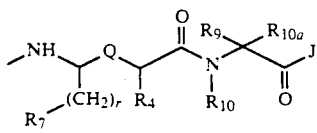

wherein r, $R_7$, $R_4$, $R_{10}$, $R_9$, $R_{10a}$, Q and J are as defined therein including r is 1-4, $R_7$ is alkyl, aryl or cycloalkyl, $R_4$ is hydrogen, alkyl, alkenyl, cycloalkyl, aryl or substituted alkyl, $R_{10}$ and $R_{10a}$ are independently selected from hydrogen and alkyl, $R_9$ is $-(CH_2)_s-NR_{11}R_{12}$ wherein s is 1-2 and $R_{11}$ and $R_{12}$ are independently selected from hydrogen, heterocyclic, aryl, cycloalkyl, alkyl, arylalkyl, (heterocyclic)alkyl, aminoalkyl, hydroxyalkyl, alkylaminoalkyl, dialkylaminoalkyl, carboxy, alkyl substituted by $-SO_3H$, aminocarbonylalkyl, alkylaminocarbonylalkyl or dialkylaminocarbonylalkyl, Q is $-CH(OH)-$, $-CH(N(R_8))-$, $-CH(OH)CH_2-$ or $-CH(N(R_8))CH_2-$ wherein $R_8$ is hydrogen, alkyl, formyl, alkanoyl, aroyl, alkoxycarbonyl, aryloxycarbonyl or araylalkoxycarbonyl and J is substituted alkylamino or substituted alkoxy;

European Patent Application No. EP0312157, published Apr. 19, 1989, discloses mimics of the Leu-Val cleavage site of angiotensinogen having the formula

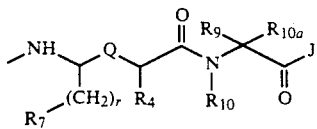

wherein r, $R_7$, $R_4$, $R_{10}$, $R_9$, $R_{10a}$, Q and J are as defined therein including r is 1-4, $R_7$ is alkyl, aryl or cycloalkyl, $R_4$ is hydrogen, alkyl, alkenyl, cycloalkyl, aryl or substituted alkyl, $R_{10}$ and $R_{10a}$ are independently selected from hydrogen and alkyl, $R_9$ is $-(CH_2)_s-NR_{11}R_{12}$ wherein s is 1-2 and $R_{11}$ and $R_{12}$ are independently selected from hydrogen, heterocyclic, aryl, cycloalkyl, alkyl, arylalkyl, (heterocyclic)alkyl, aminoalkyl, hydroxyalkyl, alkylaminoalkyl, dialkylaminoalkyl, carboxy, alkyl substituted by $-SO_3H$, aminocarbonylalkyl, alkylaminocarbonylalkyl or dialkylaminocarbonylalkyl, Q is $-CH(OH)-$, $-CH(N(R_8))-$, $-CH(OH)CH_2-$ or $-CH(N(R_8))CH_2-$ wherein $R_8$ is hydrogen, alkyl, formyl, alkanoyl, aroyl, alkoxycarbonyl, aryloxycarbonyl or araylalkoxycarbonyl and J is substituted alkylamino, substituted alkoxy, heterocyclic, heterocyclicamino or substitute guanidino;

European Patent Application No. EP0314239, published May 3, 1989, discloses mimics of the Leu-Val cleavage site of angiotensinogen having the formula

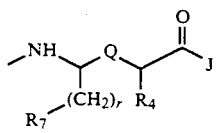

wherein r, $R_7$, $R_4$, Q and J are as defined therein including r is 1-4, $R_7$ is alkyl, aryl or cycloalkyl, $R_4$ is hydrogen, alkyl, alkenyl, cycloalkyl, aryl or substituted alkyl, Q is $-CH(OH)-$, $-CH(N(R_8))-$, $-CH(OH)CH_2-$ or $-CH(N(R_8))CH_2-$ wherein $R_8$ is hydrogen, alkyl, formyl, alkanoyl, aroyl, alkoxycarbonyl, aryloxycarbonyl or araylalkoxycarbonyl and J is amino, hydroxy, substituted alkylamino or substituted alkoxy;

South African Patent Application No. 866642, published Feb. 24, 1987, discloses mimics of the Leu-Val cleavage site of angiotensinogen having the formula

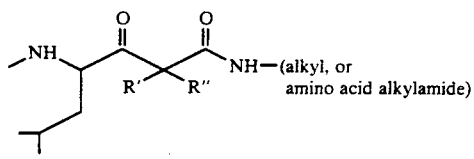

wherein R' and R" are as defined therein including R' is fluoro and R" is hydrogen or fluoro;

European Patent Application No. EP0273696, published Jul. 6, 1988, discloses mimics of the Leu-Val cleavage site of angiotensinogen having the formula

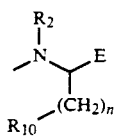

wherein n, $R_2$, $R_{10}$ and E are as defined therein including n is 0-5, $R_2$ is hydrogen or alkyl, $R_{10}$ is alkyl, cycloalkyl, cycloalkylalkyl, arylalkyl, (heterocyclic)alkyl, alkoxyalkyl, thioalkoxyalkyl, hydroxyalkyl or aminoalkyl and E is —CH(W)—G wherein W is hydroxy, amino, alkanoyloxy or alkanoyloxyalkyloxy and G is —Q—C(O)—T—U—V wherein Q is a bond or —CH($R_{13}$)— wherein $R_{13}$ is hydrogen, aryl, alkyl, cycloalkyl or substituted alkyl, T and U are independently absent or selected from an amino acid residue and V is hydroxy, substituted alkoxy, amino or substituted amino;

European Patent Application No. EP0278158, published Aug. 17, 1988, discloses mimics of the Leu-Val cleavage site of angiotensinogen having the formula

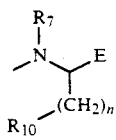

wherein n, $R_7$, $R_{10}$ and E are as defined therein including n is 0-3, $R_7$ is alkyl or substituted alkyl, $R_{10}$ is alkyl, cycloalkyl, cycloalkylalkyl, arylalkyl, (heterocyclic)alkyl, alkoxyalkyl, thioalkoxyalkyl, hydroxyalkyl or aminoalkyl and E is —CH(W)—G wherein W is hydroxy, amino, alkanoyloxy or alkanoyloxyalkyloxy and G is —Q—C(O)—T—U—V wherein Q is a bond or —CH($R_{13}$)— wherein $R_{13}$ is hydrogen, aryl, alkyl, cycloalkyl or substituted alkyl, T and U are independently absent or selected from an amino acid residue and V is hydroxy, substituted alkoxy, amino or substituted amino;

German Patent Application No. DE3721855, published Sep. 22, 1988, discloses mimics of the Leu-Val cleavage site of angiotensinogen having the formula

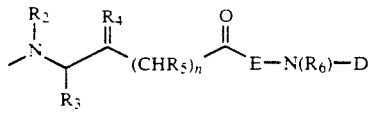

wherein n, $R_2$, $R_3$, $R_4$, $R_5$, $R_6$, E and D are as defined therein including n is 1-2, $R_2$ is hydrogen or alkyl, $R_3$ is hydrogen, alkyl, aryl, arylalkyl, (heterocyclic)alkyl, cycloalkyl, alkoxy or cycloalkylalkyl, $R_4$ is (H,OH), (H,NH$_2$) or O, $R_5$ is hydrogen or alkyl, $R_6$ is hydrogen or alkyl, E is 0-2 amino acid residues and D is —CH$_2$CHOHCH$_2$OH, substituted sulfonyl, substituted sulfonylalkyl, substituted carbonyl, substituted phosphonyl, phenyl, phenylalkyl, furyl, furylalkyl, thienyl, thienylalkyl, pyridyl, pyridylalkyl or other (heterocyclic)alkyl;

European Patent Application No. EP0309841, published Apr. 5, 1989, discloses mimics of the Leu-Val cleavage site of angiotensinogen having the formula

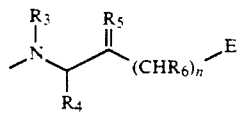

wherein n, $R_3$, $R_4$, $R_5$, $R_6$ and E are as defined therein including n is 1-2, $R_3$ is hydrogen or alkyl, $R_4$ is hydrogen, alkyl, aryl, arylalkyl, heterocyclic, (heterocyclic)alkyl, cycloalkyl, alkoxy or cycloalkylalkyl, $R_5$ is (H,OH), (H,NH$_2$ or O, $R_6$ is hydrogen, alkyl or alkenyl and E is —SR$_7$, —SOR$_7$, —SO$_2$R$_7$, —SO$_2$OR$_7$ or —SO$_2$NR$_7$R$_8$ wherein $R_7$ and $R_8$ are independently selected from $R_4$;

European Patent Application No. EP0292800, published Nov. 30, 1988, discloses mimics of the Leu-Val cleavage site of angiotensinogen having the formula

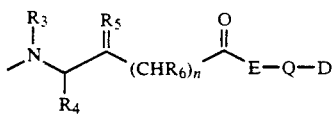

wherein n, $R_3$, $R_4$, $R_5$, $R_6$, E, Q and Y are as defined therein including n is 1-2, $R_3$ is hydrogen or alkyl, $R_4$ is hydrogen, alkyl, aryl, arylalkyl, heterocyclic, (heterocyclic)alkyl, cycloalkyl, cycloalkylalkyl or alkoxy, $R_5$ is (H,OH), (H,NH$_2$), or O, $R_6$ is hydrogen or alkyl, E is 0-2 amino acid residues, Q is O or NH and Y is H or substituted alkyl;

European Patent Application No. EP0249096, published Dec. 16, 1987, discloses mimics of the Leu-Val cleavage site of angiotensinogen having the formula

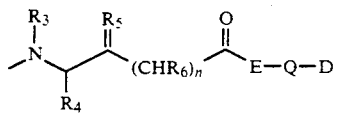

wherein n, $R_3$, $R_4$, $R_5$, $R_6$, E, Q and Y are as defined therein including n is 1-2, $R_3$ is hydrogen or alkyl, $R_4$ is hydrogen, alkyl, aryl, arylalkyl, heterocyclic, (heterocyclic)alkyl, cycloalkyl, cycloalkylalkyl or alkoxy, $R_5$ is (H,OR$_{12}$), (H,NR$_{12}$R$_{13}$), or O wherein $R_{12}$ and $R_{13}$ are independently selected from hydrogen and alkyl, $R_6$ is hydrogen or alkyl, E is 0-2 amino acid residues, Q is O or NH and Y is H or substituted alkyl; and European Patent Application No. EP0264795, published Apr. 27, 1988, discloses mimics of the Leu-Val cleavage site of angiotensinogen having the formula

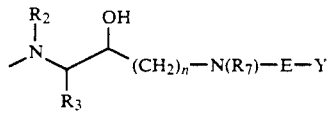

wherein n, R2, R3, R4, E and Y are as defined therein including n is 1-2, R2 is hydrogen or alkyl, R3 is hydrogen, alkyl, aryl, arylalkyl, heterocyclic, (heterocyclic)alkyl, cycloalkyl, cycloalkylalkyl or alkoxy, R4 is hydrogen or alkyl, E is —C(O)NH—, —C(S)NH—, —C(O)O—, —SO$_2$—, —SO$_2$NH—, or —PO(OA)O— wherein A is hydrogen or alkyl and Y is carboxy, carboxyalkyl, substituted carboxyalkyl, alkoxycarbonyl, alkoxycarbonylalkyl, substituted alkoxycarbonylalkyl, aminocarbonyl, substituted aminocarbonyl, aminocarbonylalkyl, substituted aminocarbonylalkyl, hydrogen, alkyl, aryl, arylalkyl, cycloalkyl or cycloalkylalkyl; or E-Y is pyrrolidinocarbonyl, piperidinocarbonyl, morpholinocarbonyl, pyrrolidinosulfonyl, piperidinosulfonyl or morpholinosulfonyl.

The term "substituted methylene group" as used herein refers to:

(I) —CHR$_{13}$R$_{14}$ wherein
  1) R$_{13}$ is
    i) hydrogen or
    ii) hydroxy and
  2) R$_{14}$ is i) hydrogen,
ii) loweralkyl,
iii) hydroxy,
iv) hydroxyalkyl,
v) alkoxy,
vi) alkoxyalkyl,
vii) azido,
viii) azidoalkyl,
ix) amino,
x) (N-protected)amino,
xi) aminoalkyl,
xii) (N-protected)aminoalkyl,
xiii) alkylamino,
xiv) (N-protected)(alkyl)amino,
xv) alkylaminoalkyl,
xvi) (N-protected)(alkyl)aminoalkyl,
xvii) dialkylamino,
xviii) dialkylaminoalkyl,
xix) carboxyalkyl
xx) thioalkoxy,
xxi) thioalkoxyalkyl,
xxii) alkylsulfonyl,
xxiii) alkylsulfonylalkyl,
xxiv) thioaryloxy,
xxv) thioaryloxyalkyl,
xxvi) arylsulfonyl,
xxvii) arylsulfonylalkyl,
xxviii) (unsubstituted heterocyclic)alkyl or
xxix) (substituted heterocyclic)alkyl
such that when $R_{13}$ is hydroxy then $R_{14}$ is not hydroxy, alkoxy, azido, amino, alkylamino, dialkylamino, (N-protected)amino, (N-protected)(alkyl)amino, thioalkoxy, alkylsulfonyl or arylsulfonyl, and such that when $R_{13}$ is hydrogen then $R_{14}$ is not hydrogen or loweralkyl;
(II) $-C(=CH_2)C(O)NHR_{15}$,
(III) $-C(OH)(R_{16})C(O)NHR_{15}$ or
(IV) $-CH(R_{16})C(O)NHR_{15}$ wherein
1) $R_{15}$ is
i) loweralkyl,
ii) hydroxyalkyl,
iii) alkoxyalkyl,
iv) aminoalkyl,
v) alkylaminoalkyl,
vi) dialkylaminoalkyl,
vii) heterocyclic,
viii) aryl,
ix) (heterocyclic)alkyl or
x) arylalkyl and
2) $R_{16}$ is
i) hydrogen,
ii) loweralkyl,
iii) hydroxyalkyl,
iv) haloalkyl or
v) azidoalkyl;

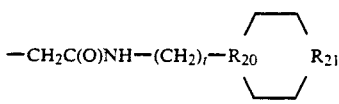 (V)

wherein
1) t is 0 to 3,
2) $R_{20}$ is
i) $CH_2$ or
ii) N and
3) $R_{21}$ is i) NH,
ii) O,
iii) S or
iv) $SO_2$,
such that when t is 0 then $R_{20}$ is $CH_2$ and when t is 1 to 3 then $R_{20}$ is N,
(VI) $-CH_2CH(R_{22})C(O)NHR_{23}$ wherein
1) $R_{22}$ is
i) loweralkyl or
ii) cycloalkylalkyl and
2) $R_{23}$ is
i) loweralkyl,
ii) hydroxyalkyl,
iii) alkoxyalkyl,
iv) aminoalkyl,
v) alkylaminoalkyl,
vi) dialkylaminoalkyl,
vii) heterocyclic,
viii) aryl,
ix) (heterocyclic)alkyl,
x) arylalkyl or

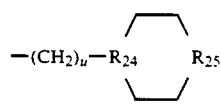 xi)

wherein
a) u is 0 to 3,
b) $R_{24}$ is $CH_2$ or N and
c) $R_{25}$ is NH, O, S or $SO_2$,
such that when u is 0 then $R_{24}$ is $CH_2$ and when u is 1 to 3 then $R_{24}$ is N;

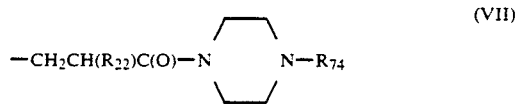 (VII)

wherein
1) $R_{22}$ is as defined above and
2) $R_{74}$ is
i) hydrogen,
ii) loweralkyl,
iii) an N-protecting group or
iv) $R_{75}-C(O)-$ wherein $R_{75}$ is aminoalkyl or (N-protected)aminoalkyl;

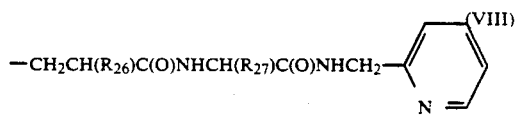 (VIII)

wherein
1) $R_{26}$ is
i) loweralkyl or
ii) cycloalkylalkyl and
2) $R_{27}$ is
i) loweralkyl or
ii) cycloalkylalkyl;
(IX) $-CH_2CH(R_{81})NHC(O)R_{82}$ or $-CH_2CH(R_{81})NHS(O)_2R_{82}$ wherein
1) $R_{81}$ is
i) loweralkyl or
ii) cycloalkylalkyl and
2) $R_{82}$ is i) loweralkyl,
ii) alkoxy,
iii) alkylamino,
iv) dialkylamino,
v) —OR* wherein R* is aminoalkyl, alkylaminoalkyl, dialkylaminoalkyl or (heterocyclic)alkyl or vi)
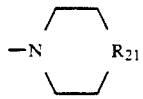

as defined above;
(X) —CH$_2$NHC(O)R$_{82}$ or —CH$_2$NHS(O)$_2$R$_{82}$ wherein R$_{82}$ is as defined above; or
(X) —CF$_2$CH(OH)R$_{83}$ wherein R$_{83}$ is loweralkyl, loweralkenyl, cycloalkyl, cycloalkenyl, cycloalkylalkyl, cycloalkenylalkyl, aryl, arylalkyl, heterocyclic or (heterocyclic)alkyl.

The chiral centers of the compounds of the invention may have either the "R", "S" or "R,S" configuration. The terms "R" and "S" configuration are as defined by IUPAC 1974 Recommendations for Section E, Fundamental Stereochemistry, Pure Appl. Chem. (1976) 45, 13–30.

The term "N-protecting group" or "N-protected" as used herein refers to those groups intended to protect nitrogen atoms against undesirable reactions during synthetic procedures or to prevent the attack of exopeptidases on the final compounds or to increase the solubility of the final compounds and includes but is not limited to acyl, acetyl, pivaloyl, t-butylacetyl, trichloroethoxycarbonyl, t-butyloxycarbonyl (Boc), benzyloxycarbonyl (Cbz) or benzoyl groups or an L- or D-aminoacyl residue, which may itself be N-protected similarly.

The term "loweralkyl" as used herein refers to straight or branched chain alkyl radicals containing from 1 to 7 carbon atoms including but not limited to methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "loweralkenyl" as used herein refers to a loweralkyl radical which contains at least one carbon-carbon double bond.

The term "aminoalkyl" as used herein refers to —NH$_2$ appended to a loweralkyl radical.

The term "hydroxyalkyl" as used herein refers to —OH appended to a loweralkyl radical.

The term "alkylamino" as used herein refers to a loweralkyl radical appended to an NH radical.

The term "cycloalkyl" as used herein refers to an aliphatic ring having 3 to 7 carbon atoms.

The term "cycloalkylalkyl" as used herein refers to an cycloalkyl group appended to a loweralkyl radical, including, but not limited to cyclohexylmethyl and the like.

The term "cycloalkenyl" as used herein refers to an aliphatic ring having 3–7 carbon atoms and also having at least one carbon-carbon double bond including, but not limited to, cyclohexenyl and the like.

The term "cycloalkenylalkyl" as used herein refers to a cycloalkenyl group appended to a loweralkyl radical.

The term "aryl" as used herein refers to a monocyclic or bicyclic carbocyclic ring system having one or more aromatic rings including, but not limited to, phenyl, naphthyl, tetrahydronaphthyl, indanyl and the like; or "aryl" refers to a heterocyclic aromatic ring as defined herein. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy and carboxamide.

The term "arylalkyl" as used herein refers to an aryl group appended to a loweralkyl radical including, but not limited to benzyl, naphthylmethyl and the like.

The terms "alkoxy" and "thioalkoxy" as used herein refer to R$_{30}$O— and R$_{30}$S+, respectively, wherein R$_{30}$ is a loweralkyl group or a cycloalkyl group.

The term "alkoxyalkoxy" as used herein refers to an alkoxy group appended to an alkoxy radical, including, but not limited to methoxymethoxy and the like.

The term "alkoxyalkyl" as used herein refers to an alkoxy group appended to a loweralkyl radical.

The term "(thioalkoxy)alkyl" as used herein refers to thioalkoxy appended to a loweralkyl radical.

The term "dialkylamino" as used herein refers to —NR$_{31}$R$_{32}$ wherein R$_{31}$ and R$_{32}$ are independently selected from loweralkyl groups.

The term "((alkoxy)alkoxy)alkyl" refers to an alkoxy group appended to an alkoxy group which is appended to a loweralkyl radical.

The term "(N-protected)amino" as used herein refers to —NHR$_{33}$ wherein R$_{33}$ is an N-protecting group.

The term "(N-protected)(alkyl)amino" as used herein refers to —NR$_{33}$R$_{34}$ wherein R$_{33}$ is an N-protecting group and R$_{34}$ is a loweralkyl group.

The term "N-protected aminoalkyl" as used herein refers to —NHR$_{35}$ appended to a loweralkyl group, wherein R$_{35}$ is an N-protecting group.

The term "alkylaminoalkyl" as used herein refers to —NHR$_{36}$ appended to a loweralkyl radical, wherein R$_{36}$ is a loweralkyl group.

The term "(N-protected)(alkyl)aminoalkyl" as used herein refers to —NR$_{35}$R$_{36}$, which is appended to a loweralkyl radical, wherein R$_{35}$ and R$_{36}$ are as defined above.

The term "dialkylaminoalkyl" as used herein refers to —NR$_{39}$R$_{40}$ is appended to a loweralkyl radical wherein R$_{39}$ and R$_{40}$ are independently selected from loweralkyl.

The term "polyalkoxy" as used herein refers to —OR$_{41}$ wherein R$_{41}$ is a straight or branched chain containing 1-5, C$_w$—O—C$_x$ linkages wherein w and x are independently selected from 1 to 3, including, but not limited to methoxyethoxymethoxy, ethoxyethoxymethoxy and the like.

The term "(polyalkoxy)alkyl" as used herein refers to a polyalkoxy group appended to a loweralkyl radical.

The term "(heterocyclic)alkyl" or "heterocyclic ring substituted alkyl" as used herein refers to a heterocyclic group appended to a loweralkyl radical, including but not limited to imidazolylmethyl, thiazolylmethyl and the like.

The term "azidoalkyl" as used herein refers to —N$_3$ appended to a loweralkyl radical.

The term "carboxyalkyl" as used herein refers to a carboxylic acid group (—COOH) appended to a loweralkyl radical.

The term "alkylsulfonyl" as used herein refers to R$_{42}$S(O)$_2$— wherein R$_{42}$ is a loweralkyl residue.

The term "alkylsulfonylalkyl" as used herein refers to an alkylsulfonyl group appended to a loweralkyl radical.

The term "thioaryloxy" as used herein refers to $R_{43}S$— wherein $R_{43}$ is an aryl group.

The term "thioaryloxyalkyl" as used herein refers to a thioaryloxy group appended to a loweralkyl radical.

The term "arylsulfonyl" as used herein refers to $R_{44}S(O)_2$— wherein $R_{44}$ is an aryl group.

The term "arylsulfonylalkyl" as used herein refers to an arylsulfonyl group appended to a loweralkyl radical.

The term "(alkoxyalkyl)(alkyl)amino" as used herein refers to $-NR_{45}R_{46}$ wherein $R_{45}$ is an alkoxyalkyl group and $R_{46}$ is a loweralkyl group.

The term "(alkoxyalkoxyalkyl)(alkyl)amino" as used herein refers to $-NR_{47}R_{48}$ wherein $R_{47}$ is an alkoxyalkoxyalkyl group and $R_{48}$ is a loweralkyl group.

The term "halo" or "halogen" as used herein refers to Cl, Br, F or I substituents.

The term "haloalkyl" as used herein refers to a loweralkyl radical in which one or more hydrogen atoms are replaced by halogen including, but not limited to, fluoromethyl, 2-chloroethyl, trifluoromethyl, 2,2-dichloroethyl and the like.

The term "0-protecting group" as used herein refers to a substituent which protects hydroxyl groups and includes but is not limited to substituted methyl ethers, for example, methoxymethyl, benzyloxymethyl, 2-methoxyethoxymethyl, 2-(trimethylsilyl)ethoxymethyl and tehahydropyranyl; substituted ethyl ethers, for example, 2,2,2-trichloroethyl, t-butyl, benzyl and triphenylmethyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

The term "heterocyclic group" or "heterocyclic" as used herein refers to any 3- or 4-membered ring containing a heteroatom selected from oxygen, nitrogen and sulfur, or a 5- or 6-membered ring containing from one to three heteroatoms selected from the group consisting of nitrogen, oxygen, and sulfur; wherein the 5-membered ring has 0-2 double bonds and the 6-membered ring has 0-3 double bonds; wherein the nitrogen and sulfur heteroatoms may optionally be oxidized; wherein the nitrogen heteroatom may optionally be quaternized; and including any bicyclic group in which any of the above heterocyclic rings is fused to a benzene ring or another 5- or 6-membered heterocyclic ring independently as defined above. Heterocyclics in which nitrogen is the heteroatom are preferred. Fully saturated heterocyclics are also preferred. Preferred heterocyclics include: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, N-methyl piperazinyl, azetidinyl, N-methyl azetidinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclics can be unsubstituted or monosubstituted or disubstituted with substitutents independently selected from hydroxy, halo, oxo (=O), alkylimino (R*N=wherein R* is a loweralkyl group), amino, alkylamino, dialkylamino, alkoxy, polyalkoxy, loweralkyl, cycloalkyl or haloalkyl.

The most preferred heterocyclics include imidazolyl, pyridyl, piperazinyl, N-methyl piperazinyl, azetidinyl, N-methyl azetidinyl, thiazolyl, thienyl, triazolyl and the following:

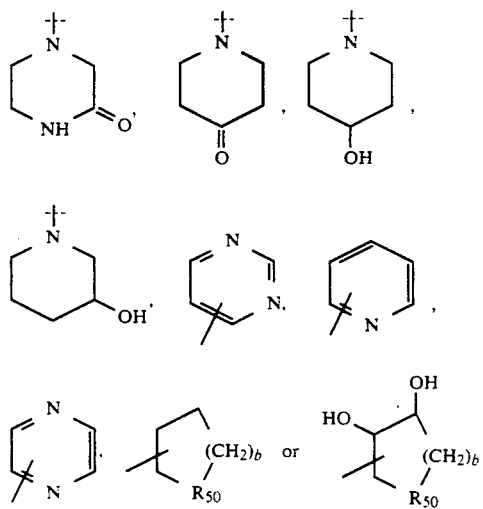

wherein b is 1 or 2 and $R_{50}$ is N, NH, O, S, provided that $R_{50}$ is the point of connection only when $R_{50}$ is N,

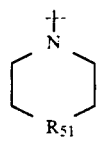

wherein $R_5$ is NH, N-loweralkyl, O, S, or $SO_2$, or

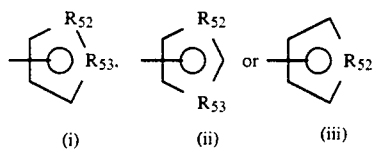

wherein the symbols (i), (ii) and (iii) represent 5-membered heterocycles containing one or more heteroatoms and containing 2 double bonds; wherein $R_{52}$ is N, O, or S and not the point of connection and $R_{53}$ is N when it is the point of connection and NH, O or S when it is not the point of connection.

The terms "Ala", "His", "Leu", "Phe", "Tyr", "Cys", "Gly", "Lys", "Sar", "Pro" and "norLeu" as used herein refer to alanine, histidine, leucine, phenylalanine, tyrosine, cysteine, glycine, lysine, sarcosine, proline and norleucine, respectively. In general, the amino acid abbreviations follow the IUPAC-IUB Joint Commission on Biochemical Nomenclature for amino acids and peptides (Eur. J. Biochem. 1984, 158, 9–31).

The compounds of the invention may be made as shown in Schemes 1-10. The syntheses of segments containing substituents $R_5$ are described in the Examples or have previously been described (Kempf, et al., J. Med. Chem. 1987, 30, 1978; Luly, et al., J. Med. Chem. 1987, 30, 1609; Buhlmayer, et al., U.S. Pat. No. 4,727,060; Morisawa, et al., European Patent Application No. 0228192; Ten Brink, PCT Patent Application No. W087/02986).

Scheme 1 discloses, a general method for the synthesis of compounds of the invention containing substituted piperazines. The process involves reaction of the appropriately substituted piperazine with an alph-halo ester. The ester 2 is hydrolyzed (LiOH/MeOH/H2O) and then coupled to the appropriately functionalized amine (in this case 2-amino-1-cyclohexyl-3,4-dihydroxy-6-methyl heptane) using a EDAC, 1-(3-dimethylaminopropyl)-3-ethylcarbodiimide hydrochloride, or other standard peptide coupling methods to provide the desired product 4.

Scheme 2 discloses a general method for the synthesis of compounds of the invention containing N-substituted benzyl piperazines. The dipeptide 5 is synthesized using a mixed anhydride coupling method. The diketopiperazine 6, which is formed by heating 5 in refluxing xylene, is reduced (excess lithium aluminum hydride (LAH) in THF) to give 7. Reaction of 7 with an alpha-bromo ester (in this case ethyl 2-bromo hexanoate) gives 8. The amine 8 is protected (Boc-anhydride in CH2Cl2) and then the ester is hydrolyzed (LiOH/MeOH/H2O). The free acid 9 is then coupled to the hydrochloride salt of the appropriately functionalized amine ( in this case 2-amino-1-cyclohexyl-3,4-dihydroxy-6-methyl heptane) using EDAC or other standard peptide coupling methods to provide 10.

Scheme 3 discloses a general method for the synthesis of benzyl ketopiperazine containing compounds of the invention. The reduced dipeptide 11 is synthesized by oxidation of the precursor protected amino alcohol, followed by a reductive amination. The free amine of 11 is reacted with an alpha-bromo ester such as benzyl bromoacetate to give 12, which is deprotected by hydrogenolysis and then cyclized with EDAC-HOBT (hydroxybenzotriazole) or other peptide or lactam forming agents. The lactam-ester 13 is hydrolyzed (LiOH/dioxane/H2O) and then coupled to the hydrochloride salt of the appropriately functionalized amine (in this case 2-amino-1-cyclohexyl-3,4-dihydroxy-6-methyl heptane) using a standard peptide coupling method such as EDAC to give the desired product 14.

Scheme 4 discloses a method for synthesizing substituted ketopiperazines of the invention which are isomeric with those prepared in Scheme 3. The methyl ester of D-Phe is protected with Boc-anhydride and then allylated with allyl bromide. The intermediate 15 is oxidized to aldehyde 16. Aldehyde 16 is coupled to an amino acid by reductive amination and then cyclized. The lactam-ester 18 is hydrolyzed (LiOH/water/dioxane) and then coupled to the hydrochloride salt of the appropriately functionalized amine (in this case 2-amino-1-cyclohexyl-3,4-dihydroxy-6-methyl heptane) to give the desired product 20.

Scheme 5 discloses the synthesis of compounds of the invention containing substitued delta-lactams. Valerolactone is alkylated (in this case with a benzyl group) by lithiation at −78° C. in THF followed by an alkyl halide (benzyl bromide). The resulting lactone 21 is transesterified with benzyl alcohol. The primary alcohol 22 is oxidized using Swern conditions and then reductively aminated with an amino acid ester such as L-norleucine methyl ester. The benzyl ester 24 is subjected to hydrogenolysis to remove the benzyl group and the amino acid is cyclized to give lactam 25 using EDAC or other standard peptide coupling or lactam forming methods. The lactam-ester is hydrolyzed and the acid is coupled to the hydrochloride salt of the appropriately functionalized amine (in this case 2-amino-1-cyclohexyl-3,4-dihydroxy-6-methyl heptane) to give the desired product 26.

Scheme 6 discloses a general method for synthesizing compounds of the invention containing amino substituted gamma- and delta-lactams. Compound 27 (J. AM. Chem. Soc. 79 5736 (1957)) is deprotonated and alkylated with allyl bromide to provide 28. Hydrolysis (aq. sodium hydroxide) followed by acidification provides the acid corresponding to 29, which is treated with excess ethereal diazomethane to provide 29. Oxidation of 29 gives aldehyde 30a. Reductive amination of 30a with the methyl ester of the desired amino acid hydrochloride salt (in this case His-OMe) provides the amino ester 31a, which is cyclized to the corresponding lactam 32 (n=1). The lactam ester 32 is hydrolyzed to the corresponding acid. The acid is coupled to the hydrochloride salt of the appropriately functionalized amine (in this case 2-amino-1-cyclohexyl-3,4-dihydroxy-6-methyl heptane) through a standard solution phase peptide coupling method using a water soluble carbodiimide to give the desired product wherein n=1.

Hydroboration of 28 followed by oxidation gives the aldehyde 30b. Reductive amination of 30b with the methyl ester of the desired amino acid hydrochloride salt (in this case L-His—OMe) provides 31b. Lactam ester 32 (n=2) is produced by refluxing a methanolic solution of 31b with isopropyl amine. Ester hydrolysis, followed by coupling to the hydrochloride salt of the appropriately functionalized amine (in this case 2-amino-1-cyclohexyl-3,4-dihydroxy-6-methyl heptane) using EDAC or other standard peptide coupling methods, provides the desired product wherein n=2.

Scheme 7 discloses a general method for synthesizing compounds of the invention containing an oxa-lactam. For example, D-phenylalanine is converted to D-3-phenyllactic acid 33, which is esterified to produce 34. The free hydroxy group is allylated with allyl bromide to provide ester 35, which is oxidized to the aldehyde 36. The aldehyde 36 is reductively aminated with the appropriate amino acid ester (in this case L-His—OMe) to give amino ester 37, which is thermally cyclized to lactam 38. Lactam ester 38 is hydrolyzed and the imidazole nitrogen is protected as the N-t-Boc derivative. The acid is then coupled to the hydrochloride salt of the appropriately functionalized amine (in this case 2-amino-1-cyclohexyl-3,4-dihydroxy-6-methyl heptane) using EDAC or other standard peptide coupling methods to produce the desired product 39.

Scheme 8 discloses a method for the synthesis of compounds of the invention containing an N-terminal substituted gamma-lactam. A mixed diester 40 is converted to acids 41 or 42, which are reduced to alcohols 43 or 44, respectively. Alcohols 43 and 44 are then oxidized to aldehydes 45 and 46. Reductive amination of 46 with the appropriate amino acid ester (in this case L-His—OMe di-p-toluenesulfonic acid salt) provides amino ester 48. This compound is converted to the free acid, which is then cyclized to 49. Similarly, reductive amination of 45 leads directly to the cyclic derivative 47. Protection of the imidazole nitrogen of 47 and 49 as the N-t-Boc derivative, followed by ester hydrolysis, leads to acids 50 and 51. Amide formation with the hydrochloride salt of the appropriately functionalized amine (in this case 2-amino-1-cyclohexyl-3,4-dihydroxy-6-methyl heptane) using EDAC or other standard peptide coupling methods, followed by imidazole deprotection, affords 52 and 53, respectively.

Scheme 9 discloses a method for the synthesis of compounds of the invention containing an unsubstituted N-terminal cyclic urea. For example, Boc-phenylalanol 54 is oxidized to the aldehyde and reductively aminated with the appropriate amino acid ester (in this case L-His—OMe di-p-toluenesulfonic acid salt) to give monoprotected diamine 55. Removal of the protecting group and cyclization affords cyclic urea 56. Protection of the imidazole nitrogen and benzyl ester hydrogenolysis provides the acid 57. Amide formation with the hydrochloride salt of the appropriately functionalized amine (in this case 2-amino-1-cyclohexyl-3,4-dihydroxy-6-methyl heptane) using EDAC or other standard peptide coupling methods, followed by imidazole deprotection, affords 58.

Scheme 10 discloses a method for the synthesis of compounds of the invention containing an N'-substituted N-terminal cyclic urea. For example, phenylalanine methyl ester hydrochloride salt is reductively alkylated with an aldehyde or ketone (in this case isobutanal) and the resulting amine is protected to provide ester 60. The ester is reduced to the alcohol and the alcohol is oxidized to the aldehyde 61. Treatment of this aldehyde as described in Scheme 9 provides the desired compound 62.

Scheme 11 discloses a general method for the synthesis of benzyl ketopiperazine containing compounds which are isomeric with the compounds of Scheme 3. Alkylation and protection of amino-alcohol 63 provides alcohol 64. Oxidation and reductive amination of 64 gives diamine 65. Ring closure to 66, followed by coupling to the hydrochloride salt of the appropriately functionalized amine (in this case 2-amino-1-cyclohexyl-3,4-dihydroxy-6-methyl heptane) using EDAC or other standard peptide coupling methods to provide 67.

Scheme 12 discloses a general method for synthesizing compounds of the invention containing a sulfonyl substituted ketopiperazine. Compound 68 is sulfonylated, followed by ring formation, to give compounds such as 70 and 72. Deprotection and coupling of the resulting acid with the appropriately functionalized amine provides products such as 71 and 72.

Scheme 13 discloses a general method for synthesizing compounds of the invention containing amino substiuted delta-lactams. Compound 32 (Scheme 6, n=2) is treated with H₂ and Pd/C in acetic acid, followed by treatment with toluenesulfonyl chloride, to produce di-tosylate 75. Treatment of 75 with LiOH, followed by ditertbutyldicarbonate, produces acid 76. Acid 76 is coupled to the appropriately functionalized amine using EDAC, or other standard peptide coupling methods, to provide the desired product wherein n=2.

Scheme 14 discloses a general method for synthesizing compounds of the invention containing amino substituted delta-lactams which do not contain histidine residues. Compound 30b (Scheme 6, n=2) is reductively alkylated with the corresponding amino acid methyl ester and the resulting product is thermally cyclized to delta-lactam 77. Treatment of 77 with HBr/HOAc, followed by reaction with sulfonyl chlorides or sulfamoyl chlorides, produces the amino protected compound 78. Ester hydrolysis of 78, followed by coupling to the appropriately functionalized amine using EDAC or other standard peptide coupling methods, provides the desired product wherein n=2.

Scheme 15 describes an improved synthesis for the amine in Example 139. The lactone 82 was reduced with LAH at room temperature in 5 min and then cyclized under Mitsonobu condition to give the tetrahydrofuran derivative 84 in high yield. The free amine 85 was obtained by deprotection of 84 under acidic condition followed by a basic work-up with saturated NaHCO₃.

Scheme 16 discloses a general method for the synthesis of the compounds of the invention containing an N,N-disubstituted terminal amino group. Treatment of lactam ester 78 with various aldehydes and sodium cyanoborohydride in inert solvents produces the N-alkyl compound 79. Standard ester hydrolysis and coupling to various amines using standard peptide coupling methods produces the final inhibitors.

Scheme 17 discloses an improved method for the synthesis of lactam intermediates such as 32 and 77 which are used in the synthesis of compounds of the invention. Compound 86 (J. Chem. Soc. (c), 329, 1) is deprotonated and alkylated with allyl bromide to provide 87. Hydrolysis (aq. lithium hydroxide followed by acidification) affords the amino acid which is treated with CBZ-NOS and then paraformaldehyde to give chiral oxazolidinone 88. Hydroboration of 88 (9-BBN then NaOOH) and oxidation to the aldehyde (PCC) is followed by reductive alkylation with amino acid esters to provide the lactams.

Scheme 1

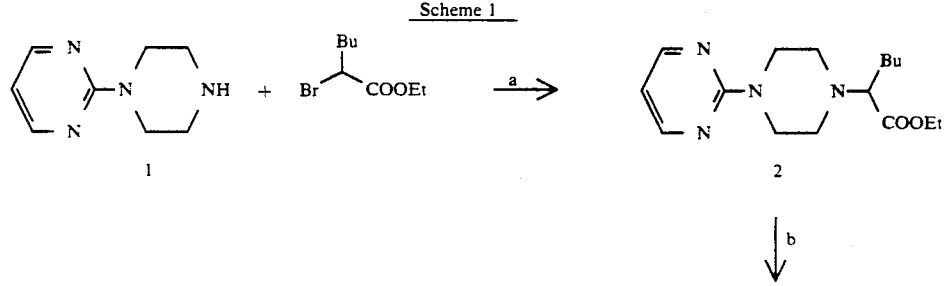

Scheme 1
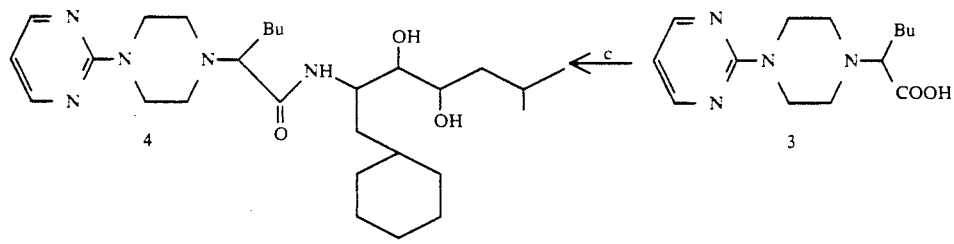
a: $K_2CO_3$, EtOH;
b: LiOH, MeOH—$H_2O$;
c: HOBT, EDAC, Amine.HCl
Scheme 2
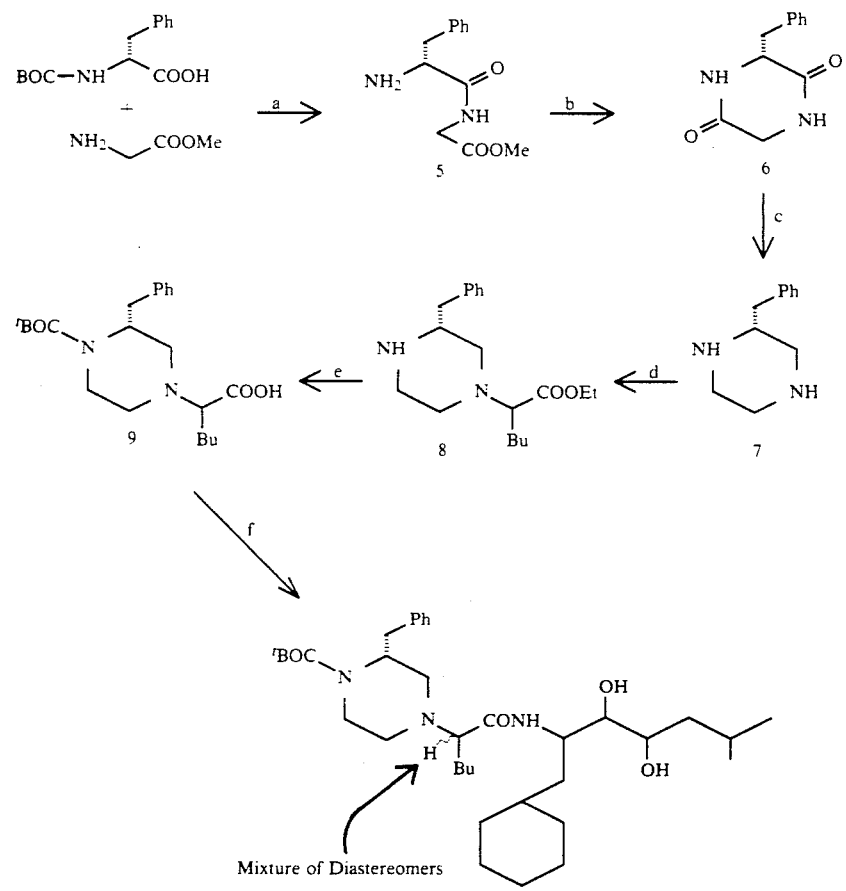
Mixture of Diastereomers
a: Mixed anhydride coupling followed by HCl/Dioxane
b: Heating in Xylene for 6 h
c: LAH in THF, Reflux overnight
d: Ethyl Bromohexanoate, $K_2CO_3$, Dioxane, Reflux for 2 h
e: $^t$BOC-Anhydride, $CH_2Cl_2$
f: Hydrolysis followed by EDAC coupling of the amine Scheme 3
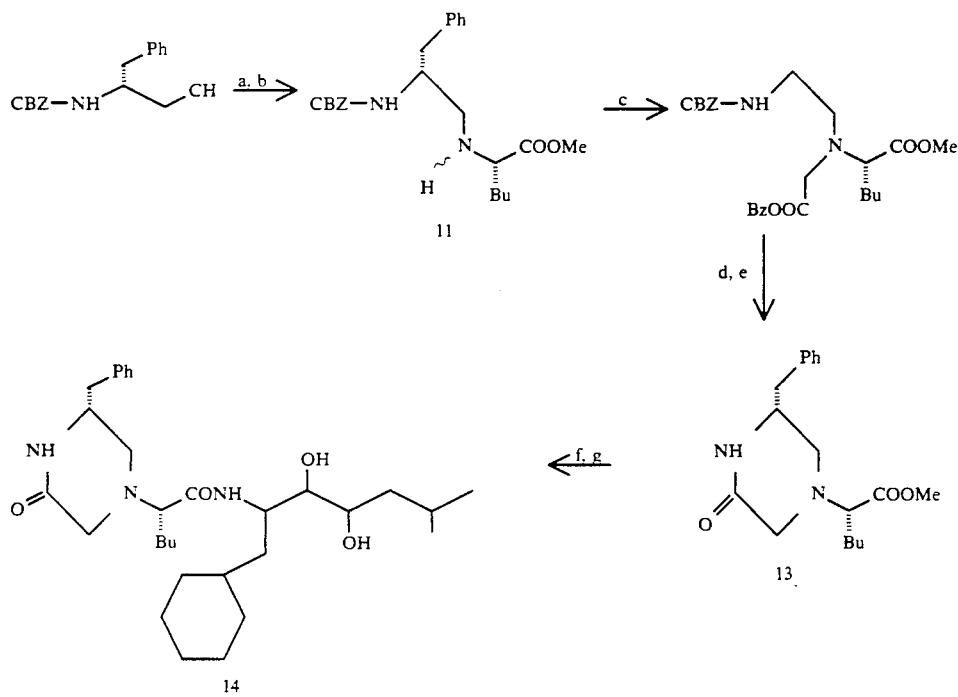
a: SO₃-Pyridine
b: nor—Leu—OMe, NaCNBH₃
c: Benzylbromoacetate, Na₂CO₃, Dioxane
d: H₂—Pd, MeOH
e: EDAC, HOBT, DMF
f: LiOH, H₂O-Dioxane
g: EDAC, HOBT, Amine.HCl, DMF
Scheme 4
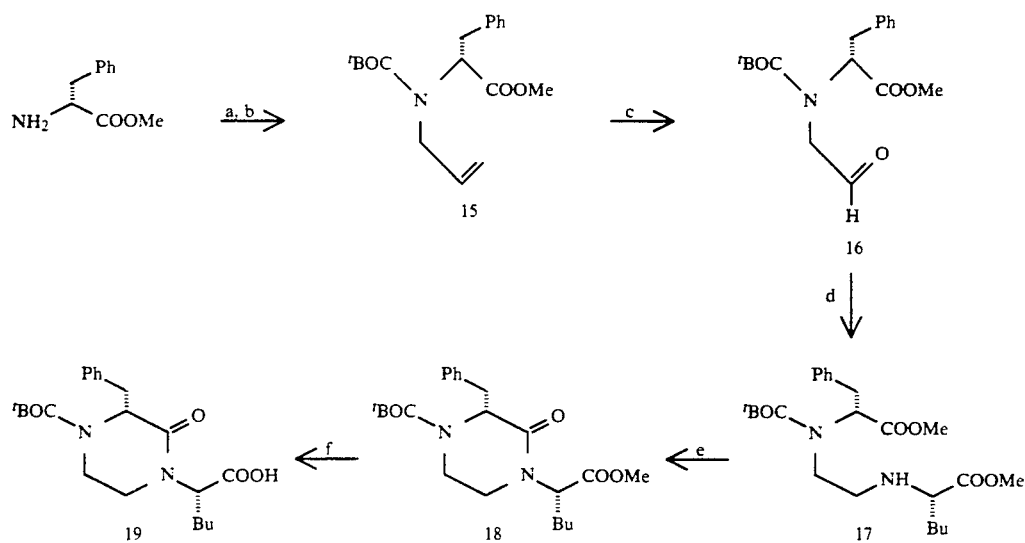

-continued
Scheme 4
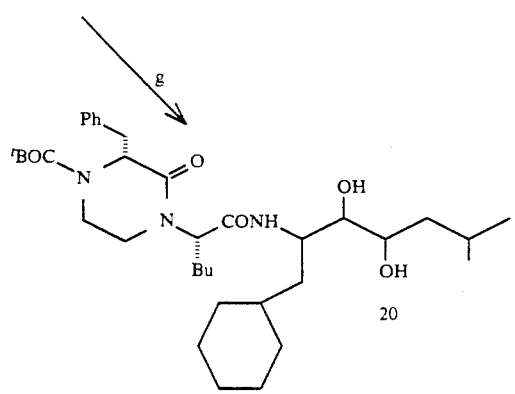
a: ᵗBOC-Anhydride, CH₂CL₂
b: NaN(TMS)₂, Allyl Bromide, DMF
c: Ozone, CH₂Cl₂
d: nor—Leu—OMe, NaCNBH₃
e: Reflux in Xylene
f: LiOH, H₂O-Dioxane
g: EDAC, HOBT, Amine.HCl, DMF
Scheme 5
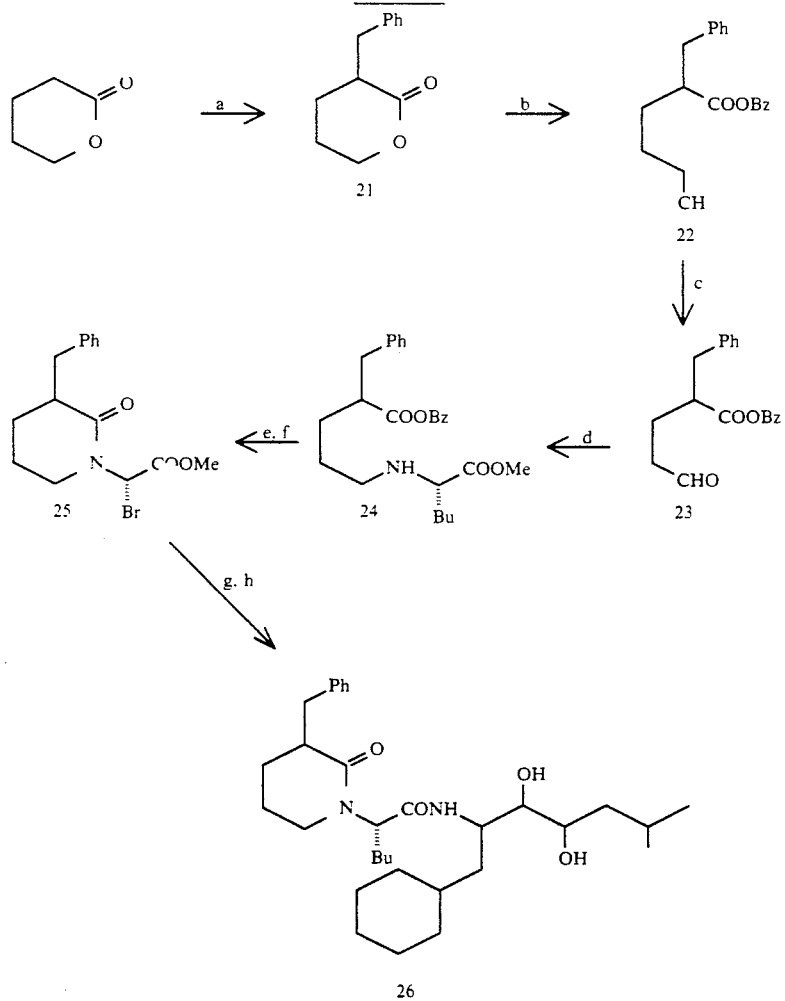
a: LDA, Benzyl Bromide, THF
b: Methanol/Sulphuric Acid followed by Benzyl Alcohol/TsOH, Reflux
c: Oxalyl Chloride, DMSO, TEA
d: L—nor—Leu—OMe, Sodium Cyanoborohydride IPA

Scheme 5
e: Hydrogen, 10% Pd-C, MeOH
f: EDAC, HOBT, TEA, DMF
g: LiOH, Diox-Water
h: HCl Amine, EDAC, HOBT, TEA, DMF
Scheme 6
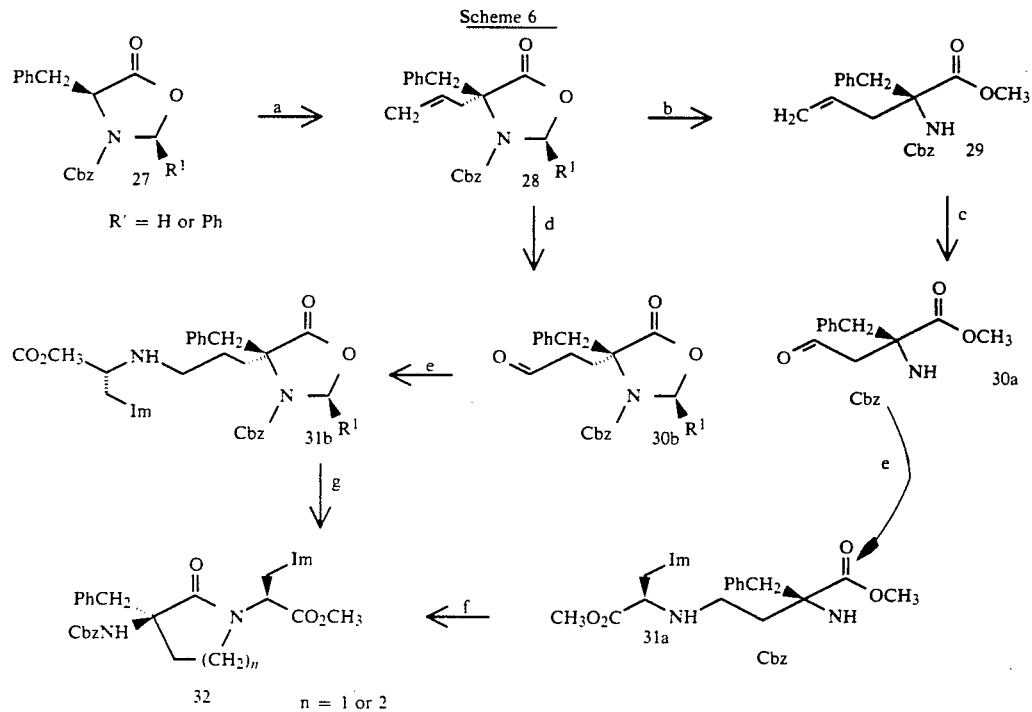
a: KHMDS, THF, −78° C., allyl bromide
b: aq. NaOH; H⁻; CH₂N₂
c: O₃, −78° C., then Me₂S
d: 9-BBN/THF, NaOOH; PPC
e: His—OMe, NaOAc, NaCNBH₃
f: HOBT, Toluene; DME, reflux
g: 2 eq. isopropylamine, MeOH, reflux
h: aq. LiOH; EDAC, Amine
Scheme 7
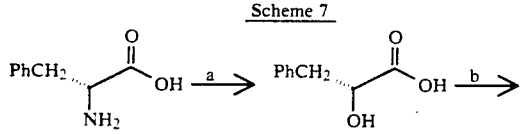
-continued
Scheme 7
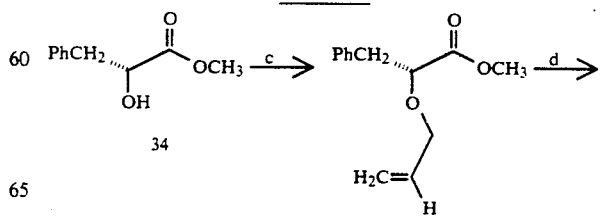

5,164,388
-continued
Scheme 7
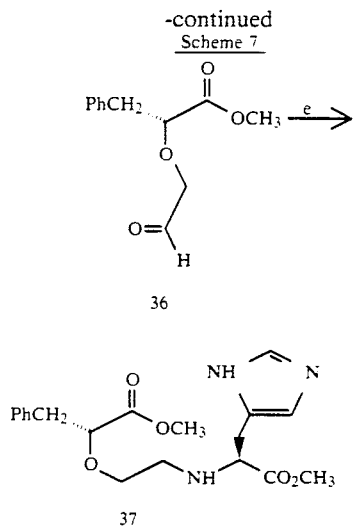
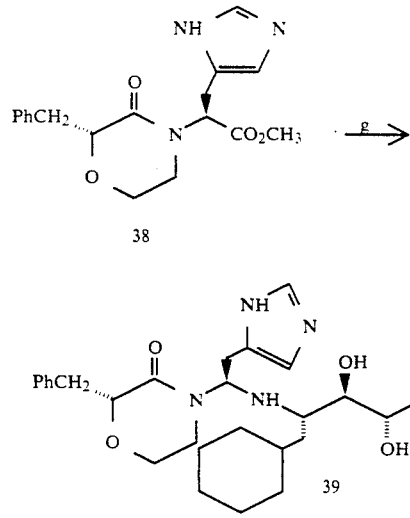
a: HNO₂
b: MeOH, TsOH, reflux
c: NaH, DMF, allyl bromide
d: O₃, −78° C., Me₂S
e: His—OCH₃, NaOAc, NaCNBH₃
f: MeOH, reflux
g: LiOH, BocOBoc, amine, EDAC, HOAc
SCHEME 8
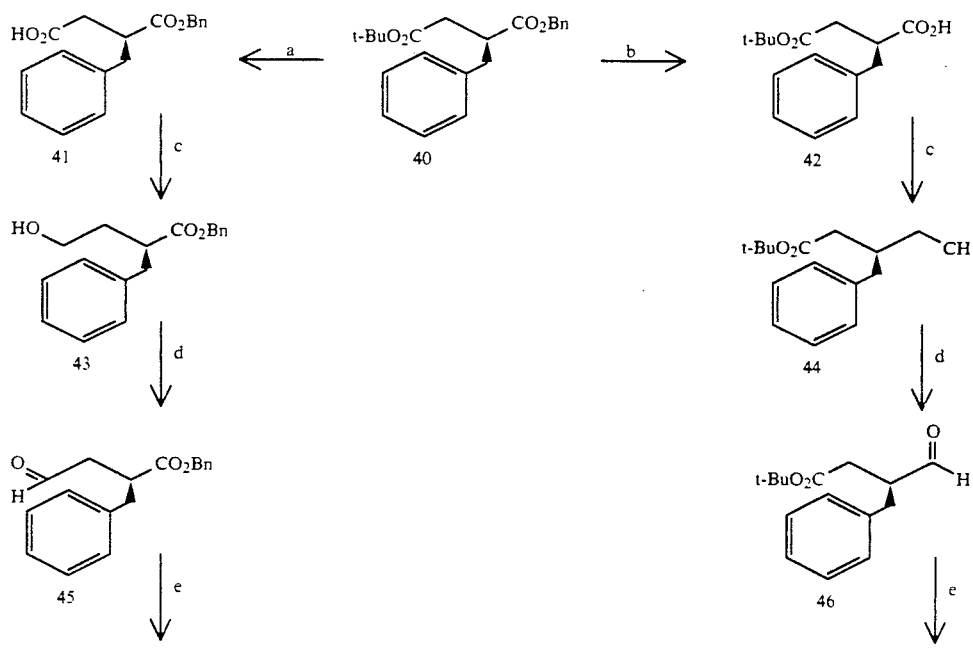

-continued
SCHEME 8
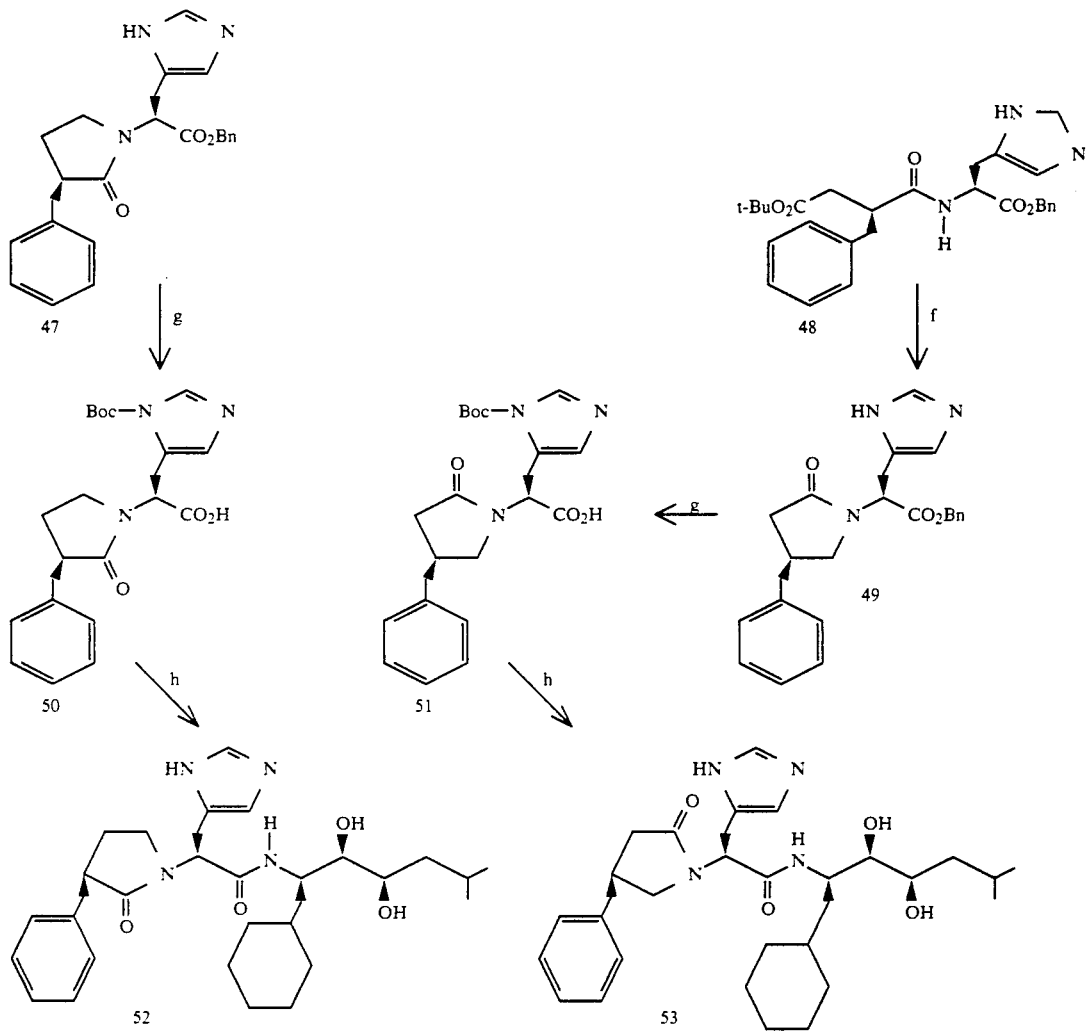
a: CF$_3$CO$_2$H;
b: H$_2$, Pd/C;
c: BH$_3$/THF;
d: ClCOCOCl, DMSO, TEA;
e: H—His—OBn.TsOH$_2$, NaOAc, NaCNBH$_3$;
f: CF$_3$CO$_2$H, then EDAC, HOBT;
g: Boc-O-Boc, then H$_2$, Pd/C;
h: EDAC, HOBT, Amine, then HOAc.
SCHEME 9

-continued
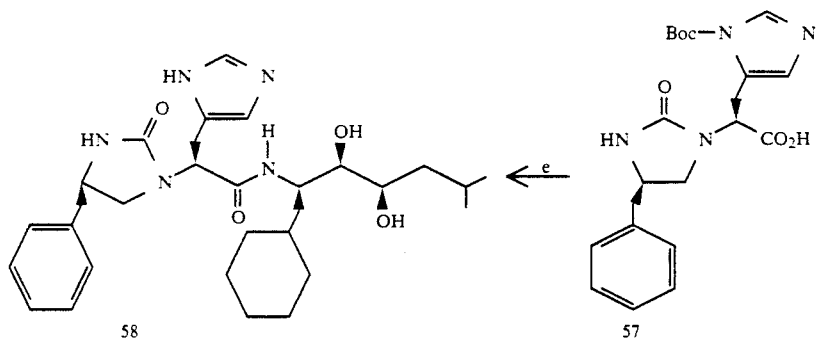
SCHEME 10
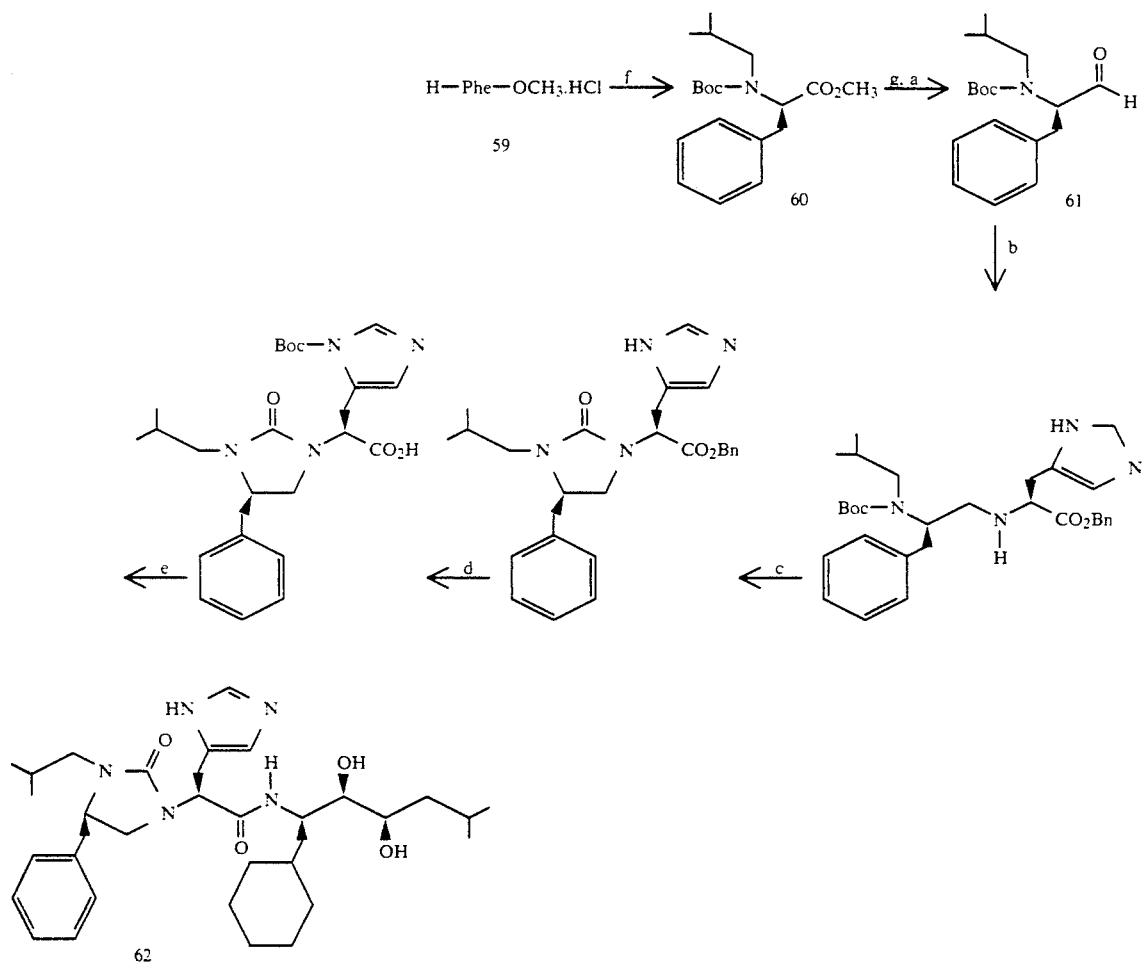
a: ClCOCOCl, DMSO, TEA;
b: H—His—OBn.TsOH$_2$, NaOAc, NaCNBH$_3$;
c: CF$_3$CO$_2$H, then CDI;
d: Boc-O-Boc, then H$_2$, Pd/C;
e: EDAC, HOBT, Amine, then HOAc;
f: (CH$_3$)$_2$CHCHO, NaOAC, NaCNBH$_3$, then Boc-O-Boc;
g: Ca(BH$_4$)$_2$.

Scheme 11
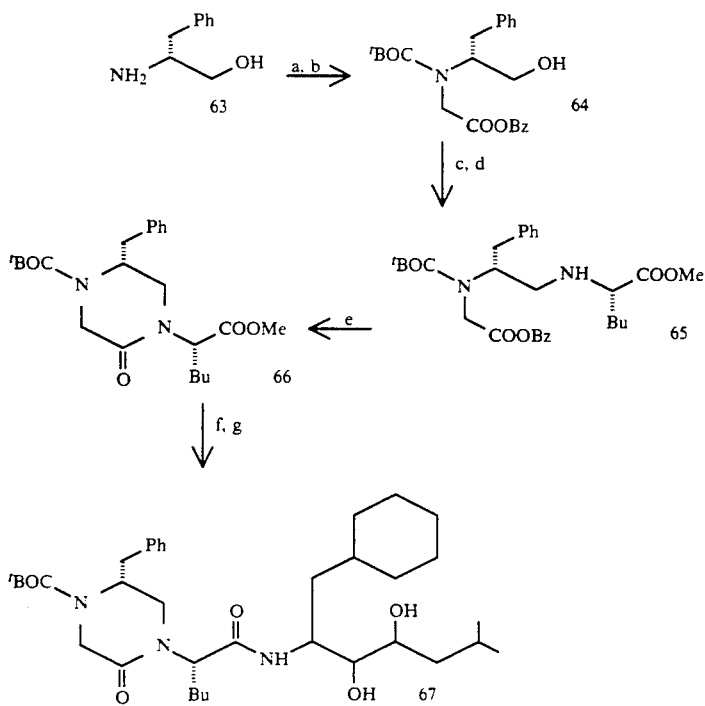
a) Benzyl bromoacetate, TEA, THF
b) BOC-Anhydride, Methylene Chloride
c) Pyridine-SO₃
d) L-nor-Leu—OMe, NaCNBH₃, IPA
e) Reflux in Xylene
f) NaOH, MeOH—H₂O
g) Amine, EDAC, HOBT, DMF, TEA
Scheme 12
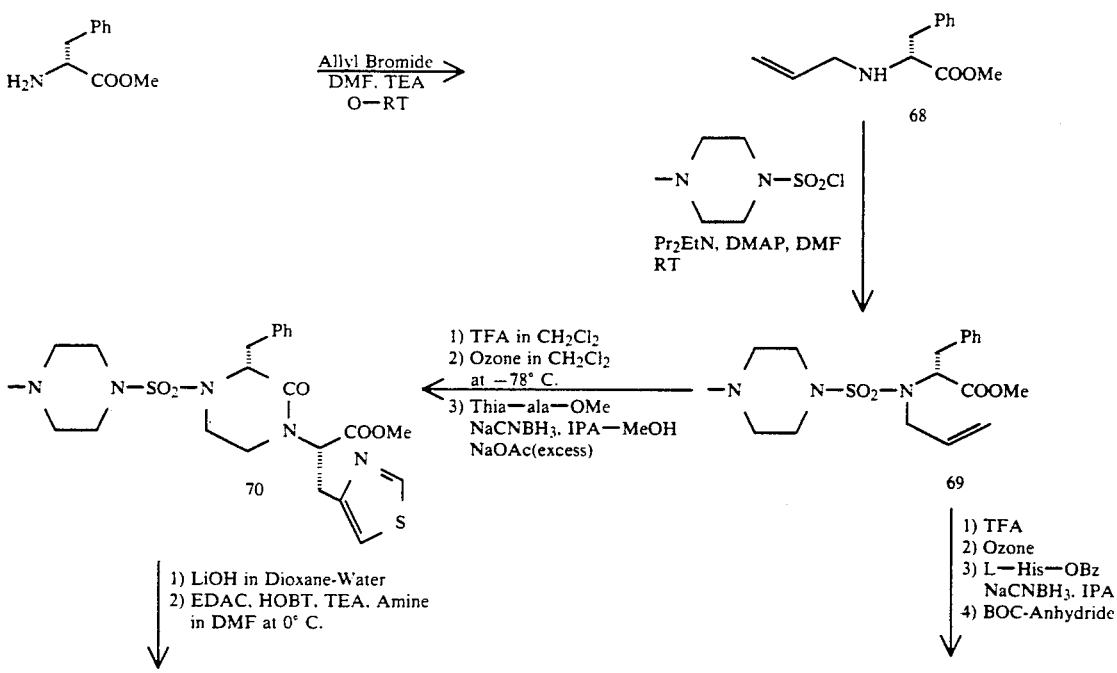

5,164,388
-continued
Scheme 12
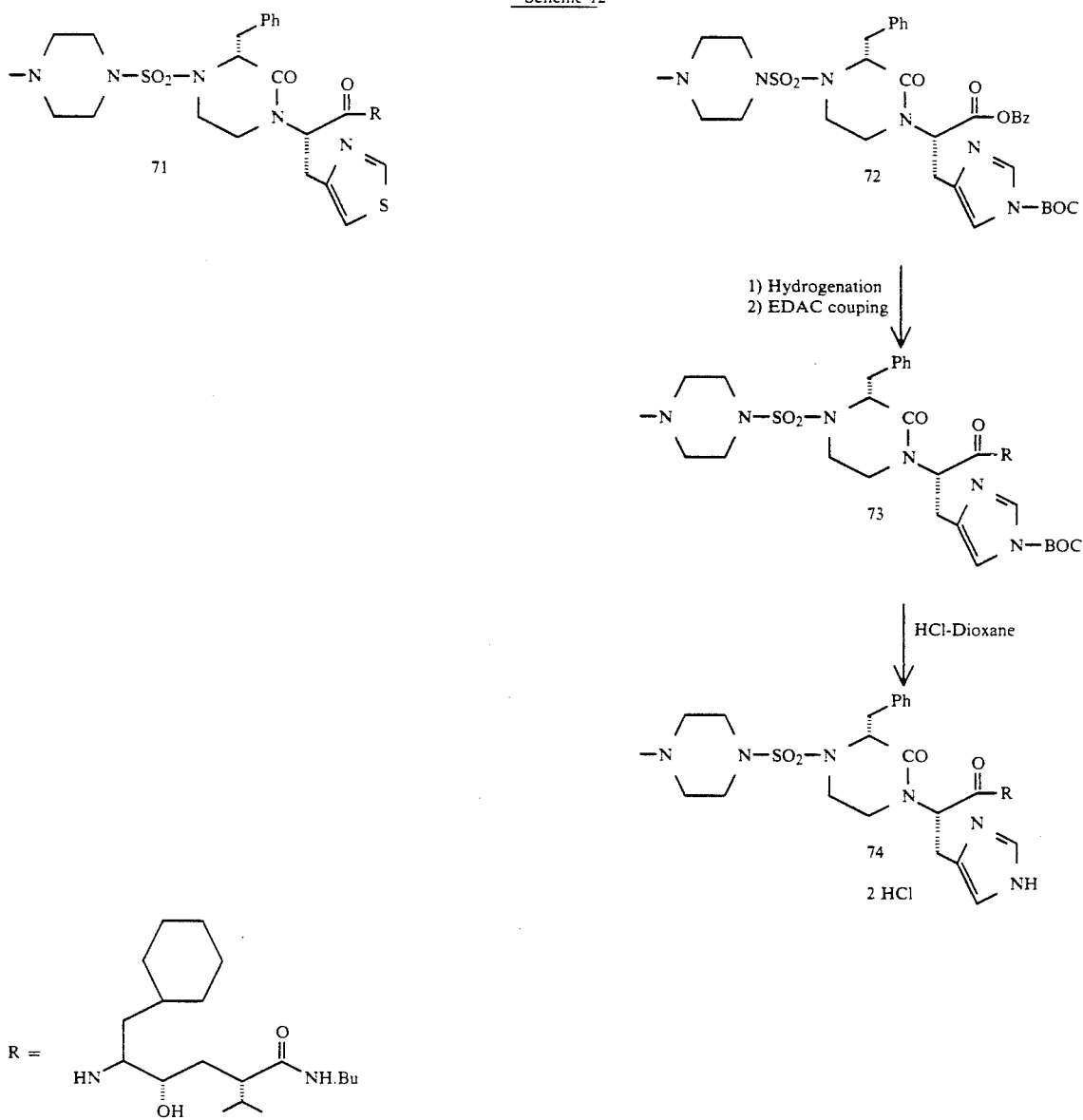
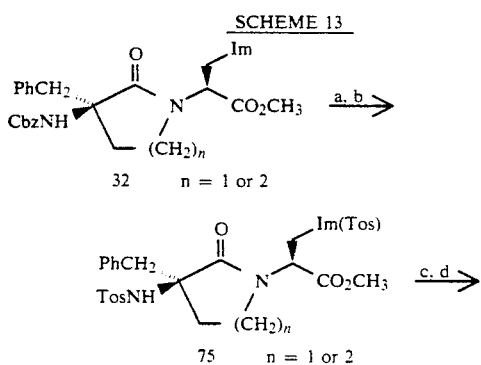
SCHEME 13
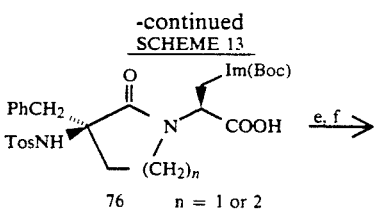
-continued
SCHEME 13
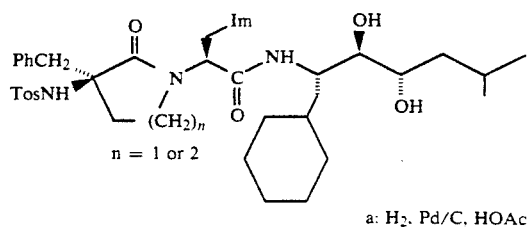
a: $H_2$, Pd/C, HOAc
b: TsCl, NMM, DMAP, $CH_2Cl_2$
c: LiOH, $H_2O$
d: BocOBoc

71
-continued
SCHEME 13
e: Amine, EDAC, HOBT
f: HOAc, THF, H$_2$O
Scheme 14
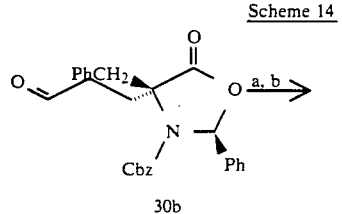
30b
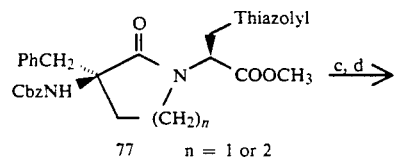
77  n = 1 or 2
72
-continued
Scheme 14
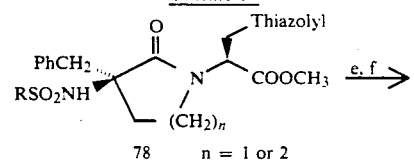
78  n = 1 or 2
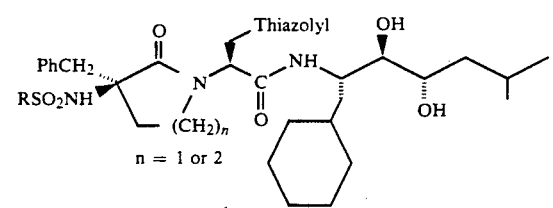
n = 1 or 2
a: Thiazolylalanine-OCH$_3$, NaCNBH$_3$, NaOAc
b: MeOH, NaOAc, Reflux
c: HBr/HOAc
d: RSO$_2$Cl, DMAP, NMM, DMF
e: LiOH, H$_2$O
f: Amine, EDAC, HOBT
Scheme-15
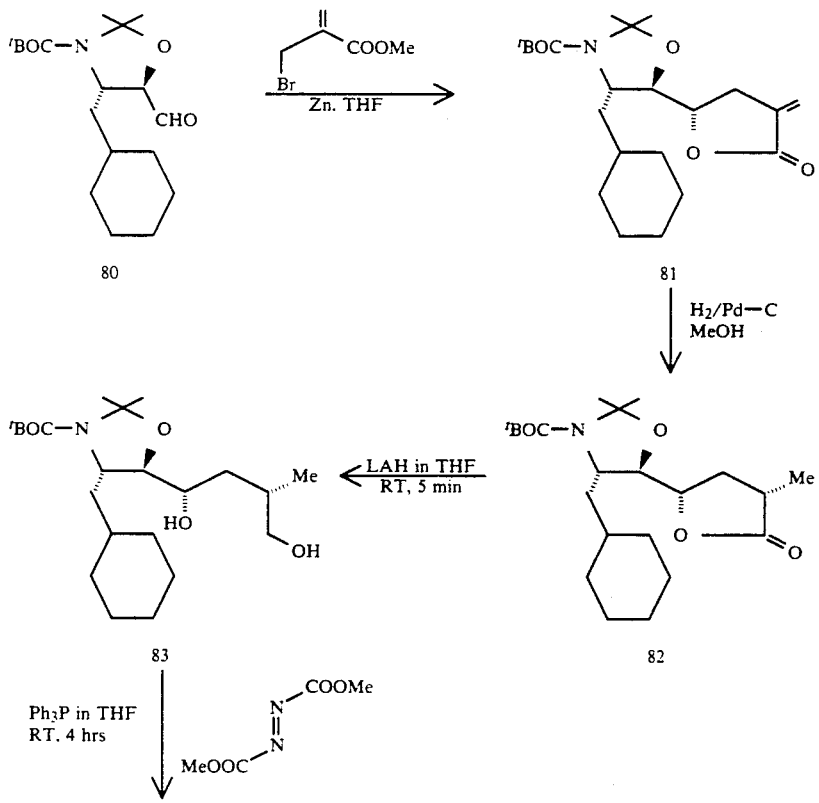

-continued
Scheme-15

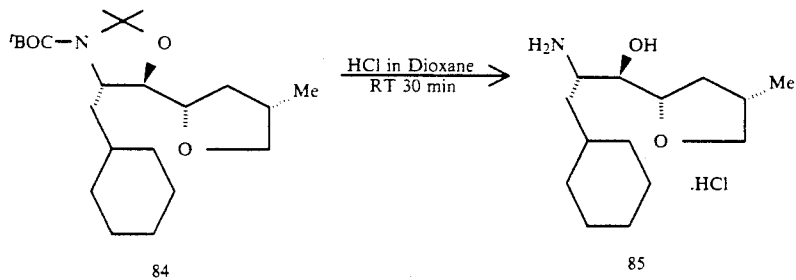

SCHEME 16

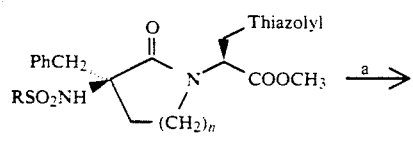
78  n = 1 or 2

R = Tosyl or N-methylpiperazinyl

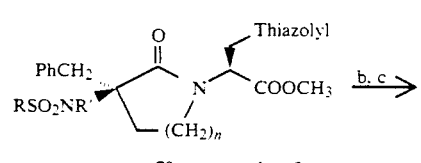
79  n = 1 or 2

R' = Methyl, Ethyl, etc.

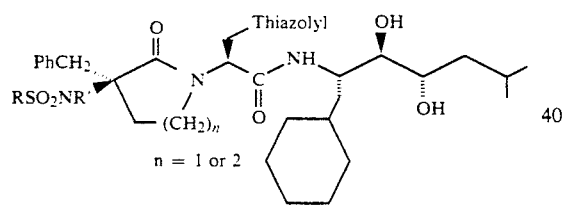
n = 1 or 2 a: R'CHO, NaCNBH₃, CH₃CN
b: LiOH, H₂O
c: Amine, EDAC, HOBT

SCHEME 17

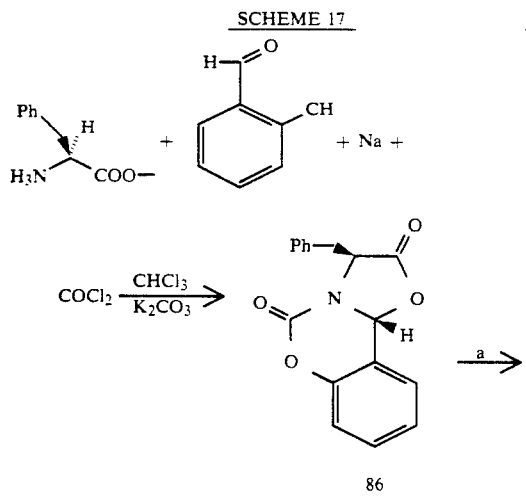

86

-continued
SCHEME 17

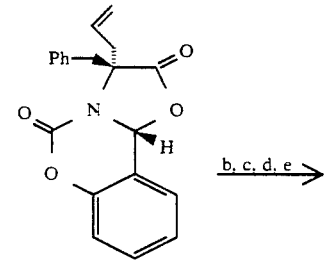
87

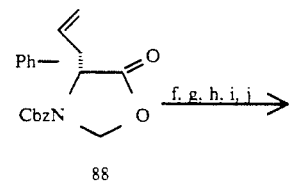
88

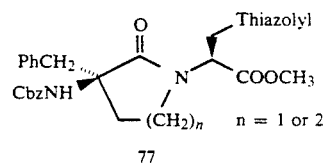
77  n = 1 or 2 a: LiHMDS, DMPU, Allyl Bromide
b: LiOH, H₂O
c: 1N HCl
d: Cbz-Nos
e: HCHO, TsOH
f: 9-BBN
g: NaOOH
h: PCC
i: Thiala-OCH₃, NaCNBH₃
j: NaOAc, MeOH, Reflux Particularly useful intermediates for the preparation of the novel compounds of this invention are compounds of the formula:

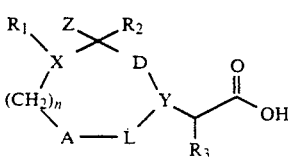

or an acid halide or activated ester derivative thereof.
X is
(I) N, (II) O or
(III) CH.
$R_1$ is
(I) absent,
(II) hydrogen,
(III) an N-protecting group,
(IV) aryl,
(V) heterocyclic, or
(VI) $R_6$—Q— wherein
  (1) $R_6$ is
    (i) loweralkyl,
    (ii) amino,
    (iii) alkylamino,
    (iv) dialkylamino,
    (v) (alkoxyalkyl)(alkyl)amino,
    (vi) (alkoxyalkoxyalkyl)(alkyl)amino,
    (vii) aryl,
    (viii) arylalkyl,
    (ix) aminoalkyl,
    (x) (N-protected)aminoalkyl,
    (xi) alkoxy,
    (xii) substituted loweralkyl wherein the substituent is selected from alkoxy, thioalkoxy, halogen, alkylamino, (N-protected)(alkyl)amino and dialkylamino, xiii)

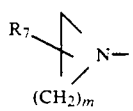

wherein m is 1 to 5 and $R_7$ is hydrogen, hydroxy, alkoxy, thioalkoxy, alkoxyalkoxy, polyalkoxy, amino, (N-protected)amino, alkylamino, (N-protected)(alkyl)amino or dialkylamino; or xiv)

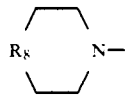

wherein $R_8$ is O, S, $SO_2$, O=C or $R_9N$ wherein $R_9$ is hydrogen, loweralkyl or an N-protecting group; and
  (2) Q is
    (i) C=O or
    (ii) $CH_2$, with the proviso that X is N when $R_1$ is an N-protecting group;
(VII) $R_{54}S(O)_2$—wherein $R_{54}$ is
  (1) amino,
  (2) alkylamino,
  (3) dialkylamino,
  (4) loweralkyl,
  (5) haloalkyl,
  (6) aryl,
  (7) p-biphenyl,
  (8) heterocyclic or
(VIII) $(R_{55})_2P(O)$—wherein $R_{55}$ is
  (1) alkoxy,
  (2) alkylamino or
  (3) dialkylamino.
A and L are independently selected from
(I) absent,
(II) C=O,
(III) $SO_2$ and
(IV) $CH_2$.
D is
(I) C=O,
(II) $SO_2$ or
(III) $CH_2$.
Y is
(I) N or
(II) CH.
$R_2$ is
(I) hydrogen,
(II) loweralkyl,
(III) cycloalkylalkyl
(IV) —$CH_2$—$R_{10}$—$(CH_2)_q$—$R_{11}$ wherein
  (1) q is 0, 1 or 2,
  (2) $R_{10}$ is absent or $R_{10}$ is O, NH or S only when q is 1 or 2, and
  (3) $R_{11}$ is
    (i) aryl or
    (ii) heterocyclic.
Z is
(I) hydrogen or
(II) —$R_{28}C(O)R_{29}$, —$R_{28}S(O)_2R_{29}$ or —$R_{28}$—$C(S)R_{29}$ wherein
  (1) $R_{28}$ is
    (i) NH,
    (ii) —N($R_{200}$)— wherein $R_{200}$ is loweralkyl or benzyl or
    (iii) $CH_2$ and
  (2) $R_{29}$ is
    (i) alkoxy,
    (ii) benzyloxy,
    (iii) alkylamino,
    (iv) dialkylamino,
    (v) aryl or
    (vi) heterocyclic.
$R_3$ is
(I) hydrogen,
(II) loweralkyl,
(III) loweralkenyl,
(IV) cycloalkylalkyl,
(V) cycloalkenylalkyl,
(VI) alkoxyalkyl,
(VII) thioalkoxyalkyl,
(VIII) (alkoxyalkoxy)alkyl,
(IX) (polyalkoxy)alkyl,
(X) arylalkyl or
(XI) (heterocyclic)alkyl.
n is 0 or 1.

Acid halide derivatives of the above intermediates include the acid chloride. Activated ester derivatives of the above intermediates include activated esters commonly used by those skilled in the art for activating carboxylic acid groups for coupling with an amine to form a peptide bond, including, but not limited to formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 4-nitrophenol derived esters, 2,4,5-trichlorophenol derived esters and the like.

Novel compounds of the invention include the following.

| Example | n | X | R₁ | A | D | L | Y | R₂ | Z | R₃ | R₄ | R₅ |
|---|---|---|---|---|---|---|---|---|---|---|---|---|
| 12 | 0 | N | piperazin-1-yl | CH₂ | CH₂ | CH₂ | N | H | H | n-butyl | cyclohexylmethyl | 1* |
| 13 | 0 | CH | benzyl | CH₂ | CH₂ | CH₂ | N | H | H | n-butyl | cyclohexylmethyl | 1* |
| 15 | 0 | N | (4-OMe)phenyl | CH₂ | CH₂ | CH₂ | N | H | H | n-butyl | cyclohexylmethyl | 1* |
| 17 | 0 | N | 2-pyridyl | CH₂ | CH₂ | CH₂ | N | H | H | n-butyl | cyclohexylmethyl | 1* |
| 18 | 0 | CH | H | CH₂ | CH₂ | CH₂ | N | benzyl | H | n-butyl | cyclohexylmethyl | 1* |
| 24 | 0 | N | H | C=O | CH₂ | CH₂ | N | benzyl | H | n-butyl | cyclohexylmethyl | 1* |
| 30 | 0 | N | t-Boc | CH₂ | CH₂ | CH₂ | N | benzyl | H | n-butyl | cyclohexylmethyl | 1* |
| 31 | 0 | N | benzyl | CH₂ | CH₂ | CH₂ | N | H | H | H | cyclohexylmethyl | 1* |
| 32 | 0 | N | benzyl | CH₂ | CH₂ | CH₂ | N | H | H | n-butyl | cyclohexylmethyl | 1* |
| 33 | 0 | N | H | CH₂ | CH₂ | CH₂ | N | benzyl | H | H | cyclohexylmethyl | 1* |
| 35 | 0 | N | Me₂NC(O)— | CH₂ | CH₂ | CH₂ | N | benzyl | H | n-butyl | cyclohexylmethyl | 1* |
| 36 | 0 | N | benzyl | CH₂ | CH₂ | CH₂ | N | benzyl | H | 4-thiazolyl-methyl | cyclohexylmethyl | 1* |
| 37 | 0 | N | 4-methyl-piperazin-1-yl-carbonyl | CH₂ | CH₂ | CH₂ | N | benzyl | H | n-butyl | cyclohexylmethyl | 1* |
| 38 | 0 | N | morpholin-1-yl-carbonyl | CH₂ | CH₂ | CH₂ | N | benzyl | H | n-butyl | cyclohexylmethyl | 1* |
| 44 | 0 | N | t-Boc | CH₂ | C=O | CH₂ | N | benzyl | H | n-butyl | cyclohexylmethyl | 1* |
| 45 | 0 | N | t-Boc | CH₂ | C=O | CH₂ | N | benzyl | H | 4-imidazolyl-methyl | cyclohexylmethyl | 1* |
| 47 | 0 | N | 4-methyl-piperazin-1-yl-carbonyl | CH₂ | C=O | CH₂ | N | benzyl | H | n-butyl | cyclohexylmethyl | 1* |
| 48 | 0 | N | N-methoxy-methoxyethyl-N-methylamino-carbonyl | CH₂ | C=O | CH₂ | N | benzyl | H | n-butyl | cyclohexylmethyl | 1* |
| 49 | 0 | N | morpholin-1-yl-carbonyl | CH₂ | C=O | CH₂ | N | benzyl | H | 4-thiazolyl-methyl | cyclohexylmethyl | 1* |
| 50 | 0 | N | morpholin-1-yl-carbonyl | CH₂ | C=O | CH₂ | N | benzyl | H | n-butyl | cyclohexylmethyl | 1* |
| 51 | 0 | N | morpholin-1-yl-carbonyl | CH₂ | C=O | CH₂ | N | benzyl | H | 4-imidazolyl-methyl | cyclohexylmethyl | 1* |
| 56 | 0 | CH | H | CH₂ | C=O | CH₂ | N | benzyl | H | n-butyl | cyclohexylmethyl | 1* |
| 63 | 0 | CH | H | — | C=O | CH₂ | N | benzyl | Cbz-NH | 4-imidazolyl-methyl | cyclohexylmethyl | 1* |
| 73 | 0 | CH | H | — | C=O | CH₂ | N | benzyl | H | 4-imidazolyl-methyl | cyclohexylmethyl | 1* |
| 86 | 0 | CH | H | CH₂ | C=O | CH₂ | N | benzyl | Cbz-NH | 4-imidazolyl-methyl | cyclohexylmethyl | 1* |
| 95 | 0 | O | — | CH₂ | C=O | CH₂ | N | benzyl | H | 4-imidazolyl-methyl | cyclohexylmethyl | 1* |
| 118 | 0 | N | isobutyl | — | CH₂ | C=O | N | benzyl | H | 4-imidazolyl-methyl | cyclohexylmethyl | 1* |
| 119 | 0 | N | isobutyl | — | CH₂ | C=O | N | benzyl | H | 4-imidazolyl-methyl | cycloheyxlmethyl | 2* |
| 120 | 0 | N | H | — | CH₂ | C=O | N | benzyl | H | 4-imidazolyl-methyl | cyclohexylmethyl | 1* |
| 121 | 0 | CH | H | — | C=O | CH₂ | N | benzyl | H | 4-imidazolyl-methyl | cyclohexylmethyl | 1* |
| 122 | 0 | CH | H | — | CH₂ | C=O | N | benzyl | H | 4-imidazolyl-methyl | cyclohexylmethyl | 1* |
| 129 | 0 | N | morpholin-1-yl-carbonyl | CH₂ | C=O | CH₂ | N | benzyl | H | 4-thiazolyl-methyl | cyclohexylmethyl | 3* |
| 130 | 0 | N | p-toluene-sulfonyl | CH₂ | C=O | CH₂ | N | benzyl | H | 4-thiazolyl-methyl | cyclohexylmethyl | 3* |
| 131 | 0 | N | p-toluene-sulfonyl | CH₂ | C=O | CH₂ | N | benzyl | H | 4-thiazolyl-methyl | cyclohexylmethyl | 1* |
| 132 | 1 | N | t-Boc | CH₂ | C=O | CH₂ | N | benzyl | H | n-butyl | cyclohexylmethyl | 1* |
| 140 | 0 | N | p-toluene-sulfonyl | CH₂ | C=O | CH₂ | N | benzyl | H | 4-thiazolyl-methyl | cyclohexylmethyl | 4* |
| 141 | 0 | N | 4-methyl-piperazin-1-yl-sulfonyl | CH₂ | C=O | CH₂ | N | benzyl | H | 4-thiazolyl-methyl | cyclohexylmethyl | 3* |
| 142 | 0 | N | 4-methyl-piperazin-1-yl-sulfonyl | CH₂ | C=O | CH₂ | N | benzyl | H | (N-Boc)-4-imidazolyl-methyl | cyclohexylmethyl | 2* |
| 143 | 0 | N | 4-methyl-piperazin-1-yl-sulfonyl | CH₂ | C=O | CH₂ | N | benzyl | H | 4-imidazolyl-methyl | cyclohexylmethyl | 2* |
| 144 | 0 | N | 4-methyl-piperazin-1-yl-sulfonyl | CH₂ | C=O | CH₂ | N | benzyl | H | (N-Boc)-4-imidazolyl-methyl | cyclohexylmethyl | 1* |
| 145 | 0 | N | 4-methyl-piperazin-1-yl-sulfonyl | CH₂ | C=O | CH₂ | N | benzyl | H | 4-imidazolyl-methyl | cyclohexylmethyl | 1* |
| 146 | 0 | N | 4-methyl-piperazin-1-yl-sulfonyl | CH₂ | C=O | CH₂ | N | benzyl | H | (N-Boc)-4-imidazolyl-methyl | cyclohexylmethyl | 4* |

-continued

| Example | n | X | R₁ | A | D | L | Y | R₂ | Z | R₃ | R₄ | R₅ |
|---|---|---|---|---|---|---|---|---|---|---|---|---|
| 147 | 0 | N | 4-methyl-piperazin-1-yl sulfonyl | CH₂ | C=O | CH₂ | N | benzyl | H | 4-imidazolyl-methyl | cyclohexylmethyl | 4* |
| 151 | 0 | CH | H | CH₂ | C=O | CH₂ | N | benzyl | 4-methyl-piperazin-1-yl-sulfonylamino | 4-thiazolyl-methyl | cyclohexylmethyl | 1* |
| 152 | 0 | CH | H | CH₂ | C=O | CH₂ | N | benzyl | 4-methyl-piperazin-1-yl-sulfonylamino | 4-thiazolyl-methyl | cyclohexylmethyl | 4* |
| 156 | 0 | CH | H | CH₂ | C=O | CH₂ | N | benzyl | p-toluene-sulfonylamino | 4-thiazolyl-methyl | cyclohexylmethyl | 1* |
| 157 | 0 | N | 4-methyl-piperazin-1-yl sulfonyl | CH₂ | C=O | CH₂ | N | benzyl | H | 4-thiazolyl-methyl | T = 5* | |
| 158 | 0 | N | 4-methyl-piperazin-1-yl sulfonyl | CH₂ | C=O | CH₂ | N | benzyl | H | 4-thiazolyl-methyl | T = 6* | |
| 159 | 0 | N | 4-methyl-piperazin-1-yl sulfonyl | CH₂ | C=O | CH₂ | N | benzyl | H | 4-thiazolyl-methyl | T = 7* | |
| 160 | 0 | N | 4-methyl-piperazin-1-yl sulfonyl | CH₂ | C=O | CH₂ | N | benzyl | H | 4-thiazolyl-methyl | T = 8* | |
| 161 | 0 | N | 4-methyl-piperazin-1-yl sulfonyl | CH₂ | C=O | CH₂ | N | benzyl | H | 4-thiazolyl-methyl | T = 9* | |
| 162 | 0 | N | 4-methyl-piperazin-1-yl sulfonyl | CH₂ | C=O | CH₂ | N | benzyl | H | 4-thiazolyl-methyl | T = 10* | |
| 163 | 0 | N | 4-methyl-piperazin-1-yl sulfonyl | CH₂ | C=O | CH₂ | N | benzyl | H | 4-thiazolyl-methyl | T = 11* | |
| 164 | 0 | N | 4-methyl-piperazin-1-yl sulfonyl | CH₂ | C=O | CH₂ | N | benzyl | H | 4-thiazolyl-methyl | T = 12* | |
| 165 | 0 | N | 4-methyl-piperazin-1-yl sulfonyl | CH₂ | C=O | CH₂ | N | benzyl | H | 4-thiazolyl-methyl | T = 13* | |
| 166 | 0 | N | 4-methyl-piperazin-1-yl sulfonyl | CH₂ | C=O | CH₂ | N | benzyl | H | 4-thiazolyl-methyl | T = 14* | |
| 167 | 0 | N | 4-methyl-piperazin-1-yl sulfonyl | CH₂ | C=O | CH₂ | N | benzyl | H | 4-thiazolyl-methyl | T = 15* | |
| 168 | 0 | N | 4-methyl-piperazin-1-yl sulfonyl | CH₂ | C=O | CH₂ | N | benzyl | H | 4-thiazolyl-methyl | T = 16* | |
| 169 | 0 | CH | H | CH₂ | C=O | CH₂ | N | benzyl | 4-methyl-piperazin-1-yl-sulfonylamino | 4-thiazolyl-methyl | T = 5* | |
| 170 | 0 | CH | H | CH₂ | C=O | CH₂ | N | benzyl | 4-methyl-piperazin-1-yl-sulfonylamino | 4-thiazolyl-methyl | T = 6* | |
| 171 | 0 | CH | H | CH₂ | C=O | CH₂ | N | benzyl | 4-methyl-piperazin-1-yl-sulfonylamino | 4-thiazolyl-methyl | T = 7* | |
| 172 | 0 | CH | H | CH₂ | C=O | CH₂ | N | benzyl | 4-methyl-piperazin-1-yl-sulfonylamino | 4-thiazolyl-methyl | T = 8* | |
| 173 | 0 | CH | H | CH₂ | C=O | CH₂ | N | benzyl | 4-methyl-piperazin-1-yl-sulfonylamino | 4-thiazolyl-methyl | T = 9* | |
| 174 | 0 | CH | H | CH₂ | C=O | CH₂ | N | benzyl | 4-methyl-piperazin-1-yl-sulfonylamino | 4-thiazolyl-methyl | T = 10* | |
| 175 | 0 | CH | H | CH₂ | C=O | CH₂ | N | benzyl | 4-methyl-piperazin-1-yl-sulfonylamino | 4-thiazolyl-methyl | T = 11* | |
| 176 | 0 | CH | H | CH₂ | C=O | CH₂ | N | benzyl | 4-methyl-piperazin-1-yl-sulfonylamino | 4-thiazolyl-methyl | T = 12* | |
| 177 | 0 | CH | H | CH₂ | C=O | CH₂ | N | benzyl | 4-methyl-piperazin-1-yl-sulfonylamino | 4-thiazolyl-methyl | T = 13* | |
| 178 | 0 | CH | H | CH₂ | C=O | CH₂ | N | benzyl | 4-methyl-piperazin-1-yl-sulfonylamino | 4-thiazolyl-methyl | T = 14* | |
| 179 | 0 | CH | H | CH₂ | C=O | CH₂ | N | benzyl | 4-methyl-piperazin-1-yl-sulfonylamino | 4-thiazolyl-methyl | T = 15* | |

-continued

| Example | n | X | R₁ | A | D | L | Y | R₂ | Z | R₃ | R₄ | R₅ |
|---|---|---|---|---|---|---|---|---|---|---|---|---|
| 180 | 0 | CH | H | CH₂ | C=O | CH₂ | N | benzyl | 4-methyl-piperazin-1-yl-sulfonylamino | 4-thiazolyl-methyl | T = 16* | |
| 182 | 0 | CH | H | CH₂ | C=O | CH₂ | N | benzyl | N-methyl-N-(4-methyl-piperazin-1-yl-sulfonyl)amino | 4-thiazolyl-methyl | R₄ = cyclohexylmethyl | R₅ = 4* |
| 183 | 0 | CH | H | CH₂ | C=O | CH₂ | N | benzyl | N-methyl-N-(4-methyl-piperazin-1-yl-sulfonyl)amino | 4-thiazolyl-methyl | R₄ = cyclohexylmethyl | R₅ = 1* |

1* = —CH(OH)CH₂CH(CH₃)₂
2* = 3-ethyloxazolidin-2-on-5-yl
3* = —CH₂CH(CH(CH₃)₂)—C(O)NH-n-butyl
4* = 4-methyltetrahydrofur-2-yl
5* = —NHCH(CH2cyclohexyl)CH(OH)CH2CH(CH3)CH2SO2CH(CH3)2
6* = —NHCH(CH2cyclohexyl)CH(OH)CO2CH(CH3)2
7* = —NHCH(CH2cyclohexyl)CH(OH)CH2C(O)NHCH2CH2morpholin-4-yl
8* = —NHCH(CH2cyclohexyl)CH(OH)CH2CH(CH(CH3)2)—CH=CH2
9* = —NHCH(CH2cyclohexyl)CH(OH)CH2CH(CH(CH3)2)C(O)-Ile-NHCH2-pyrid-2-yl
10* = —NHCH(CH2CH(CH3)2)CH(OH)CH2CH(CH(CH3)2)C(O)-Ile-NHCH2-pyrid-2-yl
11* = —NHCH(CH2CH(CH3)2)CH(OH)CF2C(O)-Ile-NHCH2-pyrid-2-yl
12* = —NHCH(CH2cyclohexyl)CH(OH)CF2C(O)NHCH2CH(CH3)2
13* = —NHCH(CH2cyclohexyl)CH(OH)CH2SO2CH(CH3)2
14* = —NHCH(CH2cyclohexyl)CH(OH)CH2C(=CH)C(O)NH(CH2CH(CH3)2)
15* = —NHCH(CH2CH(CH3)2)CH(OH)CH=CH—C(O)NH(CH2CH(CH3)2)
16* = —NHCH(CH2cyclohexyl)CH(OH)CH2CH2SO2-morpholin-4-yl Preferred compounds of the invention include:
3-(3-Thiazolyl)-2-(3R-benzyl-4-N-(N-methylpiperazyl)-sulfonyl-2-keto-piperazin-1-yl)-propionic acid Amide of Butyl 5(S)-amino-6-cyclohexyl-4(S)-hydroxy-2(R)-isopropylhexan-amide;

3-(3N-tert-butyloxycarbonyl-2-imidazolyl)-2-(3R-benzyl-4-N-(N-methylpiperazyl)-sulfonyl-2-keto -piperazin-1-yl)-propionic acid Amide of (2'S,1'R,5S)-3-Ethyl-5-(1'-hydroxy-2'-amino-3'-cyclohexylpropyl) oxazolidin-2-one;

3-(2-imidazolyl)-2-(3R-benzyl-4-N-(N-methylpiperazyl)sulfonyl-2-keto-piperazin-1-yl)-propionic acid Amide of (2'S,4'R,5S)-3-Ethyl-5-(1'-hydroxy-2'-amino-3'-cyclohexylpropyl)oxazolidin -2-one;

3-(3N-tert-butyloxycarbonyl-2-imidazolyl)-2-(3R-benzyl-4N-(N-methylpiperazyl)-sulfonyl-2-keto -piperazin-1-yl)propionic acid Amide of 2(S)-Amino-1-cyclohexyl-3(R),4(S)-dihydroxy-6-methylheptane;

3-(2-imidazolyl)-2-(3R-benzyl-4N-(N-methylpiperazyl)-sulfonyl-2-keto-piperazin-1-yl)-propionic acid Amide of 2(S)-Amino-1-cyclohexyl-3(R),4(S)-dihydroxy-6-methylheptane;

3-(3N-tert-butyloxycarbonyl-2-imidazolyl)-2-(3R-benzyl-4N-(N-methylpiperazyl)-sulfonyl-2-keto -piperazin-1-yl)-propionic acid Amide of 2(S)-Amino-3-cyclohexyl-1(R)-hydroxy)propyl-4(S)-methyltetrahydrofuran;

3-(2-imidazolyl)-2-(3R-benzyl-4N-(N-methylpiperazyl)-sulfonyl-2-keto-piperazin-1-yl)-propionic acid Amide of 2(S)-Amino-3-cyclohexyl-1(R)-hydroxy)propyl-4(S)-methyltetrahydrofuran;

(2S)-((3S)-((N-methylpiperazinsulfonyl)-amino-3-phenylmethyl-2-oxo-1-piperidinyl)3-(4-thiazolyl) -propionic acid amide of 2(S)-Amino-1-cyclohexyl-3(R),4(S)-dihydroxy-6-methylheptane;

(2S)-Methyl-((3S)-((N-methylpiperazinsulfonyl)-amino-3-phenylmethyl-2-oxo-1-piperidinyl)-3-(4-thiazolyl)-propionic acid amide of 2(S)-Amino-1-cyclohexyl-3(R),4(S)-dihydroxy-6-methylheptane; and (2S)-2-((1-tert-butyloxycarbonyl)-1-imidazol-4-yl-methyl)-3-((3(S)-(4-methyl -benzenesulfonyyl)-amino-3-phenylmethyl-2-oxo-1-piperidinyl) amide of 2(S)-Amino-1-cyclohexyl-3(R),4(S)-dihydroxy-6-methylheptane.

The following examples will serve to further illustrate preparation of the novel compounds of the invention.

EXAMPLE 1

2(S)-t-Butyloxycarbonylamino-1-cyclohexyl-6-methyl-hept-3-ene

To a stirred —78° C. solution of Boc-cyclohexylalanine methyl ester (40 g, 140 mmol) in anhydrous toluene (250 ml) was added diisobutylaluminum hydride (130M %, 1.5M solution in toluene, 121.4 ml) at a rate to keep the internal temperature below —60° C. After stirring for an additional 20 minutes at —78° C., the aldehyde solution is used immediately as described below.

To a potassium hydride (35% dispersion in oil, 32.09 g) suspension in a 0° C. mixture of anhydrous THF/DMSO (1000 ml/200 ml) under dry N₂ was added 1,1,1,3,3,3-hexamethyldisilazane (209M %, 49.07 g) dropwise. After stirring at 0° C. for 1 hour, the resulting solution was added via cannula to a 0° C. flask containing isopentyltriphenylphosphonium bromide (209M %, 125.66 g). The mixture was stirred vigorously for 1 hour at which time it was cooled to —78° C. The —78° C. aldehyde solution prepared above was then added via cannula. After stirring at —78° C. for 15 minutes, the mixture was allowed to slowly warm to room temperature and then heated to 40° C. for 12 hours. The mixture was then cooled to room temperature and quenched with methanol (7.65 ml) followed by aqueous Rochelle salts (100 ml saturated solution and 500 ml H₂O). The mixture was then extracted with ethyl acetate (2×). The combined extracts were washed with water and brine. Drying (MgSO₄) and evaporating provided crude alkene which was chromatographed on silica gel (ether/hexane) to give 16.5 g (38%) of the desired compound as an 85:15 mixture of cis:trans isomers. m.p.=53°–55° C. Mass spectrum: M⁺=309.

Anal. Calcd. for C₁₉H₃₅NO₂: C, 73.7; H, 11.4; N, 4.5. Found: C, 73.8; H, 11.4; N, 4.5.

EXAMPLE 2

2(S)-Amino-1-cyclohexyl-3,4-dihydroxy-6-methylheptane: The 3(R)4(S), 3(S)4(S), 3(R)4(R), and 3(S)4(R) Diastereomers To a solution of the resultant compound of Example 1 (8.50, 27.5 mmol) in dry THF (150 ml) were added OsO4 (2.8 ml of a 2.5% solution in t-butanol and N-methylmorpholine N-oxide (9.28 g, 68.7 mmol). After 4 days the mixture was partitioned between ether (200 ml) and brine (100 ml). The aqueous layer was back-extracted with ether (2×100 ml), and the combined organic phase was washed with 10% $Na_2SO_3$, 0.1M $H_3PO_4$, and brine. Drying ($MgSO_4$) and evaporating provided a residue (10.81 g) which was chromatographed on silica gel to elute a 60% yield of the 4 diols in the following order.

3(R),4(S) Mass spectrum: $(M+H)^+ = 344$.
Anal. Calcd. for $C_{19}H_{37}NO_4$: C, 66.4; H, 10.9; N, 4.1.
Found: C, 66.4; H, 10.8; N, 3.9.
3(S),4(S) Mass spectrum: $(M+H)^+ = 344$.
Anal Calcd. for $C_{19}H_{37}NO_4$: C, 66.4; H, 10.9; N, 5.1.
Found: C, 66.4; H, 11.1; N, 4.0.
3(R),4(R) Mass spectrum: $(M+H)^+ = 344$.
3(S),4(R) Mass spectrum: $(M+H)^+ = 344$.
Anal Calcd. for $C_{19}H_{37}NO_4$: C, 66.4; H, 10.9; N, 4.1.
Found: C, 66.0; H, 10.7; N, 4.0.

The 3(R),4(S)-isomer was converted to the corresponding free amine or its hydrochloride salt following the procedure given below. A 0.17 g (0.50 mmol) portion of the 3(R),4(S)-isomer was added to 5 ml of 4M-HCl-Dioxane at room temperature. After 1 h at this temperature, solvent and excess HCl was removed under reduced pressure. The residual liquid was dissolved in $CH_2Cl_2$-toluene (1:4 ratio) and then concentrated under reduced pressure which gave the solid hydrochloride salt. To obtain the free amine, the HCl-salt was added to a stirring slurry of $NH_3$-$H_2O$/AcOEt. The organic layer was separated, dried over $MgSO_4$, and concentrated in vacuo to produce the desired free amine.

EXAMPLE 3

4(S)-t-Butyloxycarbonylamino-5-cyclohexyl-3(R,S)-hydroxy-1-pentene

To a stirred −78° C. solution of Boc-cyclohexylalanine methyl ester (10.2 g, 35.8 mmol) in dry toluene (60 ml) was added diisobutylaluminum hydride (34 ml of a 1.5M solution in toluene). After 30 min, vinyl magnesium bromide (108 ml of 1M solution in tetrahydrofuran (THF)) was added. After stirring for 15 h at 0° C., the mixture was carefully quenched with methanol, treated with Rochelle salts (22 ml of saturated aqueous solution in 140 ml $H_2O$), and filtered. After extracting the solids 5 times with ethyl acetate, the extracts and filtrate were combined and the organic phase was washed with brine, dried, filtered and evaporated to an oil (10.2 g). Chromatography on silica gel eluting with hexane/ethyl acetate mixtures provided 6.1 g (60%) of the desired product.
Anal. Calcd. for $C_{16}H_{29}NO_3 \cdot \frac{1}{4} H_2O$: C, 66.8; H, 10.3; N, 4.9.
Found: C, 66.9; H, 10.2; N, 4.7.

EXAMPLE 4

4(S)-Cyclohexylmethyl-5(R,S)-vinyl-2-oxazolidinone

The resultant product of Example 3 (2.80 g, 9.88 mmol) in dry dimethylformamide (DMF) (50 ml) was added to a stirred suspension of NaH (593 mg of a 60% dispersion in oil, 14.8 mmol, hexane washed) in dry DMF (50 ml). After 3 h, the mixture was quenched (750 ml water+100 ml brine) and extracted with ether (5×100 ml). The combined organic phase was washed with brine (3×50 ml), dried ($MgSO_4$), filtered and evaporated to an oil (2.23 9). The NMR spectrum of the crude product revealed an 82:18 mixture of 5S:5R diastereomers. Silica gel chromatography gave 80% recovery of pure diastereomers. 5S:
Anal. Calcd. for $C_{12}H_{19}NO_2$: C, 68.9; H, 9.1; N, 6.7.
Found: C. 68.4; H, 9.2; N, 6.5. Mass spectrum: $(M+1)^+ = 210$. 5R: Mass spectrum: $(M+1)^+ = 210$.

EXAMPLE 5

(3S,4S)-3-Hydroxy-4-amino-5-cyclohexyl-1-pentene

To the resultant 5S-diastereomer from Example 4 (2.06 g, 9.84 mmol) in dioxane (180 ml) and water (120 ml) was added barium hydroxide octahydrate (6.24 g, 19.8 mmol). The mixture was refluxed for 18 h, cooled, filtered, concentrated, taken up in water and extracted with ethyl acetate which was dried over $Na_2SO_4$ and evaporated to afford 1.64 9 (91%) of the desired product, m.p.: 59°–61° C.
Anal. Calcd. for $C_{11}H_{21}NO$: C, 72.08; H, 11.55; N, 7.64.
Found: C, 71.67; H, 11.68; N, 7.36.

EXAMPLE 6

(3S,4S)-3-Hydroxy-4-tert-butyloxycarbonylamino-5-cyclohexyl-1-pentene

To the resultant compound from Example 5 (1.62 g, 8.84 mmol) in methylene chloride (20 ml) was added di-tert-butyldicarbonate (1.93 g, 8.84 mmol). The mixture was stirred for 14 h, diluted with ethyl acetate, washed sequentially with 0.5M $H_3PO_4$, saturated $NaHCO_3$ solution and brine, then dried over $Na_2SO_4$ and evaporated to afford 2.51 g (100%) of the desired compound.

EXAMPLE 7

(3S,4S)-3-Methoxyethoxymethoxy-4-tert-butyloxycarbonylamino-5-cyclohexyl-1-pentene To the resultant compound from Example 6 (2.51 g, 8.84 mmol) in methylene chloride (20 ml) was added diisopropylethylamine (4.60 ml, 26.4 mmol) and methoxyethoxychloromethane (3.00 ml, 26.3 mmol). After stirring at room temperature for 24 h the mixture was concentrated, diluted with ethyl acetate, washed with 0.5M $H_3PO_4$, saturated $NaHCO_3$ solution, then brine, dried over $Na_2SO_4$, and evaporated. Chromatography on silica gel with ethyl acetate/ hexane mixtures afforded 2.63 g (80%) of the desired product as an oil. EI-MS: $M^+ = 371$.

EXAMPLE 8

(2RS,3R,4S)-3-Methoxyethoxymethoxy-4-tert-butyloxycarbonylamino-5-cyclohexyl-1,2-oxopentane To the resultant compound from Example 7 (5.41 g, 14.56 mmol) in methylene chloride (50 ml) was added 3-chloroperbenzoic acid (6.28 g). After stirring at room temperature for 60 h the mixture was concentrated, diluted with ethyl acetate, washed with cold 1:1 15% aqueous $Na_2SO_3$ solution/saturated $NaHC)_3$ solution (2×200 ml), saturated $NaHCO_3$ solution (3×100 ml then brine (1×100 ml), dried over $Na_2SO_4$, and evaporated to afford 4.57 g (81%) product as an oil. EI-MS: $M^+ = 387$.

EXAMPLE 9

(2'S,1'R,5S)-3-Ethyl-5-(1'-methoxyethoxymethoxy-2'-tert-butyloxycarbonylamino-3'-cyclohexylpropyl)oxazolidin-2-one.

To the resultant compound from Example 8 (310 mg, 0.80 mmol) in isopropanol (5 ml) was added ethylamine (200 mg, 4 mmol). The mixture was heated at 70° C. for 48 h, evaporated and dissolved in methylene chloride (5 ml). To this solution was added triethylamine (0.34 ml, 2.4 mmol) and phosgene in toluene (1.0 ml, 1.2 mmol, 12.5% solution). After 2 h the mixture was diluted with ethyl acetate, washed with 0.5M $H_3PO_4$, saturated $NaHCO_3$ solution then brine, dried over $Na_2SO_4$ and evaporated. Chromatography of the residue on silica gel with 1:1 ethyl acetate/hexane provided 14.3 mg (4%) of the 5R isomer followed by 63.0 mg (17%) of the desired 5S isomer, both as oils.

5S-Isomer: $^1$H-NMR (CDCl$_3$,TMS) δ 4.83 (d,1H), 4.80 (d,1H), 4.58 (m,1H), 3.49 (s,3H), 1.43 (s,9H), 1.15 (t,3H).

5R-Isomer: MS (M+H) =459.

EXAMPLE 10

Ethyl 2-(4-(2-pyrimidyl)-piperazyl)-hexanoate

A suspension of 1-(2-pyrimidyl)piperazine (6 g, 36.6 mmol), ethyl 2-bromohexanoate (8.16 g, 1 equiv) and powdered $K_2CO_3$ (5 g, 2 molar equiv) in EtOH (50 ml) was heated under reflux for 3.5 h. The reaction was diluted with $H_2O$/AcOEt. The organic layer was washed with brine, dried over $MgSO_4$ and concentrated in vacuo to give 9.2 g crude oil (82% crude yield): DCI-NH$_3$-MS, m/z (relative intensity), 307 (MH$^+$, 100%), and 233 (8%); 1H NMR (CDCl$_3$, 300 MHz) δ 8.30 (d,J=5Hz,2H), 6.48 (t,J=5Hz,1H), 4.20 (m,2H), 3.90-3.70 (m,4H), 3.21 (dd,J=6,8Hz,1H), 2.75-2.60 (m,4H), 2.10-1.20 (m,9H), and ↩.90 (6t,J=7Hz,3H).

EXAMPLE 11

2-(4-(2-Pyrimidyl)-piperazyl)-hexanoic Acid

The ester from Example 10 (4.66 g, 15.23 mmol) was dissolved in MeOH (100 ml) and hydrolyzed with LiOH (2 equiv in 30 ml $H_2O$) at room temperature for 2 h. At the end, the free acid was generated by adding HCl-Dioxane solution (4.5M in HCl, 8.8 ml used). The sample was evaporated to dryness and extracted with $CH_2Cl_2$. Evaporation of solvent under reduced pressure and drying under high vacuum gave 3.95 9 crude acid (84%); DCI-NH$_3$-MS, m/z (relative intensity), 279 (MH$^+$, 100%), 233 (10%), and 164 (16%).

EXAMPLE 12

2-(4-(2-Pyrimidyl)-piperazin-1-yl)-hexanoic acid Amide of 2(S)-Amino-1-cyclohexyl-3(R),4(S)-dihydroxy-6-methylheptane To a solution containing the free amine from Example 2 (218 mg, 0.89 mmol), HOBT (365 mg, 3 equiv), acid (250 mg, 0.89 mmol) from Example 11 in dry DMF (10 ml) at 0° C. under $N_2$, was added EDAC (173 mg, 1 equiv). The reaction was stirred at 0° C. for 2 h and then at room temperature overnight. The light yellow solution was diluted with sat $NaHCO_3$ and AcOEt. The organic layer was washed with brine, dried over $MgSO_4$ and concentrated in vacuo. The chromatographic purification (silica gel, AcOEt-Hexane, 1:1) of the crude product gave two diastereomers 12A and 12B (275 mg, total yield 61%):

(12A): R$_f$=0.51 (AcOEt); m.p. 150°-151° C.; DCI-NH$_3$-MS, m/z (relative intensity) 504 (MH$^+$, 100%), 416 (5%), and 278 (8%); $^1$H NMR (CDCl$_3$, 300 MHz) δ: 8.31 (d,J=5Hz,2H), 7.00 (NH,d,J=9Hz,1H), 6.51 (t,J=5Hz,1H), 4.48 (b s,1H), 4.35 (m,1H), 3.90-3.72 (m,4H), 3.23 (b s,2H), 2.98 (t,J=6Hz,1H), 2.70-2.55 (m,4H), 2.00-1.10 (m,≈22H), and 1.00-0.80 (m,9H); Anal. ($C_{28}H_{49}O_3N_5$) C,H,N.

(12B): R$_f$=0.41 (AcOEt); m.p. 217°-218° C.; DCI-NH$_3$-MS, m/z (relative intensity), 504 (MH$^+$, 100%), 416 (8%), and 278 (18%); $^1$H NMR (CDCl$_3$, 300 MHz) δ: 8.32 (d,J=5Hz,2H), 6.85 (d,NH,J=9Hz,1H), 6.51 (t,J=5Hz,1H), 4.34 (m,1H), 3.85 (t,J=4.5Hz,2H), 3.24 (b s,1H), 2.90 (dd,J=5,7Hz,1H), 2.70-2.50 (m,2H), 2.00-1.10 (m,≈22H), and 1.00-0.80 (m,9H); Anal. ($C_{28}H_{49}O_3N_5$) C,H,N.

EXAMPLE 13

2-(4-Benzylpiperidin-1-yl)-hexanoic acid Amide of 2(S)-Amino-1-cyclohexyl-3(R),4(S)-dihydroxy-6-methylheptane The desired compound was made following the procedure as described in Example 10, 11, and 12. In this case, 4-benzyl piperidine was used as starting material.

Less polar diastereomer: R$_f$=0.16 (hexane-AcOEt. 3:1); DCI-NH$_3$-MS, m/z (relative intensity), 515 (MH$^+$, 100%), 342 (20%), 289 (7%), 244 (41%), and 174 (52%); 1H NMR (CDCl$_3$, 300 MHz) δ: 7.32-7.10 (m5H), 7.08 (d,J=9Hz,1H), 4.53 (b s,1H), 4.29 (t of d,J=3,9Hz,1H), 3.20 (b s,2H), 2.90 (t,J=6Hz,1H), 2.80 (b t,J=10Hz,2H), 2.55 (b d,J=7Hz,2H), 2.29 (t,J=11, 11Hz,1H), 2.10 (t,J=11Hz,1H), 1.90 (m,1H), 1.80-1.05 (m,≈27H), 0.98-0.80 (m,9H); Anal. ($C_{32}H_{54}O_3N_2$) C,H,N.

EXAMPLE 14

2-(4-Benzylpiperidin-1-yl)-hexanoic acid Amide of 2(S)-Amino-1-cyclohexyl-3(R1,4(S)-dihydroxy-6-methylheptane This is the more polar diastereomer of the compound described in Example 13.

R$_f$=0.14 (Hexane-AcOEt, 3:1); DCI-NH$_3$-MS, m/z (relative intensity), 515 (MH$^+$, 100%), 342 (17%), 289 (15%), 244 (67%), and 174 (40%); $^1$H NMR (CDCl$_3$, 300 MHz) δ: 7.31-7.10 (m,5H), 6.89 (d,J=3Hz,1H), 4.30 (m,1H), 3.21 (b s,1H), 2.90-2.70 (m,2H), 2.53 (d,J=7Hz,1H), 2.20-1.10 (m,≈27H), 1.00-0.80 (m,9H); Anal. ($C_{32}H_{54}O_3N_2$) C,H,N.

EXAMPLE 15

2-(4-(4-Methoxyphenyl)-piperazin-1-yl)-hexanoic acid Amide of 2(S)-Amino-1-cyclohexyl-3(R),4(S)-dihydroxy-6-methylheptane The desired compound was made following the procedure described in Example 10, 11, and 12. In this case (4-methoxyphenyl)-piperazine was used as the starting material.

Less polar diastereomer: m.p. 152°–153° C.; $R_f$=0.30 (Hexane-AcOEt, 1:1); DCI-NH$_3$-MS, m/z (relative intensity), 532 (MH$^+$, 100%), 261 (18%), and 191 (8%); $^1$H NMR (CDCl$_3$, 300 MHz) δ: 6.98 (d,J=9Hz,1H), 6.92–6.80 (m,4H), 4.47 (b s,1H), 4.33 (t of d,J=4,9,9Hz,1H), 3.78 (s,—OCH$_3$,3H), 3.24 (b s,2H), 3.10 (m,4H), 2.98 (dd,J=6,7Hz,1H), 2.23 (m,4H), 1.92 (m,1H), 1.80–1.08 (m,≈22H), and 1.00–0.80 (m,9H); Anal. (C$_{31}$H$_{53}$O$_4$N$_3$), C,H,N.

EXAMPLE 16

2-(4-(4-Methoxyphenyl)-piperazin-1-yl)-hexanoic acid Amide of 2(S)-Amino-1-cyclohexyl-3(R1,4(S)-dihydroxy-6-methylheptane This is the more polar diastereomer of the compound described in Example 15.

m.p. 147°–148° C.; $R_f$=0.25 (Hexane-AcOEt, 1:1); DCI-NH$_3$-MS (relative intensity, 532 (MH$^+$, 100%), 342 (4%), 261 (23%), and 193 (8%); $^1$H NMR (CDCl$_3$, 300 MHz) δ: 6.92–6.80 (m,4H), 4.65 (b s,1H), 4.32 (t of d,J=5,9,9Hz,1H), 3.78 (s,—OCH$_3$,3H). 3.25 (b s,2H), 3.10 (t,J=4,4Hz,4H), 2.91 (dd,J=5,7Hz,1H), 2.80–2.62 (m,4H), 1.93 (m,1H), 1.80–1.10 (m,≈22H), and 1.00–0.80 (m,9H); Anal. (C$_{31}$H$_{53}$O$_4$N$_3$) C,H,N.

EXAMPLE 17

2-(4-(2-Pyridyl)-piperazin-1-yl)-hexanoic acid Amide of 2(S)-Amino-1-cyclohexyl-3(R),4(S)-dihydroxy-6-methylheptane The desired compound was synthesized following the procedure described in Example 10, 11, and 12. 2-Pyridylpiperazine was used as the starting material.

Less polar diastereomer: DCI-NH$_3$-MS, m/z (relative intensity) 503 (MH$^-$, 100%), 485 (6%), 415 (7%), and 277 (7%); $^1$H NMR (CDCl$_3$, 300 MHz) δ: 8.20 (m,1H), 7.49 (t,J=7,7Hz,1H), 7.00 (d,J=9Hz,1H), 6.64 (m,2H), 4.45 (b s,1H), 4.34 (t of d,J=4,9,9Hz,1H), 3.63–3.45 (m,4H), 3.25 (b s,2H). 2.98 (t,J=7Hz,1H), 2.80–2.60 (m,4H), 1.93 (m,1H), 1.80–1.05 (m, H), and 1.00–0.80 (m,9H); Anal. (C$_{29}$H$_{49}$N$_4$O$_3$) C,H,N.

EXAMPLE 18

2-(3-Benzylpiperidin-1-yl)-hexanoic acid Amide of 2(S)-Amino-1-cyclohexyl-3(R),4(S)-dihydroxy-6-methylheptane The title compound was made starting with 3-benzylpiperidine and following the procedure as described in Example 10, 11, and 12. This synthesis produced four possible diastereomers and the spectral data for three active diastereomers are given in Example 18 (Rf=0.49,Hexane-EtoAc 1:1). DCI-NH$_3$-MS, m/z (relative intensity), 515 (MH$^+$, 100%), 244 (30%), and 174 (24%); $^1$H NMR (CDCl$_3$, 300 MHz) δ: 7.34–7.10 (m,5H), 7.02 (b s,1H), 4.30 (m,1H), 3.22 (m,2H), 2.89 (m,1H), 2.79 (m,2H), 2.60–2.45 (m,2H), 2.30–1.05 (m,≈31H), and 1.05–0.75 (m,9H); Anal. (C$_{32}$H$_{54}$O$_3$N$_2$) C,H,N.

EXAMPLE 19

2-(3-Benzylpiperidin-1-yl)-hexanoic acid Amide of 2(S)-Amino-1-cyclohexyl-3(R),4(S)-dihydroxy-6-methylheptane The title compound was made starting with 3-benzylpiperidine and following the procedure as described in Example 10, 11, and 12. This synthesis produced four possible diastereomers and the spectral data for three active diastereomers are given in Example 18, 19, and 20. DCI-NH$_3$-MS, m/z (relative intensity), 515 (MH$^+$, 100%), 342 (18%), 289 (16%), 244 (40%), 174 (43%); $^1$H NMR (CDCl$_3$, 300 MHz) δ: 7.32–7.10 (m,5H), 6.93 (d,J=9Hz,1H), 4.28 (m,1H), 3.23 (b s,2H), 2.87 (t,J=6Hz,1H), 2.75 (b d,J=10Hz,2H), 2.58 (dd,J=7,13Hz,1H), 2.44 (dd,J=7,13Hz,1H), 2.25-1.10 (m,31H), 0.95–0.83 (m,9H); Anal. (C$_{32}$H$_{54}$O$_3$N$_2$) C,H,N.

EXAMPLE 20

2(3-Benzylpiperidin-1-yl)-hexanoic acid Amide of 2(S)-Amino-1-cyclohexyl-3(R),4(S)-dihydroxy-6-methylheptane The title compound was made starting with 3-benzylpiperidine and following the procedure as described in Example 10, 11, and 12. This synthesis produced four possible diastereomers and the spectral data for three active diastereomers are given in Example 18, 19, and 20. DCI-NH$_3$-MS, m/z (relative intensity), 515 (MH$^+$, 100%), 342 (6%), 244 (41%), 202 (21%), and 174 (61%);

EXAMPLE 21

Methyl 2S-(2R-Benzyl-2-benzyloxycarbonyl amino-ethylaminol-hexanoate

D-Phenylalaninol (7.89 g, 52.18 mmol) and N-(benzyloxycarbonyloxy)-succinimide (13 g, 52.18 mmol) were combined in 150 ml of CH$_2$Cl$_2$ and stirred for 21 h at room temperature. After this time, the solution was washed with saturated NaHCO$_3$, dried over MgSO$_4$, and concentrated in vacuo to yield 14.9 g (100%) of solid product which was used for the following reaction without further purification.

SO$_3$-Pyridine (8.36 g, 52.5 mmol) was dissolved into 20 ml of dry DMSO at room temperature. This solution was then added to a solution of CBZ-D-phenylalaninol (5 g, 17.5 mmol) and triethylamine (5.30 g, 52.5 mmol) in 100 ml of CH$_2$Cl$_2$ at 0° C. After stirring for 1 h, the reaction mixture was partitioned with 200 ml of AcOEt and 200 ml of brine. The organic layer was dried over MgSO$_4$ and concentrated in vacuo to give 4.95 g of the desired aldehyde which was used for the following reaction without further purification.

CBZ-D-Phenylalaninal (4.95 g, 17.5 mmol) and L-norLeucine methyl ester (Hydrochloride salt, 3.18 g, 17.5 mmol) were stirred in 100 ml of dry methanol at 0° C. Anhydrous NaOAc (2.87 g. 35 mmol) was added as a solid, and the reaction was stirred at 0° C. for 2 h. After this time, NaCNBH$_3$ (1.09 g, 17.5 mmol) was added portionwise over one half hour, and the reaction was stirred an additional one hour. At the end, excess borohydride was quenched with dilute HCl and the aqueous layer was basified with Na$_2$CO$_3$. The crude product was extracted with AcOEt and purified by column chromatography. DCI-NH$_3$-MS, m/z (relative intensity), 413 (MH$^+$, 100%).

EXAMPLE 22

Methyl 2S-(N-(2R-Benzyl-2-benzyloxycarbonyl-aminoethyl)-N-(benzyloxycarbonyl-methyl)-amino-hexanoate To a suspension containing the amino ester from Example 21 (2 g, 4.85 mmol) and K$_2$CO$_3$ (1.34 g, 9.70 mmol) in 55 ml dioxane at room temperature, was added benzyl bromoacetate (2.22 g, 9.69 mmol). The contents were heated under reflux for 9 h and then poured onto a slurry of H₂O-AcOEt. The organic layer was washed with brine, dried over MgSO₄ and finally concentrated in vacuo. The crude product was purified by column chromatography (silica gel, Hex-AcOEt, 2:1) and which gave the desired title compound (2.24 g, 82%): $^1$H NMR (CDCl₃, 300 MHz) δ: 7.40–7.10 (m,15H), 5.22–5.00 (m,6H), 3.88 (m,1H), 3.62 (s,—OCH₃,minor L-Phe-L-NorLeu component), 3.53 (s,—OCH₃,major D-Phe,L-NorLeu component), 3.55–3.25 (m,3H), 3.08–2.65 (m,2H), 2.43 (t,J=12Hz,1H), 1.70–1.10 (m,6H), and 0.81 (m,3H).

EXAMPLE 23

Methyl 2S-(3R-benzyl-5-oxo)-piperazin-1-yl)-hexanoate

The benzyl ester from Example 22 (1.85 g, 3.30 mmol) was dissolved in AcOEt (100 ml) and reduced with 10% Pd/C (1 g), under H₂ (4 atmosphere) at room temperature for 2 h. At the end, the catalyst was removed by filtration and the crude product (1.08 g, 90% yield) was dried under high vacuum: DCI-NH₃-MS; m/z (relative intensity), 337 (MH⁺, 8%), 319 (MH⁺—H₂O, 100%). The amino acid obtained above was subjected to cyclization with DCC (663 mg, 3.21 mmol) and HOBT (1.30 g, 9.62 mmol) in CH₂Cl₂ (30 ml) at room temperature for 9 h. The solid urea was removed by filtration and the crude product was purified by column chromatography (silica gel, 100% AcOEt) which gave 420 mg (40% after two steps, considerable amount of starting material remained unreacted) of the desired cyclic product: DCI-NH₃-MS, m/z (relative intensity), 319 (MH⁺, 100%), and 259 (11%); $^1$H NMR (CDCl₃, 300 MHz) δ: 7.38–7.20 (m,3H), 7.18 (d,J=7Hz,2H), 6.27 (b s,1H), 3.72 (s,—OCH₃,3H), 3.38

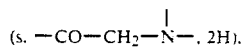

(s, —CO—CH₂—N—, 2H).

3.28 (t,J=7Hz,1H), 2.90–2.62 (m,5H), 1.80–1.58 (m,2H), 1.40–1.20 (m,4H), and 0.90 (t,J=7Hz,3H).

EXAMPLE 24

2(S)-(3R-benzyl-5-oxo)-piperazin-1-yl)-hexanoic acid Amide of 2(S)-Amino-1-cyclohexyl-3-(R),4(S)-dihydroxy-6-methylheptane The cyclized ester from Example 23 (256 mg, 0.80 mmol) was dissolved in dioxane (20 ml) and reacted with LiOH (300 mg, 7.14 mmol, in 2 ml H₂O) at room temperature overnight. The next day, the solution was cooled to 0° C. and neutralized with HCl-Dioxane (4.5M solution, 1.58 ml used). Solvent was removed under reduced pressure and the acid was extracted with CH₂Cl₂ (trace MeOH). Evaporation of solvent under reduced pressure and drying under high vacuum gave the corresponding crude acid (251 mg). DCI-NH₃-MS, m/z (relative intensity), 305 (MH⁺, 18%), 259 (8%), 225 (11%), and 138 (100%).

The acid (300 mg, 0.986 mmol) obtained in the previous reaction was dissolved in DMF (10 ml) and reacted with Amine.HCl from Example 2 (279 mg, 1 mmol), EDAC (193 mg, 1 equiv), HOBT (405 mg, 3 equiv), and Et₃N (278 μl, 2 equiv) at 0° C. for 2 h and then at room temperature overnight. At the end, the reaction mixture was poured onto EtOAc-sat. aq. NaHCO₃. The organic layer was washed with brine, dried over MgSO₄ and concentrated in vacuo. The crude product was purified by column chromatography (silica gel, Hexane-AcOEt, 1:1) to give 289 mg (55% from acid) of the desired product (less polar diastereomer): DCI-NH₃-MS, m/z (relative intensity), 530 (MH⁺, 100%), and 442 (6%); $^1$H NMR (CDCl₃, 300 MHz) δ: 7.40–7.10 (m,5H), 5.96 (b s,1H), 4.33 (m,1H), 3.73 (m,1H), 3.45 (d,J=16Hz,1H), 3.30–3.15 (m,2H), 2.97 (d,J=16Hz,1H), 2.84 (dd,J=5,14Hz,1H), 2.60 (dd,J=9,13Hz,1H), 2.45 (t,J=10Hz,1H), 2.05 (m,1H), 1.90 (m,1H), 1.80–1.10 (m,25H), and 1.00–0.70 (m,9H).

EXAMPLE 25

CBZ-D-Phe-Gly-OMe

To a solution containing CBZ-D-Phe (15 g, 50 mmol) and N-methylmorpholine (5.5 ml, 50 mmol) in CH₂Cl₂ (200 ml) at 0° C., was added isobutylchloroformate (6.8 ml, 1 equiv). The reaction was stirred at 0° C. for 8 min followed by the addition of N-methylmorpholine (5.5 ml, 50 mmol) and the hydrochloride salt of glycine methyl ester 16.30 g, equiv). The reaction was stirred at 0° C. for 1 h and then at room temperature for 4 h. The crude mixture was added to a slurry of H₂O-AcOEt. The organic layer was washed with brine, dried over MgSO₄ and finally the dipeptide was crystallized from Hex-AcOEt to give 17.5 g of white solid (m.p. 114°–115° C.): R$_f$=0.55 (Hex-AcOEt, 1:1); DCI-NH₃-MS, m/z (relative intensity), 388 (MNH₄⁺, 41%), 371 (MH⁺, 100%); $^1$H NMR (CDCl₃, 300 MHz) δ: 7.40–7.15 (m,10H), 5.10 (s,2H), 4.45 (m,1H), 3.98 (dd,J=4,16Hz,1H), 3.74 (s,3H), 3.10 (d,J=7Hz,2H).

EXAMPLE 26

2-(R)-Benzyl-3,6-diketo-piperazine

CBZ-D-Phe-Gly-OMe (9.5 9. 26 mmol) was dissolved in MeOH (150 ml) and subjected to hydrogenolysis in the presence of 10% Pd/C (1 g) and H₂-atmosphere (balloon filled with H₂) for 4 h at room temperature. At the end, the catalyst was removed by filtration through a celite bed and the removal of MeOH under reduced pressure gave 6 g of D-Phe-Gly-OMe (≈100%, crude yield).

The crude product D-Phe-Gly-OMe (6 g, 25 mmol) was powdered and then dispersed in 100 ml toluene and heated at reflux overnight. The reaction flask was cooled to 0° C. and the solid product (3.50 9, 69%) was collected by filtration: m.p. 256°–257° C.; DCI-NH₃-MS, m/z (relative intensity), 222 (MNH₄⁺, 100%), 205 (MH⁺, 31%);

EXAMPLE 27

2-(R)-Benzyl-piperazine

2-Benzyl 3,6-diketopiperazine (3 g, 17 mmol) from Example 26 was suspended in THF (200 ml) and heated at reflux with LAH (2 g, 53 mmol) for 15 h. At the end, the solution was cooled to 0° C. and the excess LAH was destroyed with aqueous NaOH (10%, 20 ml used). The free amine was extracted with AcOEt which on drying over MgSO₄ and evaporation under reduced pressure gave 2.30 9 (77% yield) of 2-R-benzyl piperazine: DCI-NH₃-MS, m/z (relative intensity, 177 (MH⁺, 100%).

EXAMPLE 28

Ethyl 2-(R,S)-(3-R-Benzyl-piperazin-1-yl)-hexanoate

A suspension of 2R-benzyl-piperazine (2.30 9, 13 mmol), ethyl 2-bromohexanoate (6.22 ml, 34 mmol) and anhydrous powdered $K_2CO_3$ (7 g, 50 mmol) in 1,4-dioxane (100 ml) was heated at reflux for 13 h. At the end, the solid residue was removed by filtration and the crude product was purified by column chromatography (silica gel, Hexane-AcOEt, 1:1) to give ethyl 2-(3R-benzylpiperazyl)-hexanoate (2.5 g, 60% yield): $MH^+$, 319 ($MH^+$, 100%).

EXAMPLE 29

Ethyl 2-(R,S)-(3-R-Benzyl-4-N-tert-butyloxycarbonylpiperazin-1-yl)-hexanoate

Ethyl 2-(3R-benzyl-piperazino)hexanoate (2.5 g, 7.86 mmol) was dissolved in $CH_2Cl_2$ (20 ml) and reacted with ($^tBoc)_2O$ (1.70 9, 7.86 mmol) at 0° C. for 2 h and at room temperature overnight. The following day, solvent was removed under reduced pressure and the crude product was purified by column chromatography (silica gel, Hexane-AcOEt, 2:1) to give 3.10 9 (95% yield) of ethyl 2-(3R-benzyl-4-tert-butoxycarbonyl)-hexanoate: $DCI-NH_3$-MS, m/z (relative intensity), 419 ($MH^+$, 100%); $^1H$ NMR ($CDCl_3$, 300 MHz, dl-mixture at the n-butyl site) δ: 7.40–7.10 (m,5H), 4.30–4.10 (m,4H), 3.20–2.20 (m,8H), 1.80–1.20 (m,6H), 1.40,1.35 (two singlets of tBu, two diastereomers, total 9H), 1.25 (two overlapping triplets, total 3H, —O—$CH_2$—$\underline{CH_3}$), and 0.93 (two overlapping triplets, total 3H).

EXAMPLE 30

2-(R,S)-(3R-Benzyl-4-N-tert-butyloxycarbonylpiperazin-1-yl)-hexanoic acid Amide of 2(S)-Amino-1-cyclohexyl-3(R),4(S)-dihydroxy-6-methylheptane The ethyl ester (1.10 g, 2.63 mmol) from Example 29 was dissolved in ethanol (30 ml) and aqueous LiOH (1N solution, 4 ml used). The clear solution was heated at reflux for 3 h. At the end, solvent was removed under reduced pressure and the sodium salt (1 g, 97% yield) thus obtained was directly used for the coupling reaction as described below.

The sodium salt (800 mg, 2.05 mmol), HOBT (830 mg, 6.15 mmol), the hydrochloride salt of the amine from Example 2 and EDAC (394 mg, 2.05.mmol) were dissolved in DMF (25 ml) and cooled to 0° C. To this solution was then added N-methylmorpholine (450 μl, 4 mmol) and the reaction was stirred at room temperature overnight. The following day, the contents were poured onto a slurry of saturated $NaHCO_3$ and AcOEt. The organic layer was washed with brine, dried over $MgSO_4$ and concentrated in vacuo. The crude product was carefully purified by column chromatography (silica gel, 10% AcOEt in Hexane) which gave two desired diastereomers (total yield 950 mg, 77%).

(30A) Less Polar Diastereomer: m.p. 148°–149° C.; $DCI-NH_3$-MS, m/z (relative intensity), 616 ($MH^+$, 100%), and 345 (23%); $^1H$ NMR ($CDCl_3$, 300 MHz) a: 7.35–7.15 (m,5H), 6.55 (d,J=8Hz,1H), 4.55 (b s,1H), 4.40–4.25 (m,2H), 3.95 (b s,1H), 3.25 (m,2H), 3.15 (t d,J=3,12,12Hz,1H), 2.98 (b s,2H), 2.85–2.70 (m,3H), 2.35–2.20 (m,2H), 1.93 (m,1H), 1.80–1.55 (m,8H), 1.45–1.10 (m,14H), 1.35 (s,tBu,9H), and 1.00–0.80 (m,methyl isopropyl,9H); Anal. ($C_{36}H_{61}N_3O_5$) C,H,N.

(30B) More Polar Diastereomer: m.p. 187°–188° C.; $DCI-NH_3$-MS, m/z (relative intensity), 616 ($MH^+$, 100%), 390 (10%), 345 (41%), and 275 (43%); Anal. ($C_{36}H_{61}N_3O_5$) C,H,N.

EXAMPLE 31

2-(4-(N-benzyl)-piperazin-1-yl)-acetic acid Amide of S(S)-Amino-1-cyclohexyl-3(R),4(S)-dihydroxy-6-methylheptane The title compound was made using the procedure of Example 10, 11, and 12 and the α-bromohexanoate was replaced with benzyl bromoacetate. $DCI-NH_3$-MS, m/z 460 ($MH^+$, 100%); Anal. ($C_{27}H_{45}N_3O_3$) C,H,N; m.p. 169°–171° C.

EXAMPLE 32

2-(4-Benzyl-piperazin-1-yl)-hexanoic acid Amide of 2(S)-Amino-1-cyclohexyl-3(R),4(S)-dihydroxy-6-methylheptane The desired final product was made using the same procedure as described in Example 10, 11, and 12.

(32A) Less Polar Diastereomer: $DCI-NH_3$-MS, m/z 516 ($MH^+$, 100%) and 245 (48%); Anal. ($C_{31}H_{53}N_3O_3$.-$H_2O$) C,H,N.; m.p. 146°–147° C. (32B) More Polar Diastereomer: MS m/z 516 ($MH^+$, 100%), m.p. 150°–151° C.

EXAMPLE 33

2-(3R-Benzyl-piperazin-1-yl)-hexanoic acid Amide of 2(S)-Amino-1-cyclohexyl-3(R),4(S)-dihydroxy-6-methylheptane Made using the procedure as described in Example 28, 29, and 30.

(33A) Less Polar Diastereomer: $DCI-NH_3$-MS, m/z relative intensity), 516 ($MH^+$, 100%), 428 (10%), 290 (15%), 245 (58%); $^1H$ NMR ($CDCl_3$, 300 MHz) δ: 7.32–7.20 (m,5H), 6.96 (d,J=9Hz,1H), 4.43 (b s,1H), 4.32 (t d,J=11Hz,1H), 3.23 (m,2H), 2.93 (m,3H), 2.78 (t d,J=11Hz,4H), 2.60 (dd,J=11Hz,1H), 2.48 lb s,1H), 2.18 (b s,1H), 2.0ε (t,J=11Hz,1H), 1.92 (b s,1H), 1.70 (m,8H), 1.40–1.15 (m,14H), 0.89 (t,J=7Hz,3H); Anal. $C_{31}H_{53}N_3O_3$) C,H,N; m.p. 130°–132° C.

(33B) More Polar Diastereomer: MS, m/z 516 ($MH^+$, 100%); m.p. 150°–151° C.

EXAMPLE 34

2-(3S-Benzyl-4-N-tert-butyloxycarbonyl-piperazin-1-yl)-hexanoic acid Amide of 2(S)-Amino-1-cyclohexyl-3(R),4(S)-dihydroxy-6-methylheptane The title compound was synthesized following the procedure described in Example 28, 29, 30.

(34A) Less Polar Diastereomer: $DCI-NH_3$-MS, m/z relative intensity), 616 ($MH^+$, 100%), 345 (40%); $^1H$ NMR ($CDCl_3$, 300 MHz), 7.38–7.12 (m,7H), 6.85 (d,J=10.5Hz,1H), 4.43–4.27 (m,3H), 3.9 (b s,1H), 3.27–3.12 (m,3H), 2.97 (t,J=6.0Hz,1H), 2.81 (m,2H), 2.72 (d,J=12Hz,1H), 2.25 (m,2H), 1.96–1.6 (m,10H), 1.57–1.4 (m,4H), 1.36 (s,9H), 1.35–1.12 (m,8H), 0.86 (t,J=7Hz,3H); Anal. ($C_{36}H_{61}N_3O_5$) C,H,N; m.p. 158°–160° C.

(34B) More Polar Diastereomer: MS, m/z 616 ($MH^+$, 100%); m.p. 130°–132° C.

EXAMPLE 35

2-(3R-Benzyl-4-N-dimethylaminocarbonyl-piperazin-1-yl)-hexanoic acid Amide of 2(S)-Amino-1-cyclohexyl-3(R),4(S)-dihydroxy-6-methylheptane The title compound was synthesized following the procedure described in Example 28, 29, and 30.

(35A) Less Polar Diastereomer: FAB-MS, m/z (relative intensity), 587 (MH$^+$, 40%), 316 (100%), 286 (20%), 271 (18%), 244 (50%), 224 (20%); Anal. ($C_{34}H_{58}N_4O_4.\frac{1}{2}H_2O$) C,H,N; m.p. 150°-151° C.

(35B) More Polar Diastereomer: MS, m/z 587 (MH$^+$); m.p. 85°-86° C.

EXAMPLE 36

3-(4-Thiazolyl)-2-(R,S)-(3R-benzyl-4-N-benzylpiperazin-1-yl)-propionic acid Amide of 2(S)-Amino-1-cyclohexyl-3(R),4(S)-dihydroxy-6-methylheptane Methyl 2-(3R-Benzyl-4N-benzyl-piperazyl)-acetate was deprotonated with NaN(TMS)$_2$ in THF at 0° C. The carbanion was then reacted with 3-chloromethyl thiazole and which on aqueous work-up and purification gave methyl 3-(3-thiazolyl)-2-(3R-benzyl-4N-benzyl-piperazyl)-propionate. The methyl ester was hydrolyzed with LiOH and then coupled to the amine following the procedure in Example 32. FAB-MS, m/z 647 (MH$^-$, 100%); Anal. ($C_{38}H_{54}N_4O_3S.2\ H_2O$) C,H,N; m.p. 63°-65° C.

EXAMPLE 37

2-(3R-Benzyl-4-N-(4-N'-methylpiperazin-1-yl-carbonyl)piperazin-1-yl)-hexanoic acid Amide of 2(S)-Amino-1-cyclohexyl-3(R),4(S)-dihydroxy-6-methylheptane The title compound was made following the procedure described in Example 28, 29, and 30.

Mixture of Diastereomers: FAB-MS, m/z 642 (MH$^+$, 100%), 371 (68%) and 271 (40%); Anal. ($C_{37}H_{63}N_5O_4.1.5\ H_2O$) C,H,N; m.p. 155°-157° C.

EXAMPLE 38

2-(3R-Benzyl-4-N-(morpholin-1-yl-carbonyl)-piperazin)-1-yl-hexanoic acid Amide of 2(S)-Amino-1-cyclohexyl-3(R),4(S)-dihydroxy-6-methylheptane The title compound was made following the procedure described in Example 28, 29, and 30.

(38A) Less Polar Diastereomer: FAB-MS, m/z (relative intensity), 629 (MH$^+$, 60%), and 358 (100%); $^1$H NMR (CDCl$_3$, 300 MHz) δ: 7.30-7.14 (m,5H), 6.69 (d,J=9Hz,1H), 4.48 (b s,1H), 4.37 (t of d,J=11Hz,1H), 4.15 (b s,1H), 3.54-3.32 (m,6H), 3.24 (b s,2H), 3.17-2.74 (m,10H), 2.58 (dd,J=12Hz,1H), 2.31 (t d,J=12Hz,1H), 2.12 (b s,1H), 1.94 (m,1H), 1.67 (m,9H), 1.40-1.15 (m,11H), 0.91 (t,J=7Hz,3H); Anal. ($C_{36}H_{60}N_4O_5.\frac{1}{2}H_2O$) C,H,N; m.p. 173°-174° C.

(38B) More Polar Diastereomer: FAB-MS, m/z (relative intensity), 629 (MH$^+$, 88%), and 358 (100%); $^1$H NMR (CDCl$_3$, 300 MHz) δ: 7.31-7.16 (m,5H), 6.54 (d,J=9Hz,1H), 4.57 (b s,1H), 4.37 (m,1H), 4.22 (b s,1H), 3.57-3.30 (m,6H), 3.25 (b s,2H), 3.14-2.74 (m,10H), 2.45 (dd,J=11Hz,1H), 2.32 (t d,J=11Hz,1H), 1.94 (b s,1H), 1.80-1.60 (m,10H), 1.44-1.14 (m,11H), 0.92 (m,6H), 0.88 (t,J=7Hz,3H); Anal. $C_{36}H_{60}N_4O_5.H_2O$) C,H,N; m.p. 104°-105° C.

EXAMPLE 39

N-tert-Butyloxycarbonyl-N-allyl-D-Phe-OMe

D-Phe-OMe (20.75 g, 116 mmol) was dissolved in CH$_2$Cl$_2$ (200 ml) and reacted with $^t$Boc-anhydride (25.31 g, 116 mmol) at 0° C. for 16 h. At the end, solvent and $^t$BuOH was removed under high vacuum which gave 29.5 g (91% yield) of the desired $^t$Boc-Phe-OMe; R$_f$=0.45 (Hexane-AcOEt, 2:1); $^1$H NMR (CDCl$_3$, 60 MHz) δ: 7.13 (m,5H), 4.93 (m,1H), 4.50 (m,1H), 3.65 (s,—OCH$_3$,3H), 3.05 (d,J=6Hz,2H), and 1.43 (s,$^t$Bu,9H). Boc-Phe-OMe (20 g, 72 mmol) from the previous reaction was dissolved in THF (90 ml) and cooled to −78° C. To this was added sodium bis(trimethylsilyl)-amide (1M in THF, 78 ml) over 5 min period. The yellow solution was stirred at −78° C. for 1 h and then reacted with allyl bromide (12 ml, 138 mmol) at −78° C. for 2 h and then at room temperature overnight. The reaction was diluted with ether-hexane (1:1) and 2N HCl (pH≈3). The organic layer was washed with brine, dried over MgSO$_4$ and concentrated in vacuo to give 21.56 g crude product which on chromatographic purification (silica gel, Hexane-AcOEt, 4:1) gave 1.80 g starting material and 18.20 g (80% yield) of the desired N-allylated product; R$_f$=0.40 (Hex-AcOEt, 2:1, R$_f$=0.31 for starting material); DCI-NH$_3$-MS, m/z (relative intensity), 320 (MH$^+$, 100%), 281 (23%), and 264 (20%).

EXAMPLE 40

N-tert-Butyloxycarbonyl-N-formylmethyl-D-Phe-OMe

Ozone was passed into a solution containing the allyl ester from Example 39 (4 g, 12.5 mmol) in 180 ml CH$_2$Cl$_2$ at −78° C. until the color turned light blue. Excess O$_3$ was blown out with O$_2$ and the ozonide was cleaved by adding Me$_2$S (6 ml). The reaction mixture was kept stirring at room temperature overnight. At the end, solvent was removed under reduced pressure and the crude product was purified by column chromatography (silica gel, Hex-AcOEt, 3:1) which on drying gave 3.50 9 (86% yield) of the desired aldehyde; R$_f$=0.40 (Hex-AcOEt, 1:1, R$_f$=0.64 for the starting material); NMR shows two sets of signals which we believe could be due to the presence of rotamers. For convenience, we will assign the letter 'L' for the major component and 'M' for the minor component. These two components were inseparable by tlc: $^1$H NMR (CDCl$_3$, 300 MHz) δ: 9.39 (t,M,J=1Hz,-CHO), 9.29 (t,L,J=1Hz,—CHO), 7.33-7.10 (m,5H), 5.15 (dd,L,J=6,10Hz, NH—CH—COOCH$_3$), 4.68 (dd,M,J=4,5,10Hz,NH—CH—COOCH$_3$), 3.77 (s,M,—OCH$_3$), 3.75 (s,L,—OCH$_3$), 3.33 (m,2H), 2.97 (m,2H), 1.36 (s,M,—O$^t$Bu) and 1.34 (s,L,—O$^t$Bu).

EXAMPLE 41

Dimethyl (2R-Benzyl-7S-butyl-3-tert-butyloxycarbonyl-3,6-diaza)-suberate

Sodium cyanoborohydride (685 mg, 10.9 mmol) was slowly added to a solution containing the aldehyde from Example (3.50 g, 10.9 mmol) and nor-Leu-OMe (1.58 g, 10.9 mmol) in isopropanol (50 ml) at 0° C. The reaction was stirred at room temperature overnight. At the end, excess borohydride was quenched with dil HCl at 0° C. (pH adjusted to 3–4) and then basified with K$_2$CO$_3$. The crude product was extracted with AcOEt and purified by column chromatography (silica gel, Hex-AcOEt, 3:1, during this process, part of the open form starts cyclizing and produces the lactam) which on further drying under reduced pressure gave 4.05 g (82% yield) of the desired product; DCI-NH$_3$-MS, m/z (relative intensity), 451 (MH$^+$, 100%) and 158 (25%); $^1$H NMR (CDCl$_3$, 300 MHz) δ: 7.30–7.10 (m,5H), 5.12 (dd,J=5,10Hz,1H), 4.72 (m,1H), 3.75 (b s,2H), 3.70 (s,—OCH$_3$,3H), 3.68 (s,—OCH$_3$,3H), 3.35–3.10 (m,2H), 2.80 (m,2H), 2.48 (m,2H), 1.90 (m,1H), 1.45 (s,$^t$Bu,9H), 1 60–1.20 (m,1H), and 0.88 (t,J=7,7Hz,3H).

EXAMPLE 42

Methyl
2-(3R-Benzyl-4N-tert-butyloxycarbonyl-2-keto-piperazin-1-yl)-hexanoate

The amine ester (4 gm, 8.88 mmol) from Example 41 was dissolved in xylene (50 ml) and heated at reflux for 2 h. At the end, solvent was removed under reduced pressure and the crude product was purified by column chromatography (silica gel, Hex-AcOEt, 9:1) to give 3.60 g (97% yield) of the desired lactam; DCI-NH$_3$-MS, m/z (relative intensity), 436 (MNH$_4$$^+$, 30%) and 419 (MH$^-$, 100%); $^1$H NMR (CDCl$_3$, 300 MHz) δ: 7.30–7.10 (m,5H), 5.15 (dd,J=5,10Hz,1H), 4.75 (m,1H), 4.08 (b d,J=12Hz,1H), 3.70 (s,—OCH$_3$,3H), 3.40–3.05 (m,3H), 2.88 (t,J=12Hz,1H), 1.99 (m,1H), 1.70 (m,1H), 1.30 (s,$^t$Bu,9H), 1.50–1.20 (m,5H), and 0.90 (t,J=7Hz,3H); High Res. Mass: Calculated 419.2546 for C$_{23}$H$_{35}$N$_2$O$_5$, found 419.2546; Anal. (C$_{23}$H$_{34}$N$_2$O$_5$) C,H,N.

EXAMPLE 43

2-(3R-Benzyl-4N-tert-butyloxycarbonyl-2-keto-piperazin-1-yl)-hexanoic acid

The ester from Example 42 (0.65 9, 1.56 mmol) was dissolved in MeOH (10 ml) and hydrolyzed with LiOH (2 ml of 1N solution in H$_2$O) at room temperature overnight. The reaction was acidified with HCl-Dioxane (4.5M in HCl, 0.45 ml used) and the solvent was removed under reduced pressure. The crude acid thus detained was used for the next reaction without further purification. DCI-NH$_3$-MS, m/z (relative intensity), 422 (MNH$_4$$^+$, 18%), 405 (MH$^+$, 100%), 361 (21%), 349 (40%), 305 (18%), and 230 (20%).

EXAMPLE 44

2(S)-(3R-Benzyl-4N-tert-butyloxycarbonyl-2-keto-piperazin-1-yl)-hexanoic acid Amide of
2(S)-Amino-1-cyclohexyl-3(R),4(S)-dihydroxy-6-methylheptane The crude acid (300 mg, 0.74 mmol) from Example 43 was dissolved in DMF (6 ml) and coupled to the amine from Example 2 (207 mg, 0.74 mmol) in the presence of EDAC (142 mg, 0.74 mmol), HOBT (300 mg, 2.22 mmol), and N-methylmorpholine (0.081 ml, 0.74 mmol) at −20° C. for 2 h and then at room temperature overnight. The following day, the reaction mixture was poured onto a slurry of aqueous NaHCO$_3$ and AcOEt. The organic layer was washed with brine, dried over MgSO$_4$ and finally concentrated in vacuo. Purification of the crude product by column chromatography (silica gel, Hex-AcOEt, 4:1) gave 354 mg of the desired product (76% yield); FAB-MS, 630 (MH$^+$); $^1$H NMR (CDCl$_3$, 300 MHz) δ: 7.30–7.10 (m,5H), 6.58 (b s,1H), 4.99 (t,J=7Hz,1H), 4.75 (b s,1H), 4.40–4.15 (m,2H), 3.80–3.60 (m,2H), 3.40–2.80 (m,5H), 2.05–1.05 (overlapping multiplets,22H), 1.20 (s,$^t$Bu,9H), 0.97 (t,J=7Hz,3H), 0.88 (d,J=7Hz,6H); Anal. (C$_{36}$H$_{59}$n$_3$O$_6$) C,H,N; m.p. 87°–88° C.

EXAMPLE 45

3R-(4-Imidazolyl)-2(R)-(3R-benzyl-4-N-tert-butyloxycarbonyl-2-keto-piperazin-1-yl)-propionic acid Amide of
2(S)-Amino-1-cyclohexyl-3(R),4(S)-dihydroxy-6-methylheptane The title compound was made following the procedure described in Example 39-44. The nor-Leu-OMe was replaced with His-OME.

R$_f$=0.74 (CH$_2$Cl$_2$-EtOH, 9:1, NH$_3$-tank); DCI-NH$_3$-MS, m/z (relative intensity), 654 (MH$^+$, 100%), 636 (10%), and 554 (6%); $^1$H NMR (CDCl$_3$, 300 MHz) δ: 7.53 (d,J=1Hz,1H), 7.30–7.10 (m,6H), 6.88 (s,1H), 6.71 (d,J=9Hz,1H), 5.39 (m,1H), 4.72 (m,1H), 4.35 9m,1H), 4.17 (m,1H), 3.50–2.70 (m,8H), 1.90–1.50 (m,8H), 1.50–1.10 (m,11H), 1.20 (s,$^t$Bu,9H), 0.93 (d,J=7Hz,3H), and 0.81 (d,J=7Hz,3H); Anal. (C$_{36}$H$_{55}$O$_6$N$_5$). C,H,N.

EXAMPLE 46

3S-(4-Imidazolyl)-2(S)-(3R-benzyl-4-N-tert-butyloxycarbonyl-2-keto-piperazin-1-yl)-hexanoic ac:d Amide of
2(S)-Amino-a-cyclohexyl-3(R),4(S)-dihydroxy-6-methylheptane This is the less polar diastereomer of the compound as described in Example 45.

R$_f$=0.80 (CH$_2$Cl$_2$-EtOH, 9:1, NH$_3$-tank); DCI-NH$_3$-MS, m/z (relative intensity) 654 (MH$^+$, 100%), 636 (45%), 596 (16%), (14%), and 411 (8%).

EXAMPLE 47

2(S)-(3R-Benzyl-4-N-(4-(N'-methyl)-piperazin-1-yl-carbonyl)-2-keto-piperazin-1-yl)-hexanoic acid Amide of
2(S)-Amino-1-cyclohexyl-3(R),4(S)-dihydroxy-6-methylheptane The title compound was made following the procedure as described in Example 39-44. The N-methylpiperazyl group was attached using dry phosgene gas.

DCI-NH$_3$-MS, m/z (relative intensity), 656 (MH$^+$, 100%), 638 (15%), 413 (63%), 342 (15%), and 317 (24%)., Anal. (C$_{33}$H$_{61}$N$_5$O$_5$.H$_2$O) C,H,N; m.p. 132°–134° C.

EXAMPLE 48

2(S)-(3R-Benzyl-4-N-(N-methyl-N-(methoxymethoxyethyl)-aminocarbonyl)-2-keto-piperazin-1-yl)-hexanoic acid Amide of
2(S)-Amino-1-cyclohexyl-3(R),4(S)-dihydroxy-6-methylheptane This compound was made using the procedure described in Example 39-44. N-methylethanolamine was first protected as MOM ether and then coupled to the ring nitrogen using phosgene gas.

DCI-NH$_3$-MS, m/z (relative intensity), 675 (MH$^+$, 98%), 657 (20%), 432 (100%), 336 (80%), 314 (45%), and 304 (20%); Anal. (C$_{37}$H$_{62}$N$_4$O$_7$) C,H,N; m.p. 68°–69° C.

EXAMPLE 49

3-(4-Thiazolyl)-2-(3R-benzyl-4-N-morpholin-1-yl-carbonyl-2-keto-piperazin-1-yl)-propionic acid Amide of 2(S)-Amino-1-cyclohexyl-3(R),4(S)-dihydroxy-6-methylheptane This compound was made following the procedure described in Example 39-44. A racemic mixture of thiazole alanine was used as the starting material. The morpholine group was attached using phosgene reaction.

(52A) Less Polar Diastereomer: DCI-$NH_3$-MS, m/z (relative intensity), 684 ($MH^+$, 100%), 666 (75%), 473 (32%), 461 (28%), 441 (50%), and 304 (24%); Anal. ($C_{36}H_{53}N_5O_6S \cdot \frac{1}{2} H_2O$) C,H,N; m.p. 80°-81° C. (52B) More Polar Diastereomer: $MH^+$ at 684; m.p. 179°-180° C.

EXAMPLE 50

2(S)-(3R-Benzyl-4-N-morpholin-1-yl-carbonyl-2-keto-piperazin-1-yl)-hexanoic acid Amide of 2(S)-Amino-1-cyclohexyl-3(R),4(S)-dihydroxy-6-methylheptane The title compound was synthesized following the procedure described in Example 39-44. The morpholine was attached using phosgene as the carbonyl anchor.

FAB-MS, m/z (relative intensity). 643 ($MH^+$, 30%), 627 (38%), 400 (100%), 344 (35%), and 257 (30%); Anal. ($C_{36}H_{58}N_4O_6 \cdot \frac{1}{2}H_2O$), C,H,N; m.p. 139°-140° C.

EXAMPLE 51

3-(4-Imidazolyl)-2(S)-(3R-benzyl-4-N-morpholin-1-yl-carbonyl-2-keto-piperazin-1-yl)-propionic Acid Amide of 2(S)-Amino-1-cyclohexyl-3(R),4(S)-dihydroxy-6-methylheptane The desired compound was made following the procedure described in Example 39-44. The morpholine group was attached using phosgene method. In this case His-OMe was used as one of the starting materials.

DCI-$NH_3$-MS, m/z (relative intensity), 667 ($MH^+$, 86%), 649 (100%), and 304 (50%); Anal. ($C_{36}H_{54}N_6O_6 \cdot 2\frac{1}{2} H_2O$) C,H,N; m.p. 176°-177° C.

EXAMPLE 52

Benzyl 2-Benzyl-5-hydroxy-pentanoate

δ-Valerolactone (7.14 g, 71.35 mmol) was slowly added to a flask containing freshly made LDA (80 mmol) in 200 ml of dry THF at −78° C. under $N_2$. After stirring the solution for 40 min at −78° C., benzyl bromide (12.20 g, 71 mmol) was added. The bath was removed and the reaction was stirred at room temperature for 40 min. At the end, the crude mixture was poured to a slurry of AcOEt-Hexane and 0.5 N $H_2SO_4$. The organic layer was washed with brine, dried over $MgSO_4$ and concentrated in vacuo. The crude product was then dissolved in 60 ml of MeOH and 10 ml of concentrated $H_2SO_4$. After stirring the solution at room temperature overnight, the acid was neutralized with aqueous $NaHCO_3$. The crude product was extracted with AcOEt-Hexane and purified by column chromatography (silica gel, AcOEt-Hexane, 1:3) which gave 6.2 g (40% yield) of methyl 2-benzyl-5-hydroxy-pentanoate; 1H NMR ($CDCl_3$, 300 MHz) δ: 7.30-7.10 (m,5H), 3.58 (s,3H,$OCH_3$, 3.56 (t,J=6Hz,2H), 2.95 (dd,J=7,12Hz,1H), 2.75 (dd,J=6,12Hz,1H), 2.69 (m,1H), 2.15 (s,1H,-OH), and 1.70-1.50 (m,4H).

The methyl ester (4 g, 18 mmol) from the above reaction was dissolved in 10 ml of benzyl alcohol and 50 ml of Benzene. After adding TsOH.$H_2O$ (0.5 g, 2.63 mmol), the contents were heated under reflux for 2 h. Once the required amount of $H_2O$ had been collected, the solution was concentrated under reduced pressure. The crude product was purified by column chromatography (silica gel, Hexane-AcOEt, 3:1) which gave 3.8 g (71%) of the title compound: 7.40-7.10 (m,10H), 5.03 (s,2H), 3.57 (t,J=6Hz,2H), 3.00-2.60 (m,≈4H), and 1.80-1.40 (m,4H).

EXAMPLE 53

Benzyl 2-Benzyl-5-oxo-pentanoate

A solution of oxalyl chloride (0.9 ml, 10 mmol in 25 ml of $CH_2Cl_2$) was slowly added to a flask containing DMSO (1.5 ml, 21 mmol in 3 ml $CH_2Cl_2$ at −60° C. under $N_2$. After 5 min, the alcohol from Example 52 (3 g, 10 mmol, 5 ml $CH_2Cl_2$) was added dropwise over 5 min period. After stirring the contents for 30 min, $Et_3N$ (6.3 ml, 45 mmol) was added and the mixture was warmed to room temperature. The suspension was stirred for 1 h and then poured to a slurry of $CH_2Cl_2$-$H_2O$-ice. The organic layer was washed with dilute HCl, brine, dried over $MgSO_4$, and finally concentrated in vacuo. The crude product was purified by column chromatography (silica gel, Hexane-AcOEt, 4:1) which gave 2.85 g (95%) of the title compound: 1H NMR ($CDCl_3$, 300 MHz) δ: 9.70 (t,J=1Hz,1H,—CHO), 7.40-7.10 (m,10H), 5.05 (s,2H), 3.95 (t,J=6Hz,1H), 2.75 (m,2H), 2.41 (m,2H), and 1.90 (m,2H); DCI-$NH_3$-MS, m/z 314 ($MNH_4^+$, 100%), and 297 ($MH^+$, 20%).

EXAMPLE 54

Methyl 2-(4-Benzyl-4-carbobenzyloxy-butyl-amino)-hexanoate

To a flask containing the aldehyde from Example 53 (0.9 g, 3 mmol) and methyl ester of L-nor-leucine (440 mg, 3 mmol) in isopropanol (3 ml) at 0° C. under $N_2$, was added $NaCNBH_3$ (190 mg, 3 mmol). The suspension was stirred at 0° C. for 2 h and then at room temperature for 12 h. The following day, the flask was cooled to 0° C. and the excess $NaCNBH_3$ was destroyed with aqueous dilute HCl. After basification of the aqueous layer with $Na_2CO_3$, the crude product was extracted with AcOEt, and purified by column chromatography which gave 1.20 g (94%) of the title compound.

EXAMPLE 55

Methyl 2-(3-Benzyl-2-oxo-piperidin-1-yl)-hexanoate

The benzyl ester from Example 54 was dissolved in 10 ml of MeOH and hydrogenolyzed ($H_2$ in balloon in the presence of 10% Pd/C, 0.3 g) at room temperature for 3 h. At the end, the catalyst was removed by filtration and the crude product, after removal of MeOH under reduced pressure, was added to a flask containing HOBT (967 mg, 7.16 mmol), $Et_3N$ (0.33 ml, 2.4 mmol) in 10 ml of DMF at 0° C. After 5 min, EDAC (458 mg, 2.38 mmol) was added and the reaction was slowly brought to room temperature. At the end of 13 h at room temperature, the contents was poured onto a slurry of aqueous $NaHCO_3$ and AcOEt. The product was extracted and purified by Column chromatography (silica gel, Hexane-AcOEt, 4:1) which gave a mixture of two diastereomers (340 mg, 45%, 1:1 ratio, dl mixture at the benzyl centre): DCI-NH$_3$-MS, m/z 318 (MH$^+$, 100%).

EXAMPLE 56

2(RS)-(3-Benzyl-2-oxo-1-piperidin-1-yl)-hexanoic acid Amide of 2(S)-Amino-1-cyclohexyl-3(R),4(S)-dihydroxy-6-heptane The methyl ester (305 mg, 0.73 mmol) from Example 55 was dissolved in MeOH-Oioxane (3 ml+3 ml) and hydrolyzed with LiOH (100 mg, 3 ml of H$_2$O) at room temperature for 3 h. At the end, the flask was cooled to 0 C and the pH was adjusted to 2 with dilute HCl. The free acid after extraction with AcOEt, was dried under high vacuum for 2 h.

The crude acid (305 mg, 1 mmol) was then dissolved in DMF (4 ml) and coupled to amine.HCl (from Example 2, 280 mg) in the presence of HOBT (405 mg, 3 mmol), EDAC (192 mg, 1 mmol), and Et$_3$N (0.139 ml, 1 mmol). The reaction was stirred at 0° C. for 3 h and then at room temperature overnight. The following day, the contents were diluted with aqueous NaHCO$_3$, and AcOEt. The organic layer was washed with brine, dried over MgSO$_4$, and concentrated in vacuo. The crude product (containing two diastereomers) was carefully purified by column chromatography (silica gel, Hexane-AcOEt, 4:1) which gave 392 mg (74% total yield) of the title compound.

(56A) Less Polar Diastereomer DCI-NH$_3$-MS, m/z 529 (MH$^+$, 100%), and 286 (41%);

(56B) More Polar Diastereomer DCI-NH$_3$-MS, m/z 529 (MH$^+$, 100%).

EXAMPLE 57

(4S)-3-Benzyloxycarbonyl-4-phenylmethyl-5-oxooxazolidine

Following the procedure of Ben-Ishai (J. Am. Chem. Soc., 1957, 79, 5736), N-Cbz-L-phenylalanine (10.0 gm, 33.4 mmol), paraformaldehyde (3.0 gm, 100.2 mmol), and p-toluenesulfonic acid (0.64 gm, 3.3 mmol) were suspended in toluene (150 ml). The reaction was brought to reflux and water removed azeotropically through the agency of a Dean-Stark trap until collection of water ceased (0.5-2.0 h). After cooling, the reaction mixture was diluted with ethyl ether, washed (1X, saturated aqueous NaHCO$_3$; 1X, brine), dried (Na$_2$SO$_4$), filtered, and concentrated in vacuo to provide a solid after cooling. Recrystallization from ethyl acetate/hexanes provided, after the collection of two crops, the pure title compound (9.26 gm, 89%). m.p.=85.5°-86.5° C.; MS (CI) (M+NH$_4$)$^+$=329, (M+H)$^+$=312; Anal. Calcd. for C$_{18}$H$_{17}$NO$_4$: C, 69.44; H, 5.50; N, 4.50. Found: C, 69.33; H, 5.48; N, 4.40.

EXAMPLE 58

(4S,4R)-3-Benzyloxycarbonyl-4-phenylmethyl-4-(1-(2-propenyl))-5-oxooxazolidine

A 250 ml round bottom flask was charged with the resultant compound from Example 57 (5.32 g, 17.1 mmol), THF (40 ml), and a magnetic stir bar. The flask was fit with a septum, a gas outlet, and cooled to −78° C. while flushing with N$_2$. To the flask was added via syringe potassium hexamethyldisilylamide (36.6 ml, 18.8 mmol, 0.5M solution in toluene); the resulting solution was stirred 0.5 h at −78° C. The allyl bromide (2.22 ml, 25.6 mmol) was passed through a neutral alumina pad just prior to addition as a single neat portion to the enolate solution. The reaction was quenched with saturated aqueous NH$_4$Cl after being judged complete (1-2 h). The quenched mixture was partitioned between brine and ethyl ether. The organic layer was washed (1X, brine), dried (Na$_2$SO$_4$), and concentrated in vacuo to provide a free-flowing light brown liquid. Purification by plug filtration through a pad of silica gel (100 g; 20% ethyl acetate/hexanes; 20 ml fractions) provided the pure title compound (4.56 g, 76%) as a colorless thick oil. MS (EI) M$^+$=351 (weak), (M-CH$_2$CHCH$_2$)$^+$=310; Anal. Calcd. for C$_{21}$H$_{21}$NO$_4$.0.25 H$_2$O: C, 70.92; H, 6.09; N, 3.94. Found: C, 70.69; H. 6.07; N, 3.94.

EXAMPLE 59

(2R,2S)-Methyl-2-((benzyloxycarbonyl)amino)-2-(phenylmethyl)-pent-4-eneoate

A 100 ml round bottom flask was charged with a magnetic stir bar, the resultant compound from Example 58 (4.28 g, 2.2 mmol), 95% ethanol (50 ml), water (10 ml), and sodium hydroxide (0.97 g, 24.4 mmol). The reaction was refluxed under N$_2$ for 1 h, cooled, concentrated in vacuo, and the resulting slurry poured into excess 10% aqueous HCl. The aqueous solution was extracted with ethyl ether (2X). The combined organic layers were washed (2X, brine), dried (Na$_2$SO$_4$), filtered, and concentrated in vacuo to ~100 ml. The ethereal solution was cooled to 0° C. and treated with excess diazomethane and slowly warmed to rt over 1 h. Glacial acetic acid was added dropwise until the excess diazomethane was consumed. The resulting solution was concentrated in vacuo and chased with toluene (2×, 150 ml) to provide a light brown liquid. Filtration through a short silica gel column (100 gm; 20% ethyl acetate/hexane; 100 ml fractions) provided the pure title compound (3.91 g, 91%).

EXAMPLE 60

(2R,2S)-Methyl-2-((benzyloxycarbonyl)amino)-2-(methylcarboxaldehyde)-3-phenyl-propanoate A 250 ml round bottom flask was charged with the resultant compound from Example 59 (0.619 g, 1.75 mmol), dichloromethane (20 ml), and a magnetic stir bar. The reaction solution was cooled to −78° C. and ozone bubbled into the solution until a light blue color persisted. The excess ozone was purged from the reaction with N$_2$ until the blue color was removed. Excess methyl sulfide (390 mcL, 5.25 mmol) was added to the −78° C. solution, the cooling bath removed, and the reaction warmed to −0° C. Concentration in provided the title compound (0.69 g, 110%). The unpurified aldehyde was used without further purification and could be stored in the freezer (T≅10° C.) for up to 2 months. MS (EI) (M+H)$^+$=356 (weak).

EXAMPLE 61

(2S)-Methyl-((3R,3S)-((benzyloxycarbonyl)amino)-3-phenylmethyl-2-oxo-1-pyrrolidinyl)-3-(4-imidazolyl)-propionate An adaptation of the procedure of Borch (J. Am. Chem. Soc., 1971, 93, 2897) was followed for the reductive amination step. A flask was charged with the aldehyde resulting from Example 63 (217 mg, 0.611 mmol), the bis hydrochloride salt of methyl L-histidine (148 mg, 0.611 mmol), anhydrous sodium actetate (100 mg, 1.22 mmol), and freshly activated 4 Å molecular sieves (0.61 gm). The sodium cyanoborohydride (77 mg, 1.22 mmol) was added in a single portion and the reaction stirred at rt for 3 h. Excess 10% aqueous HCl was added to adjust the pH to ~2. The resulting mixture was then adjusted to pH≅10 with saturated aqueous Na₂CO₃ and extracted with ethyl acetate (2×). The combined organic layers were washed (2×, brine), dried (Na₂SO₄), filtered, and concentrated in vacuo to provide the unpurified aminodiesters (230 mg). The title compounds were obtained by heating the aminodiesters (186.3 mg, 0.372 mmol) in an ~0.1M solution of 1:1 (v:v) toluene:-dimethoxyethane containing HOBT (49 mg, 0.372 mmol) at 100° C. in a resealable tube for 3-8 h. The volatiles were removed in vacuo and the resulting slurry taken up in ethyl acetate, washed (1×, saturated aqueous Na₂CO₃; 1×, brine), dried (Na₂SO₄), filtered, and concentrated in vacuo. Purification by silica gel chromatography using methanol:chloroform mixtures provided the title compounds as a 1:1 mixture at the lactam quaternary center. MS (CI) $(M+H)^+ = 477$; Anal. Calcd. for $C_{26}H_{28}N_4O_5 \cdot 0.75\ H_2O$: C, 63.73; H, 6.07; N, 11.43. Found: C, 63.43; H, 5.76; N, 11.08.

EXAMPLE 62

(2S)-((3R,3S)-((Benzyloxycarbonyl)amino)-3-phenyl-methyl-2-oxo-1-pyrrolidinyl)-3-(4-imidazolyl)propionic acid The resultant compound from Example 61 (103 mg, 0.22 mmol) was dissolved in dimethoxyethane (1 ml) and water added until the solution just clouded. To the resulting solution was added LiOH.H₂O (10.0 mg, 0.24 mmol). The mixture was stirred at rt for 1 h, neutralized with HCl (105 μl of 4.1M HCl in dioxane), concentrated in vacuo, and dried under high vacuum to provide the title compound. MS (CI) $(M+H)^+ = 463$.

EXAMPLE 63

(3-((Benzyloxycarbonyl)amino)-3-phenylmethyl-2-oxo-1-pyrrolidinyl)-3-(4-imidazolyl)propionic acid Amide of
(2S,3R,4S)-2-amino-1-cyclohexyl-3,4-dihydroxy-6-methylheptane The resultant compounds of Example 62 (99.9 mg, 0.22 mmol) and 2 (60.4 mg, 0.22 mmol). HOBT (87.6 mg, 0.65 mmol), and N-methylmorpholine (47.m μl, 0.43 ml) were dissolved in dry DMF (0.86 ml) and cooled to −23° C. (CCl₄/dry ice bath) under N₂. To this mixture was added (3-dimethylaminopropyl)-3-ethylcarbodiimide hydrochloride (41.4 mg, 0.22 mmol) in a single portion. The reaction was stirred 3 h at −23° C. and warmed to rt as it stirred overnight. The reaction was poured into saturated aqueous NaHCO₃ and the resulting mixture extracted (2×, ethylacetate). The combined organic extracts were washed (1×, brine), dried (Na₂SO₄), filtered, and concentrated in vacuo. The resulting foam was purified by silica gel chromatography eluting with methanol chloroform mixtures to provide in the order of elution.

(63A): m.p.=(softening at 145° C.) 198.5°-201° C., Anal. Calcd. for $C_{39}H_{53}N_5O_6 \cdot 0.5\ H_2O$: C, 67.22; H, 7.81; N, 10.04. Found C, 67.29; H, 7.72; N, 9.70.

(63B): m.p.=113°-116° C. (bubbling); Anal. Calcd. for $C_{39}H_{53}N_5O_6$: C, 68.10; N, 7.77; N, 10.18. Found C, 67.76; H, 7.82; N, 9.88.

(63C): m.p.=88.5°-93° C. (bubbling).

EXAMPLE 64

(4R,5S)-4-methyl-5-phenyl-oxazolidine-2-one

Into a dry 300 ml single-necked, round-bottom flask equipped for magnetic stirring was placed 40.2 g (0.27 mol) of (1S,2R)-2-amino-2-phenylpropanol, 36 ml (35.1 g, 0.30 mol) of diethyl carbonate, and approximately 2 g of anhydrous potassium carbonate. The flask was fitted for distillation through a 12" vigreux column and placed in an oil bath preequilibrated to 150° C. The stirred solution was heated until ethanol distillation ceased (overnight). Upon cooling to room temperature, the contents of the flask solidified. The reaction product was dissolved in dichloromethane (200 ml), washed once with brine (50 ml), dried over anhydrous sodium sulfate, filtered, and concentrated under reduced pressure to give a colorless solid. Recrystallization from toluene afforded 40.8 g (85%) of A as a white solid, mp 120°-122° C. (Lit. mp 116°-117° C., Newman, M. S. et al., J. Amer Chem. Soc., 1951, 73:4199-4203).

EXAMPLE 65

(4R,5S)-4-methyl-5-phenyl-3-(3-phenyl-propionyl)ox-azolidine-2-one

A mechanically stirred solution of the resultant compound from Example 64 (10 g, 56.4 mmol) in dry THF (200 ml) under an atmosphere of nitrogen was treated with n-butyl-lithium in hexanes (1.05 equiv, 22.6 ml, 56.4 mmol, 2.5M) at −78° C. After stirring for an additional 20 min at −78° C., hydrocinnamoyl chloride (9.4 ml, 62 mmol, 1.1 equiv) was added and the reaction was allowed to warm to room temperature with stirring over 2 h. The clear reaction mixture was poured into 100 ml of saturated NH₄Cl. The organic layer was removed and the resulting aqueous layer extracted three times with dichloromethane. The combined organic extracts were washed once with brine, dried (anhydrous sodium sulfate), filtered, and concentrated under reduced pressure to afford a crude solid. This material was recrystallized from hot ethyl acetate/hexane at 0°-5° C. overnight. First crop yielded 12.9 g, mp 99°-100° C. Second crop afforded 3.6 g. Total yield 16.5 g (95%).

EXAMPLE 66

(4R,5S)-3[(2S)-3t-butoxycarbonyl-2-benzylpropionyl]-4-methyl-5-phenyl-oxazolidine-2-one To a stirred solution of the resultant compound from Example 65 (12.9 g, 41.7 mmol) in dry THF (100 ml) under nitrogen was added at −78° C. a solution of sodium hexamethyldisilylamide 45.9 ml (1M in THF). After 30 min, t-butyl bromoacetate (13.6 ml, 83.4 mmol) was added as a solution in THF. The resulting reaction mixture was stirred for 1 h at −78° C., quenched with sat. NH₄Cl solution (50 ml) and the entire reaction mixture partitioned between diethyl ether and water. The organic layer was separated and the aqueous layer extracted once with ether. The combined organic solutions were washed with 10% HCl, sat. NaHC₃O, brine, dried (Na₂SO₄). filtered, and concentrated. The resulting yellow oil was submitted to silica gel chromatography (flash): yield 12.4 g (70%).

EXAMPLE 67

Preparation of Benzyl
(2S)-2-Benzyl-3-t-butoxycarbonyl Propionate

To a stirred solution of dry benzyl alcohol (6.1 ml, 58.4 mmol) in dry THF (100 ml) and cooled to 0°–5° C. (ice-water bath) was added 17.5 ml (2.5M, 43.8 mmol) of n-butyl-lithium in hexane. After the addition was complete, a solution of the resultant compound from Example 66 (12.3 g, 29.2 mmol) in THF was added dropwise. After 1 h at 0°–5° C. the reaction was quenched by adding excess saturated aqueous NH₄Cl. The reaction mixture was poured into a separatory funnel and extracted with diethyl ether (2×100 ml). The combined extracts were washed with brine, dried (NaSO₄) and concentrated to give the desired product and benzyl alcohol as a yellow oil. The benzyl alcohol was removed and the product purified by flash chromatography; yield 9 g (87%).

EXAMPLE 68

(3R)-3-Benzyloxycarbonyl-3-phenylmethylpropionic acid

The resultant compound from Example 67 (2.5 g, 7.1 mmol) in methylene chloride (5 ml) was treated with trifluoro-acetic acid (5 ml). After stirring at 25° C. for 90 min, the solvent was evaporated to afford the title compound as a colorless solid (2.05 9. 100%); mp 48°–52° C.

EXAMPLE 69

Benzyl (2S)-4-hydroxy-2-phenylmethylbutanoate

Following the procedure described in Example 100, the resultant compound from Example 68 (2 g, 7.1 mmol) was converted to the title compound. MS (DCI): 302 $(M+NH_4)^+$, 285 $(M+H)^+$.

EXAMPLE 70

(3S)-3-Benzyloxycarbonyl-3-phenylmethylpropanal

Following the procedure described in Example 101, the resultant compound from Example 69 (350 mg, 1.2 mmol) was converted to the title compound.

EXAMPLE 71

Benzyl (2S)-2-(Imidazol-4-yl
methyl)-2-((3S)-phenylmethyl-2-oxopyrrolidin-1-yl)acetate Following the procedure described in Example 103, the resultant compound from Example 70 (450 mg, 1.6 mmol) was converted into the title compound. MS (DCI): 404 $(M+H)^+$.

EXAMPLE 72

(2S)-2-((1-tert-Butyloxycarbonyl)-imidazol-4-yl
methyl)-2-((3S)-phenylmethyl-2-oxopyrrolidinyl-1-yl)acetic acid Following the procedure described in Example 104, the resultant compound from Example 71 (390 mg, 0.79 mmol) was converted into the title compound. MS (DCI): 414 $(M+H)^+$.

EXAMPLE 73

(2S)-2-(Imidazol-4-yl
methyl)-2-((3S)-phenylmethyl-2-oxo-pyrrolidin-1-yl)acetic acid amide of
(2S,3R,4S)-2-amino-1-cyclohexyl-3,4-dihydroxy-6-methylheptane The resultant compound from Example 72 (160 mg, 0.4 mmol) was treated according to the procedure in Example 118 to afford the title compound; mp 109°–114° C. MS (DCI): 539 $(M+H)^+$.

Anal. Calcd. for $C_{31}H_{46}N_4O_4$.7 H₂O: C, 67.53; H, 8.67; N, 10.16. Found: C, 67.18; H, 8.45; N, 10.09.

EXAMPLE 74

(2S,4S)-3-Benzyloxycarbonyl-2-phenyl-4-phenylmethyl-5-oxooxazolidine

Following the procedure of Karady, Tett. Lett., 1984, 25:4337. N-Cbz-L-phenylalanine (25 g, 83.5 mmol), benzaldehyde (18 g, 170 mmol), and p-toluenesulfonic acid (11.2 g, 58 mmol) were suspended in 1,1,1-trichloroethane (300 ml). The solution was refluxed for 18 hr and the water was removed by azeotropic distillation using a Dean-Stark trap for liquids heavier than water. After cooling, the reaction was washed with saturated aqueous NaHCO₃ (3×50 ml), water (1×50 ml), dried over sodium sulfate and concentrated in vacuo to produce an orange oil. After about 1 h a solid crystallized from the oil and it was collected by vacuum filtration. The orange solid was recrystallized from ethyl acetate/hexane to produce colorless crystals (4.0 g, 12%); mp 120°–122° C. MS (CI): 405 $(M+NH_4)^+$, 388 $(M+H)^+$.

EXAMPLE 75

(2R,4R)-3-Benzyloxycarbonyl-2-phenyl-4-phenylmethyl-5-oxooxazolidine

Following the procedure described in Example 74, N-Cbz-D-phenylalanine (25 g, 83.5 mmol) was converted into the title compound.

EXAMPLE 76

(2S,4S)-3-Benzyloxycarbonyl-2-phenyl-4-phenylmethyl-4-(1-(2-propenyl))-5-oxooxazolidine A 250 ml round-bottom flask was charged with the resultant compound from Example 74 (3.75 g, 9.7 mmol), THF (100 ml), and a magnetic stir bar. While under a nitrogen atmosphere, the flask was cooled to −78° C. and via syringe potassium hexamethyldisilylamide (25 ml, 12.5 mmol, 0.5M solution in toluene) was added dropwise. After 15 min at −78° C., allyl bromide (1.76 g. 14.6 mmol, passed through neutral alumina prior to addition) was added over 1 min. After 1.5 h the reaction was quenched with saturated aqueous NH₄Cl (100 ml) and the layers were separated. The aqueous layer was extracted with ethyl acetate (3×100 ml) and the combined organic extracts were washed with saturated aqueous NaCl (2×50 ml), dried over Na₂SO₄ and concentrated in vacuo to afford a light yellow oil (4.4 g). Flash chromatography (100 g silica gel, 20% ethyl acetate/hexane, 8 ml fractions) afforded the product in 28-50. Concentrate like fractions to afford the title compound as a colorless solid (3.3 g, 80%); mp 102°–104° C. MS (DCI): 445 $(M+NH_4)^+$, 428 $(M+H)^+$.

EXAMPLE 77

(2R,4R)-3-Benzyloxycarbonyl-2-phenyl-4-phenylmethyl-4-(1-(2-propenyl))-5-oxooxazolidine Following the procedure outlined in Example 76, the resultant compound from Example 75 (2.1 g, 5.4 mmol) was converted into the desired compound.

EXAMPLE 78

(2S,4S)-3-Benzyloxycarbonyl-2-phenyl-4-phenylmethyl-4-(1-(3-hydroxypropyl))-5-oxooxazolidine The resultant compound from Example 76 (3 g, 7 mmol) was dissolved in dry THF (100 ml) and then treated with 9-BBN (0.5M in THF, 21 ml, 10.5 mmol). After stirring overnight at 25° C., excess 9-BBN was quenched by the dropwise addition of water (1 ml). The reaction flask was then immersed in a 25° C. water bath followed by the concurrent and dropwise addition of 3N NaOH (23 ml, 69 mmol) and 30% $H_2O_2$ (23 ml). Stirring was continued for 10 min after the addition was completed after which the solution was saturated with solid NaCl. The layers were separated and the aqueous layer was extracted with ether ($3 \times 50$ ml). The combined organic extracts were washed with saturated aqueous $NaHCO_3$ ($2 \times 50$ ml), dried over $Na_2SO_4$, and concentrated in vacuo to afford a colorless solid. Flash chromatography (100 g silica gel, 40% ethyl acetate/hexane, 7 ml fractions) afforded the title compound as a colorless solid in fractions 29-59. Recrystallization from methylene chloride/hexane provided the title compound as colorless crystals (2.7 g, 87%); mp 130°-131° C. MS, (DCI): 463 $(M+NH_4)^+$, 446 $(M+H)^+$.

EXAMPLE 79

(2R,4R)-3-Benzyloxycarbonyl-2-phenyl-4-phenylmethyl-4-(1-(3-hydroxypropyl))-5-oxooxazolidine Following the procedure described in Example 78, the resultant compound from Example 77 (1.5 g, 3.5 mmol) was converted into the title compound.

EXAMPLE 80

(2S,4S)-3-Benzyloxycarbonyl-2-phenyl-4-phenylmethyl-4-(2-(ethylcarboxaldehyde))-5-oxooxazolidine The resultant compound from Example 78 (860 mg, 1.9 mmol) was dissolved in $CH_2Cl_2$ (10 ml) and added to a vigorously stirred mixture of PCC (1.0 g, 4.9 mmol) and 4 Å molecular sieves (4 g) in $CH_2Cl_2$ (100 ml). Additional portions of PCC (0.5 g, 2.5 mmol) were added after 30 min and 45 min. After 1 h total reaction time, the mixture was poured into moist ether (200 ml). The reaction flask was rinsed with ether ($4 \times 50$ ml) and the combined organic solutions were filtered through celite and concentrated in vacuo to afford a dark semisolid. The crude product was dissolved in $CH_2Cl_2$ and filtered through a 4 inch column of florisil. The filtrate (200 ml) was concentrated in vacuo to afford the title compound as a light yellow oil (450 mg, 52%). MS (DCI): 461 $(M+NH_4)^+$, 444 $(M+H)^+$.

EXAMPLE 81

(2R,4R)-3-Benzyloxycarbonyl-2-phenyl-4-phenylmethyl-4-(2-(ethylcarboxaldehyde))-5-oxooxazolidine Following the procedure described in Example 80, the resultant compound from Example 79 (0.6 g, 1.3 mmol) was converted into the desired product.

EXAMPLE 82

(2S)-Methyl-((3S)-((Benzyloxycarbonyl)amino)-3-phenylmethyl-2-oxo-1-piperidinyl)-3-(4-imidazolyl)propionate Following the procedure described in Example 102, the resultant aldehyde from Example 80 (443 mg, 1 mmol) was reductively aminated with the bis hydrochloride salt of L-histidine methyl ester (242 mg, 1 mmol). The resulting aminoester (600 mg, 1 mmol) was converted to the corresponding lactam by refluxing in absolute methanol (60 ml) in the presence of isopropylamine (170 μl, 1.95 mmol) under $N_2$ for 4 h. The volatiles were removed and the resulting substance was purified by flash chromatography (55 g silica gel, 5% $MeOH/CHCl_3$, 8 ml fractions), affording the title compound as a colorless foam (300 mg, 61%). MS (CI): $(M+H)^+ = 491$. Exact mass calcd. for $C_{27}H_{31}N_4O_5$ $(M+H)^+$: 491.2294. Found: 491.2294.

EXAMPLE 83

(2S) Methyl ((3R)-((benzyloxycarbonyl)amino)-3-phenylmethyl-2-oxo-1-piperidinyl)-3-(4-imidazolyl)propionate Following the procedure described in Example 102, the resultant compound from Example 81 (400 mg, 0.9 mmol) was reductively aminated with the bis hydrochloride salt of L-histidine methyl ester (218 mg, 0.9 mmol). The resulting aminoester (520 mg, 0.87 mmol) was dissolved in dry methanol (20 ml). Anhydrous sodium acetate (350 mg, 4.5 mmol) and glacial acetic acid (two drops) were added and the solution was heated in a seated tube for 15 h at 110 C. The solution was concentrated in vacuo and the resulting residue was partitioned between ethyl acetate (100 ml) and saturated aqueous $NaHCO_3$ (50 ml). The aqueous layer was further (extracted with ethyl acetate ($3 \times 50$ ml) and the combined organic extracts were dried over $Na_2SO_4$ and concentrated in vacuo to afford a yellow foam. Flash chromatography with methanol/chloroform mixtures provided the title compound as a colorless foam (180 mg, 42%). MS (CI): 491 $(M+H)^+$.

EXAMPLE 84

Lithium (2S)-2-((1-tert-Butyloxycarbonyl)-1-imidazol-4-yl methyl)-3-((3S)-((benzyloxycarbonyl)amino)-3-phenylmethyl-2-oxo-1-piperidinyl)acetate The resultant compound from Example 82 (260 mg, 0.53 mmol) was dissolved in dioxane (2 ml) and cooled to 0° C. under a $N_2$ atmosphere. Aqueous LiOH (0.5M, 1.2 ml, 0.6 mmol) was added dropwise and the solution was stirred for 2 h at 0° C. Di-tert-butyl dicarbonate (127 mg, 0.58 mmol) was added at 0° C. and the solution was warmed to room temperature over 1 h and stirred one additional h. The solution was concentrated to afford the title compound as a colorless foam.

EXAMPLE 85

Lithium (2S)-2-((1-tert-Butyloxycarbonyl)-imidazol-4-yl-methyl)-3-((3R)-((benzyloxycarbonyl)amino)-3-phenylmethyl-2-oxo-1-piperidinyl)acetate Following the procedure described in Example 84, the resulting compound from Example 83 (160 mg, 0.33 mmol) was converted into the title compound.

EXAMPLES 86 AND 87

(2R or 2S)-((3S)-(Benzyloxycarbonyl)amino)-3-phenylmethyl-2-oxo-1-piperidinyl)-3-(4-imidazolyl)propionic acid amide of (2S,3R,4S)-2-amino-1-cyclohexyl-3,4-dihydroxy-6-methylheptane The resultant compound of Example 84 (300 mg, 0.53 mmol), the resultant compound from Example 2 (148 mg, 0.53 mmol), HOBT (215 mg, 1.35 mmol), and N-methylmorpholine (59 mg, 0.58 mmol) were dissolved in dry DMF and cooled to −23° C. under $N_2$. To this solution was added EDAC (102 mg, 0.53 mmol) in one portion. The reaction was stirred for 3 h at −23° C., warmed to room temperature and stirred overnight. The reaction was poured into saturated aqueous $NaHCO_3$ (50 ml) and the resulting mixture was extracted with ethyl acetate (4×75 ml). The combined organic extracts were washed with saturated aqueous NACl (2×50 ml), dried over $Na_2SO_4$ and concentrated in vacuo to afford a yellow oil. The oil was dissolved in THF (1 ml). Acetic acid (3 ml) and water (1 ml) were added and the reaction was stirred for 2 h at 50° C. The cooled reaction was concentrated in vacuo and the resulting oil was dissolved in ethyl acetate (200 ml) and washed with saturated aqueous $NaHCO_3$ (3×50 ml), saturated aqueous NaCl (2×50 ml), dried over $Na_2SO_4$, and concentrated in vacuo to provide a yellow foam. Flash chromatography (2.5% $MeOH/CHCl_3$) afforded in the order of elution.

(86) (116 mg): mp 95°-101° C. MS (FAB): 702 $(M+H)^+$.

Anal. Calcd for $C_{40}H_{55}N_5O_6 \cdot 0.6\ H_2O$: C, 67.41, H 7.95, N, 9.83. Found: C, 67.12; H, 7.85;N, 9.87.

(87) (108 mg): mp 98°-105° C. MS (FAB): 702 $(M+H)^-$.

Anal. Calcd. for $C_{40}H_{55}N_5O_6 \cdot 0.2\ H_2O$: C, 68.10; H, 7.92; N, 9.93. Found: C, 67.79; H, 7.89;N, 9.78.

EXAMPLE 88

(2R or 2S)-((3R)-((Benzyloxycarbonyl)amino)-3-phenylmethyl-2-oxo-1-piperidinyl)-3-(4-imidazolyl)propionic acid amide of (2S,3R,4S)-2-amino-1-cyclohexyl-3,4-dihydroxy-6-methylheptane Following the procedure described in Example 86, the resultant compound from Example 85 (187 mg, 0.33 mmol) was converted into the title compounds as an inseparable mixture; mp 95°-105° C. MS (FAB): 702 $(M+H)^+$.

EXAMPLE 89

(2R)-2-Hydroxy-3-phenylpropanoic acid (J. Med. Chem., 23, 666)

Following the procedure of Johnson, 1980, D-phenylalanine (16.5 g, 100 mmol) was dissolved in 1N $H_2SO_4$ (150 ml) and cooled to 0° C. A solution of $NaNO_2$ (10.5 g. 150 mmol) in water (50 ml) was added dropwise. The mixture was stirred for 2 h at 0° C. and for 3 h at 25° C. The product was extracted into ether (5×100 ml) and the combined ether extracts were dried over $Na_2SO_4$ and concentrated in vacuo to about 100 ml. Hexane (300 ml) was added and the product which crystallized out was collected by vacuum filtration to afford the title compound as a colorless solid (9 g, 54%); mp=124°-125° C.

EXAMPLE 90

Methyl (2R)-2-Hydroxy-3-phenylpropanoate

Following the procedure of Cohen (J. Am. Chem. Soc., 1964, 86, 5326), the resultant compound from Example 89 (8.6 g, 52 mmol) was dissolved in dry methanol (250 ml). p-Toluenesulfonic acid (2 g, 10.5 mmol) was added and the solution was refluxed for 2 h. The cooled solution was concentrated in vacuo and the residue was dissolved in ether (400 ml). The ether solution was washed with saturated aqueous $NaHCO_3$ (3×50 ml), water (2×50 ml), 0.1N $H_2SO_4$ (1×50 ml), water (1×50 ml), dried over $Na_2SO_4$, and concentrated in vacuo to afford a colorless solid. The solid was recrystallized from hexane to provide the title compound as colorless needles (7.7 g, 83%); mp=46°-47° C.

EXAMPLE 91

Methyl (2R)-3-phenyl-2-(1-(2-propenoxy)propanoate

The resultant compound from Example 90 (3.B g, 21 mmol) and allyl bromide (5.1 g, 42 mmol) in dry DMF (20 ml) was cooled to 0° C. Sodium hydride (60% in oil, 556 mg, 23.2 mg) was added in portions over 1 h and stirring at 0° C was continued for 1 additional h. The solution was carefully poured into saturated aqueous $NH_4Cl$ (100 ml) and extracted with ether/hexane (1:1, 5×100 ml). The combined organic extracts were washed with saturated aqueous NaCl (2×50 ml), dried over $Na_2SO_4$, and concentrated in vacuo to afford a yellow oil (4.4 g). Flash chromatography (100 g silica gel, 40% ethyl acetate/hexane, 8 ml fractions) afforded the product in fractions 22-30 which were concentrated in vacuo to afford the title compound as a colorless oil (4 g, 80%). MS (DCI): 238 $(M+NH_4)^+$, 221 $(M+H)^+$.

EXAMPLE 92

Methyl (2R)-2(formylmethoxy)-3-phenyl propanoate

A $CH_2Cl_2$ solution (200 ml) of the resultant compound from Example 91 (3.9 g, 17.7 mmol) was cooled to −78° C. and treated with a stream of $O_3$ for 45 min. Excess ozone was removed with a stream of $N_2$ and dimethyl sulfide (4 ml) was added. After stirring overnight at room temperature, the solution was concentrated to afford the titled compound as a light yellow oil (4.0 g, 101%) which was used without further purification. MS (DCI): 256 $(M+NH_4+H_2O)^+$, 240 $(M+NH_4)^+$.

EXAMPLE 93

Methyl (2S)-2-(Imidazol-4-yl methyl)-2-(3R)-phenylmethyl-2-oxomorpholin-1-yl)acetate Following the procedure described in Example 105, the resultant aldehyde from Example 92, (1 g, 4.5 mmol) was reductively aminated with the bishydrochloride salt of L-histidine methyl ester (1.09g, 4.5 mmol). The resulting aminoester (700 mg, 1.9 mmol) was dissolved in dry methanol (20 ml) and heated in a seated tube for 45 h at 110° C. The cooled solution was concentrated and purified by flash chromatography using methanol/chloroform mixtures to afford the title compound as a light yellow foam (230 mg, 37%). MS (DCI): 344 $(M+H)^+$.

EXAMPLE 94

Lithium (2S)-2-((1-tert-Butyloxycarbonyl)-1-imidazol-4-yl-methyl)-((3R)-phenylmethyl-2-oxomorpholin-1-yl)acetate Following the procedure described in Example 87, the resultant compound from Example 93, (220 mg, 0.6 mmol) was treated with LiOH (0.5M, 1.2 ml, 0.6 mmol) and then di-tert-butyl dicarbonate (131 mg, 0.6 mmol) to afford the title compound as a light yellow foam.

EXAMPLE 95

(2R or 2S)-((3R)-3-phenylmethyl-2-oxo-1-moroholin-1-yl)-3-(4-imidazolyl)propionic acid amide of (2S,3R,4S)-2-amino-1-cyclohexyl-3,4-dihydroxy-6-methylheptane Following the procedure described in Example 92, the resultant compound from Example 94, the resultant compound from Example 2 (168 mg, 0.6 mmol), HOBT (243 mg, 1.8 mmol), N-methylmorpholine (67mg, 0.66 mmol) and EDAC (115 mg, 0.6 mmol) provided the intermediate compound which was treated with HOAc/THF/H20 (3:1:1) at 50° C. for 4 h. Normal workup afforded a crude product which was purified on silica gel using chloroform/methanol mixtures to afford in the order of elution.

(95A) (110 mg): mp 125°–127° C. MS (FAB): 555 $(M+H)^+$.

(95B) (85 mg): mp 105°–107° C. MS (FAB): 555 $(M+H)^+$.

EXAMPLE 96

(4R)-3-(3-Phenylpropionyl)-4-(2-propyl)-oxazolidine-2-one

To a stirred solution of 4-(2-propyl)-oxazolidine-2-one in anhydrous tetrahydrofuran (250 ml) under a nitrogen atmosphere at −78° C. was added in a dropwise fashion a solution of n-butyllithium in hexane (50 ml, 77.4 mmol) over 5 to 10 min. After stirring an additional 20 min at −78° C. 3-phenylpropionyl chloride (12.7 ml, 85.2 mmol) was added neat. The reaction was warmed to room temperature and stirred 1 to 2 h. The reaction was quenched by adding 100 ml of saturated aqueous ammonium chloride and the volatiles were removed by rotary evaporation. The resulting aqueous residue was extracted three times with ether and the combined organic phases were washed with brine, dried (Na2SO4), filtered and concentrated in vacuo. Recrystallization from hexanes/ethyl acetate provided the title compound (16.6 9, 82%). m.p.=86.5°–87.5° C. Mass spectrum: $(M+NH_4)^+ = 279$, $(M+H)^+ = 262$.

EXAMPLE 97

(4R)-3-((2R)-3-t-butoxycarbonyl-2-benzylpropionyl)-4-(2-propyl)-oxazolidine-2-one To a stirred solution of the product resulting from Example 96 (2.28 g, 8.72 mmol), in anhydrous tetrahydrofuran (30 ml) under a nitrogen atmosphere at −78° C. was added a solution of sodium hexamethyldisilylamide (9.6 ml, 9.59 mmol) in tetrahydrofuran. After stirring for 30 min at −78° C., t-butyl bromoacetate (2.21 g, 11.34 mmol) was added in anhydrous tetrahydrofuran and the resulting solution stirred 1 h at −78° C. The reaction was quenched by adding 20 ml of saturated aqueous ammonium chloride and then partitioning the mixture between water and ether. The aqueous layer was drawn off and extracted with ether. The combined organic phases were washed with 10% aqueous HCl, saturated aqueous NaHCO3 and brine, dried (Na2SO4), filtered, and concentrated in vacuo. Recrystallization from acetone/hexanes provided the desired purified product (2.59 g, 79%). m.p.=167°–168° C. Mass spectrum: $(M+NH_4)^+ = 393$, $(M+H)^+ = 376$.

EXAMPLE 98

Benzyl-(2R)-3-(t-butoxycarbonyl)-2-benzyl-propionate.

To a stirred solution of dry benzyl alcohol (0.55 ml, 5.33 mmol) in anhydrous tetrahydrofuran (18 ml) under a nitrogen atmosphere at 0° C. was added a hexane solution of n-butyllithium (2.58 ml, 4.00 mmol). To this solution was added the product from Example 97 in anhydrous tetrahydrofuran (10 ml). After stirring 1 h at 0° C. the reaction was quenched by adding excess saturated aqueous ammonium chloride. The volatiles were removed by rotary evaporation and the resulting aqueous residue extracted two times with ether. The combined organic layers were washed with brine, dried (Na2SO4), filtered, and concentrated in vacuo provided an oil which was purified by chromatography on SiO2 (15% ether acetate/hexanes) to provide the desired product (0.89 g, 94%) as a colorless oil. Mass spectrum: $(M)^+ = 354$.

EXAMPLE 99

(2R)-3-tert-Butyloxycarbonyl-2-phenylmethylpropionic Acid

The diester from Example 98 (1.41 g) and 10% palladium on carbon (0.70 g) in methanol were stirred under a hydrogen atmosphere for 2 h. Filtration and solvent evaporation afforded 1.03 g (98%) of the desired product as an oil. $^1$H NMR (CDCl3, TMS) δ 7.1–7.4 (m,5H), 2.95–3.15 (m,2H), 2.72 (dd,1H), 2.56 (dd,1H), 2.32 (dd,1H), 1.40 (s,9H).

EXAMPLE 100 tert-Butyl (3R)-4-Hydroxy-3-phenylmethylbutanoate

To the resultant acid from Example 99 (1.03 g, 3.90 mmol) in tetrahydrofuran (4 ml, THF) at 0° C. was added BH3 in THF (5.8 ml, 5.8 mmol, 1.0 molar) over 2 min. After 2 h at 0° C. the mixture was brought to room temperature and stirred for 2 h. The reaction was poured into saturated NaHCO3 solution and extracted into ethyl acetate which was dried over Na2SO4 and evaporated. Chromatography of the residue on silica gel with ethyl acetate/hexane mixtures afforded 0.55 g (56%) of the desired product as an oil. $^1$H NMR (CDCl3, TMS) δ 7.15–7.35 (m,5H), 3.65 (m,1H), 3.52 (m,1H), 2.65 (m,2H), 2.30 (m,2H), 1.90 (m,1H), 1.46 (s,9H).

EXAMPLE 101

(2R)-1-tert-Butyloxycarbonyl-2-phenylmethylpropanal

To oxalyl chloride (0.30 ml, 3.52 mmol) in methylene chloride (4 ml) at −69° C. was added dimethylsulfoxide (0.35 ml, 4.9 mmol) in methylene chloride (5 ml). After 5 min the resultant compound from Example 100 (547.0 mg, 2.19 mmol) in methylene chloride (9 ml) was added. After an additional 10 min at −69° C. triethylamine (1.20 ml, 8.56 mmol) was added dropwise. After 15 min the reaction was quenched with 2M HCl (10 ml), poured into hexane and washed with water and brine, then dried over Na₂SO₄ and evaporated to afford 529.5 mg (98%) of the desired aldehyde as an oil. 1H NMR (CDCl₃, TMS) δ 9.80 (s,1H), 7.15–7.35 (m,5H), 3.10 (m,1H), 2.70–2.90 (m,2H), 2.57 (m,1H), 2.37 (m,1H), 1.43 (s,9H).

EXAMPLE 102

N-((2R)-1-tert-Butyloxycarbonyl-2-phenylmethylpropyl)histidine Benzyl Ester

To the resulting aldehyde from Example 101 (526.0 mg, 2.12 mmol) in isopropanol (40 ml) was added L-histidine benyl ester di-p-toluenesulfonic acid salt (1.31 g, 2.22 mmol), anhydrous sodium acetate (0.52 g, 6.3 mmol) and sodium cyanoborohydride (0.20 g, 3.18 mmol). After 80 h at room temperature the mixture was poured into saturated NaHCO₃ solution and extracted into ethyl acetate which was dried over Na₂SO₄ and evaporated.

Chromatography of the residue on silica gel with methanol-chloroform mixtures afforded 254.8 mg (25%) of the desired product as an oil. 1H NMR (CDCl₃, TMS) δ 7.51 (d,1H), 7.10–7.40 (m,10H), 6.75 (s,1H), 5.12 (s,2H), 2.98 (dd,1H), 1.45 (s,9H).

EXAMPLE 103

Benzyl (2S)-2-(imidazol-4-ylmeth_1)-2-((4R)-phenylmethyl-2-oxopyrrolidin-1-yl)acetate The resultant compound from Example 102 (247.2 mg, 0.518 mmol) was stirred for 90 min in trifluoroacetic acid. After solvent evaporation the residue was dissolved in water and lyopholized to a white powder. 1-Hydroxybenztriazole (190 mg, 1.41 mmol), dimethylformamide (5 ml) and N-methylmorpholine (125 μl, 1.14 mmol) were added, then the mixture was cooled to −23° C. and treated with 1-(3-dimethylaminopropyl)-3-ethylcarbodiimide hydrochloride (140 mg, 0.73 mmol). After 2 h at −23° C. and 16 h at room temperature the mixture was poured into saturated NaHCO₃ solution and extracted into ethyl acetate which was washed with water and brine, then dried over Na₂SO₄ and evaporated.

Chromatography of the residue on silica gel with methanol-chloroform mixtures afforded 194.0 mg (93%) of the desired product as an oil. 1H NMR (CDCl₃, TMS) δ 7.52 (s,1H), 7.00–7.40 (m,10H), 6.81 (s,1H), 5.25 (m,2H), 5.12 (m,1H), 3.42 (dd,1H), 3.31 (dd,1H), 3.10 (m,2H), 2.51 (m,2H), 2.38 (dd,1H), 2.12 (dd,1H).

EXAMPLE 104

(2S)-2-((1 tert-Butyloxycarbonyl)-imidazol-4-ylmethyl)-2-((4R)-phenylmethyl-2-oxopyrrolidin-1-yl)acetic Acid The resultant compound from Example 103 (191.0 mg, 0.473 mmol) and di-tert-butyldicarbonate (115.0 mg, 0.527 mmol) in methylene chloride (1.5 ml) were stirred at room temperature for 16 h. After solvent evaporation the residue was treated with 10% palladium on carbon (200 mg), taken up in methanol (5 ml), and stirred under a hydrogen atmosphere for 2 h. The mixture was filtered and the solvent was evaporated to afford 177.8 mg (91%) of the desired acid as a foam. 1H NMR (CDCl₃, TMS) δ 8.05 (d,1H), 1.61 (s,9H).

EXAMPLE 105

(3R)-3-Benzyloxycarbonyl-3-phenylmethylpropionic Acid

The resultant compound from Example 98 (11.76 g, 33.2 mmol) in methylene chloride (25 ml) was treated with trifluoroacetic acid (25 ml). After stirring at room temperature for 90 min the solvent was evaporated to afford 9.91 g (100%) of the desired product as a solid, m.p. 48°–51° C.

EXAMPLE 106

Benzyl (2R)-4-Hydroxyl-2-phenylmethylbutanoate

The resultant compound from Example 105 (537.2 mg. 1.801 mmol) was treated according to the procedure of Example 100 to afford 341.8 mg (67%) of the desired product as an oil. 1H NMR (CDCl₃, TMS) δ 7.10–7.40 (m,10H), 5.05 (s,2H), 3.65 (m,2H), 3.02 (dd,1H), 2.92 (m,1H), 2.80 (dd,1H), 1.93 (m,1H), 1.82 (m,1H).

EXAMPLE 107

(3R)-3-Benzyloxycarbonyl-3-phenylmethylpropanal

The resultant compound from Example 106 (338.0 mg, 1.19 mmol) was reacted according to the procedure of Example 101 to afford 328.1 mg (98%) of the desired product as an oil. 1H NMR (CDCl₃, TMS) δ 9.70 (s,1H), 7.10–7.40 (m,10H), 5.11 (s,2H), 3.15–3.30 (m,1H), 3.07 (dd,1H), 2.40–2.90 (m,3H).

EXAMPLE 108

Benzyl (2S)-2-(Imidazol-4-ylmethyl)-2-((3R)-phenylmethyl-2-oxopyrrolidin-1-yl)acetate The resultant compound from Example 107 (155.8 mg, 0.552 mmol) was reductively aminated according to the procedure of Example 102. The resulting amine spontaneously cyclised to afford after chromatography 142.0 mg (64%) of the desired product as an oil. 1H NMR (CDCl₃, TMS) δ 7.51 (d,1H), 7.10–7.40 (m,10H), 6.78 (s,1H), 5.21 (d,1H), 5.18 (d,1H), 5.13 (dd,1H), 3.20–3.35 (m,3H), 3.10 (m,2H), 2.70 (m,1H), 2.39 (dd,1H), 1.95 (m,1H), 1.58 (m,1H).

EXAMPLE 109

(2S)-2-((1-tert-Butyloxycarbonyl)-imidazol-4-ylmethyl)-2-((3R)-phenylmethyl-2-oxopyrrolidin-1-yl)acetic Acid The resultant compound from Example 108 (142.0 mg, 0.352 mmol) was treated according to the procedure of Example 104 to provide 133.1 mg (91%) of the desired product as a foam. 1H NMR (CDCl₃, TMS) δ 8.03 (s,1H), 1.60 (s,9H).

EXAMPLE 110

N-((2S)-tert-Butyloxycarbonylamino-3-phenylpropyl)-histidine Benzyl Ester

Boc-phenylalanal (479.9 mg, 1.997 mmol) was reductively aminated according to the procedure of Example 102 to provide 643.1 mg (67%) of the desired product as a foam. 1H NMR (CDCl₃, TMS) δ 7.50 (s,1H), 7.10–7.40 (m,10H), 6.71 (s,1H), 5.15 (d,1H), 5.11 (d,1H), 4.77 (br,1H), 3.87 (br,1H), 3.50 (dd,1H), 3.02 (dd,1H), 2.42 (dd,1H), 1.41 (s,9H).

EXAMPLE 111

Benzyl
(2S)-2-(Imidazol-4-ylmethyl)-2-((4S)-phenylmethyl-imidazolidin-2-one-1-yl)acetate The resultant compound from Example 110 (295.0 mg, 0.616 mmol) was deprotected with trifluoroacetic acid as described in Example 103. The resultant powder was dissolved in methylene chloride (4 ml), treated with N-methylmorpholine (0.21 ml, 1.91 mmol), cooled to 0° C., and then treated with carbonyldiimidazole (121 mg, 0.746 mmol) in methylene chloride (8 ml). After 90 min at 0° C. and 18 h at room temperature the mixture was poured into saturated $NaHCO_3$ solution and then extracted into ethyl acetate which was dried and evaporated. Chromatography of the residue on silica gel with methanol-chloroform mixtures afforded 162.9 mg (65%) of the desired product. $^1H$ NMR ($CDCl_3$, TMS) δ 7.50 (s,1H), 7.05-7.40 (m,10H), 6.83 (s,1H), 5.25 (d,1H), 5.18 (d,1H), 3.76 (m,1H), 3.55 (m,1H), 3.30 (dd,1H), 3.22 (dd,1H), 3.08 (dd,1H), 2.72 (dd,1H), 2.64 (dd,1H).

EXAMPLE 112

(2S)-2-((1-tert-Butyloxycarbonyl)-imidazole-4-ylmethyl)-2-((4S)-phenylmethylimidazolidin-2-one-1-yl)acetic Acid The resultant compound from Example 111 (189.5 mg, 0.469 mmol) was treated according to the procedure of Example 104 to provide 176.7 mg (91%) of the desired product as a foam. $^1H$ NMR ($CDCl_3$, TMS) δ 8.00 (s,1H), 1.59 (s,9H).

EXAMPLE 113

Boc-N-Isobutyl-L-Phe Methyl Ester

To L-Phe methyl ester hydrochloride (0.54 g, 2.5 mmol) in isopropanol (50 ml) was added isobutyraldehyde (0.24 ml, 2.6 mmol), anhydrous sodium acetate (0.41 g, 5.0 mmol), and sodium cyanoborohydride (0.24 g, 3.8 mmol). After 16 h the reaction was worked up as described in Example 108 to provide a residue which was taken up in chloroform and filtered. The filtrate was evaporated to afford 0.58 g (98%) of N-isobutylPhe methyl ester as a mobile oil. This product was dissolved in methylene chloride (5 ml), treated with di-tert-butyldicarbonate (0.55 g, 2.5 mmol), and stirred at room temperature for 26 h. Evaporation of the solvent and chromatography of the residue on silica gel with ethyl acetate-hexane mixtures afforded 0.58 g (71%) of the desired product as an oil. $^1H$ NMR ($CDCl_3$, TMS) δ 7.10-7.30 (m,5H), 3.73 (s,3H), 1.46 (s,9H), 0.65-0.85 (m,6H).

EXAMPLE 114

Boc-N-Isobutylphenylalanol

To the resultant compound from Example 113 (0.58 g, 1.73 mmol) in ethanol (4 ml) at 0° C. was added ground $CaCl_2$ (0.38 g, 3.4 mmol), tetrahydrofuran (4 ml), and then sodium borohydride (0.26 g, 6.9 mmol). After 24 h at 0° C. the reaction was poured slowly into a mixture of citric acid (4 g) and ice (20 g) and extracted into ethyl acetate which was dried over $Na_2SO_4$ and evaporated. Chromatography of the residue on silica gel with ethyl acetate-hexane mixtures afforded 0.43 g (81%) of the desired product as an oil. $^1H$ NMR ($CDCl_3$, TMS) δ 7.15-7.30 (m,5H), 3.82 (m,2H), 1.47 (s,9H), 0.82 (d,3H), 0.75 (d,3H).

EXAMPLE 115

N-((2S)-tert-Butyloxycarbonyl(isobutyl)amino-3-phenylpropyl)histidine Benzyl Ester The resultant compound from Example 114 (435.6 mg, 1.417 mmol) was reacted according to the procedure of Example 101 and the resulting aldehyde was reductively aminated according to the procedure of Example 102 to provide 405.3 mg (53%) of the desired product as a foam. $^1H$ NMR ($CDCl_3$, TMS) δ 7.49 (s,1H), 7.10-7.40 (m,10H), 6.74 (s,1H), 5.11 (s,2H), 1.43 (s,9H), 0.78 (d,3H), 0.72 (d,3H).

EXAMPLE 116

Benzyl
(2S)-2-(Imidazol-4-ylmethyl)-2-(3-isobutyl-(4S)-phenylmethylimidazolidin-2-one-1-yl)acetate The resultant compound from Example 115 (402.0 mg, 0.752 mmol) was reacted according to the procedure of Example 111 to provide 109.2 mg (32%) of the desired product as a foam. $^1H$ NMR ($CDCl_3$, TMS) δ 7.47 (d,1H), 7.00-7.40 (m,10H), 5.25 (d,1H), 5.16 (d,1H), 4.93 (dd,1H), 3.68 (m,1H), 2.95-3.30 (m,6H), 2.85 (dd,1H), 2.44 (dd,1H), 1.83 (m,1H), 0.88 (d,3H), 0.75 (d,3H).

EXAMPLE 117

(2S)-2-((1-tert-Butyloxycarbonyl)-imidazole-4-ylmethyl)-2-(3-isobutyl-(4S)-phenylmethylimidazolidin-2-one-1-yl)acetic Acid The resultant compound from Example 116 (109.0 mg, 0.237 mmol) was treated according to the procedure of Example 104 to afford 101.2 mg (91%) of the desired product as a foam. $^1H$ NMR ($CDCl_3$, TMS) δ 8.04 (d,1H), 1.60 (s,9H), 0.92 (d,3H), 0.84 (d,3H).

EXAMPLE 118

(2S)-2-(Imidazol-4-ylmethyl)-2-(3-isobutyl-(4S)-phenylmethylimidazolidin-2-one-1-yl)acetic Acid Amide of (2)-Amino-1-cyclohexyl-3(R),4(S)-dihydroxy-6-methylheptane To the resultant compound from Example 117 (49.8 mg, 0.106 mmol) in methylene chloride (3 ml) at −10° C. was added N-methylmorpholine (0.014 ml, 0.127 mmol) followed by isobutyl chloroformate (0.014 ml, 0.107 mmol). After 3 min the resultant 3(R),4(S) amine from Example 2 (26.0 mg, 0.17 mmol) was added, the mixture was stirred at −10° C. for 15 min and then at room temperature for 2 h. The solvent was evaporated and the residue was dissolved in acetic acid (3 ml), tetrahydrofuran (1 ml) and water (1 ml), and heated at 45°-50° C. for 12 h. After solvent evaporation the residue was partitioned between saturated $NaHCO_3$ solution and ethyl acetate, and then extracted into ethyl acetate which was dried over $Na_2SO_4$ and evaporated. Chromatography of the residue on silica gel with methanol-chloroform mixtures afforded 32.6 mg (52%) of the desired product as a solid, m.p. 105°-110° C.

Anal. Calcd. for $C_{34}H_{53}N_5O_4 \cdot 0.25 H_2O$: C, 68.03; H, 8.98; N, 11.66. Found: C, 68.01; H, 8.92; N, 11.41.

EXAMPLE 119

(2S)-2-(Imidazol-4-ylmethyl)-2-(3-isobutyl-(4S)-phenylmethylimidazolidin-2-one-1-yl)acetic Acid Amide of (2'S,1'R,5S)-3-Ethyl-5-(1'-hydroxy-2'-amino-3'-cyclohexylpropyl)oxazolidin-2-one Using the procedure of Example 118 but replacing the resultant amine of Example 2 with the compound from Example 9 which had been deprotected according to the procedure of Example 2 provided the desired product as a solid.

Exact Mass Calcd. for $C_{34}H_{51}N_6O_5$ (M+H): 623.3921.

Found: 623.3919.

$^1$H NMR (CDCl$_3$, TMS) δ 7.66 (s,1H), 7.10–7.40 (m,5H), 6.96 (d,1H), 6.85 (s,1H), 4.55 (m,1H), 2.91 (dd,1H), 0.91 (m,6H), 0.84 (t,3H).

EXAMPLE 120

(2S)-2-(Imidazol-4-ylmethyl)-2-((4S)-phenylmethylimidazolidin-2-one-1-yl)acetic Acid Amide of (2S)-Amino-1-cyclohexyl-3(R),4(S)-dihydroxy-6-methylheptane Using the procedure of Example 118 with the resultant acid from Example 112 afforded the desired product as a solid, m.p. 117°–119° C.

Anal. Calcd. for $C_{30}H_{45}N_5O_4 \cdot 0.40\ H_2O$: C, 65.88; H, 8.44; N, 12.80. Found: C, 66.22; H, 8.50; N, 12.37.

EXAMPLE 121

(2S)-2-(Imidazol-4-ylmethyl)-2-((3R)-phenylmethyl-2-oxopyrrolidin-1-yl)acetic Acid Amide of (2S)-Amino-1-cyclohexyl-3(R),4(S)-dihydroxy-6-methylheptane Using the procedure of Example 118 with the resultant acid from Example 109 afforded the desired product as a solid, m.p. 92°–95° C.

Anal Calcd. for $C_{31}H_{46}N_4O_4$: C, 69.12; H, 8.61; N, 10.40. Found: C, 68.90; H, 8.55; N, 10.14.

EXAMPLE 122

(2S)-2-(Imidazol-4-ylmethyl)-2-((4R)-phenylmethyl-2-oxopyrrolidin-1-yl)acetic Acid Amide of (2S)-Amino-1-cyclohexyl-3(R),4(S)-dihydroxy-6-methylheptane Using the procedure of Example 118 with the resultant acid from Example 104 afforded the desired product as a solid, m.p. 83°–86° C.

Anal. Calcd. for $C_{31}H_{46}N_4O_4 \cdot 0.5\ H_2O$: C, 67.98; H, 8.65; N, 10.23. Found: C, 68.19; H, 8.54; N, 10.18.

EXAMPLE 123

3-[3(R)-[3-(tert-Butyloxycarbonyl)-2,2-dimethyl-4(S)-cyclohexylmethyl-5(R)-oxazolidinyl]-3-hydroxy-2(R)-isopropyl-1-oxopropyl]-4(R)-methyl-5(S)-phenyl-2-oxazolidinone Prepared from (S)-cyclohexylalaninol in analogy to the procedure of S. Thaisrivongs, D. T. Pals, L. T. Knoll, S. R. Turner, and F. S. Han, J. Med. Chem., 1987, 30, 976–982.

$^1$H NMR (CDCl$_3$) δ 0.91 (d,3H), 1.06(d,3H), 1.1 (d,3H), 0.9–1.4 (several bm), 1.48 (2S,9H), 1.5–1.9 (several bm), 2.12 (bd,1H), 2.3 (m,1H), 3.81 (dd,1H), 3.94 (td,1H), 4.04 (bm,1H), 4.22 (dd,1H), 4.84 (dq,1H), 5.61 (d,1H), 7.31–7.45 (m,5H); $^{13}$C NMR (CDCl$_3$) δ 14.72, 19.43, 20.09, 26.02, 26.30, 26.43, 26.49, 26.88, 27.51, 28.48 (3C), 29.00, 32.51, 34.37, 34.76, 50.78, 54.89, 56.15, 70.63, 78.47, 79.81, 81.64, 94.24, 125.61 (2C), 128.70 (2C), 128.75, 133.31, 151.64, 152.54, 173.40. Mass spectrum: (M+H)$^+$ = 587.

EXAMPLE 124

3-[3(R)-[3-(tert-Butyloxycarbonyl)-2,2-dimethyl-4(S)-cyclohexylmethyl-5-(R)-oxazolidinyl]-3-[(1-imidazolyl)thionyloxy]-2(R)-isopropyl-1-oxopropyl]-4(R)-methyl-5(S)-phenyl-2-oxazolidinone The resultant compound from Example 123 (1.840 g, 3.136 mmol) and 1,1'-thiocarbonyldiimidazolide (1.128 g, 6.330 mmol) were refluxed in 8 ml dry 1,2-dichloroethane under a nitrogen atmosphere for 24 h. The mixture was concentrated and the residue was purified by flash chromatography on silica gel (2.5% methanol in dichloromethane), affording 1.896 g (87%) of the desired compound. $^1$H NMR (CDCl$_3$) δ 0.93 (d,3H), 1.04 (d,3H), 1.08 (d,3H), 0.9–1.1 (bm), 1.1–1.4 (bm), 1.5 (bs,9H), 1.6–1.9 (several bm), 2.05 (m,1H), 4.13 (bm,1H), 4.23 (dd,1H), 4.81 (dd,1H), 4.94 (dq,1H), 5.70 (d,1H), 6.33 (dd,1H), 7.06 (bs,1H), 7.3–7.5 (m,5H), 7.61 (bs,1H), 8.40 (bs,1H). Mass spectrum: (M+H)$^+$ = 697.3629. Calcd. for $C_{37}H_{53}N_4O_7S$: 697.3635.

EXAMPLE 125

3-[3-[3-(tert-Butyloxycarbonyl)-2,2-dimethyl-4(S)-cyclohexylmethyl-5(S)-oxazolidinyl]-2(R)-isopropyl-1-oxopropyl]-4(R)-methyl-5(S)-phenyl-2-oxazolidinone The resultant product from Example 124 (129 mg, 0.185 mmol) was dissolved in 10 ml dry toluene and added slowly dropwise over 30 min to a refluxing solution of tri-n-butyltin hydride (93 μl, 100 mg, 0.346 mmol) in 15 ml dry toluene under a nitrogen atmosphere. Reflux was continued for an additional 10 h. The resulting solution was cooled, concentrated in vacuo, and the residue was triturated with four 10 ml portions of acetonitrile, with gentle warming. The combined acetonitrile extracts were washed with three 20 ml portions of hexane, then the combined hexane phases were back-extracted with 20 ml of acetonitrile. All acetonitrile phases were combined and concentrated in vacuo. The crude product was purified by silica gel chromatography (hexane-ethyl acetate 9:1) to give 73 mg (69%) of the desired product. $^1$H NMR (CDCl$_3$) δ 0.90 (d,3H), 0.92 (d,3H), 0.9–1.1 (bm,3H), 1.06 (d,3H), 1.15–1.35 (bm,3H), 1.51 (bs,9H), 1.57–2.14 (several bm), 3.84 (m,1H), 3.97 (m,1H), 4.85 (dq,1H), 5.68 (d,1H), 7.3–7.46 (m,5H). Mass spectrum: (M+H)$^+$ = 571.

EXAMPLE 126

2(S)-[[3-(tert-Butyloxycarbonyl)-2,2-dimethyl-4(S)-cyclohexylmethyl-5(S)-oxazolidinyl]methyl]-3-methylbutanoic acid The resultant product from Example 125 (842 mg, 1.476 mmol) was dissolved in 15 ml tetrahydrofuran and 5 ml water, and treated with a solution of lithium hydroxide manohydrate (125 mg, 2.98 mmol) in 30% aqueous hydrogen peroxide (1.1 ml, 366 mg hydrogen peroxide, 10.77 mmol). The resulting mixture was stirred 21 h at ambient temperature. The mixture was cooled to 0° and treated with 8.6 ml of 1.5M aqueous sodium sulfite. After 3 h, the mixture was concentrated in vacuo, then the aqueous residue was diluted with 35 ml dichloromethane, cooled to 0°, and acidified to pH 2 with 1M aqueous sodium bisulfate. The crude product was isolated by extraction with four 50 ml portions of dichloromethane, which were combined, washed with 50 ml brine and dried over magnesium sulfate. Concentration and silica gel chromatography of the residue gave 471 mg (77%) of the desired product. $^1$H NMR (CDCl$_3$) δ 0.96 (d,3H), 1.00 (d,3H), 1.1–1.3 (bm,5H), 1.48 (s,9H), 1.5–1.9 (several bm,15H), 2.0 (m,1H), 2.66 (m,1H), 3.7 (bm,1H), 3.90 (m,1H). Mass spectrum: (M+H)$^+$ =412.

EXAMPLE 127

Butyl 2(S)-[[3-(tert-butyloxycarbonyl)-2,2-dimethyl-4(S)-cyclohexylmethyl-5(S)-oxazolidinyl]methyl]-3-methyl-butanamide The resultant product from Example 126 (446 mg, 1.085 mmol) was treated with 1-hydroxybenztriazole monohydrate (216 mg, 1.41 mmol), 4-methylmorpholine (285 mg, 2.82 mmol) and 1-(dimethylamino propyl)-3-ethylcarbodiimide hydrochloride (301 mg, 1.10 mmol) in 10 ml anhydrous dimethylformamide at −20°, under a nitrogen atmosphere. The reaction solution was stirred at −20° for 10 min, then allowed to react at 0 for 3 days. To this solution was added n-butylamine (163 mg, 2.22 mmol), and the resulting solution was stirred at 0° for 2 h, then at ambient temperature for an additional 22 h. The solution was concentrated, and the residue partitioned between 30 ml sat. aqueous sodium bicarbonate and 50 ml ethyl acetate. The aqueous layer was further extracted with three 30 ml portions of ethyl acetate, and the combined organic phases were washed with 50 ml brine, dried over sodium sulfate and concentrated in vacuo. Purification by silica gel chromatography (ethyl acetate-hexane 1:4) afforded 483 mg (95%) of the desired product. $^1$H NMR (CDCl$_3$) a 0.91 (t,3H), 0.93 (d,3H), 0.95 (d,3H), 1.1–1.3 (m,4H), 1.3–1.9 (several m, approximately 21H), 1.49 (s,9H), 2.0 (m,1H), 3.28 (qd,2H), 3.63 (bm,1H), 3.75 (ddd,1H), 5.63 (bt,1H); $^{13}$C NMR (CDCl$_3$) δ 13.71, 20.12, 20.30, 21,06, 26.09, 26.28, 26.60, 27.99, 28.62 (3C), 30.68, 31.94, 32.81, 34.54, 35.01, 36.21, 39.12, 51.02, 61.21, 79.05, 79.76, 93.80, 152.02, 174.53.

EXAMPLE 128

Butyl 5(S)-amino-6-cyclohexyl-4(S)-hydroxy-2(R)-isopropyl-hexan-amide

A solution of the resultant compound from Example 127 (520 mg, 1.11 mmol) in 8 ml dry methanol was treated at 0° C. with acetyl chloride (0.68 ml, 0.75 g, 9.6 mmol). The resultant solution was allowed to warm slowly to room temperature, and was further stirred for 48 h. The reaction was carefully basified with an excess of solid NaHCO$_3$, then the mixture was diluted with 15 ml CH$_2$Cl$_2$ and filtered through a plug of celite, using a total of 100 ml CH$_2$Cl$_2$ to wash the solids. The filtrate was rotoevaporated to a cloudy residue, which was then redissolved in 50 ml CH$_2$Cl$_2$ and refiltered through celite as above. Evaporation produced a yellow oil, which was triturated with hot hexanes to afford 272 mg (75%) of the desired compound as white needles; m.p. 89°–90° C.; [α]$_D$= −24.6 C. (CHCl$_3$, C=1.055); $^1$H NMR (CDCl$_3$) δ 0.94 (m,10H), 1.05–1.80 (several bm,1BH), 1.86 (m,1H), 2.08 (ddd,1H), 2.57 (ddd,1H), 3.07 (ddd,1H), 3.22 (m,1H), 3.30 (m,5H), 5.79 (bt,1H); Mass spectrum: (M+H)$^+$ =327.

Anal. Calcd. for C$_{19}$H$_{38}$N$_2$O$_2$: C, 69.9; H, 11.7; N, 8.6. Found: C, 69.5; H, 11.5; N, 8.5.

EXAMPLE 129

3-(3-Thiazolyl)-2-(3R-benzyl-4-N-morpholin-1-yl-carbonyl-2-keto-piperazin-1-yl)-propionic acid Amide of Butyl 5(S)-amino-6-cyclohexyl-4(S)-hydroxy-2(R)-isopropyl-hexan-amide The morpholine group was attached to the piperazine ring by phosgene method and the title compound was then synthesized by attaching the amine from Example 128 to the appropriate acid by EDAC coupling method. DCI-NH$_3$-MS, m/e, 767 (MH$^+$, 100%), 749 (40%), 694 (25%), and 441 (32%).

Anal. (C$_{41}$H$_{62}$O$_6$N$_6$S.½ H$_2$O) C,H,N.

$^1$H NMR (300 MHz, CDCl$_3$) δ: 8.71 (d,J=1 Hz,H), 7.30–7.08 (m,7H), 6.50 (d,J=9 Hz,H), 5.89 (t,J=6 Hz,H), 5.47 (t,J=8 HzH), 4.69 (dd,J=5,9 Hz,H), 4.08 (d,J=4 Hz,H), 3.88 (m,H), 3.60–3.10 (m,≈17H), 3.03 (m,2H), 2.78 (m,2H), 2.02 (m,H), 1.95–1.05 (m,15H) and 0.95–0.80 (m,9H).

EXAMPLE 130

3-(4-Thiazolyl)-2-(3R-benzyl-4-N-p-toluene-sulfonyl-2-keto-piperazin-1-yl)-propionic acid Amide of Butyl 5(S)-amino-6-cyclohexyl-4(S)-hydroxy-2(R)-isopropyl-hexan-amide The sulfonamide linkage was formed by adding p-toluene sulfonyl chloride to the corresponding piperazine system in pyridine. The resulting acid was then coupled to the amine from Example 128 by EDAC coupling method. DCI-NH$_3$-MS, m/e, 808 (M$^+$, 23%), 790 (33%), and 482 (100%).

Anal. (C$_{43}$H$_{61}$O$_6$N$_5$S$_2$), C,H,N.

$^1$H NMR (300 MHz,CDCl$_3$)δ: 8.69 (d,J=1Hz,H), 7.37 (d,J=8 Hz,2H), 7.20 (m,3H), 7.14 (d,J=8 Hz,2H), 7.05(m,2H), 6.95 (d,J=1 Hz,H), 6.41 (d,J=9 Hz,H), 5.99 (t,J=6 Hz,H), 5.31 (t,J=6 Hz,H), 4.45 (dd,J=5,7 Hz,H), 4.16 (m,I:), 3.B3 (m,H), 3.69 (6d,J=15H,H), 3.60–2.90 (m,≈10H), 2.40 (s,3H), 2.02 (m,H), 1.90–1.00 (m,≈20H) and 1.00–0.80 (m,9H).

EXAMPLE 131

3-(3-Thiazolyl)-2-(3R-benzyl-4-N-p-toluene-sulfonyl-2-keto-piperazin-1-yl)-propionic acid Amide of 2(S)-amino-1-cyclohexyl-3(R),4(S)-dihydroxyl-6-methylheptane The piperazine ring system was synthesized following the procedure described in Example 130 and the acid was then coupled to the amine from Example 3 by EDAC coupling method. DCI-NH$_3$-MS, m/e, 725 (MH$^+$, 100%), 707 (10%), and 482 (21%).

Anal. (C$_{38}$H$_{52}$O$_6$N$_4$S$_2$), C,H,N.

$^1$H NMR (300 MHz,CDCl$_3$)δ: 8.73(d,J=1Hz,H), 7.35 (d,J=7 Hz,2H), 7.20 (m,2H), 7.13 (d,J=7 Hz,2H), 7.02 (m,3H), 6.50 (d,J=9 Hz,H), 5.20 (6t,J=6 Hz,H), 4.45 (m,H), 4.30 (m,H), 4.08 (6S,H), 3.70 (d,J=13 Hz,H), 3.55 (m,H), 3.47 (t,J=7 Hz,H), 3.25–3.10 (m,4H), 3.00 (m,2H), 2.40 (Δ,3H), 2.28 (6Δ,H), 1.85 (m,H), 1.80–1.00 (m,17H), 0.95 (d,J=7 Hz,3H), and 0.85 (d,J=7 Hz,3H).

EXAMPLE 132

2(S)-(3R-Benzyl-4N-tert-butyloxycarbonyl-2-keto-homopiperazin-1-yl)-hexanoic acid Amide of 2(S)-Amino-1-cyclohexyl-3(R),4(S)-dihydroxy-6-methylheptane Synthesized according to Scheme 4. For this synthesis allyl bromide was replaced with homoallyl bromide. MH+(OCl-NH$_3$) at 644; Anal. (C$_{37}$H$_{61}$O$_6$N$_3$), C,H,N.

EXAMPLE 133

4(S)-t-Butyloxycarbonylamino-5-cyclohexyl-3(R,S)-hydroxy-1-pentene

To a stirred −78° C. solution of Boc-cyclohexylalanine methyl ester (10.2 g, 35.8 mmol) in dry toluene (60 ml) was added diisobutylaluminum hydride (34 ml of a 1.5M solution in toluene). After 30 min, vinyl magnesium bromide (108 ml of 1M solution in tetrahydrofuran (THF)) was added. After stirring for 15 h at 0° C., the mixture was carefully quenched with methanol, treated with Rochelle salts (22 ml of saturated aqueous solution in 140 ml H$_2$O), and filtered. After extracting the solids 5 times with ethyl acetate, the extracts and filtrate were combined and the organic phase was washed with brine, dried, filtered and evaporated to an oil (10.2 g). Chromatography on silica gel eluting with hexane/ethyl acetate mixtures provided 6.1 g (60%) of the desired product.

Anal. Calcd. for C$_{16}$H$_{29}$NO$_3$·¼ H$_2$O: C, 66.8; H, 10.3; N, 4.9. Found: C, 66.9; H, 10.2; N, 4.7.

EXAMPLE 134

3-(t-Butyloxycarbonyl)-4-(cyclohexylmethyl)-2,2-dimethyl-5-vinyloxazolidine

The procedure of S. Thaisrivong (J. Med. Chem. 1987, 30, 976) was employed. A solution of 40 g of the resultant compound of Example 133 and 102 g of 2-methoxypropene in 250 ml of dichloromethane was stirred at room temperature. Solid pyridinium p-toluenesulfonate (PPTS) (177 g) was added slowly to the reaction mixture. After addition was complete, the reaction was stirred for 1 h and neutralized by addition of solid sodium bicarbonate. The solids were filtered and the filtrate was concentrated. Flash chromatography on silica gel gave 57 g of the desired compound. IR (CDCl$_3$) 1690 (C=O carbamate) cm$^{-1}$; $^1$H NMR (CDCl$_3$) δ 5.95 (m,1H), 5.32 (m,1H), 5.20 (dt,1H), 4.27 (dd,1H), 1.47 (s,9H).

Anal. Calcd. for C$_{19}$H$_{33}$NO$_3$: C, 70.55; H, 10.28; N, 4.33. Found: C, 70.47; H, 10.27; N, 4.09.

EXAMPLE 135

3-(t-Butyloxycarbonyl)-4-(cyclohexylmethyl)-2,2-dimethyloxazolidine-5-carboxaldehyde A solution of 10 g of the resultant compound of Example 134 in 150 ml of 2:1 dichloromethane:methanol was cooled in an dry-ice acetone bath. Ozone was bubbled through the solution until a blue color persisted (1 h). Dry nitrogen was then bubbled through the reaction mixture to remove excess dissolved ozone. The reaction mixture was cannulated into a suspension of 8 g zinc dust, 8 ml glacial acetic acid, 200 ml water, and 200 ml of methanol cooled to −45° C. After 5 min the bath was removed and the mixture allowed to warm to room temperature overnight. 100 ml of saturated sodium chloride was added and the entire reaction mixture extracted with two 300 ml portions of dichloromethane. The combined dichloromethane extracts were decanted, dried (MgSO$_4$), filtered, and evaporated. The crude aldehyde was purified by flash chromatography (1:4) ethyl acetate:hexane to give 9.7 g of the desired compound as a mixture of diastereomers (3:1 trans:cis) as judged by the integrated resonances of the two aldehyde protons. IR (CDCl$_3$) 1735 (C=O aldehyde), 1690 (C=O carbamate) cm$^{-1}$; $^1$H NMR (CDCl$_3$) δ 9.83 (s,1H,CHO), 9.73 (d,1H,CHO cis diastereomer), 4.14 (m,1H), 1.46 (s,9H).

Anal. Calcd. for C$_{18}$H$_{31}$NO$_4$: C, 66.43; H, 9.60; N, 4.30. Found: C, 65.27; H, 9.79; N, 4.20.

Equilibration of Aldehyde Isomers

A suspension of 25 g of the above aldehyde in 300 ml of methanol and powdered potassium carbonate (10.7 g) was stirred at room temperature for 6 h. The reaction mixture was cooled in an ice-water bath and treated with 9.3 g of glacial acetic acid for 5 min. A solution of 0.5M sodium dihydrogen phosphate (300 ml) was added to the mixture. After 30 min, the solution was concentrated to one-half the volume under reduced pressure and extracted with ether (600 ml). The combined ether extracts were dried (MgSO$_4$), filtered, and concentrated. The aldehyde was purified by flash chromatography using (1:4) ethyl acetate:hexane to give 19.5 g of the desired compound as an 8:1 mixture of trans:cis diastereomers.

EXAMPLE 136

(5S,4′S,5′R)-5-(3-(t-Butyloxycarbonyl)-4-hexylmethyl)-2,2-dimethyloxazolidin-5-yl)-3-methylenedihydrofuran-2(4H)-one A solution of 16.52 g (51 mmol) of the resultant compound of Example 135 in 15 ml of anhydrous tetrahydrofuran was treated with 3.98 g (61 mmol) of freshly activated zinc dust. With vigorous stirring, the mixture was treated with 10 g (56 mmol) of methyl 2-(bromomethyl)acrylate at a rate which maintained the temperature at 50°-60° C. Upon completion of the addition, the mixture was stirred at 50° C. for 1 h. After being allowed to cool, the mixture was poured into 100 ml of cold 1M HCl and extracted with dichloromethane (3×100 ml). The combined organic layers were washed successively with saturated aqueous NaHCO$_3$ and H$_2$O, dried over Na$_2$SO$_4$, and concentrated. Silica gel chromatography using 9:1 hexane:ethyl acetate provided 10.83 g (61%) of the desired compound. $^1$H NMR (CDCl$_3$) δ -.8–2.0 (br envelope), 1.49 (s,9H), 1.54 (s,3H), 1.57 (s,3H), 2.93 (ddt,J=18,6,3 Hz,1H), 3.05 (m,1H). 3.70 (m,1H), 4.07 (m,1H), 4.47 (ddd,J=13,9,6 Hz,1H), 5.70 (br t,J=3 Hz,1H), 6.28 (t,J=3 Hz,1H). Mass spectrum: (M+H)+ =394.

Anal. Calcd. for C$_{22}$H$_{35}$NO$_5$: C, 67.15; H, 8.96; N, 3.56. Found: C, 67.66; H, 9.11; N, 3.60.

EXAMPLE 137

(3S,5S,4′S,5′R)-5-(3-(t-Butyloxycarbonyl)-4-(cyclohexylmethyl)-2,2-dimethyloxazolidin-5-yl)-3-methyldihydrofuran-2(3H)-one A mixture of 8.03 g (20 mmol) of the resultant compound of Example 136 and 0.81 g of 10% palladium on carbon in 200 ml of ethyl acetate was shaken under 4 atmospheres of H$_2$. After filtration, concentration of the filtrate gave 7.58 g (94%) of the desired compound. $^1$H NMR (CDCl$_3$) δ 0.8–2.0 (br envelope), 1.31 (s,3H), 1.48 (s,9H), 1.54 (s,3H), 1.58 (s,3H), 2.57 (m,1H), 2.68 (m,1H), 3.74 (m,1H), 4.04 (m,1H), 4.31 (ddd,J=13,9,6 Hz,1H). Mass spectrum: (M+H)$^+$=396.

EXAMPLE 138

3-(t-Butyloxycarbonyl)-4-(cyclohexylmethyl)-5-(1,4-dihydroxy-3-methylbutyl)-2,2-dimethyloxazolidine A mixture of 0.50 g (1.26 mmol) of the resultant compound of Example 137 and 0.15 g (4 mmol) of sodium borohydride in 50 ml of tetrahydrofuran was heated at reflux under N$_2$ atmosphere for 48 h. After being allowed to cool, the mixture was treated cautiously with aqueous NH$_4$Cl, extracted with ether, washed with saturated brine, dried over MgSO$_4$, and concentrated in vacuo. Silica gel chromatography using 2:1 chloroform/ethyl acetate gave 0.37 g (73%) of the desired compound. $^1$H NMR (CDCl$_3$) δ 0.7–2.0 (br envelope), 0.94 (d,J=7 Hz,3H), 1.49 (s,9H), 1.52 (s,3H), 1.55 (s,3H), 3.43 (dd,J=11,8 Hz,1H), 3.55–3.7 (m,3H), 4.09 (br d,1H). Mass spectrum: (M+H)$^+$=400.

EXAMPLE 139

3-(t-Butyloxycarbonyl)-4-(cyclohexylmethyl)-2,2-dimethyl-5-(4-methyltetrahydrofuran-2-yl)oxazolidine A solution of 51 mg (0.13 mmol) of the resultant compound of Example 138 and 0.037 ml (0.27 mmol) of triethylamine in 2 ml of dichloromethane was cooled to 0° C. under N$_2$ atmosphere and treated with 0.012 mol (0.15 mmol) of methanesulfonyl chloride. After 1 h, the solution was diluted with dichloromethane, washed successively with 10% citric acid, water and saturated aqueous NaHCO$_3$, dried over Na$_2$SO$_4$, and concentrated in vacuo. The crude mesylate thus produced (59 mg) was taken up in 8 ml of dry detrahydro furan, treated with 20 mg (0.50 mmol) of sodium hydride (60% dispersion in oil), and heated at reflux for 2 h. After being allowed to cool, the solution was treated cautiously with saturated aqueous NH$_4$Cl, extracted with ether, dried over MgSO$_4$ and concentrated. Silica gel chromatography using 9:1 hexane/ethyl acetate gave 30 mg (75%) of the desired compound. $^1$H NMR (CDCl$_3$) δ 0.7–2.4 (br envelope), 1.06 (d,J=7 Hz,3H),1.48 (s,9H),1.52 (s,3H), 1.56 (s,3H),3.30 (t,J=9 Hz,1H), 3.66 (m,1H), 3.9–4.0 (m,3H). Mass spectrum: (M+H)$^+$=382.

The amine hydrochloride was obtained by treating the resultant compound with HCl-dioxane at 0° C. for 3 h.

EXAMPLE 140

3-(S-Thiazolyl)-2-(3R-benzyl-4-N-p-toluene-sulfonyl-2-keto-piperazin-1-yl)-propionic acid Amide of
2(S)-(2(S)-Amino-3-cyclohexyl-1(R)-hydroxy)propyl-4(S)-methyltetrahydrofuran The piperazine ring system was synthesized following the procedure described in Example 130 and the acid was then coupled to the amine from Example 139 by EDAC coupling method. DCI-NH$_3$-MS, m/c. 723 (MH$^+$, 100%), 705 (42%) and 482 (31%); $^1$H NMR (CDCl$_3$,300 MHz) δ:7.40 (d,2H,J=9 Hz), 7.30–7.05 (m,8H), 6.95 (d,1H,J≈1 Hz), 6.43 (d,1H,J=9 Hz), 5.36(t,1H,J=7 Hz), 4.50(dd,1H,J=5,6 Hz), 4.02 (m,1H), 3.88 (t,2H,J=7 Hz), 3.78–2.90 (m,≈8H), 2.40 (s,3H), 2.25 (m,H), 1.90 (m,H), 1.80 (d,H,J=12 Hz), 1.70–0.80 (m,16H) and 1.03 (d,3H,J=6H).

EXAMPLE 141

3-(3-Thiazolyl)-2-(3R-benzyl-4-N-methylpiperazyl)-sulfonyl-2-keto-piperazin-1-yl)-propionic acid Amide of Butyl
5(S)-amino-6-cyclohexyl-4(S)-hydroxy-2(R)-isopropyl-hexan-amide This compound was synthesized following the same procedure as described in Scheme 4. A minor change was made (see Scheme 10) at the allylamine stage 68. The intermediate 68 was sulfonated with N-methylpiperazyl sulfonyl chloride (J. Med. Chem. 15, 538, 1972) to give 69 in moderate yield (40–65%). The acid obtained following the hydrolysis of 70 with LiOH was coupled under standard EDAC condition to give the final product 71. DCI-NH$_3$-MS, m/e. 816 (MH$^+$, 60%), 798 (10%), 750 (3%) and 327 (100%); $^1$H NMR (300 MHz, CDCl$_3$) δ:8.75 (d,J=2 Hz,H), 7.35–7.20 (m,5H), 7.12 (d,J=2 Hz,H), 6.58 (d,J=9 Hz,H), 6.01 (t,J=5 Hz,H), 5.18 (6m,H), 4.26 (dd,J=9.4 Hz), 4.06 (m,H), 3.90–3.00 (m), 3.00–2.70 (m), 2.20 (s,3H), 2.20–1.05 (m) and 0.90 (m,9H); Anal. (C$_{44}$H$_{65}$N$_7$O$_6$S$_2$) C,H,N.

EXAMPLE 142

3-(3N-tert-butyloxycarbonyl-2-imidazolyl)-2-(3R-benzyl-4-N-(N-methylpiperazyl)-sulfonyl-2-keto-piperazin-1-yl)-propoionic acid Amide of
(2'S,1'R,5S)-3-Ethyl-5-(1'-hydroxy-2'-amino-3'-cyclohexylpropyl)oxazolidin-2-one This analog was synthesized following the procedure as described in Scheme 12 and the experimental conditions were similar to that of in Example 141. DCI-NH$_3$-MS, m/e. (MH$^+$, 100%), 743 (99%) and 460 (26%).

EXAMPLE 143

3-(2-imidazolyl)-2-(3R-benzyl-4-N-(N-methylpiperazyl)-sulfonyl-2-keto-piperazin-1-yl)-propionic acid Amide of
(2'S,1'R,5S)-3-Ethyl-5-(1'-hydroxy-2'-amino-3'-cyclohexylpropyl)oxazolidin-2-one The analog from Example 142 was deprotected with HCl-dioxane and the dihydrochloride was crystallized from EtOAc-EtOH; DCI-NH$_3$-MS, m/e. 743 ('.1H$^+$, 100%), 725 (65%), 699 (25%); Anal. (C$_{36}$H$_{54}$N$_8$O$_7$S.2 HCl H$_2$O) C,H,N.

EXAMPLE 144

3-(3N-tert-butyloxycarbonyl-2-imidazolyl)-2-(3R-benzyl-4N-(N-methylpiperazyl)-sulfonyl-2-keto-piperazin-1-yl)-propionic acid Amide of
2(S)-Amino-1-cyclohexyl-3(R),4(S)-dihydroxy-6-methylheptane This compound was made following the same procedure as described in Scheme 12. The acid derived from the hydrogenation of 72 was coupled to amine from Example 2. DCI-NH$_3$-MS, m/e. 816 (MH$^+$, 82%), 716 (83%) and 505 (100%); Anal. (C$_{41}$H$_{65}$N$_7$O$_8$ S,H$_2$O) C,H,N.

EXAMPLE 145

3-(2-imidazolyl)-2-(3R-benzyl-4N-(N-methylpiperazyl)-sufonyl-2-keto-piperazin-1-yl-propionic acid Amide of
2(S1-Amino-1-cyclohexyl-3(R1),4(S)-dihydroxy-6-methylheptane The compound in Example 144 was deprotected with HCl-dioxane and the product was finally crystallized from EtOAc-Hexane-EtOH: FAB-MS, m/e. 716 (MH+, 100%), 307 (58%) and 289 (40%); $^1$H NMR (300 MHz, free base CDCl$_3$) δ:7.60 (s,H), 7.40–7.20 (m,5H), 6.93 (d,J=9 Hz,H), 6.88 (s,H), 5.28 (m,H), 4.40 (m,2H), 3.82 (m,H), 3.70–2.70 (m), 2.20 (s,3H), 2.30–1.10 (m), 0.95 (d,J=7 Hz, 3H) and 0.82 (d,J=7 Hz, 3H).

EXAMPLE 146

3-(3N-tert-butyloxycarbonyl-2-imidazolyl)-2-(3R-benzyl-4N-(N-methylpiperazyl)-sulfonyl-2-keto-piperazin-1-yl)-propionic acid Amide of 2(s)-(2(s)-Amino-3-cyclohexyl-1(R) hydroxy)propyl-4(S)-methyltetrahydrofuran This compound was made following a procedure described in Example 144. The acid derived from the hydrogenation of 72 was coupled to the amine from Example 139 to get the final product. FAB-MS, m/e. 814 (MH+,82%), and 714 (100%); Anal. (C$_{41}$H$_{63}$N$_7$O$_8$.0.5 H$_2$O) C,H,N.

EXAMPLE 147

3-(2-imidazolyl)-2-(3R-benzyl-4-N-(N-methyl-piperazyl)-sulfonyl-2-keto-piperazin-1-yl)-propionic acid Amide of 2(S)-2(S)-Amino-3-cyclohexyl-1(R)-hydroxy) propyl-4(S)-methyltetrahydrofuran The compound in Example 146 was deprotected with HCl-dioxane and then crystallized from EtOAc-hexane-EtOH DCI-NH$_3$-MS, m/e. 714 (MH+, 20%), 696 (17%), 643 (100%) and 625 (95%); $^1$H NMR (300 MHz, free base, CDCl$_3$) δ:7.60 (6s,H), 7.35–7.20 (m,5H), 6.90 (6s,H), 6.65 (d,J=9 Hz,H), 5.20 (m,H), 4.90 (6s), 4.38 (dd,J=4.9 Hz,H), 3.90 (t,J=7 Hz,H), 3.80–2.70 (m), 2.21 (s,3H), 2.30–0.80 (m), and 1.04 (d,J=7 Hz,3H).

EXAMPLE 148

(2S)-Methyl-((3S)-((Benzyloxycarbonyl) amino-3-phenylmethyl-2-oxo-1-piperidinyl)-3-(4-thiazolyl)propionate Following the procedure described in Example 102, the resultant compound from Example 80 (1 g, 2.2 mmol) was reductively aminated with the bis hydrochloride salt of (L)-(4-thiazolyl)alanine (620 mg, 2.4 mmol). Following the procedure described in Example 83, the resulting aminoester was treated with anhydrous sodium acetate (1.8 g, 22 mmol) and glacial acetic acid (5 drops) in dry MeOH (30 mL). After heating for 72 hr at 110° C., the reaction was treated as in Example 83 to afford a yellow foam. Flash chromatography with ethyl acetate/hexane mixtures provided the title compound as a light yellow semi-solid (660 mg, 59%). MS(FAB): 508 (M+H)+.

EXAMPLE 149

(2S)-Methyl-((3S)-((amino-3-phenylmethyl-2-oxo-1-piperidinyl)-3-(4-thiazolyl)propionate The resultant compound from Example 148 (2.5 g, 4.9 mmol) was dissolved in glacial acetic acid (10 ml) and then treated with HBr/HOAc (10 ml). After stirring for 45 min, the orange solution was concentrated in vacuo. The residue was dissolved in 50 ml H$_2$O and washed with CCl$_4$ (4×). Solid NaHCO$_3$ was added to the aqueous layer to bring the pH to 9 and the aqueous layer was extracted with CH$_2$Cl$_2$ (2×) and ethyl acetate (2X). The combined organic extracts were dried (Na$_2$SO$_4$) and concentrated in vacuo to afford a yellow oil (1.8 g). MS(DCI): 374 (M+H)+.

EXAMPLE 150

(2S)-Methyl-((3S)-((N-methylpiperazinsulfonyl) amino-3-phenylmethyl-2-oxo-1-piperidinyl)-3-(4-thiazolyl)propionate The resultant compound from Example 149 (250 mg, 0.67 mmol) was dissolved in 5 ml dry dimethylformamide. To this solution was added N-methylmorpholine (407 mg, 4 mmol), N,N-dimethylaminopyridine (42 mg, 0.34 mmol) and N-methylpiperidinesulfamoyl chloride (470 mg, 2 mmol). After stirring for 18 hr, the solution was diluted with ethyl acetate (150 ml) and washed with saturated brine (3×), dried (Na$_2$SO$_4$) and concentrated in vacuo to afford a yellow oil. Flash chromatography with methanol/chloroform mixtures provided the title compound as a colorless foam (180 mg, 50%). MS(CI): 536(M+H)+.

EXAMPLE 151

(2S)-(3S)-((N-methylpiperazinsulfonyl)-amino-3-phenylmethyl-2-oxo-1-piperidinyl)-3-(4-thiazolyl) propionic acid amide of (2S.3R,4S)-2-amino-1-cyclohexyl-3,4-dihydroxy-6-methylheptane The resultant compound from Example 150 (500 mg, 0.93 mmol) was dissolved in dioxane (9 ml) and cooled to 0° C. under a N$_2$ atmosphere. A solution of LiOH (98 mg, 2.3 mmol) in water (3 ml) was added dropwise and the solution was stirred for 15 min at 0° C. and at 1 hr at 25° C. The reaction was neutralized with HCl/dioxane (500 μl, 2.3 mmol) and the solution was concentrated in vacuo and dried overnight on the HI-vac. The resultant colorless acid, the resultant compound of Example 2 (226 mg, 0.93 mmol), HOBT (377 mg, 2.8 mmol), and N-methylmorpholine (104 mg, 1.02 mmol) were dissolved in dry DMF and cooled to −23° C. To this solution was added EDAC (178 mg, 0.93 mmol) in one portion. The reaction was stirred for 3 h at −23° C., warmed to 25° C., and stirred overnight. The reaction was poured into saturated aqueous NaHCO$_3$ (50 ml) and extracted with ethyl acetate (4×). The combined organic extracts were washed with saturated aqueous NaCl (2×) dried over Na$_2$SO$_4$ and concentrated in vacuo to afford a yellow oil. Flash chromatography with methanol/methylene chloride mixtures afforded the product as a colorless powder (110 mg, 16%).

Mp 93°–97° C. MS(DCI): 747 (M+H)+.
MS(Hi-Res): Calcd. Mass for C$_{37}$H$_{59}$N$_6$O$_6$S$_2$=747.3937
Measured Mass=747.3929.

EXAMPLE 152

(2S1-((3S)-((N-methylpiperazinsulfonyl) amino-3-phenylmethyl-2-oxo-1-piperidinyl)-3-(4-thiazolyl)propionic acid amide of (2S,4S,1'R,2'S)-2-(2'-amino-3'-cyclohexyl-1'-hydroxypropyl)-4-methyltetrahydrofuran Following the procedure described in Example 151, the resultant compound from Example 150 (611 mg, 1.14 mmol), LiOH (144 mg, 3.42 mmol), dioxane (9 ml), and H$_2$O (3 ml) were mixed at 0° C. and then stirred at 25° C. for 1 hr. Following neutralization with HCl/dioxane, the solution was concentrated in vacuo and dried on Hi-vac. The resultant colorless acid, the amine from Example 139 (275 mg, 1.14 mmol), HOBT (462 mg, 3.42 mmol), and N-methylmorpholine (115 mg, 1.14 mmol) were dissolved in dry DMF and cooled to −23°C. Following the addition of EDAC (218 mg, 1.14 mmol), the reaction was treated as in Example 151. Extractive workup afforded a yellow foam. Flash chromatography with methanol/methylene chloride mixtures produced the title compound as a colorless powder (115 mg, 14%).

Mp=85°–89° C., MS(DCI): 746(M+H)+.

EXAMPLE 153

(2S)-Methyl-((3S)-amino-3-phenylmethyl-2-oxo-1-piperidinyl)-3-(4-imidazolyl)propionate The resultant lactam from Example 82 (640 mg, 1.3 mmol) and 10% palladium on carbon in glacial acetic acid were stirred under a hydrogen atmosphere for 12 hrs. Filtration and solvent evaporation afforded a colorless oil which was dissolved in H$_2$O (25 ml) and made basic with saturated NaHCO$_3$ solution. The aqueous layer was extracted with methylene chloride (5×) and the combined organic extracts were dried (Na$_2$SO$_4$) and concentrated in vacuo to afford a colorless foam (390 mg, 84%). MS(DCI): 357(M+H)+.

EXAMPLE 154

(2S)-Methyl-2-((4-methylbenzenesulfonyl)-1-imidazol-4-yl methyl)-3-(3S)-((4-methyl-benzenesulfonyl)amino)-3-phenylmethyl-2-oxo-1-piperidinyl)acetate The resultant amine from Example 153 (180 mg, 0.5 mmol), p-toluenesulfonyl chloride (280 mg, 1.26 mmol), N,N-dimethylamino-pyridine(15 mg 0.126 mmol), and N-methylmorpholine (141 mg, 1.4 mmol) in methylene chloride were refluxed for 6 hr. The solution was cooled and diluted with ethyl acetate and then washed with saturated aqueous brine (2×), dried (Na$_2$SO$_4$) and concentrated in vacuo to afford a yellow oil. Flash chromatography with methanol/chloroform mixtures produced the title product as a colorless foam (290 mg, 86%).

MS(DCI): 665(M+H)+.

EXAMPLE 155

(2S)-2-((1-tert-Butyloxycarbonyl)-1-imidazol-4-yl methyl)-3-((3S)-(4-methyl-benzenesulfonyl)amino)-3-phenylmethyl-2-oxo-1-piperdinyl)acetic acid The resultant ditosylate from Example 154 was dissolved in dioxane (4 ml) and cooled to 0° C. A solution of LiOH (28 mg, 0.68 mmol) in H$_2$O (2 ml) was added and the solution was warmed to 25° C. and stirred an additional 2 h. The solution was cooled to 0° C. and a solution of ditertbutyldicarbonate (44 mg, 0.202 mmol) in dioxane (1 ml) was added. The cooling bath was removed and the solution stirred for 4 hr at 25° C. The solution was diluted with H$_2$O (25 ml) and extracted with ether (2×) after which it was acidified and extracted with methylene chloride (5×). The combined organic extracts were dried (Na$_2$SO$_4$) and concentrated in vacuo to afford a colorless powder (61 mg, 76%).

MS(DCI): 497(M-C$_5$H$_9$O$_2$)+.

EXAMPLE 156

(2S)-2-(1-imidazol-4-yl methyl)-3-((3S)-(4-methyl benzenesulfonyl)amino)-3-phenylmethyl-2-oxo-1-piperdinyl)amide of (2S,3R,4S)-2-amino-1-cyclohexyl-3,4-dihydroxy-6-methylheptane The resultant acid from Example 155 (80 mg, 0.134 mmol), the resultant compound from Example 2 (33 mg, 0.134 mmol), HOBT (55 mg, 0.422 mmol), and N-methylmorpholine (15 mg, 0.15 mmol) were dissolved in dry DMF and cooled to −23° C. To this solution was added EDAC (26 mg, 0.134 mmol) in one portion. The reaction was treated as in Examples 86 and 87 to provide the imidazole protected product which was dissolved in THF (2 ml). Acetic acid (6 ml) and water (2 ml) were added and the reaction was stirred for 3 h at 50° C. The cooled reaction was worked up to provide the crude product as a colorless foam. Flash chromatography with methanol/methylene chloride mixtures provided the title compound as a colorless powder (35 mg, 36%).

Mp=125°–132° C. MS(FAB): 722(M+H)+.
MS(Hi-Res): Calcd. Mass for C$_{39}$H$_{55}$N$_5$O$_6$S=722.3951
Measured Mass=722.3958

EXAMPLE 157

3-(3-Thiazolyl)-2-(3R-benzyl-4-N-(N-methylpiperazyl)-sulfonyl-2-keto-piperazine-1-yl)-propionic acid Amide of 5-Amino-6-cyclohexyl-4-hydroxy-1-isopropylsulfonyl-2-methylhexane The acid from the hydrolysis of 70 (Scheme 12) is coupled to 5-Amino-6-cyclohexyl-4-hydroxy-1-isopropylsulfonyl-2-methylhexane (Tet. Lett. 30, 2653, 1989) to obtain the title compound.

EXAMPLE 158

3-(3-Thiazolyl)-2-(3R-benzyl-4-N-(N-methylpiperazyl)-sulfonyl-2-keto-piperazin-1-yl)-propionic acid Amide of Isopropyl 3-amino-4-cyclohexyl-2-hydroxybutyrate The acid from Example 157 is coupled to isopropyl 3-amino-4-cyclohexyl-2-hydroxybutyrate (Japanese Patent Application No. J63275552, published Nov. 14, 1988) to obtain the title compound.

EXAMPLE 159

3-(3-Thiazolyl)-2-(3R-benzyl-4-N-(N-methylpiperazyl)-sulfonyl-2-keto-piperazine-1-yl)-propionic acid Amide of ACHPA amide of 2-morpholino-ethyl amine The acid from Example 157 is coupled to ACHPA amide of 2-morpholino-ethyl amine (Japanese Patent No. J62246-546, published Oct. 27, 1987; European Patent Application No. EP 0274259, published Jul. 13, 1988) to obtain the title compound.

EXAMPLE 160

3-(3-Thiazolyl)-2-(3R-benzyl-4-N-(N-methylpiperazyl)-sulfonyl-2-keto-piperazine-1-yl)-propionic acid Amide of 6-Amino 7-cyclohexyl-5-hydroxy-3-isopropyl-1-heptane The acid from Example 157 is coupled to 6-Amino 7-cyclohexyl-5-hydroxy-3-isopropyl-1-heptane (European Patent Application No. EP 0310918, published Apr. 12, 1989) to obtain the title compound.

EXAMPLE 161

3-(3-Thiazolyl)-2-(3R-benzyl-4-N-(N-methylpiperazyl)-sulfonyl-2-keto-piperazine-1-yl)-propionic acid Amide of
5-Amino-6-cyclohexyl-4-hydroxy-2-isopropylhexanoyl-L-isoleucyl-2-pyridylmethylamine The acid from Example 157 is coupled to 5-Amino-6-cyclohexyl-4-hydroxy-2-isopropylhexanoyl-L-isoleucyl-2-pyridylmethylamine (J. Med. Chem., 29, 2080, 1986) to obtain the title compound.

EXAMPLE 162

3-(3-Thiazolyl)-2-(3R-benzyl-4-N-(N-methylpiperazyl)-sulfonyl-2-keto-piperazine-1-yl)-propionic acid amide of
5-Amino-6-isopropyl-4-hydroxy-2-isopropylhexanoyl-L-isoleucyl-2-pyridylmethylamine The acid from Example 157 is coupled to 5-Amino-6-isopropyl-4-hydroxy-2-isopropylhexanoyl-L-isoleucyl-2-pyridylmethylamine (U.S. Pat. No. 4,705,846, issued Nov. 10, 1987; J. Med. Chem. 29, 2088, 1986) to obtain the title compound.

EXAMPLE 163

3-(3-Thiazolyl)-2-(3R-benzyl-4-N-(N-methylpiperazyl)-sulfonyl-2-keto-piperazine-1-yl)-propionic acid Amide of
4-Amino-2,2-difluoro-3-hydroxy-6-methylheptanoyl-L-isoleucyl-2-pyridylmethylamine The acid from the hydrolysis of 70 (Scheme 12) is coupled to 4-Amino-2,2-difluoro-3-hydroxy-6-methylheptanoyl-L-isoleucyl-2-pyridylmethylamine (J. Med. Chem., 29,2080, 1986) to obtain the desired compound.

EXAMPLE 164

3-(3-Thiazolyl)-2-(3R-benzyl-4-N-(N-methylpiperazyl)-sulfonyl-2-keto-piperazine-1-yl)-propionic acid Amide of ACHPA-difluorostatine amide of
(2-methyl-propyl)-amine The acid from Example 157 is coupled to ACHPA-difluorostatine amide of (2-methyl-propyl)-amine (J. Med. Chem., 29, 2080, 1986) to obtain the desired analog.

EXAMPLE 165

3-(3-Thiazolyl)-2-(3R-benzyl-4-N-(N-methylpiperazyl)-sulfonyl-2-keto-piperazine-1-yl)-propionic acid Amide of
3-Amino-4-cyclohexyl-2-hydroxy-1-isopropylsulfonyl-butane The acid synthesized in Example 157 is coupled to 3-Amino-4-cyclohexyl-2-hydroxy-1-isopropylsulfonyl-butane (U.S. Pat. No. 4,826,815, issued May 2, 1989) to obtain the title compound.

EXAMPLE 166

3-(3-Thiazolyl)-2-(3R-benzyl-4-N-(N-methylpiperazyl)-sulfonyl-2-keto-piperazine-1-yl)-propionic acid Amide of
(4S,5S)-N-Isobutyl-4-hydroxy-5-amino-6-cyclohexyl-hex-1-ene-2-carboxamide The acid from Example 157 is coupled to (4S,5S)-N-Isobutyl-4-hydroxy-5-amino-6-cyclohexyl-hex-1-ene-2-carboxamide (J. Org. Chem., 51, 3921, 1986) to obtain the desired product.

EXAMPLE 167

3-(3-Thiazolyl)-2-(3R-benzyl-4-N-(N-methylpiperazyl)-sulfonyl-2-keto-piperazine-1-yl)-propionic acid Amide of (4S,5S)-5-Amino-4-hydroxy-7-methyl-2E-octenoic acid isobutylamide The acid from Example 157 is coupled to (4S,5S)-5-Amino-4-hydroxy-7-methyl-2E-octenoic acid isobutylamide (European Patent Application No. EP 0272583, published Jun. 19, 1988) to obtain the desired title compound.

EXAMPLE 168

3-(3-Thiazolyl)-2-(3R-benzyl-4-N-(N-methylpiperazyl)-sulfonyl-2-keto-piperazine-1-yl)-propionic acid Amide of
(1R,3S,4S)-4-Amino-5-cyclohexyl-3-hydroxy-1-isopropyl-pentane sulfonic acid morpholino amide The acid from Example 157 is coupled to (1R,3S,4S)-4-Amino-5-cyclohexyl-3-hydroxy-1-isopropyl-pentane sulfonic acid morpholino amide (European Patent Application No. EP 0309841, published Apr. 5, 1989) to obtain the title compound.

EXAMPLE 169

(2S)-((3S)-((N-methylpiperazinsulfonyl)-amino-3-phenylmethyl-2-oxo-1-piperidinyl)-3-(4-thiazolyl) propionic acid amide of
5-Amino-6-Cyclohexyl-4-hydroxy-1-isopropylfulfonyl-2-methylhexane Following the procedure described in Example 152, the acid obtained in Example 152 is coupled to 5-Amino-6-Cyclohexyl-4-hydroxy-1-isopropylfulfonyl-2-methylhexane (Tetrahedron Letters, 1989, 30, 2653) to afford the title compound.

EXAMPLE 170

(2S)-((3S)-((N-methylpiperazinsulfonyl)-amino-3-phenylmethyl-2-oxo-1-piperidinyl)-3-(4-thiazolyl) propionic acid amide of Isopropyl 3-Amino-4-Cyclohexyl 2-hydroxybutyrate Following the procedure described in Example 152, the acid from Example 152 is coupled to isopropyl 3-amino-4-cyclohexyl-2-hydroxybutyrate (Japanese Patent Application No. J63275552, published Nov. 14, 1988) to afford the title compound.

EXAMPLE 171

(2S)-((3S)-((N-methylpiperazinsulfonyl)-amino-3-phenylmethyl-2-oxo-1-piperidinyl)-3-(4-thiazoyly) propionic acid amide of ACHPA amide of 2-morpholinoethyl amine.

Following the procedure described in Example 152, the acid obtained in Example 152 is coupled to ACHPA amide of 2-morpholinoethyl amine (Japanese Patent Application No. J62246546, published Oct. 27, 1987; European Patent Application No. EP027425, published Jul. 13, 1988) to afford the title compound.

EXAMPLE 172

(2S)-((3S)-((N-methylpiperazinsulfonyl)-amino-3-phenylmethyl-2-oxo-1-piperidinyl)-3-(4-thiazolyl) propionic acid amide of 6-Amino-7-Cyclohexyl-5-Hydroxy-3-Isopropyl-1-heptene Following the procedure described in Example 152, the acid from 152 is coupled to 6-Amino-7-Cyclohexyl-5-Hydroxy-3-Isopropyl-1-heptene (European Patent Application No. EP0310918, published Apr. 12, 1989) to afford the title compound.

EXAMPLE 173

(2S)-((3S)-((N-methylpiperazinsulfonyl)-amino-3-phenylmethyl-2-oxo-1-piperidinyl)-3-(4-thiazolyl) propionic acid amide of 5-Amino-6-cyclohexyl-4-hydroxy-2-isopropylhexanoyl-L-isoleucyl-2-pyridylmethylamine Following the procedure described in Example 152, the acid obtained in Example 152 is coupled to 5-Amino-6-cyclohexyl-4-hydroxy-Z-isopropylhexanoyl-L-isoleucyl-2-pyridylmethylamine (J. Med. Chem., 1986, 29, 2080) to afford the title compound.

EXAMPLE 174

(2S)-((3S)-((N-methylpiperazinsulfonyl)-amino-3-phenylmethyl-2-oxo-1-piperidinyl)-3-(4-thiazolyl) propionic acid amide of 5-Amino-6-isopropyl-4-hydroxy-2-Isopropylhexanoyl-L-isoleucyl-2-pyridylmethylamine Following the procedure described in Example 152, the acid obtained in Example 152 is coupled to 5-Amino-6-Isopropylhexanoyl-L-isoleucyl-2-pyridylmethylamine (U.S. Pat. No. 4,705,846, issued Nov. 10, 1987; J. Med. Chem., 1986, 29, 2088) to afford the title compound.

EXAMPLE 175

(2S)-((3S)-((N-methylpiperazinsulfonyl)-amino-3-phenylmethyl-2-oxo-1-piperidinyl)-3-(4-thiazolyl) propionic acid amide of 4-Amino-2,2-difluoro-3-hydroxy-6-methylheptanoyl-L-isoleucyl-2-pyridylmethylamine Following the procedure described in Example 152, the acid obtained in Example 152 is coupled to 4-Amino-2,2-difluoro-3-hydroxy-6-methylheptanoyl-L-isoleucyl-2-pyridylmethylamine (J. Med. Chem., 1986, 29, 2080) to afford the title compound.

EXAMPLE 176

(2S)-((3S)-((N-methylpiperazinsulfonyl)-amino-3-phenylmethyl-2-oxo-1-piperidinyl)-3-(4-thiazolyl) propionic acid amide of ACHPA-difluorostatine amide of 2-methylbutylamine Following the procedure described in Example 152, the acid obtained in Example 152 is coupled to ACHPA-difluorostataine amide of 2-methylbutylamine (J. Med. Chem., 1986, 29, 2080) to afford the title compound.

EXAMPLE 177

(2S)-((3S)-((N-methylpiperazinsulfonyl)-amino-3-phenylmethyl-2-oxo-1-piperidinyl)-3-(4-thiazolyl) propionic acid amide of 3-Amino-4-cyclohexyl-2-hydroxyl-1-isopropylsulfonylbutane Following the procedure described in Example 152, the acid obtained in Example 152 is coupled to 3-Amino-4-cyclohexyl-2-hydroxyl-1-isopropylsulfonylbutane (U.S. Pat. No. 4,826,815, issued May 2, 1989) to afford the title compound.

EXAMPLE 178

(2S)-((3S)-((N-methylpiperazinsulfonyl)-amino-3-phenylmethyl-2-oxo-1-piperidinyl)-3-(4-thiazolyl) propionic acid amide of (4S,5S)-N-Isobutyl-4-hydroxy-5-amino-6-cyclohexyl-hex-1-ene-2-carboxamide Following the procedure described in Example 152, the acid obtained in Example 152 is coupled to (4S,5S)-N-Isobutyl-4-hydroxy-5-amino-6-cyclohexyl-hex-1-ene-2-carboxamide (J. Org. Chem., 1986, 51, 3921) to afford the title compound.

EXAMPLE 179

(2S)-((3S)-((N-methylpiperazinsulfonyl)-amino-3-phenylmethyl-2-oxo-1-piperidinyl)-3-(4-thiazolyl) propionic acid amide of (4S,5S)-5-Amino-4-hydroxy-7-methyl-2E-octenoic acid isobutylamide Following the procedure described in Example 152, the acid obtained in Example 152 is coupled to (4S,5S)-5-Amino-4-hydroxy-7-methyl-2E-octenoic acid isobutylamide (European Patent Application No. EP 0272583, published Jun. 19, 1988) to afford the title compound.

EXAMPLE 180

(2S)-((3S)-((N-methylpiperazinsulfonyl)-amino-3-phenylmethyl-2-oxo-1-piperidinyl)-3-(4-thiazolyl) propionic acid amide of (1R,3S,4S)-4-Amino-5-cyclohexyl-3-hydroxyl-1-isopropylpentanesulfonic acid morpholinoamide Following the procedure described in Example 152, the acid obtained in Example 152 is coupled to (1R,3S,4S)-4-Amino-5-cyclohexyl-3-hydroxy-1-isopropylpentanesulfonic acid morpholinoamide (European Patent Application No. EP 0309841, published Apr. 5, 1989) to obtain the title compound.

EXAMPLE 181

(2S)-Methyl-((3S)-((N-methyl-N-methyl-piperazinsulfonyl)amino-3-phenylmethyl-2-oxo-1-piperidinyl)-3-(4-thiazolyl)propionate The resultant compound from Example 150 is mixed with aqueous formaldehyde, and sodium cyanoborohydride in acetonitrile and stirred until the reaction is complete. Normal workup affords the title compound.

EXAMPLE 182

(2S)-((3S)-((N-methyl-N-methylpiperazin-sulfonyl-)amino-3-phenylmethyl-2-oxo-1-piperidinyl)-3-(4-thiazolyl)propionic acid amide of (2S,4S,1'R,2'S)-2-(2'-amino-3'-cyclohexyl-1'-hydroxypropyl)-4-methyltetrahydrofuran Following the procedure described in Example 151, the resultant compound from Example 181 is hydrolyzed to the free acid and coupled to the amine from Example 139 to afford the title compound.

EXAMPLE 183

(2S)-((3S)-((N-methyl-N-methyl-piperazinsalfonyl-)amino-3-phenylmethyl-2-oxo-1-piperidinyl)-3-(4-thiazolyl)propionate amide of (2S,3R,4S)-2-amino-1-cyclohexyl-3,4-dihydroxy-6-methylheptane Following the procedure described in Example 151, the resultant compound from Example 181 is hydrolyzed and coupled to the resultant compound of Example 2 to afford the title compound.

EXAMPLE 184

An improved synthesis of (2S)-Methyl-((3S)-((Benzyloxycarbonyl)amino-3-phenylmethyl-2-oxo-1-piperidinyl)-3-phenylmethyl-2-oxo-1-piperidinyl)-3-(4-thiazolyl)propionate a: (3S,11R)-3-Phenylmethyl-10bH-oxazolo[3,2-c][1,3]benzoxazine-2(3H),5-dione Following the procedure of H. Block (J. Chem. Soc. (c), 329, 1071), Na metal (1.15 g, 50 mmol) was dissolved in 500 ml of absolute ethanol. L-Phenylalanine (8.26 g, 50 mmol) and salicylaldehyde (6.11 g, 50 mmol) were then added and the yellow-green solution was concentrated in vacuo and further dried for 3 h at 50° C. under hi-vac. The yellow residue was suspended in dry, ethanolfree chloroform (200 ml), treated with $K_2CO_3$ (60 g, 450 mmol), and cooled in an ice-$H_2O$ bath. A solution of phosgene (5.5 g, 55 mmol) in chloroform (100 ml) was added dropwise over 1 h and the reaction was stirred for an additional 2 h at 25° C.. Excess phosgene was removed with a stream of dry $N_2$ and the organic solution was decanted. The salts remaining in the reaction flask were washed with several portions of chloroform and the combined organic solutions were washed with water (2×), half-saturated aqueous NaCl (2×), saturated aqueous NaCl (1×), dried ($MgSO_4$) and concentrated in vacuo to afford a pale yellow solid. Recrystallization from ethyl acetate/hexane provided the title compound as a colorless solid (7.2 g, 58%).
MS(DCI): 296 (M+H)+.

b: (3S,11R)-3-Phenylmethyl-3-(1-(2-propenyl)-10bH-oxazolo [3,2-c][1,3]benzoxazine-2(3H), 5-dione A solution of the resultant compound from Example 184a (886 mg, 3 mmol) in dry THF (15 ml) was cooled to −78° C. and then treated with a THF solution of lithium bis(trimethylsilyl)amide (1N, 2.94 ml, 2.94 mmol). After the addition of DMPU (1.15 g, 9 mmol), the solution was stirred for 15 min at −78° C. and then treated with allyl bromide (725 mg, 6 mmol). The reaction was stirred for 2 h at −78° C. and then warmed to −20° C. over 2 hr. The reaction was recooled to −78° C. and then acetic acid (100 μl) was added. The solution was concentrated in vacuo and the residue was partitioned between ethyl acetate (200 ml) and saturated aqueous citric acid (100 ml). The layers were separated and the organic layer was washed with additional saturated aqueous citric acid (2×), water (1×), saturated brine (1×), dried ($Na_2SO_4$) and concentrated in vacuo to afford a yellow oil. The oil was dissolved in methylene chloride and passed through a 6" plug of silica gel eluting with 12.5% ethyl acetate/hexane. The eluent (200 ml) was concentrated in vacuo to afford the title compound as a colorless oil (940 mg, 82%).
MS(DCI): 336(M+H)+, 353(M+NH4)+.

c: (S)-2-Amino-2-phenylmethyl-4-pentenoic acid.

A solution of the resultant compound from Example 184b (210 mg, 0.63 mmol) was dissolved in dioxane (9 ml) and treated with a solution of LiOH-$H_2O$ (105 mg, 2.5 mmol) in 4 ml $H_2O$. The green solution was stirred for 1 h at room temperature and then acidified with 10% HCl to pH=1. After stirring 2 h at R.T. the solution was concentrated in vacuo The residue was dissolved in 10% HCl (5 ml) and extracted with diethyl ether (4×). The aqueous solution was concentrated in vacuo, redissolved in 5 ml $H_2O$ and applied to 15 g of Dowex H+ form ion-exchange resin. The column was eluted with water (100 ml) and then 1.3 N ammonium hydroxide. The ninhydrin positive fractions were pooled and concentrated in vacuo. The residue was dissolved in 10 ml water and concentrated in vacuo; repeat once more. Finally, the residue was dissolved in water and passed through a C-18 Sep Pak cartridge which was then eluted with 20% methanol/water. The eluent was concentrated in vacuo and dried overnight under hi-vac (50° C., 0.3 mmHg) to afford a colorless powder (85 mg, 65%).
MS(DCI): 206(M+H)+, 223(M+NH4)+.

d: (S)-2-Benzyloxycarbonylamino-2-phenylmethyl-4-pentenoic acid

The resultant compound from Example 184c is dissolved in saturated aqueous sodium bicarbonate and heated with excess N-(benzyloxycarbonloxy)succinimide until no more amino acid remains. The solution is cooled and extracted with ether. The solution is then acidified and extracted with ethyl acetate which is dried and concentrated to afford the title compound.

e: (4S)-3-Benzyloxycarbonyl-4-phenylmethyl-4-(1-(2-propenyl))-5-oxooxazolidine

The resultant compound from Example 184d (2.30 g, 6.78 mmol), paraformaldehyde (0.75 g, 25 mmol) and toluenesulfonic acid (0.13 g, 0.68 mmol) were dissolved in toluene and refluxed for 2.5 h during which time the water produced in the reaction was removed by a Dean-Stark trap. The reaction was cooled and diluted with ether. The organic solution was washed with saturated aqueous sodium bicarbonate (2×), saturated aqueous sodium chloride (1×), dried ($Na_2SO_4$) and concentrated in vacuo to provide a yellow oil. Flash chromatography with ethyl acetate/hexane mixtures afforded the title compound as a colorless oil (1.53 g, 64%).
MS(DCI): 352(M+H)+, 369(M+NH4)+.

f:
(2S)-3-Benzyloxycarbonyl-4-(1-(3-hydroxypropyl)-4-phenylmethyl-5oxooxazolidine The resultant compound from Example 184e (1.40 g, 3.98 mmol) was dissolved in dry THF and treated dropwise with 9-BBN (11.95 ml, 5.98 mmol). After stirring overnight the mixture was quenched with one ml of water. The reaction flask was immersed in a 25° C. water bath followed by the concurrent and dropwise addition of 3N NaOH (10 ml, 30 mmol) and 30% $H_2O_2$ (10 ml). Stirring was continued for 10 min after the addition was completed after which the solution was saturated with solid NaCl. The layers were separated and the aqueous layer was extracted with ether (3×). The combined organic extracts were washed with saturated aqueous $NaHCO_3$ solution, dried over $Na_2SO_4$ and concentrated in vacuo. Flash chromatography with ethyl acetate/hexane mixtures provided the title compound as a colorless oil (1.12 g, 76%).

MS(DCI): 387(M+NH$_4$)+.

g: (2S)-3-Benzyloxycarbonyl-4-(2-(ethyl carboxaldehyde)-4-phenylmethyl-5-oxooxazolidine The resultant compound from Example 184f (1.11 g, 3 mmol) was dissolved in $CH_2Cl_2$ (5 ml) and added to a vigorously stirred mixture of PCC (1.75 g, 4. mmol) and 4 Å molecular sieves (4 g) in $CH_2Cl_2$ (100 ml). Additional portions of PCC (0.8 g, 2 mmol) were added after 30 min and 45 min. After 1 h total reaction time, the mixture was poured into moist ether (200 ml). The reaction flask was washed with ether (4×) and the combined organic solutions were filtered through celite and concentrated in vacuo to afford a dark semisolid. The crude product was dissolved in $CH_2Cl_2$ and filtered through a 4 inch column at florisil. The filtrate (200 ml) was concentrated in vacuo to afford the title compound as a light yellow oil (0.63 g, 57%).

MS(DCI): 385(M+NH4)+.

h:
(2S)-Methyl-((3S)-((Benzyloxycarbonyl)lamino-3-phenylmethyl-2-oxo-1-piperidinyl)-3-(4-thiazolyl)propionate Following the procedure described in Example 102, the resultant product from Example 184g (630 mg, 1.71 mmol) was reductively animated with the bis hydrochloride salt of L-(4-thiazolyl)alanine (0.44 g, 1.71 mmol). Following the procedure described in Example 83, the resulting aminoester was treated with anhydrous sodium acetate (1.42 g, 17 mmol) and glacial acetic acid (7 drops) in dry MeOH (30 ml). After heating for 18 h at 110° C. the reaction mixture was treated as in Example 83 to afford a yellow foam. Flash chromatography with ethyl acetate/hexane mixtures provided the title compound as a light yellow foam (463 mg, 53%).

MS(DCI): 508(M+H)+.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The compounds of the present invention can also be used in the form of prodrugs which include esters. Examples of such esters include a hydroxyl-substituted compound of formula I which has been acylated with a blocked or unblocked amino acid residue, a phosphate function, or a hemisuccinate residue. The amino acid esters of particular interest are glycine and lysine; however, other amino acid residues can also be used. Other esters include the compounds of formula I wherein a carboxylic acid group has been esterified to provide esters which include, but are not limited to, methyl, ethyl or benzyl esters. These esters serve as pro-drugs of the compounds of the present invention and serve to increase the solubility of these substances in the gastrointestinal tract. The prodrugs are metabolically converted in vivo to the parent compound of formula I. The preparation of the pro-drug esters is carried out by reacting a hydroxyl-substituted compound of formula I with an activated amino acyl, phosphoryl or hemisuccinyl derivative. The resulting product is then deprotected to provide the desired pro-drug ester. Prodrugs which are esters of carboxylic acid group containing compounds of formula I are prepared by methods known in the art.

The novel compounds of the present invention possess an excellent degree of activity and specificity in treating hypertension in a host. The novel compounds of the present invention are also useful for treating congestive heart failure. The ability of the compounds of the invention to inhibit human renal renin can be demonstrated in vitro by reacting a selected compound at varied concentrations with human renal renin, free from acid proteolytic activity, and with renin substrate (human angiotensinogen) at 37 degrees C. and pH of 6.0. At the end of the incubation, the amount of angiotensin I formed is measured by radioimmunoassay and the molar concentration required to cause 50% inhibition, expressed as the IC$_{50}$, is calculated. When tested in accordance with the foregoing procedure, the compounds of the invention demonstrated IC$_{50}$'s in the range of $10^{-7}$ to $10^{-10}$ M as seen in Table I.

TABLE I

| Example | IC$_{50}$(nM) |
| --- | --- |
| 12A | 770 |
| 13 | 430 |
| 18 | 920 |
| 20 | 240 |

TABLE I-continued

| Example | IC$_{50}$(nM) |
| --- | --- |
| 21 | 62 |
| 22 | 300 |
| 24 | 170 |
| 32A | 810 |
| 34A | 100 |
| 35A | 91 |
| 36 | 330 |
| 38A | 6.2 |
| 44 | 15 |
| 45 | 13 |
| 47 | 81 |
| 48 | 22 |
| 49B | 32 |
| 50 | 22 |
| 51 | 230 |
| 56A | 410 |
| 63B | 15 |
| 63C | 4.5 |
| 73 | 67 |
| 87 | 1.4 |
| 88 | 28 |
| 118 | 150 |
| 119 | 150 |
| 120 | 650 |
| 121 | 430 |
| 122 | 580 |
| 129 | 1.3 |
| 130 | 0.73 |
| 131 | 3 |
| 132 | 340 |
| 140 | 3.4 |
| 141 | 1.5 |
| 142 | 5.0 |
| 143 | 1.7 |
| 144 | 6.6 |
| 145 | 1.7 |
| 146 | 1.6 |
| 147 | 1.0 |
| 151 | 0.32 |
| 152 | 0.55 |
| 156 | 1.4 |
| 141 | 1.5 |
| 142 | 5.0 |
| 143 | 1.7 |
| 144 | 6.6 |
| 145 | 1.7 |
| 146 | 1.6 |
| 147 | 3.3 |
| 151 | 0.32 |
| 152 | 0.55 |
| 156 | 1.4 |

The ability of the compounds of the invention to decrease blood pressure and plasma renin activity in vivo can be determined using the following method.

In Vivo Activity

Male cynomolgous monkeys housed under constant temperature and lighting conditions and weighing 3–5 kg were instrumented with chronic indwelling arterial and venous catheters. Following pretreatment by salt-depletion, the monkeys were dosed by nasogastric tube with 3 mg/kg of the compound of Example 152. The results with three monkeys are shown in Table II.

TABLE II

Effect of the Compound of Example 152 on Blood Pressure (BP, mmHg) and Plasma Renin Activity (PRA, ng/ml/hr) in Three Salt Depleted Monkeys Following Oral Dosing (3 mg/kg)

| Time (min) | Monkey 1 BP | Monkey 1 PRA | Monkey 2 BP | Monkey 2 PRA | Monkey 3 BP | Monkey 3 PRA | Mean BP | Mean PRA |
| --- | --- | --- | --- | --- | --- | --- | --- | --- |
| 0 | 75 | 12.6 | 105 | 34.2 | 77 | 18.4 | 86 | 21.7 |
| 5 | 75 | 2.2 | 99 | 0.1 | 82 | 0.1 | 85 | 0.8 |
| 15 | 75 | 0.44 | 92 | 0.0 | 69 | 0.2 | 79 | 0.2 |
| 30 | 71 | 0.0 | 82 | 0.0 | 69 | 0.0 | 74 | 0.0 |
| 60 | 70 | 0.0 | 85 | 0.0 | 65 | 0.1 | 73 | 0.0 |
| 90 | 74 | 0.1 | 85 | 0.0 | 70 | 0.0 | 76 | 0.0 |
| 120 | 68 | 0.0 | 80 | 0.3 | 82 | 0.0 | 77 | 0.1 |
| 180 | 72 | 0.1 | 92 | 0.2 | 72 | 0.1 | 79 | 0.1 |
| 360 | 72 | 0.2 | 93 | 0.7 | 84 | 0.7 | 83 | 0.5 |

These results indicate that the compound caused a decrease in blood pressure accompanied by suppression of PRA when administered orally.

The compounds of the invention may also be used with one or more antihypertensive agents selected from the group consisting of diuretics, and/or β-adrenergic blocking agents, central nervous system -acting agents, adrenergic neuron blocking agents, vasodilators, angiotensin I converting enzyme inhibitors, and other antihypertensive agents.

Total daily dose administered to a host in single or divided doses may be in amounts, for example, from 0.001 to 10 mg/kg body weight daily and more usually 0.01 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The present invention also relates to the use of novel compounds, pharmaceutical compositions containing the novel compounds and the use of the compounds and compositions to inhibit renin for treating glaucoma or reducing and/or controlling intraocular pressure. The present invention also relates to the use of novel compounds and pharmaceutical compositions which inhibit renin in combination with a beta-adrenergic antagonist agent or an angiotensin converting enzyme inhibiting compound for treating glaucoma or reducing and/or controlling intraocular pressure.

The present invention also relates to pharmaceutical compositions for treating the increase in intraocular pressure associated with the administration of steroidal antiinflammatory agents comprising novel renin inhibiting compounds in combination with a steroidal antiinflammatory compound in a pharmaceutically acceptable vehicle.

The present invention also relates to a kit comprising in individual containers in a single package a novel renin inhibiting compound in a suitable pharmaceutical vehicle and a steroidal antiinflammatory compound in a suitable pharmaceutical vehicle and/or a beta-adrenergic antagonist agent in a suitable pharmaceutical vehicle or an angiotensin converting enzyme inhibiting compound in a suitable pharmaceutical vehicle.

The compositions of the invention are administered as topical or systemic pharmaceutical compositions when used for treating or reducing and/or controlling intraocular pressure.

These compositions are preferably administered as topical pharmaceutical compositions suitable for ophthalmic administration, in a pharmaceutically acceptable vehicle such as pharmaceutically acceptable sterile aqueous or nonaqueous solutions, suspensions, emulsions, ointments and solid inserts.

Examples of suitable pharmaceutically acceptable vehicles for ophthalmic administration are water, propylene glycol and other pharmaceutically acceptable alcohols, sesame or peanut oil and other pharmaceutically acceptable vegetable oils, petroleum jelly, water soluble ophthalmologically acceptable non-toxic polymers such as methyl cellulose, carboxymethyl cellulose salts, hydroxyethyl cellulose, hydroxypropyl cellulose; acrylates such as polyacrylic acid salts; ethylacrylates; polyacrylamides; natural products such as gelatin, alginates, pectins, tragacanth, karaya, agar, acacia; starch derivatives such as starch acetate, hydroxyethyl starch ethers, hydroxypropyl starch; as well as other synthetic derivatives such as polyvinyl alcohol, polyvinyl pyrrolidone, polyvinyl methyl ether, polyethylene oxide, carbopol and xantham gum; and mixtures of these polymers. Such compositions may also contain adjuvants such as buffering, preserving, wetting, emulsifying, and dispersing agents. Suitable preserving agents include antibacterial agents such as quaternary ammonium compounds, phenylmercuric salts, benzyl alcohol, phenyl ethanol; and antioxidants such as sodium metabisulfite, butylated hydroxyanisole and butylated hydroxytoluene. Suitable buffering agents include borate, acetate, gluconate and phosphate buffers.

The pharmaceutical ophthalmic compositions of the invention may also be in the form of a solid insert. A solid water soluble or water swellable polymer such as dextran, hydroxyloweralkyl dextran, carboxymethyl dextran, hydroxyloweralkyl cellulose, loweralkyl cellulose, carboxymethyl cellulose, polyvinyl alcohol, dextrin, starch, polyvinyl pyrrolidone and polyalkylene glycols may be used as the carrier for the drug.

Dosage levels of the active compound in the compositions for treating glaucoma or reducing and/or controlling intraocular pressure may be varied so as to obtain a desired therapeutic response to a particular composition. Generally, the active compound will be administered as an isotonic aqueous solution of from 0.00001 to 1.0 (w/v) percent concentration. More preferably the active compound will be administered as an isotonic aqueous solution of from 0.00001 to 0.1 (w/v) percent concentration.

The term "controlling intraocular pressure" as used herein means the regulation, attenuation and modulation of increased intraocular tension. The term also means that the decrease, in the otherwise elevated intraocular pressure, obtained by the methods and compositions of the invention is maintained for a significant period of time as, for example, between consecutive doses of the composition of the invention.

The novel renin inhibiting compounds of the invention may be the only active ingredient for controlling intraocular pressure in the methods and compositions of the invention or may be used in combination with other ingredients which control intraocular pressure such as beta-adrenergic antagonist compounds. The term "beta-adrenergic antagonist" as used herein means a compound which by binding to betaadrenergic plasma membrane receptors reduces or eliminates sympathetic activity or blocks the effects of exogenously administered catecholamines or adrenergic drugs. Examples of beta-adrenergic antagonists are atenolol, metopropol, nadolol, propranolol, timolol, labetalol, betaxolol, carteolol and dilevalol and pharmaceutically acceptable salts thereof. Most preferably the beta-adrenergic antagonist is timolol.

Timolol is currently used for treating glaucoma or reducing and/or controlling intraocular pressure, but it has a number of adverse side effects. Accordingly, administration of a composition comprising a combination of a beta-adrenergic antagonist and a novel renin inhibiting compound of the invention could produce a reduction in intraocular pressure equivalent to that produced by a beta-adrenergic antagonist alone, but at a reduced dose level of the beta-adrenergic antagonist. This will result in a reduced level of the beta-adrenergic antagonist related adverse side effects.

The combination composition is administered as a single dosage form containing both the novel renin inhibitor and the beta-adrenergic antagonist. The beta adrenergic antagonist may comprise from 5 mg to about 125 mg of the composition of the invention. The preferred ranges of the components in the composition of the invention in unit dosage form are:

Renin inhibitor: 1 ng to 0.1 mg
Beta-adrenergic antagonist: 5 ug to 125 ug

When the beta-adrenergic antagonist and the novel renin inhibitor are administered as separate compositions the present invention relates to a kit comprising in two separate containers a pharmaceutically acceptable beta-adrenergic antagonist composition and a pharmaceutically acceptable novel renin inhibitor composition, in a single package. A preferred kit comprises a beta-adrenergic antagonist composition and a topical novel renin inhibitor composition. A most preferred kit comprises a topical ophthalmological beta-adrenergic antagonist composition and a topical ophthalmological novel renin inhibitor composition.

The novel renin inhibiting compounds of the invention may also be administered in combination with an angiotensin converting enzyme (ACE) inhibiting compound. Examples of angiotensin converting enzyme inhibiting compounds are captopril and enalapril. As was previously mentioned, ACE inhibitors have some undesirable side effects. Accordingly, administration of an ACE inhibitor in combination with a renin inhibitor could produce a reduction in intraocular pressure greater than or equivalent to that of an ACE inhibitor alone, but at a reduced dose level of the ACE inhibitor. This will result in a reduced level of the ACE inhibitor related adverse side effects.

The combination composition is administered as a single dose form containing both the novel renin inhibitor and the angiotensin converting enzyme inhibitor. The ACE inhibitor may comprise from 5 ng to about 50 ug of the composition of the invention. The preferred ranges of the components in the composition of the invention in unit dosage form are:

Renin inhibitor: 1 ng to 0.1 mg
ACE inhibitor: 5 ng to 50 ug

When the ACE inhibitor and the novel renin inhibitor are administered as separate compositions the present invention relates to a kit comprising in two separate containers a pharmaceutically acceptable ACE inhibitor composition and a pharmaceutically acceptable novel renin inhibitor composition, in a single package. A preferred kit comprises an ACE inhibitor composition and a topical novel renin inhibitor composition. A most preferred kit comprises a topical ophthalmological ACE inhibitor composition and a topical novel renin inhibitor composition.

Dosage levels of the active compounds in the compositions of the invention may be varied so as to obtain a desired therapeutic response depending on the route of administration, severity of the disease and the response of the patient.

Topical, ophthalmic and systemic administration of steroidal antiinflammatory agents can cause an increase in intraocular pressure. The increase in intraocular pressure can be reduced by the administration of a novel renin inhibiting compound of the invention. Steroidal antiinflammatory agents include hydrocortisone, cortisone, prednisone, prednisolone, dexamethasene, methylprednisolone, triamcinolone, betamethasone, alclometasone, flunisolide, beclomethasone, clorocortolone, diflorasone, halcinonide, fluocinonide, fluocinolone, desoximetasone, medrysone, paramethasone, and fluorometholone, and their pharmaceutically acceptable salts and esters. Preferred steroidal antiinflammatory agents are hydrocortisone, prednisolone, dexamethasone, medrysone and fluorometholone and their pharmaceutically acceptable salts and esters. The novel renin inhibitor is administered after use of a steroidal antiinflammatory agent or at the same time, causing reduction and/or control of intraocular pressure.

Various combinations of a topical or oral or injectible dosage form of a steroidal antiinflammatory agent and a topical or oral dosage form of the novel renin inhibitor may be used. A preferred combination comprises a topical steroidal antiinflammatory and a topical novel renin inhibitor. More preferred is a topical ophthalmic dosage form comprising both a steroidal antiinflammatory and a novel renin inhibitor.

When the steroidal antiinflammatory agent and the novel renin inhibitor are administered as separate compositions the present invention relates to a kit comprising in two separate containers a pharmaceutically acceptable steroidal antiinflammatory agent composition and a pharmaceutically acceptable novel renin inhibitor composition, in a single package. A preferred kit comprises a steroidal antiinflammatory composition and a topical novel renin inhibitor composition. A most preferred kit comprises a topical ophthamological steroidal antiinflammatory composition and a topical ophthamological novel renin inhibitor composition.

The combination composition of the invention may contain from about 0.00001 to 1.0 (w/v) percent of the novel renin inhibitor for combined or separate topical administration. More preferably the amount of the novel renin inhibitor is about 0.00001 to 0.1 (w/v) percent of the composition. The amount of the novel renin inhibitor in a unit dosage form for topical administration to the eye is from about 5 ng to about 0.5 mg, preferably from about 5 ng to about 25 ng. The dose required will depend on the potency of the particular novel renin inhibitor, the severity of the intraocular pressure increase and the response of the individual patient.

The combination composition of the invention may contain from about 0.05 to 1.5 (w/v) percent of the steroidal antiinflammatory for combined or separate topical administration. The amount of the steroidal antiinflammatory in a unit dosage form for topical administration to the eye is from about 20 ug to about 600 ug. The dose required will depend on the potency of the particular steroidal antiinflammatory, the severity of the disease and the response of the individual patient.

When the steroidal antiinflammatory agent of the combination therapeutic method of the invention is administered other than ophthalmically, appropriate doses are well known in the art.

The compositions of the invention may include other therapeutic agents in addition to the novel renin inhibitor, and other agents which reduce and/or control intraocular pressure.

The effect on intraocular pressure of the novel compounds of the invention can be determined in rabbits by using the following method.

Effects of Topically Administered Renin Inhibiting Compounds on Intraocular Pressure of Rabbits a. Method The antiglaucoma activity of the compounds was tested by measuring the effect on intraocular pressure in rabbits as described by Tinjum, A.M., Acta Ophthalmologica, 50, 677 (1972). Male albino, New Zealand rabbits were placed in restraining devices and the intraocular pressure was measured with an applamatic tonometer. Exactly 0.1 ml of an isotonic saline solution containing a test compound was instilled into the conjuctival sac and the intraocular pressure was measured at 5, 15, 30, 60, 90, 120 and 180 minutes afterwards.

The present invention is also directed to the use of compounds of the formula I in combination with one or more antihypertensive agents independently selected from diuretics, adrenergic blocking agents, vasodilators, calcium channel blockers, angiotensin converting enzyme (ACE) inhibitors, potassium channel activators and other antihypertensive agents.

Representative diuretics include hydrochlorothiazide, chlorothiazide, acetazolamide, amiloride, bumetanide, benzthiazide, ethacrynic acid, furosemrde, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Other representative antihypertensive agents include sympatholytic agents such as methyldopa, clonidine, guanabenz, reserpine and the like or a pharmaceutically acceptable salt thereof.

Synergistic combinations of a compound of formula I with one or more of the above-mentioned antihypertensive agents are useful for the treatment of hypertension or congestive heart failure.

The compound of formula I and the antihypertensive agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

In addition, the present invention is directed to the use of a compound of formula I to inhibit retroviral proteases and in particular to inhibit HIV-1 protease and HIV-2 protease. Compounds of formula I are useful for treatment or prophylaxis of diseases caused by retroviruses, especially acquired immune deficiency syndrome or an HIV infection.

The antiviral activity of compounds of the invention can be demonstrated using the following method.

A mixture of 0.1 ml (4×10⁶ cells/ml) of H9 cells and 0.1 ml (100 infectious units) of HIV-1₃ₐ was incubated on a shaker for 2 h. The resulting culture was washed three times, resuspended into 2 ml of medium, and treated with 10 µl of the compound of the invention (5 mM in dimethylsulfoxide). The control culture was treated in an identical manner except the last step was omitted. After incubation of the culture for eight days without change of medium, an aliquot (0.1 ml) of the supernatent was withdrawn and incubated with fresh H9 cells on a shaker for 2 h. The resulting culture was washed three times, resuspended into 2 ml of medium, and incubated. Virus infectivity was determined using the Abbott HTLV-III antigen E.I.A. method (Paul, et al., J. Med. Virol., 22 357 (1987)).

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula

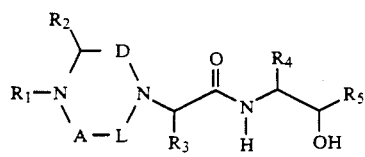

wherein
$R_1$ is
(I) hydrogen,
(II) benzyl,
(III) pyrimidinyl,
(V) pyridyl,
(VI) $R_6$—C(O)—wherein $R_6$ is
 (i) loweralkyl,
 (ii) amino,
 (iii) alkylamino,
 (iv) dialkylamino,
 (v) (alkoxyalkyl)(alkyl)amino,
 (vi) (alkoxyalkoxyalkyl)(alkyl)amino,
 (vii) aryl wherein aryl is an unsubstituted or substituted phenyl, naphthyl, tetrahydronaphthyl or indanyl group wherein a substituted phenyl, naphthyl, tetrahydronaphthyl or indanyl is substituted with one or two substituents independently selected from loweralkyl, haloalkyl, alkoxy, thioalkoxy, amino, alkylamino, dialkylamino, hydroxy, halo, mercapto, nitro, carboxaldehyde and carboxamide,
 (viii) arylalkyl wherein aryl is defined as above,
 (ix) aminoalkyl,
 (x) alkoxy,
 (xi) substituted loweralkyl wherein the substituent is selected from alkoxy, thioalkoxy, halogen, alkylamino and dialkylamino,

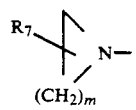

(xii)

wherein m is 1 to 5 and $R_7$ is hydrogen, hydroxy, alkoxy, thioalkoxy, alkoxyalkoxy, polyalkoxy, amino, alkylamino or dialkylamino or

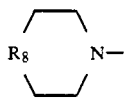

(xxii)

wherein R₈ is O, S, SO₂, O=C or R₉N wherein R₉ is hydrogen or loweralkyl or
—(VII) R₅₄S(O)₂— wherein R₅₄ is
  (i) amino,
  (ii) alkylamino,
  (iii) dialkylamino,
  (iv) loweralkyl,
  (v) haloalkayl,
  (vi) aryl wherein aryl is defined as above,
  (vii) p-biphenyl or
  (viii) morpholinyl, piperidinyl, piperazinyl or 4-methylpiperazinyl;
A is CH₂ and D is CH₂ or A is CH₂ and D is C=O or A is C=) and D is CH₂;
L is CH₂;
R₂ is
  (I) hydrogen,
  (II) loweralkyl,
  (III) cycloalkylalkyl or
  (IV) benzyl;
R₃ is
  (I) hydrogen,
  (II) loweralkyl,
  (III) loweralkenyl,
  (IV) cycloalkylalkyl,
  (V) cycloalkenylalkyl,
  (VI) alkoxyalkyl,
  (VII) thioalkoxyalkyl,
  (VIII) (alkoxyalkoxy)alkyl,
  (IX) (polyalkoxy)alkyl,
  (X) arylalkyl wherein aryl is defined as above,
  (XI) imidazolylmethyl or
  (XII) thiazolylmethyl;
R₄ is
  (I) loweralkyl,
  (II) cycloalkylalkyl or
  (III) arylalkyl wherein aryl is defined as above; and
R₅ is
  (I)—CH(OH)R₁₄ wherein R₁₄ is loweralkyl or
  (II) —CH₂CH(R₂₂)C(O)NHR₂₃ wherein R₂₂ is loweralkyl or cycloalkylalkyl and R₂₃ is
    (i) loweralkyl,
    (ii) hydroxyalkyl,
    (iii) alkoxyalkyl,
    (iv) aminoalkyl,
    (v) alkylaminoalkyl,
    (vi) dialkylaminoalkyl or
    (vii)

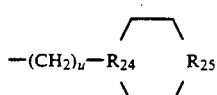

wherein u is 0 to 3, R₂₄ is CH₂ or N and R₂₅ is NH, O, S or SO₂; or a pharmaceutically acceptable salt or ester thereof.

2. The compound of claim 1 wherein R₂ is benzyl, R₃ is loweralkyl, R₄ is cyclohexylmethyl and R₅ is —CH₂CH(R₂₂)C(O)NHR₂₃ wherein R₂₂ is loweralkyl and R₂₃ is loweralkyl.

3. A pharmaceutical composition for inhibiting renin, comprising a pharmaceutical carrier and a therapeutically effective amount of a compound of claim 1.

4. A method for inhibiting renin comprising administering to a host in need of such treatment a therapeutically effective amount of a compound of claim 1.

5. A method for treating hypertension comprising administering to a host in need of such treatment a therapeutically effective amount of a compound of claim 1.

6. A method for treating congestive heart failure comprising administering to a host in need of such treatment a therapeutically effective amount of a compound of claim 1.

7. The compound of claim 1 wherein R₂ is benzyl, R₃ is loweralkyl, R₄ is cyclohexylmethyl and R₅ is —CH₂CH(R₂₂)C(O)NHR₂₃ wherein R₂₂ is loweralkyl and R₂₃ is loweralkyl.

8. A compound of the formula:

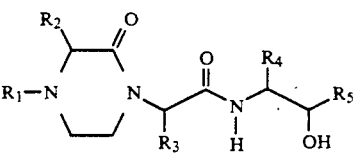

wherein
R₁ is
  (I) hydrogen,
  (II) benzyl,
  (III) (4-OMe)benzyl,
  (IV) pyrimidinyl,
  (V) pyridyl,
  (VI) R₆—C(O)— wherein R₆ is
    (i) loweralkyl,
    (ii) amino,
    (iii) alkylamino,
    (iv) dialkylamino,
    (v) (alkokxyalkyl)(alkyl)amino,
    (vi) (alkoxyalkoxyalkyl)(alkyl)amino,
    (vii) aryl wherein aryl is an unsubstituted or substituted phenyl, naphthyl, tetrahydronaphthyl or indanyl group wherein a substituted phenyl, naphthyl, tetrahydronaphthyl or indanyl is substituted with one or two substituents independently selected from loweralkyl, haloalkyl, alkoxy, thioalkoxy, amino, alkylamino, dialkylamino, hydroxy, halo, mercapto, nitro, carboxaldehyde and carboxamide,
    (viii) arylalkyl wherein aryl is defined as above,
    (ix) aminoalkyl,
    (x) alkoxy,
    (xi) substituted loweralkyl wherein the substituent is selected from alkoxy, thioalkoxy, halogen, alkylamino and dialkylamino,

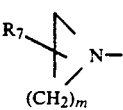

(xii)

wherein m is 1 to 5 and R₇ is hydrogen, hydroxy, alkoxy, thioalkoxy, alkoxyalkoxy, polyalkoxy, amino, alkylamino or dialkylamino or

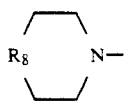
(xxii)

wherein $R_8$ is O, S, $SO_2$, O=C or $R_9$ N wherein $R_9$ is hydrogen or loweralkyl or (VII) $R_{54}S(O)_2$—wherein $R_{54}$ is
(i) amino,
(ii) alkylamino,
(iii) dialkylamino,
(iv) loweralkyl,
(v) haloalkyl,
(vi) aryl wherein aryl is defined as above,
(vii) p-biphenyl or
(viii) morpholinyl, piperidinyl, piperazinyl or 4-methylpiperazinyl;

$R_2$ is
(I) hydrogen,
(II) loweralkyl,
(III) cycloalkylalkyl or
(IV) benzyl;

$R_3$ is
(I) hydrogen,
(II) loweralkyl,
(III) loweralkenyl,
(IV) cycloalkylalkyl,
(V) cycloalkenylalkyl,
(VI) alkoxyalkyl,
(VII) thioalkoxyalkyl,
(VIII) (alkoxyalkoxy)alkyl,
(IX) (polyalkoxy)alkyl,
(X) arylalkyl wherein aryl is defined as above,
(XI) imidazolylmethyl or
(XII) thiazolylmethyl;

$R_4$ is
(I) loweralkyl,
(II) cycloalkylalkyl or
(III) arylalkyl wherein aryl is defined as above; and $R_5$ is
(I) —CH(OH)$R_{14}$ wherein $R_{14}$ is loweralkyl or (II) —CH$_2$CH($R_{22}$)C(O)NHR$_{23}$ wherein $R_{22}$ is loweralkyl or cycloalkylalkyl and $R_{23}$ is
(i) loweralkyl,
(ii) hydroxyalkyl,
(iii) alkoxyalkyl,
(iv) aminoalkyl,
(v) alkylaminoalkyl,
(vi) dialkylaminoalkyl or
(vii)

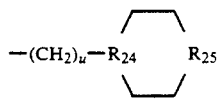

wherein u is 0 to 3, $R_{24}$ is $CH_2$ or N and $R_{25}$ is NH, O, S or $SO_2$; or a pharmaceutically acceptable salt or ester thereof.

9. 3-(3-Thiazolyl)-2-(3R-benzyl)-4-N-p-toluenesulfonyl-2-keto-piperazin-1-yl)-propionic acid amide of 2(S)-amino-1-cyclohexyl-3(R), 4(S)-dihydroxy-6-methylheptane, or a pharmaceutically acceptable salt or ester thereof.

10. 3-(3-Thiazolyl)-2-(3R-benzyl-4-N-morpholin-1-yl-carbonyl-2-keto-piperazin-1-yl)-propionic acid amide of Butyl 5(S)-amino-6-cyclohexyl-4(S)-hydroxy-2(R)-isopropylhexanamide, or a pharmaceutically acceptable salt or ester thereof.

11. A pharmaceutical composition for inhibiting renin comprising a pharmaceutical carrier and a therapeutically effective amount of a compound of claim 8.

12. A method for inhibiting renin comprising administering to a host in need of such treatment a therapeutically effective amount of a compound of claim 8.

13. A method for treating hypertension comprising administering to a host in need of such treatment a therapeutically effective amount of a compound of claim 8.

14. A method for treating congestive heart failure comprising administering to a host in need of such treatment a therapeutically effective amount of a compound of claim 8.

* * * * *

UNITED STATES PATENT AND TRADEMARK OFFICE
CERTIFICATE OF CORRECTION

PATENT NO. : 5,164,388
DATED : November 17, 1992
INVENTOR(S) : Biswanath De, et. al.

It is certified that error appears in the above-indentified patent and that said Letters Patent is hereby corrected as shown below:

Column 142, line 34, change "pyrimidinyl" to --(4-OMe)benzyl-- and insert between (III) and (V) --(IV) pyrimidinyl, --.
Column 143, line 14, delete, "haloalkayl", insert --haloalkyl--.
Column 143, line 21, delete ")", insert --O--.

Signed and Sealed this

Seventh Day of June, 1994

Attest:

BRUCE LEHMAN

Attesting Officer   Commissioner of Patents and Trademarks